US007718688B2

(12) United States Patent
Denny et al.

(10) Patent No.: US 7,718,688 B2
(45) Date of Patent: May 18, 2010

(54) NITROBENZINDOLES AND THEIR USE IN CANCER THERAPY

(75) Inventors: William Alexander Denny, Auckland (NZ); William Robert Wilson, Waluki (NZ); Ralph James Stevenson, Auckland (NZ); Moana Tercel, Auckland (NZ); Graham John Atwell, Auckland (NZ); Shangjin Yang, Auckland (NZ); Adam Vorn Patterson, Auckland (NZ); Frederik Bastlaan Pruijn, Auckland (NZ)

(73) Assignee: Auckland Uniservices Limited, Auckland (NZ)

( * ) Notice: Subject to any disclaimer, the term of this patent is extended or adjusted under 35 U.S.C. 154(b) by 305 days.

(21) Appl. No.: 11/666,014

(22) PCT Filed: Oct. 21, 2005

(86) PCT No.: PCT/NZ2005/000278

§ 371 (c)(1),
(2), (4) Date: Jun. 28, 2007

(87) PCT Pub. No.: WO2006/043839

PCT Pub. Date: Apr. 27, 2006

(65) Prior Publication Data

US 2008/0119442 A1    May 22, 2008

(30) Foreign Application Priority Data

Oct. 22, 2004    (NZ) .................................... 536107

(51) Int. Cl.
*A61K 31/403*    (2006.01)
*C07D 209/60*    (2006.01)

(52) U.S. Cl. ...................................... 514/411; 548/427
(58) Field of Classification Search ................ 514/411; 548/427

See application file for complete search history.

(56) References Cited

FOREIGN PATENT DOCUMENTS

| WO | WO 98/11101 | 3/1998 |
| WO | WO 03/097635 A1 | 11/2003 |

OTHER PUBLICATIONS

Alberts et al. Clinical Cancer Research 1998, 4, 2111-2117.*
Alberts et al. J. Gastrointest. Cancer 2007, 38, 10-14.*
Markovic et al. Am. J. Clin. Oncol (CCT) 2002, 25(3), 308-312.*
Boger et al. J. Med. Chem. 2001, 66(7), 2207-2216.*
Boger et al. J. Am. Chem. Soc. 2007, 129(49), 15391-15397.*
Boger et al. Tet. Lett. 1998, 39, 2227-2230.*
STN File CA, Abstract No. 140:246365, & Kline, T., et al; *Molecular Pharmaceutics* (2004), 1(1), pp. 9-22.
STN File CA, Abstract No. 139:100997, & Hay, M.P., et al; *Journal of Medicinal Chemistry* 46(12), pp. 2456-2466.
STN File CA, Abstract No. 131:286452, & Hay, M.P., et al; *Bioorganic & Medicinal Chemistry Letters* (1999), 9(16), pp. 2237-2242.
Atwell, G.J., et al; "Synthesis and cytotoxicity of amino analogues of the potent DNA alkylating agent seco-CBI-TMI"; *Bioorganic & Medicinal Chemistry Letters*, Pergamon, Elsevier Science, GB, vol. 7, No. 12, pp. 1493-1496 (1997) (XP004136243).

* cited by examiner

*Primary Examiner*—Rebecca L Anderson
*Assistant Examiner*—Jason M Nolan
(74) *Attorney, Agent, or Firm*—Nixon & Vanderhye

(57) ABSTRACT

The present invention relates generally to nitro-1,2-dihydro-3H-benzo[e]indoles and related analogues, to their preparation, and to their use as hypoxia-selective drugs and radiosensitizers for cancer therapy, both alone or in combination with radiation and/or other anticancer drugs.

31 Claims, 1 Drawing Sheet

NITROBENZINDOLES AND THEIR USE IN CANCER THERAPY

This application is the U.S. National Phase of International Application PCT/NZ2005/000278, filed 21 Oct. 2005, which designated the U.S. PCT/NZ2005/000278 claims priority to New Zealand Application No. 536107 filed 22 Oct. 2004. The entire content of these applications are incorporated herein by reference.

TECHNICAL FIELD

The present invention relates generally to nitro-1,2-dihydro-3H-benzo[e]indoles and related analogues, to their preparation, and to their use as hypoxia-selective drugs and radiosensitizers for cancer therapy, both alone or in combination with radiation and/or other anticancer drugs, and to their use for gene-directed enzyme-prodrug therapy (GDEPT) and antibody-directed enzyme-prodrug therapy (ADEPT).

BACKGROUND TO THE INVENTION

It has been established that many human tumours contain a significant proportion of hypoxic cells (Kennedy et al., *Int. J. Radiat. Oncol. Biol. Phys.*, 1997, 37, 897-905; Vaupel et al., *Semin. Oncol.*, 2001, 28, 25-35). The presence of hypoxic cells arises because of chaotic growth and an inefficient microvasculature system within the tumour, so that tumours often exhibit large intercapillary distances and variable blood flow. Reduction of oxygen tension in tumours leads to radioresistance. Up to a three-fold increase in radiation dose may be required to kill anoxic tumour cells. A link has been identified between the presence of tumour hypoxia and failure of local control by radiation therapy (Nordsmark et al., *Radiother. Oncol.*, 1996, 41, 31-39; Brizel et al., *Radiother. Oncol.*, 1999, 53, 113-117). This phenomenon of tumour hypoxia has been exploited in the development of a class of anticancer agents termed 'hypoxia-activated prodrugs' which are also sometimes referred to as 'bioreductive drugs' although the latter term also encompasses prodrugs activated by reduction under oxic conditions (Brown et al., *Semin. Radiat. Oncol.*, 1966, 6, 22-36; Denny et al., *Br. J. Cancer*, 1996, 74 (Suppl XXVII) 32-38; Stratford & Workman, *Anti-Cancer Drug Des.*, 1998, 13, 519-528).

Various nitro(hetero)aromatic compounds have been reported as hypoxia-activated prodrugs. These include
- the nitroimidazole (i), which is proposed to undergo fragmentation following nitro group reduction by endogenous cellular nitroreductase enzymes (McClelland et al., *Biochem. Pharmacol.*, 1984, 33, 303-309),
- the dinitrobenzamide mustard (ii) and analogues, where similar reduction of the nitro group activates the mustard (Palmer et al., *J. Med. Chem.* 1996, 39, 2518; Helsby et al., *Chem. Res. Toxicol.*, 2003, 16, 469-478; Denny et al., NZ Provisional Patent Application 529249), and
- the nitrobenzindoline (iii) and analogues have been reported as potential bioreductive drugs activated by the *E. coli* NR enzyme (Denny et al., PCT Int. Appl. WO 98/11101 A2, 1998; Atwell et al., *J. Org. Chem.* 1998, 63, 9414-9420; Atwell et al., *Bioorg. Med. Chem. Lett.* 1997, 7, 1493-1496.)

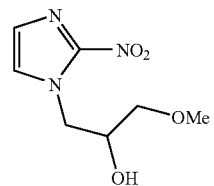

I

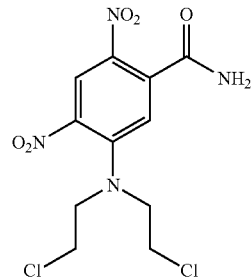

II

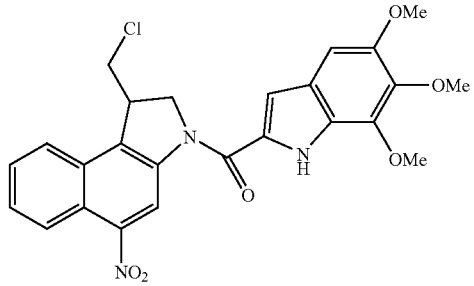

III

It is an object of the present invention to provide a specific class of nitro-1,2-dihydro-3H-benzo[e]indoles, and their corresponding phosphates, as bioreductive prodrugs for use in cancer therapy or to at least provide the public with a useful alternative.

SUMMARY OF THE INVENTION

In a first aspect, the present invention provides a compound of Formula I,

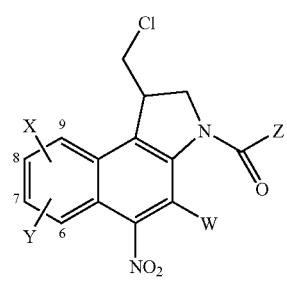

(I)

Wherein X, Y, and W are independently selected from H, halogen, $C_{1-4}$alkyl, $OR^1$, $OP(O)(OH)_2$, $SR^1$, $NR^1{}_2$, $COR^1$, $SOR^1$, $SO_2R^1{}_2$, $SO_2NR^1{}_2$, $SO_2NR^1R^1{}_2$, $SO_2NR^1NR^1{}_2$, $SO_2NHCOR^1$, $CO_2R^1$, $CONR^1{}_2$, $CONHSO_2R^1$, $CF_3$, $CN$, $NO_2$, where X and Y are located at any one of the available positions 6-9, and where each $R^1$ independently represents H or a $C_{1-4}$alkyl, optionally substituted with one or more hydroxyl or amino groups, each hydroxyl group being further optionally substituted with a phosphate [P(O)(OH)$_2$] group, and each amino group being further optionally substituted with one or two C$_{1-4}$alkyl groups, and wherein Z may be selected from the following structures (Ia-Ic)

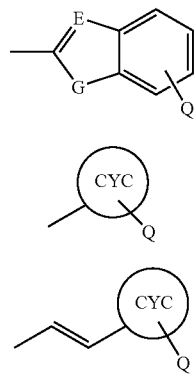

wherein E may be selected from —N= or —H=, G may be selected from O, S, or NH, Q may be independently selected from one to three of R$^2$, OR$^2$, OP(O)(OH) halogen, NR$^2_2$, NO$_2$, CO$_2$R$^2$, CONR$^2_2$, NR$^2$COR$^2$, where each R$^2$ independently represents H, lower C$_{1-4}$ alkyl, optionally substituted with one or more hydroxyl or amino groups, each hydroxyl group being further optionally substituted with a phosphate [P(O)(OH)$_2$] group, each amino group being optionally substituted with one or two C$_{1-4}$alkyl groups; and CYC may represent a 5- or 6-membered carbocycle, or heterocycle containing one or two atoms independently selected from N, O and S, and physiologically functional salt derivatives thereof, with the proviso that when W represents H, X and Y do not each represent H.

Preferably, in one embodiment of a compound of formula I, Z is selected from the following:

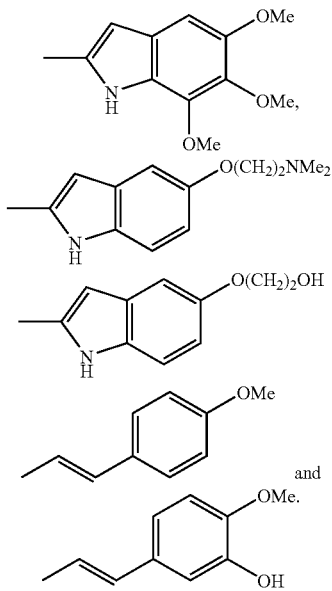

Preferably, the compound of Formula I is selected from one of the following 1-(Chloromethyl)-5,6-dinitro-3-(5,6,7-trimethoxyindol-2-carbonyl)-1,2-dihydro-3H-benzo[e]indole;

1-(Chloromethyl)-3-{5-[2-(dimethylamino)ethoxy]indol-2-carbonyl}-5,6-dinitro-1,2-dihydro-3H-benzo[e]indole;

6-Acetyl-1-(chloromethyl)-5-nitro-3-(5,6,7-trimethoxyindol-2-carbonyl)-2-dihydro-3H-benzo[e]indole;

6-Acetyl-1-(chloromethyl)-3-{5-[2-(dimethylamino) ethoxy]indol-2-carbonyl}-5-nitro-1,2-dihydro-3H-benzo[e]indole;

7-Acetyl-1-(chloromethyl)-5-nitro-3-(5,6,7-trimethoxyindol-2-carbonyl)-1,2-dihydro-3H-benzo[e]indole;

7-Acetyl-1-(chloromethyl)-3-{5-[2-(dimethylamino) ethoxy]indol-2-carbonyl}-5-nitro-1,2-dihydro-3H-benzo[e]indole;

1-(Chloromethyl)-3-{5-[2-dimethylamino)ethoxy]indol-2-carbonyl)}-5-nitro-1,2-dihydro-3H-benzo[e]indole-6-sulfonamide;

1,2-(Chloromethyl)-3-{5-[2-(dimethylamino)ethoxy]indol-2-carbonyl}-5-nitro-1,2-dihydro-3H-benzo[e]indole-7-sulfonamide;

1-(Chloromethyl)-3-[(2E)-3-(3-hydroxy-4-methoxyphenyl)-2-propenoyl]-5-nitro-1,2-dihydro-3H-benzo[e]indole-7-sulfonamide;

1-(Chloromethyl)-3-[5-(2-hydroxyethoxy)indol-2-carbonyl]-5-nitro-1,2-dihydro-3H-benzo[e]indole-7-sulfonamide;

1-(Chloromethyl)-3-{5-[2-(dimethylamino)ethoxy]indol-2-carbonyl}-N-methyl-5-nitro-1,2-dihydro-3H-benzo[e]indole-7-sulfonamide;

1-(Chloromethyl)-N-(2-hydroxyethyl)-5-nitro-3-(5,6,7-trimethoxyindol-2-carbonyl)-1,2-dihydro-3H-benzo[e]indole-7-sulfonamide;

1-(Chloromethyl)-N-(2-hydroxyethyl)-3-[(E)-4-methoxycinnamoyl]-5-nitro-1,2-dihydro-3H-benzo[e]indole-7-sulfonamide;

1-(Chloromethyl)-3-{5-[2-(dimethylamino)ethoxy]indol-2-carbonyl}-N-(2-hydroxyethyl)-5-nitro-1,2-dihydro-3H-benzo[e]indole-7-sulfonamide;

1-(Chloromethyl)-3-{5-[2-(dimethylamino)ethoxy]indol-2-carbonyl}-N,N-dimethyl-5-nitro-1,2-dihydro-3H-benzo[e]indole-7-sulfonamide;

1-(Chloromethyl)-3-{5-[2-(dimethylamino)ethoxy]indol-2-carbonyl}-N-[2-(dimethylamino)ethyl]-5-nitro-1,2-dihydro-3H-benzo[e]indole-7-sulfonamide;

1-(Chloromethyl)-3-{5-[2-(dimethylamino)ethoxy]indol-2-carbonyl}-5-nitro-1,2-dihydro-3H-benzo[e]indol-6-carbonitrile;

1-(Chloromethyl)-3-{5-[2-(dimethylamino)ethoxy]indol-2-carbonyl}-5-nitro-1,2-dihydro-3H-benzo[e]indole-6-carboxamide;

1-(Chloromethyl)-5,7-dinitro-(5,6,7-trimethoxyindol-2-carbonyl)-1,2-dihydro-3H-benzo[e]indole;

1-(Chloromethyl)-3-{5-[2-(dimethylamino)ethoxy]indol-2-carbonyl}-5,7-dinitro-1,2-dihydro-3H-benzo[e]indole;

1-(Chloromethyl)-5,9-dinitro-(5,6,7-trimethoxyindol-2-carbonyl)-1,2-dihydro-3H-benzo[e]indole;

1-(Chloromethyl)-3-{5-[2-(dimethylamino)ethoxy]indol-2-carbonyl}-5,9-dinitro-1,2-dihydro-3H-benzo[e]indole;

1 (Chloromethyl)-5-nitro-3-[5,6,7-trimethoxyindol-2-carbonyl]-1,2-dihydro-3H-benzo[e]indole-7-carboxamide;

1-(Chloromethyl)-3-{5-[2-(dimethylamino)ethoxy]indol-2-carbonyl}-5-nitro-1,2-dihydro-3H-benzo[e]indole-7-carboxamide;

1-Chloromethyl)-5-nitro-3-5,6,7-trimethoxyindol-2-carbonyl)-1,2-dihydro-3H-benzo[e]indole-7-carbonitrile;

1-(Chloromethyl)-3-{5-[2-(dimethylamino)ethoxy]indol-2-carbonyl}-5-nitro-1,2-dihydro-3H-benzo[e]indole-7-carbonitrile;
1-(Chloromethyl)-N-(2-hydroxyethyl)-5-nitro-3-(5,6,7-trimethoxyindol-2-carbonyl)-1,2-dihydro-3H-benzo[e]indole-7-carboxamide;
1-(Chloromethyl)-N-(2-hydroxyethyl)-3-[(E)-4-methoxycinnamoyl]-5-nitro-1,2-dihydro-3H-benzo[e]indole-7-carboxamide;
1-(Chloromethyl)-3-{5-[2-(dimethylamino)ethoxy]indol-2-carbonyl}-N-(2-hydroxyethyl)-5-nitro-1,2-dihydro-3H-benzo[e]indole-7-carboxamide;
Methyl 1-(chloromethyl)-3-(5,6,7-trimethoxyindol-2-carbonyl)-5-nitro-1,2-dihydro-3H-benzo[e]indole-7-carboxylate;
Methyl 1-(chloromethyl)-3-{5-[2-(dimethylamino)ethoxy]indol-2-carbonyl}-5-nitro-1,2-dihydro-3H-benzo[e]indole-7-carboxylate;
1-(Chloromethyl)-N-[2-(dimethylamino)ethyl]-5-nitro-3-(5,6,7-trimethoxyindol-2-carbonyl)-1,2-dihydro-3H-benzo[e]indole-7-carboxamide;
1-(Chloromethyl)-7-methylsulfonyl)-5-nitro-3-(5,6,7-trimethoxyindol-2-carbonyl)-1,2-dihydro-3H-benzo[e]indole;
1-Chloromethyl)-3-{5-[2-(dimethylamino)ethoxy]indol-2-carbonyl}-7-(methylsulfonyl)-5-nitro-1,2-dihydro-3H-benzo[e]indole;
8-Acetyl-1-(chloromethyl)-3-{5-[2-(dimethylamino)ethoxy]indol-2-carbonyl}-5-nitro-1,2-dihydro-3H-benzo[e]indole;
Methyl 1-(chloromethyl)-3-{5-[2-(dimethylamino)ethoxy]indol-2-carbonyl}-5-nitro-1,2-dihydro-3H-benzo[e]indole-8-carboxylate;
1 (Chloromethyl)-N-[2-(dimethylamino)ethyl]-5-nitro-3-(5,6,7-trimethoxyindol-2-carbonyl)-1,2-dihydro-3H-benzo[e]indole-8-carboxamide;
1-(Chloromethyl)-3-{5-[2-(dimethylamino)ethoxy]indol-2-carbonyl}-5-nitro-1,2-dihydro-3H-benzo[e]indole-8-carboxamide;
1-(Chloromethyl)-3-{5-[2-(dimethylamino)ethoxy]indol-2-carbonyl}-5-nitro-1,2-dihydro-3H-benzo[e]indole-8-carbonitrile;
1-(Chloromethyl)-8-(methylsulfonyl)-5-nitro-3-(5,6,7-trimethoxyindol-2-carbonyl)-1,2-dihydro-3H-benzo[e]indole;
1-(Chloromethyl)-3-{5-[2-dimethylamino)ethoxy]indol-2-carbonyl}-8-(methylsulfonyl)-5-nitro-1,2-dihydro-3H-benzo[e]indole;
1-Chloromethyl)-5-nitro-3-(5,6,7-trimethoxyindol-2-carbonyl)-1,2-dihydro-3H-benzo[e]indole-8-sulfonamide;
1-(Chloromethyl)-3-{5-[2-(dimethylamino)ethoxy]indol-2-carbonyl}-5-nitro-1,2-dihydro-3H-benzo[e]indole-8-sulfonamide;
7-Amino-1-(chloromethyl)-3-{5-[2-(dimethylamino)ethoxy]indol-2-carbonyl}-5-nitro-1,2-dihydro-3H-benzo[e]indole;
1-(Chloromethyl)-3-{5-[2-(dimethylamino)ethoxy]indol-2-carbonyl}-N-hydroxy-5-nitro-1,2-dihydro-3H-benzo[e]indole-7-sulfonamide;
1-(Chloromethyl)-3-{5-[2-(dimethylamino)ethoxy]indol-2-carbonyl}-5-nitro-1,2-dihydro-3H-benzo[e]indole-7-sulfonohydrazide;
1-(Chloromethyl)-3-{5-[2-(dimethylamino)ethoxy]indol-2-carbonyl}-5-nitro-N-propionyl-1,2-dihydro-3H-benzo[e]indole-7-sulfonamide; and
1-(Chloromethyl)-3-{5-[2-(dimethylamino)ethoxy]indol-2-carbonyl}-5,7-dinitro-1,2-dihydro-3H-benzo[e]indole-8-sulfonamide.

Preferably, in a further embodiment of a compound of Formula I at least one of X, Y, W or Q is substituted with a phosphate $[P(O)(OH)_2]$ group.

Preferably, the compound of Formula I is selected from one of the following:
2-{[1-(Chloromethyl)-5-nitro-3(5,6,7-trimethoxyindol-2-carbonyl)-1,2-dihydro-3H-benzo[e]indol-7-yl]sulfonyl}aminoethyl dihydrogen phosphate;
2-{[1-(Chloromethyl)-5-nitro-3-{5-[2-(dimethylamino)ethoxy]indol-2-carbonyl}-1,2-dihydro-3H-benzo[e]indol-7-yl]sulfonyl}aminoethyl dihydrogen phosphate;
2-({2-[7-(Aminosulfonyl)-1-(chloromethyl)-5-nitro-1,2-dihydro-3H-benzo[e]indol-3-carbonyl]indol-5-yl}oxy) ethyl dihydrogen phosphate.

Preferably, the compound of Formula I is one as defined above but with the further proviso that when W is H, and one of X and Y represents H, the other of X and Y does not represents halogen, $CH_3$, $OR^1$, $SR^1$, $NR^1_2$, $SO_2R^1$, $CONHR_1$, CN or $CO_2R^1$, where for this proviso each $R^1$ can only independently represent H or $C_1$-$C_4$ alkyl, optionally substituted with one or more hydroxyl or amino groups, the amino groups being further optionally substituted with one or two $C_1$-$C_4$ alkyl groups.

Preferably, the compound of Formula I is one as defined above but with the further proviso that when W is H, and one of X and Y represents H, the other of X and Y is selected from halogen, $CH_3$, $OR^1$, $SR^1$, $NR^1_2$, $SO_2R^1$, $CONHR_1$, CN or $CO_2R^1$, where for this proviso each $R^1$ can only independently represent H or $C_1$-$C_4$ alkyl, optionally substituted with one or more hydroxyl or amino groups, the amino groups being further optionally substituted with one or two $C_1$-$C_4$ alkyl groups.

Preferably, the compound of Formula I is one as defined above but with the further proviso that when W is H, and one of X and Y represents H, the other of X and Y is $CONHR^1_2$, wherein $R^1$ is as defined above.

Preferably, the compound of Formula I is one as defined above but with the further proviso that when W is H, and one of X and Y represents H, then the other of X and Y is selected from $C_2$-$C_4$ alkyl, $OP(O)(OH)_2$, $COR^1$, $SOR^1$, $SO_2NR^1_2$, $SO_2NR^1OR^1$, $SO_2NR^1NR^1_2$, $SO_2NHCOR^1$, $CONHSO_2R^1$, $CF_3$ or $NO_2$, wherein $R^1$ is as defined above.

Preferably, the compound of Formula I is one as defined above but with the further proviso that when W is H, and one of X and Y represents H, then the other of X and Y is $SO_2NR^1_2$, wherein $R^1$ is as defined above.

In a second aspect, the present invention provides a compound of Formula II,

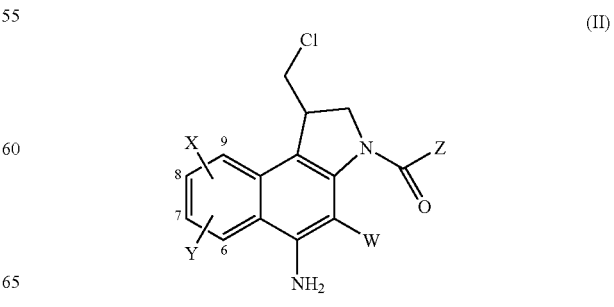

(II)

Wherein X, Y, and W are independently selected from H, halogen, $C_{1-4}$alkyl, $OR^1$, $OF(O)(OH)_2$, $SR^1$, $NR^1_2$, $COR^1$, $SOR^1$, $SO_2R^1$, $SO_2NR^1_2$, $SO_2NR^1OR^1$, $SO_2NR^1NR^1_2$, $SO_2NHCOR^1$, $CO_2R^1$, $CONR^1$, $CONHSO_2R^1$, $CF_3$, $CN$, $NO_2$, where X and Y are located at any one of the available positions 6-9, and where each $R^1$ independently represents H or a $C_{1-4}$alkyl, optionally substituted with one or more hydroxyl or amino groups, each hydroxyl group being further optionally substituted with a phosphate $[P(O)(OH)_2]$ group, and each amino group being further optionally substituted with one or two $C_{1-4}$alkyl groups, and wherein Z may be selected from the following structures (Ia-Ic)

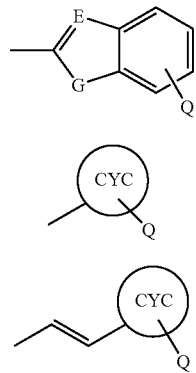

wherein E may be selected from —N= or —CH=, G may be selected from O, S, or NH, Q may be independently selected from one to three of $R^2$, $OR^2$, $OP(O)(OH)_2$ halogen, $NR^2_2$, $NO_2$, $CO_2R^2$, $CONR^2_2$, $NR^2COR^2$, where each $R^2$ independently represents H, lower $C_{1-4}$ alkyl, optionally substituted with one or more hydroxyl or amino groups, each hydroxyl group being further optionally substituted with a phosphate $[P(O)(OH)_2]$ group, each amino group being optionally substituted with one or two $C_{1-4}$alkyl groups; and CYC may represent a 5- or 6-membered carbocycle, or heterocycle containing one or two atoms independently selected from N, O and S, and physiologically functional salt derivatives thereof, with the proviso that when W represents H, X and Y do not each represent H.

Preferably, in one embodiment of a compound of formula II, Z is selected from the following:

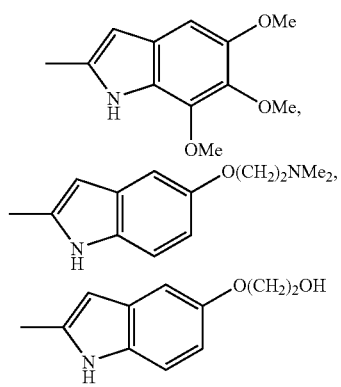

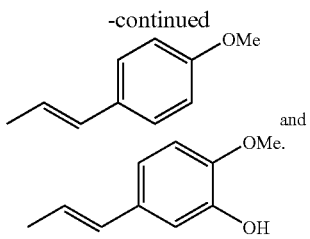

Preferably, the compound of Formula II is selected from
7-Acetyl-5-amino-1-(chloromethyl)-3-{5-[2-(dimethylamino)ethoxy]indol-2-carbonyl}-1,2-dihydro-3H-benzo[e]indole;
Methyl 5-amino-1-(chloromethyl)-3-{5-[2-(dimethylamino)ethoxy]indol-2-carbonyl}-1,2-dihydro-3H-benzo[e]indole-7-carboxylate;
5-Amino-1-(chloromethyl)-3-{5-[2-(dimethylamino)ethoxy]indol-2-carbonyl}-1,2-dihydro-3H-benzo[e]indole-7-carboxamide;
5-Amino-1-(chloromethyl)-3-{5-[2-(dimethylamino)ethoxy]indol-2-carbonyl}-1,2-dihydro-3H-benzo[e]indole-7-carbonitrile;
5-Amino-1-(chloromethyl)-7-(methylsulfonyl)-3(5,6,7-trimethoxyindol-2-carbonyl)-1,2-dihydro-3H-benzo[e]indole;
5-Amino-1-(chloromethyl)-3-{5-[2-(dimethylamino)ethoxy]indol-2-carbonyl}-7-(methylsulfonyl)-1,2-dihydro-3H-benzo[e]indole;
5-Amino-1-(chloromethyl)-3-(5,6,7-trimethyoxyindol-2-carbonyl)-1,2-dihydro-3H-benzo[e]indole-7-sulfonamide;
5-Amino-1-(chloromethyl)-3-{5-[2-(dimethylamino)ethoxy]indol-2-carbonyl}-1,2-dihydro-3H-benzo[e]indole-7-sulfonamide;
5-Amino-1-(chloromethyl)-3-{5-[2-(dimethylamino)ethoxy]indol-2-carbonyl}-N-methyl-1,2-dihydro-3H-benzo[e]indole-7-sulfonamide;
5-Amino-1-(chloromethyl)-3-{5-[2-(dimethylamino)ethoxy]indol-2-carbonyl}-N-(2-hydroxyethyl)-1,2-dihydro-3H-benzo[e]indole-7-sulfonamide;
5-Amino-1-(chloromethyl)-8-(methylsulfonyl)-3-(5,6,7-trimethoxyindol-2-carbonyl)-1,2-dihydro-3H-benzo[e]indole and
5-Amino-1-(chloromethyl)-3-{5-[2-(dimethylamino)ethoxy]indol-2-carbonyl}-8-(methylsulfonyl)-1,2-dihydro-3H-benzo[e]indole.

Preferably, the compound of Formula II is one as defined above but with the further proviso that when W is H, and one of X and Y represents H, the other of X and Y does not represent halogen, $CH_3$, $OR^1$, $SR^1$, $NR^1_2$, $SO_2R^1$, $CONHR^1$, $CN$ or $CO_2R^1$, where for this proviso each $R^1$ can only independently represent H or $C_1$-$C_4$ alkyl, optionally substituted with one or more hydroxyl or amino groups, the amino groups being further optionally substituted with one or two $C_1$-$C_4$ alkyl groups.

Preferably, the compound of Formula II is one as defined above but with the further proviso that when W is H, and one of X and Y represents H, then the other of X and Y is selected from halogen, $CH_3$, $OR^1$, $SR^1$, $NR^1_2$, $SO_2R^1$, $CONHR^1$, $CN$ and $CO_2R^1$, where for this proviso each $R^1$ can only independently represent H or $C_1$-$C_4$ alkyl, optionally substituted with one or more hydroxyl or amino groups, the amino groups being further optionally substituted with one or two $C_1$-$C_4$ alkyl groups.

Preferably, the compound of Formula II is one as defined above but with the further proviso that when W is H, and one of X and Y represents H, then the other of X and Y is $CONHR^1_2$, wherein $R^1$ is as defined above.

Preferably, the compound of Formula II is one as defined above but with the further proviso that when W is H, and one of X and Y represents H, then the other of X and Y is selected from $C_2$-$C_4$ alkyl, $OP(O)(OH)_2$, $COR^1$, $SOR^1$, $SO_2NR^1_2$, $SO_2NR^1OR^1$, $SO_2NR^1NR^1_2$, $SO_2NHCOR^1$, $CONHSO_2R^1$, $CF_3$ or $NO_2$, wherein $R^1$ is as defined above.

Preferably, the compound of Formula II is one as defined above but with the further proviso that when W is H, and one of X and Y represents H, then the other of X and Y is $SO_2NR^1_2$, wherein $R^1$ is as defined above.

In a third aspect, the present invention provides a method of providing cancer treatment which includes the step of administering to a subject in need of cancer treatment a therapeutically effects amount of a compound of Formula I as defined above to the subject.

Preferably the subject has tumour cells in a hypoxic environment.

Preferably the tumour cells are leukaemia cells, solid cancers including breast, bowel and lung tumours cells and/or small cell lung tumour cells.

Preferably the method further includes the step of administering radiotherapy to the subject before, during or after the administration of the compound of Formula I.

It is further preferred that the method of therapy further includes the steps of administrating one or more chemotherapeutic agents to the subject before, during or after the administration of the compound of Formula I as defined above to the tumour cells.

While these compounds will typically be used in cancer therapy of human subjects, they can be used to target tumour cells in other warm blooded animal subjects such as other primates, farm animals such as cattle, and sports animals and pets such as horses, dogs, and cats.

It is to be understood that the compound of Formula I can be administered alone or in combination with other chemotherapeutic agents or treatments, especially radiotherapy, either simultaneously or sequentially dependent upon the condition to be treated.

Preferred chemotherapeutic agents can be selected from:

Cisplatin or other platinum-based derivatives,

Temozolomide or other DNA methylating agents,

Cyclophosphamide or other DNA alkylating agents,

Doxorubicin, mitoxantrone, camptothecin or other topoisomerase inhibitors,

Methotrexate, gemcitabine or other antimetabolites,

Paclitaxel, Docetaxel or other tubulin-modifying agents.

Tirapazamine, Bleomycin, or other DNA-breaking agents.

In a fourth aspect of the present invention there is provided a pharmaceutical composition including a therapeutically effective amount of a compound of formula I and a pharmaceutically acceptable excipient, adjuvant, carrier, buffer or stabiliser.

The pharmaceutically acceptable excipient, adjuvant, carrier, buffer or stabiliser should be non-toxic and should not interfere with the efficacy of the active ingredient. The precise nature of the carrier or other material will depend on the route of administration, which can be oral, or by injection, such as cutaneous, subcutaneous, or intravenous injection.

Pharmaceutical compositions for oral administration can be in tablet, capsule, powder or liquid form. A tablet may comprise a solid carrier or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included. A capsule may comprise a solid carrier such as gelatin.

For intravenous, cutaneous or subcutaneous injection, the active ingredient will be in the form of a parenterally acceptable aqueous solution which is pyrogen-free and has a suitable pH, isotonicity and stability. Those of relevant skill in the art are well able to prepare suitable solutions using, for example, isotonic vehicles such as Sodium Chloride injection, Ringer's injection, Lactated Ringer's injection. Preservatives, stabilisers, buffers antioxidants and/or other additives may be included as required.

In a further aspect, the present invention further relates to the use of the compounds defined above that are suitable as substrates for nitroreductase enzymes (for example, the aerobic nitroreductase coded by the nfsB gene in *E. coli*) in methods of ADEPT and GDEPT therapy.

In a further aspect the present invention provides the use, in the manufacture of a medicament, of an effective amount of a compound of Formula I for use in treating a subject in need of cancer treatment.

Preferably the medicament is manufactured for treating tumour cells in a hypoxic environment.

Preferably the medicament is manufactured for targeting hypoxic tumour cells, such as leukemias, solid cancers including breast, bowel and lung tumours, including small cell lung tumour.

It is preferred that the medicament is manufactured such that radiotherapy can be administered to the tumour cells before, during or after the administration of the compound of Formula I as defined above.

It is flier preferred that the medicament is manufactured such that one or more chemotherapeutic agents can be administered to the tumour cells before, during or after the administration of the compound of Formula I as defined above.

While these medicaments will typically be used in cancer therapy of human subjects, they can be used to target tumour cells in other warm blooded animal subjects such as other primates, farm animals such as cattle, and sports animals and pets such as horses, dogs, and cats.

A "therapeutically effective amount", is to be understood as an amount of a compound of Formula I as defined above that is sufficient to show benefit to a subject in need of cancer treatment. The actual amount, rate and time-course of administration, will depend on the nature and severity of the disease being treated. Prescription of treatment is within the responsibility of general practitioners and other medical doctors.

A hypoxic environment is to be understood as either an in vitro or in vivo environment having a lower oxygen tension than normal tissues.

Physiologically functional salt derivatives of the compounds defined above are to be understood as including physiologically acceptable base salts, e.g. derived from an appropriate base, such as alkali metal (e.g. sodium), alkaline earth metal (e.g. magnesium) salts, ammonium and $NR^{4"}$ (wherein $R^{4"}$ is $C_{1-4}$ alkyl) salts. Other salts include acid addition salts, including the hydrochloride and acetate salts. Such salts may be prepared by techniques known per se in the art.

In a further aspect the present invention provides a method of making a compound of Formula III

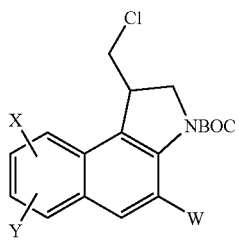

wherein W, X and Y are as defined above for a compound of Formula I, the method including reacting in a first step a compound of Formula IV

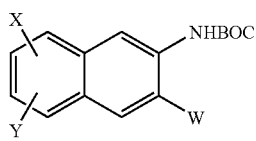

wherein W, X and Y are as defined above for a compound of Formula I, with an effective amount of a halogenating agent to provide a compound of Formula V

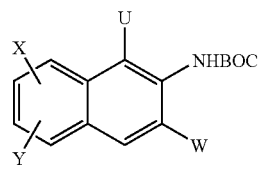

Wherein U is Br or I, W, X and Y are as defined above for a compound of Formula I and in a second step reacting the compound of Formula V with an effective amount of a strong base followed by 1,3-dichloropropene to provide a compound of Formula VI

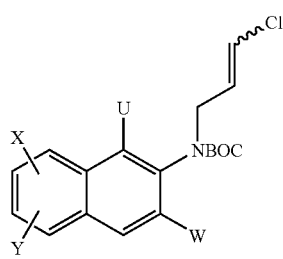

wherein U is Br or I, and W, X and Y are as defined above for a compound of Formula I, and in a third step undergoing a cyclisation reaction to provide a compound of Formula III as defined above.

Preferably the halogenation step is achieved using an effective amount of N-bromosuccinimide or N-iodosuccinimide.

Preferably the strong base utilised in the second step is sodium hydride.

Preferably the cyclisation step is achieved using an effective amount of tributyltin hydride and a radical initiator such as azobisisobutyronitrile.

Preferably the method further includes the step of making a compound of Formula IV by reacting a compound of formula VII

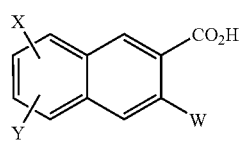

wherein W, X and Y are as defined above for a compound of Formula I, with an effective amount of t-BuOH and $Et_3N$ followed by diphenylphosphoryl azide (DPPA).

In a further aspect, the present invention provides a method of nitrating a compound of formula VIII

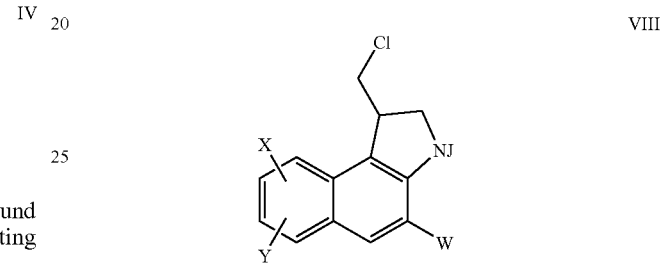

wherein W, X and Y are as defined above for Formula I, J represents H, t-butoxycarbonyl or trifluoroacetyl to provide a compound of Formula IX,

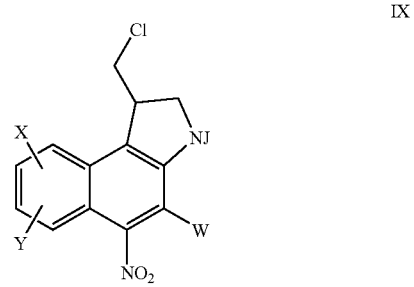

wherein W, X and Y are as defined above for Formula I, J represents H, or trifluoroacetyl.

Preferably, nitration is achieved with $KNO_3/H_2SO_4$ or with any other suitable nitrating agent.

In a further aspect the present invention provides a method of reducing a compound of Formula I, as defined above, to provide a compound of Formula II, as defined above under recucing conditions. Preferably the reduction is carried out by chemical reduction or hypoxic metabolism. Most preferably the reduction step is carried out under in vivo hypoxic conditions.

In a final aspect, the present invention provides methods of preparing compounds of the general formula I and formula II, defined above. Such methods are described below.

It is to be recognised that the compounds of the invention defined above may exist in different enantiomeric and/or diastereomeric forms. In such cases it is to be understood that formula I, may represent any possible enantiomeric or diastereomeric forms, or any mixtures of such forms, and also any physiologically functional salt derivatives thereof.

BRIEF DESCRIPTION OF THE DRAWING

While the invention is broadly defined above, it will be appreciated by those skilled in the art that further aspects of the invention will become apparent with reference to the following Description, Schemes, Examples and FIG. 1 all given by way of example only, wherein.

DETAILED DESCRIPTION OF THE INVENTION

Figure 1:
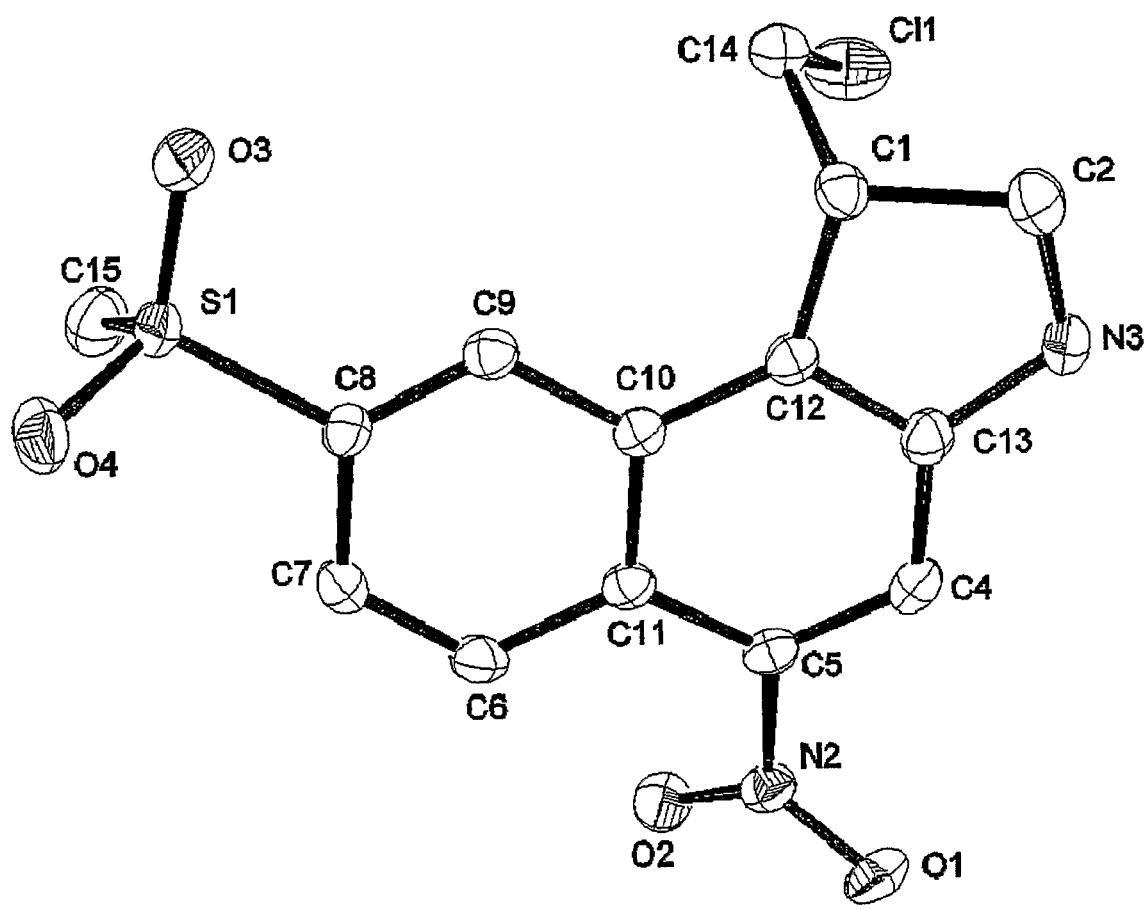
FIG. 1 shows an Oak Ridge Thermal Ellipsoid Plot (ORTEP) representation of the crystal structure of 1-(chloromethyl)-8-(methylsulfonyl)-5-nitro-1,2-dihydro-3H-benzo[e]indole (206).

As defined above, this invention provides nitrobenzindoles and their physiologically functional salt derivatives, and is particularly concerned with the use of these compounds activated under hypoxic conditions or as prodrugs activated by enzymes or by therapeutic ionising radiation, in the treatment of cancer. In particular this invention provides nitrobenzindoles that are superior to those described previously (Denny et al., PCT Int. Appl. WO 98/11101 A2, compounds of Formula I where W, X, and Y all represent H), in that the addition of a variety of substituents in a variety of positions on the dihydro-3H-benzo[e]indole core provides compounds with improved hypoxic selectivities. Examples where the substituent is a carboxamide or sulfonamide in the 7-position show especially high hypoxic selectivities.

The following Tables 1 and 2 show a representative number of compounds of the present invention.

TABLE 1

Examples of Compounds of Formula I of the Invention

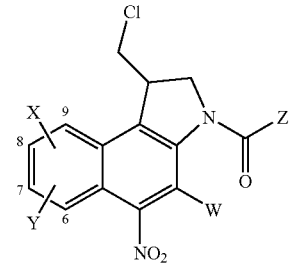

| No | Y | W | X | Z | Mp | Anal |
|---|---|---|---|---|---|---|
| 1 | H | H | 6-$NO_2$ | A | 278-279 | C, H, N |
| 2 | H | H | 6-$NO_2$ | B | 225-226 (HCl) | C, H, N (HCl•1½$H_2O$) |
| 3 | H | H | 6-COMe | A | 180-183 | C, H, N (½$H_2O$) |
| 4 | H | H | 6-COMe | B | >300 | C, H, N, Cl (½$H_2O$) |
| 5 | H | H | 6-$CONH_2$ | B | >350 | C, H, N, Cl |
| 6 | H | H | 6-CN | B | >300 | C, H, N (¼$H_2O$) |
| 7 | H | H | 6-$SO_2NH_2$ | B | >320 | C, H, N, Cl |
| 8 | H | H | 7-$NO_2$ | A | 251-252 | C, H, N |
| 9 | H | H | 7-$NO_2$ | B | 263-264 (HCl) | C, H, N (HCl) |
| 10 | H | H | 7-$NH_2$ | B | >300 | C, H (1½$H_2O$) |
| 11 | H | H | 7-COMe | A | 257-260 | C, H, N |
| 12 | H | H | 7-COMe | B | >350 | C, H, N, Cl ($H_2O$) |
| 13 | H | H | 7-$CO_2Me$ | A | 256-257 | C, H, N |
| 14 | H | H | 7-$CO_2Me$ | B | >300 (HCl) | C, H, N (HCl•½$H_2O$) |
| 15 | H | H | 7-$CONH_2$ | A | 287-289 | C, H, N |
| 16 | H | H | 7-$CONH_2$ | B | >300 (HCl) | C, H, N (HCl•$H_2O$) |
| 17 | H | H | 7-$CONH(CH_2)_2OH$ | A | 244-245 | C, H, N |
| 18 | H | H | 7-$CONH(CH_2)_2OH$ | D | 240-241 | C, H, N |
| 19 | H | H | 7-$CONH(CH_2)_2OH$ | B | 231-233 (HCl) | C, H, N, Cl (HCl) |
| 20 | H | H | 7-$CONH(CH_2)_2NMe_2$ | A | 246-248 | C, H, N (HCl) |
| 21 | H | H | 7-CN | A | 257-258 | C, H, N |
| 22 | H | H | 7-CN | B | >300 (HCl) | C, H, N (HCl•½$H_2O$) |
| 23 | H | H | 7-$SO_2Me$ | A | 296-297 | C, H, N (½$H_2O$) |
| 24 | H | H | 7-$SO_2Me$ | B | 250-252 (HCl) | C, H, N (HCl) |
| 25 | H | H | 7-$SO_2NH_2$ | A | 280-285 | C, H, N |
| 26 | H | H | 7-$SO_2NH_2$ | B | >350 (HCl) | C, H, N (HCl•½$H_2$) |
| 27 | H | H | 7-$SO_2NH_2$ | E | 220-225 | C, H, N (½$H_2O$) |
| 28 | H | H | 7-$SO_2NH_2$ | C | 231-234 | C, H, N (⅓$H_2O$) |
| 29 | H | H | 7-$SO_2NH_2$ | F | 207-211 | C, H, N (½$H_2O$) |
| 30 | H | H | 7-$SO_2NHOH$ | B | 260-265 (HCl) | C, H (HRMS) |
| 31 | H | H | 7-$SO_2NHNH_2$ | B | 280-285 (HCl) | — |
| 32 | H | H | 7-$SO_2NHMe$ | B | >350 (HCl) | C, H, N (HCl•¾$H_2O$) |
| 33 | H | H | 7-$SO_2NH(CH_2)_2OH$ | A | 257-258 | C, H, N |
| 34 | H | H | 7-$SO_2NH(CH_2)_2OPO(OH)_2$ | A | 228-233 | C, H, N |
| 35 | H | H | 7-$SO_2NH(CH_2)_2OH$ | B | 205-210 | (HRMS) |
| 36 | H | H | 7-$SO_2NH(CH_2)_2OPO(OH)_2$ | B | 171-174 (TFA) | C, H, N (TFA) |
| 37 | H | H | 7-$SO_2NH(CH_2)_2OH$ | D | 250-251 | C, H, N |
| 38 | H | H | 7-$SO_2NMe_2$ | B | >350 (HCl) | C, H, N (HCl•½$H_2O$) |
| 39 | H | H | 7-$SO_2NH(CH_2)_2NMe_2$ | B | >350 (HCl) | C, H, N (3HCl•½$H_2O$) |
| 40 | H | H | 7-$SO_2NHCOEt$ | B | 221-225 | (HRMS) |
| 41 | H | H | 8-COMe | B | 210-215 | C, H, N ($H_2O$) |

TABLE 1-continued
Examples of Compounds of Formula I of the Invention
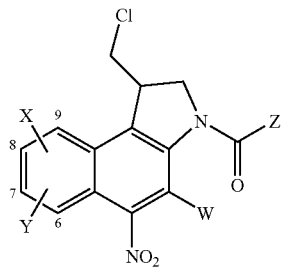
| No | Y | W | X | Z | Mp | Anal |
|----|---|---|---|---|----|------|
| 42 | H | H | 8-CO₂Me | B | >320 (TFA) | (HRMS) |
| 43 | H | H | 8-CONH₂ | B | >320 (TFA) | C, H (TFA•1¼H₂O) |
| 44 | H | H | 8-CONH(CH₂)₂NMe₂ | A | 228-229 (HCl) | C, H, N (HCl) |
| 45 | H | H | 8-CN | B | >340 | C, H, N |
| 46 | H | H | 8-SO₂Me | A | 265 | C, H, N |
| 47 | H | H | 8-SO₂Me | B | >300 (HCl) | C, H, N (HCl) |
| 48 | H | H | 8-SO₂NH₂ | A | 264-266 | C, H, N (½EtOAc) |
| 49 | H | H | 8-SO₂NH₂ | B | 260-265 | C, H, N (½H₂O) |
| 50 | 7-NO₂ | H | 8-SO₂NH₂ | B |  | (HRMS) |
| 51 | H | H | 9-NO₂ | A | 270-271 | C, H, N |
| 52 | H | H | 9-NO₂ | B | 187-191 (HCl) | C, H, N (HCl•H₂O) |
Z =
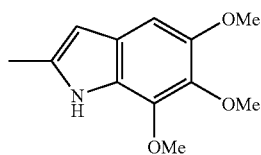
A
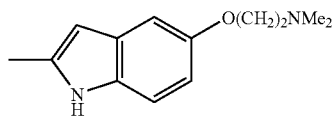
B
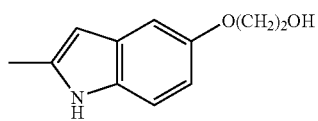
C
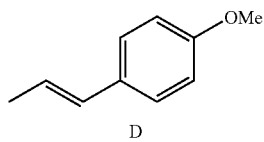
D
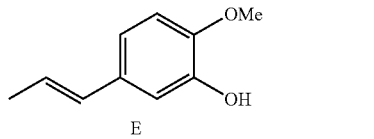
E
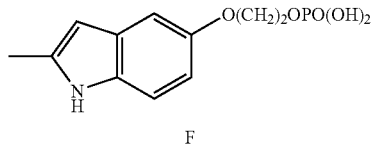
F

TABLE 2

Examples of Compounds of Formula II of the Invention

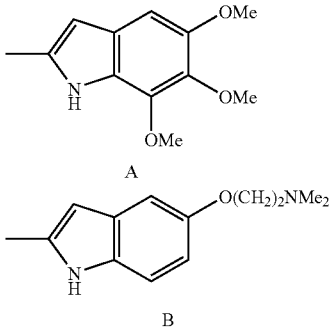

| No | Y | W | X | Z | Mp | Anal |
|---|---|---|---|---|---|---|
| 53 | H | H | 7-COMe | B | 220-224 | (HRMS) |
| 54 | H | H | 7-CO$_2$Me | B | 225-230 | C, H, N |
| 55 | H | H | 7-CONH$_2$ | B | 232-236 | C, H, N (½H$_2$O) |
| 56 | H | H | 7-CN | B | 250-255 | (HRMS) |
| 57 | H | H | 7-SO$_2$Me | A | 266-268 | C, H, N |
| 58 | H | H | 7-SO$_2$Me | B | 280-285 | C, H, N, Cl |
| 59 | H | H | 7-SO$_2$NH$_2$ | A | 240-245 | C, H, N |
| 60 | H | H | 7-SO$_2$NH$_2$ | B | 260-266 | (HRMS) |
| 61 | H | H | 7-SO$_2$NHMe | B | 260-265 | C, H, N (½H$_2$O•½EtOAc) |
| 62 | H | H | 7-SO$_2$NH(CH$_2$)$_2$OH | B | 225-230 | C, H, N (½H$_2$O) |
| 63 | H | H | 8-SO$_2$Me | A | 165-170 | C, H, N (½H$_2$O) |
| 64 | H | H | 8-SO$_2$Me | B | 235-240 | C, H, N (½H$_2$O) |

Z =

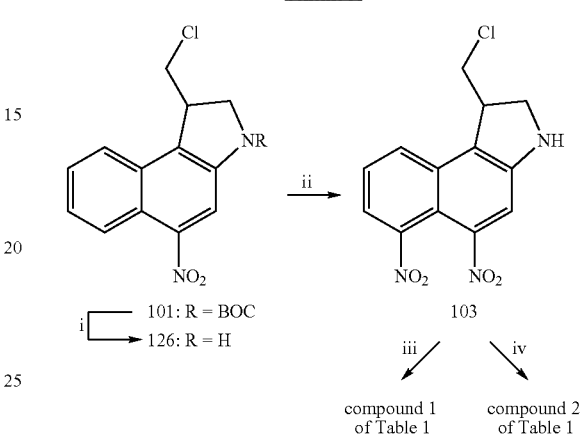

The following Schemes show schematically the methods, for preparing compounds of Formula I and Formula II of the invention. Also included in the Schemes are the details of the synthetic reagents used to achieve each of the synthetic steps. The Examples that follow the Schemes describe in full detail the actual synthetic steps and synthetic conditions.

Scheme A (i) HCl(g)/dioxane;

(ii) conc. H$_2$SO$_4$/KNO$_3$;

(iii) 5,6,7-trimethoxyindole-2-carbonyl chloride/DMAP/pyridine;

(iv) 5-[2-(dimethylamino)ethoxy]indole-2-carboxylic acid/EDCI/TsOH/DMF.

The preparation of the compound of Formula IV (104) as shown in Scheme B below can be made from a compound of 2-naphthoic acid as described in WO02/067930 and this description is hereby incorporated in its entirety.

Scheme B

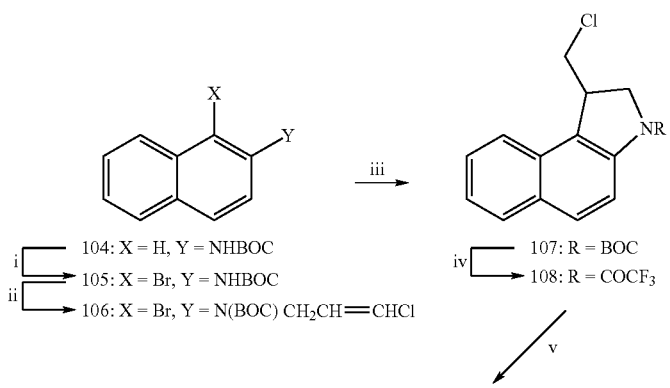

-continued
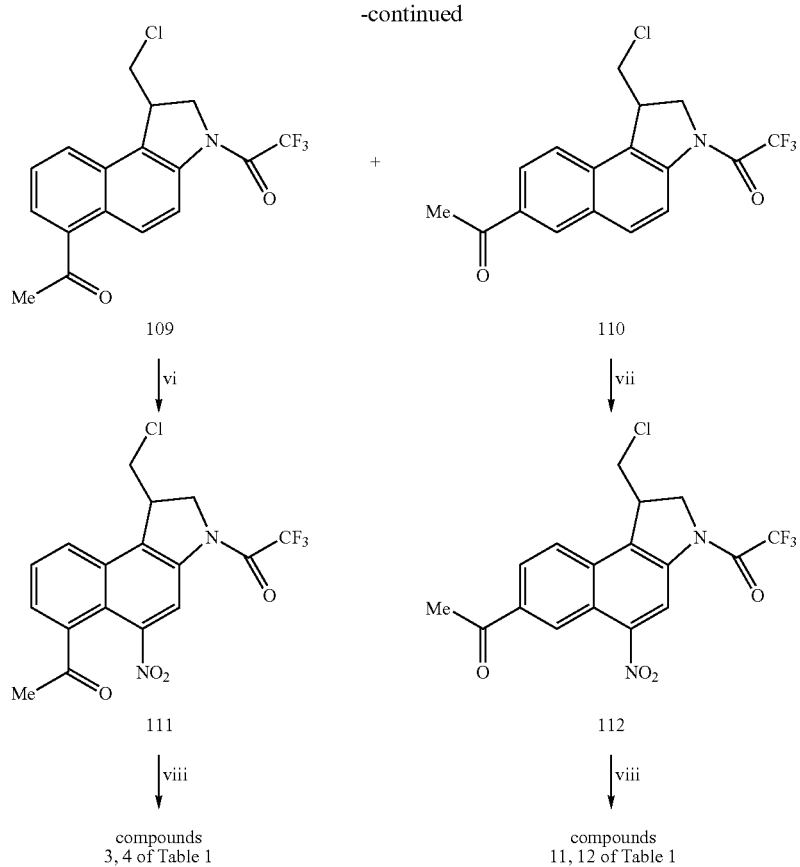
(i) NBS/MeCN;
(ii) NaH/DMF, then 1,3-dichloropropene;
(iii) Bu₃SnH/AIBN/benzene;
(iv) HCl(g)/dioxane, then (CF₃CO)₂O/pyridine;
(v) AlCl₃/AcCl/CS₂ or PhNO₂
(vi) f. HNO₃/CH₂Cl₂;
(vii) conc. H₂SO₄/KNO₃;
(viii) Cs₂CO₃/CH₂Cl₂/MeOH, then 5,6,7-trimethoxyindole-2-carbonyl chloride/pyridine, or 5-[2-(dimethylamino)ethoxy]indole-2-carboxylic acid/EDCI/TsOH/DMA.
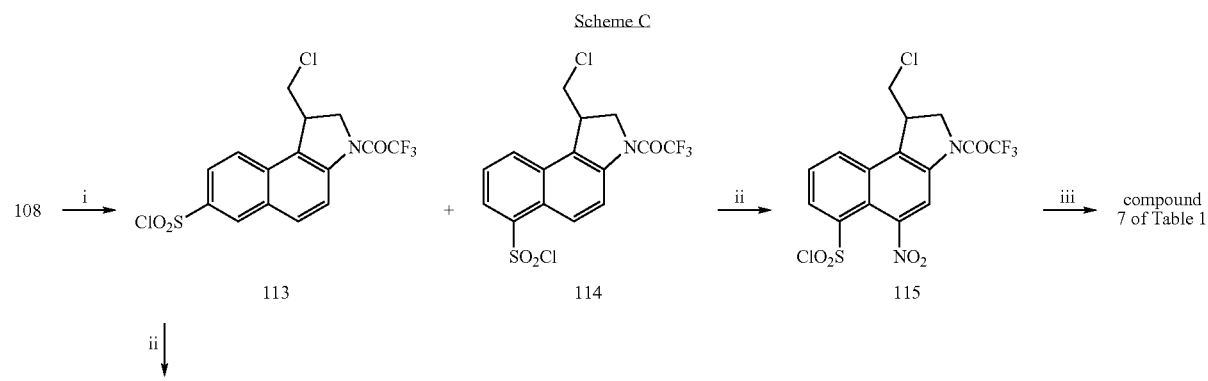

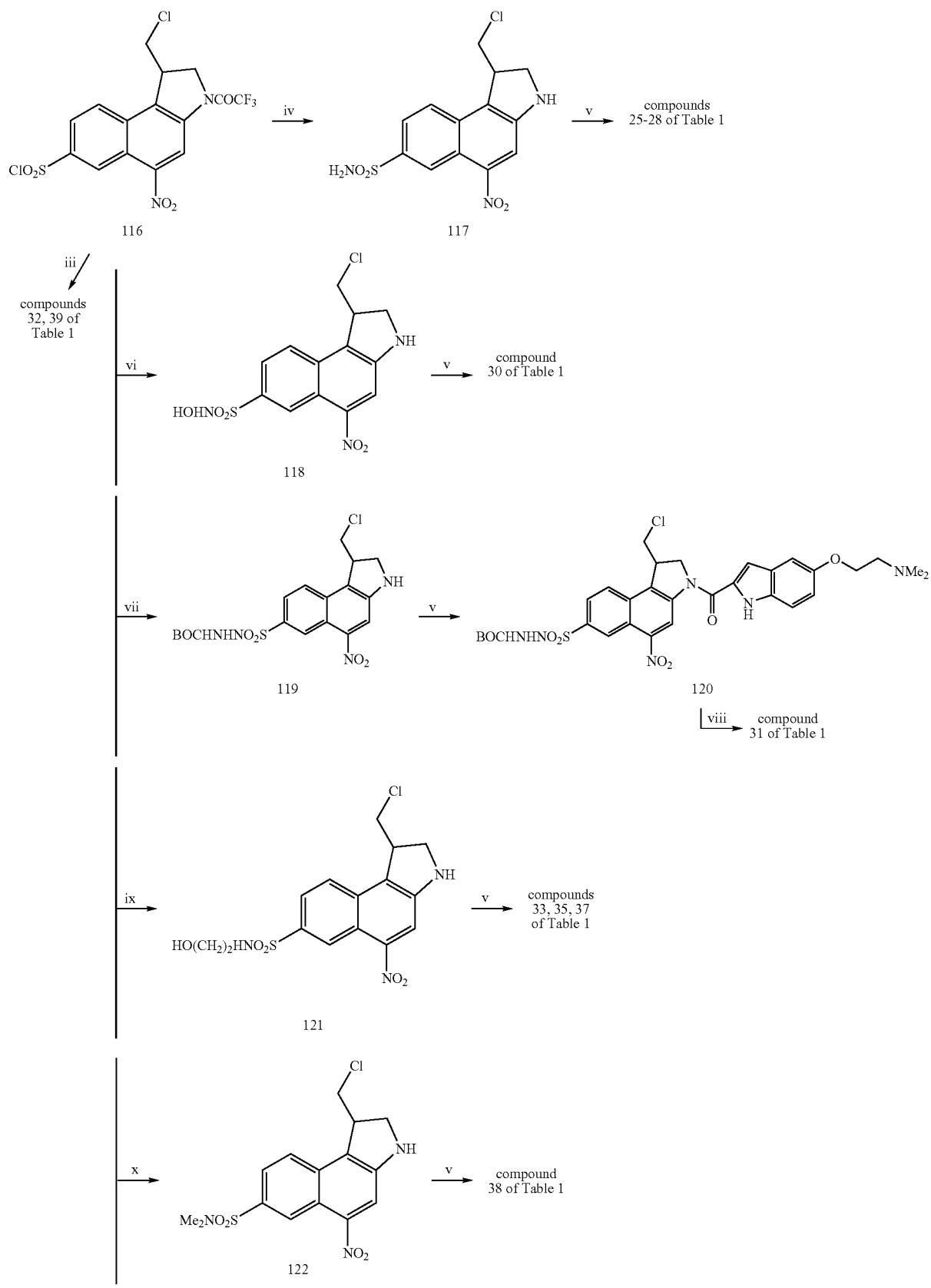

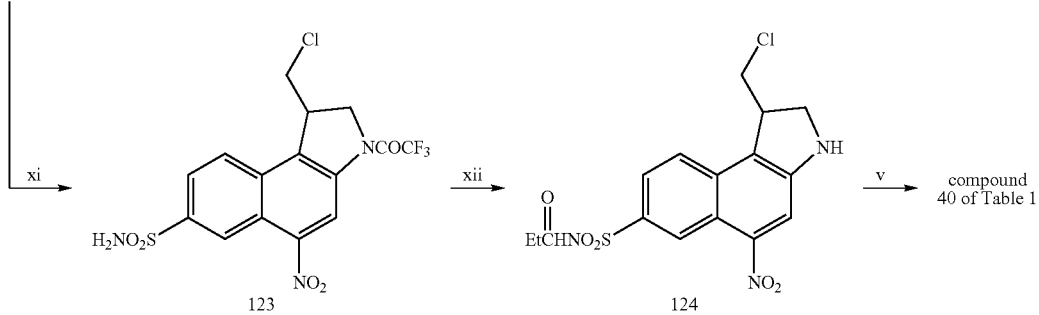

(i) ClSO$_3$H;
(ii) conc. H$_2$SO$_4$/KNO$_3$;
(iii) RNH$_2$/CH$_2$Cl$_2$/THF, then Cs$_2$CO$_3$, then HCl(g)/MeOH/ evaporate, then RCO$_2$H/EDCI/TsOH/DMA;
(iv) NH$_3$ then Cs$_2$CO$_3$/MeOH;

(ix) NH$_2$(CH$_2$)OH, then Cs$_2$CO$_3$;
(x) Me$_2$NH then Cs$_2$CO$_3$/MeOH;
(xi) NH$_3$/THF/−78° C.
(xii) (EtCO)$_2$O/Et$_3$N/DMAP then Cs$_2$CO$_3$/MeOH.

Scheme D

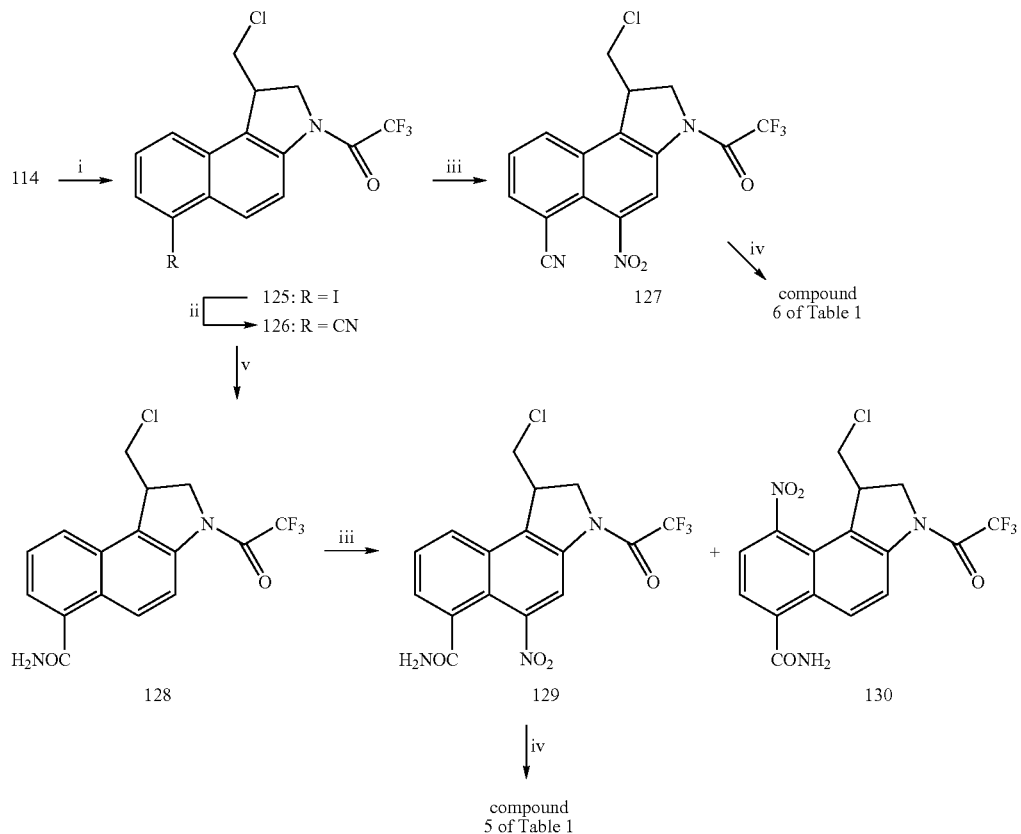

(v) RCO$_2$H/EDCI/TsOH/DMA;
(vi) NH$_2$OH then Cs$_2$CO$_3$/MeOH;
(vii) BOCNHNH$_2$ then Cs$_2$CO$_3$/MeOH;
(viii) HCl/dioxane;

(i) ZnI$_2$/LiCl/PdCl$_2$(PhCN)$_2$/Ti(OiPr)$_4$/diglyme;
(ii) KCN/Pd(PPh$_3$)$_4$CuI;
(iii) f. HNO$_3$/CH$_2$Cl$_2$;

(iv) $Cs_2CO_3/CH_2Cl_2/MeOH$, then $HCl(g)$/dioxane, evaporate, then 5-[2-(dimethylamino)ethoxy]indole-2-carboxylic acid/EDCI/TsOH;
(v) 90% $H_2SO_4$.
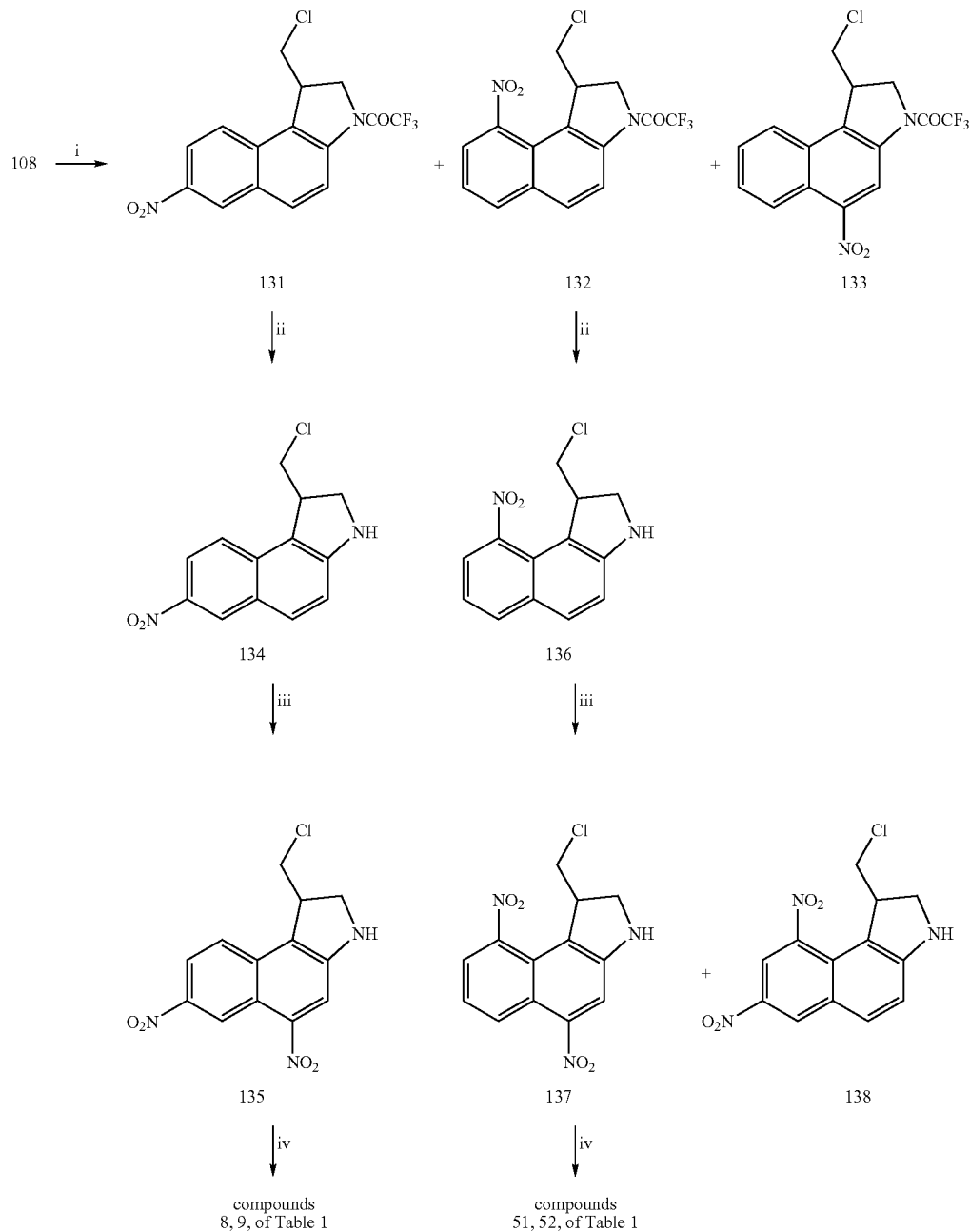
(i) f. $HNO_3/CH_2Cl_2$;
(ii) $Cs_2CO_3$/dioxane/MeOH/$H_2O$;
(iii) conc. $H_2SO_4/KNO_3$;
(iv) 5,6,7-trimethoxyindole-2-carbonyl chloride/DMAP/pyridine, or 5-[2-(dimethylamino)ethoxy]indole-2-carboxylic acid/EDCI/TsOH/DMA.

Scheme F
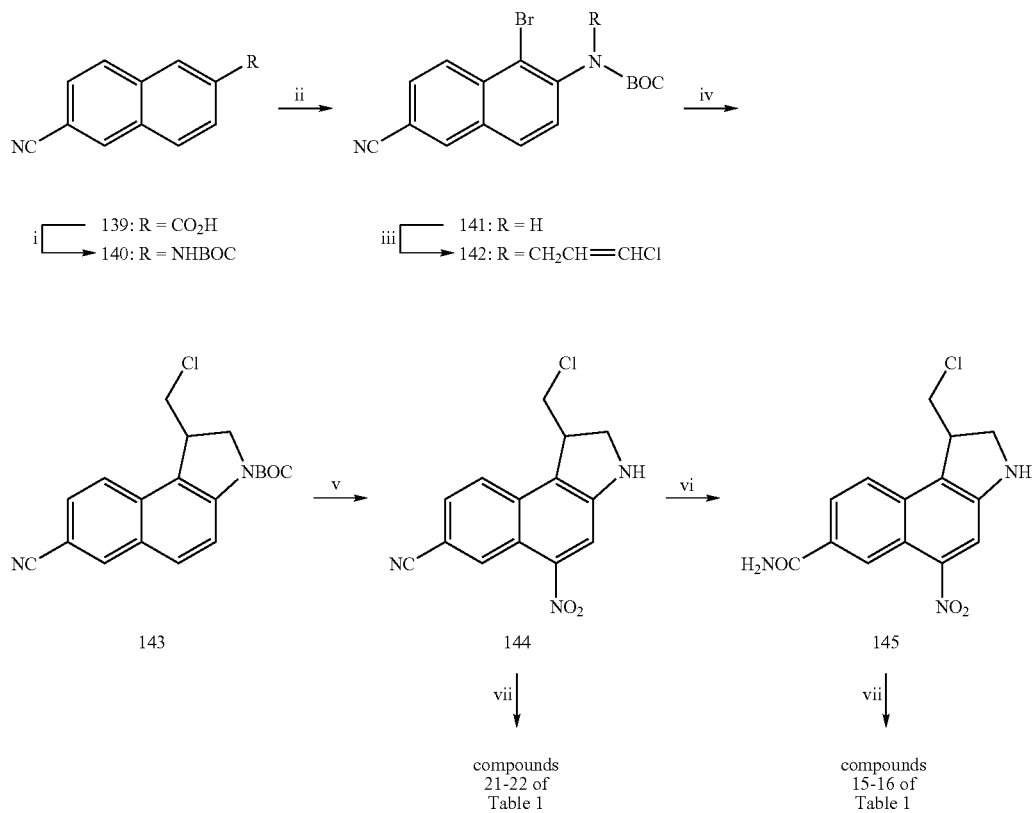
(i) DPPA/Et₃N/t-BuOH;
(ii) NBS/MeCN;
(iii) NaH/DMF, then 1,3-dichloropropene;
(iv) Bu₃SnH/AIBN/benzene;
(v) conc. H₂SO₄, then KNO₃;
(vi) aq. H₂SO₄;
(vii) 5,6,7-trimethoxyindole-2-carbonyl chloride/DMAP/pyridine, or 5-[2-(dimethylamino)ethoxy]indole-2-carboxylic acid/EDCI/TsOH/DMA.
Scheme G
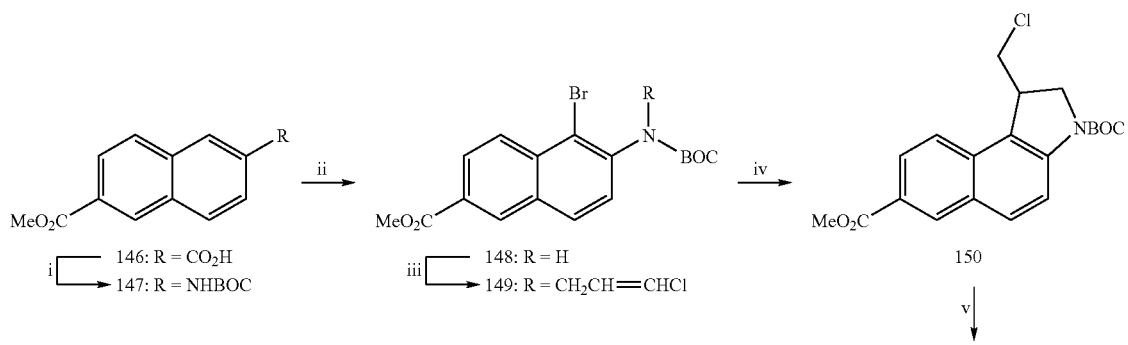

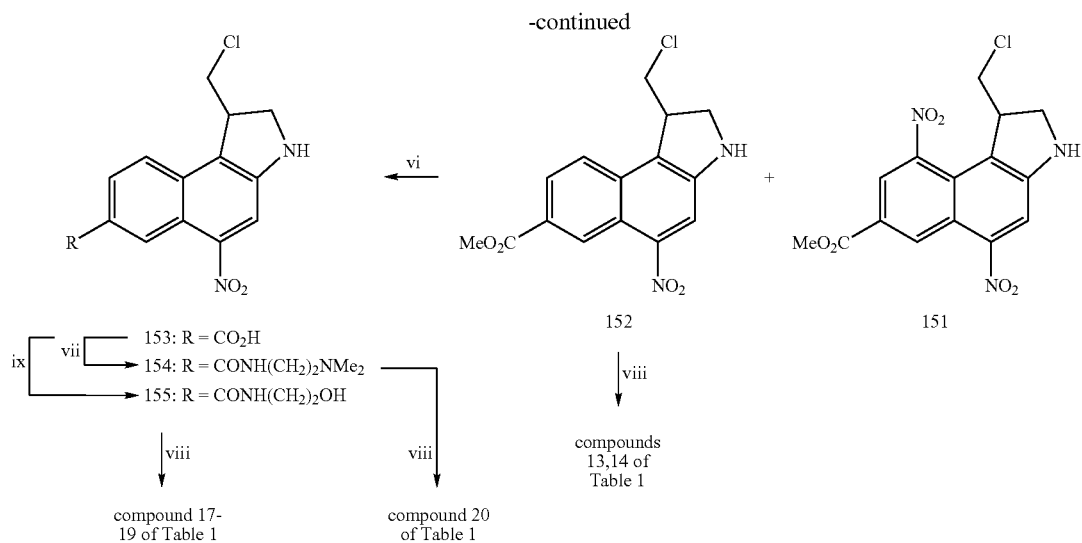

(i) DPPA/Et$_3$N/t-BuOH;
(ii) NBS/MeCN;
(iii) NaH/DMF, then 1,3-dichloropropene;
(iv) Bu$_3$SnH/AIBN/benzene;
(v) conc. H$_2$SO$_4$, then NO$_3$;
(vi) conc. HCl;
(vii) N,N-dimethyl-1,2-ethanediamine/DMF, then DECP;
(viii) 5,6,7-trimethoxyindole-2-carbonyl chloride/DMF/DMAP/pyridine, or RCO$_2$H/EDCI/TsOH/DMA;
(ix) H$_2$N(CH$_2$)$_2$OH/PyBOP/THF.

Scheme H

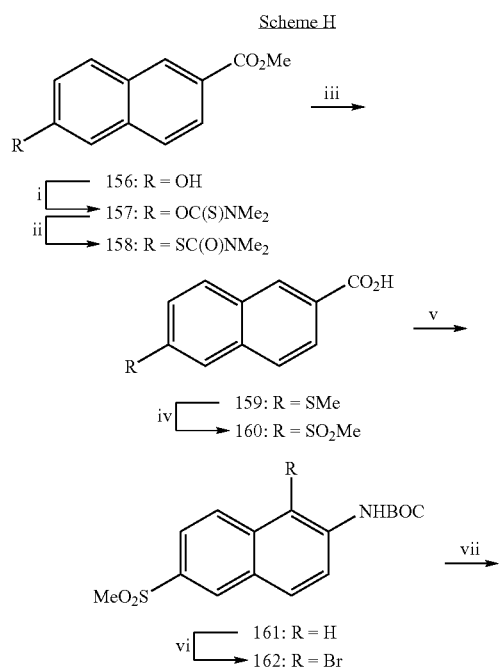

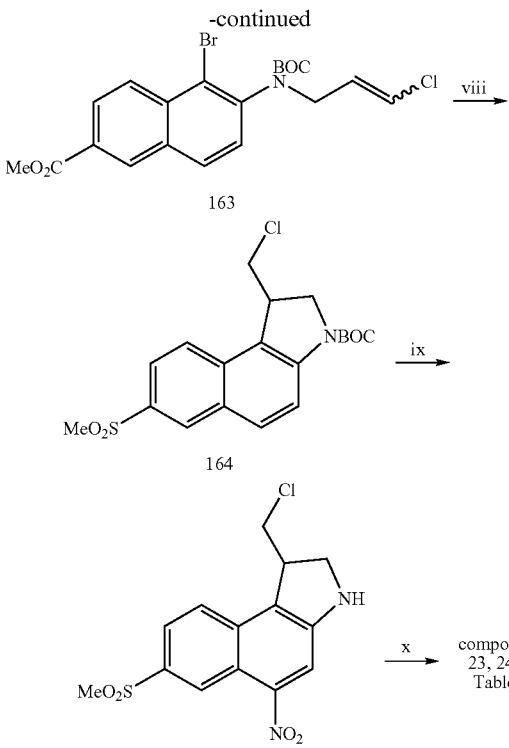

(i) (Me)$_2$NCSCl/DABCO/DMF;
(ii) 225° C.;
(iii) KOH/MeOH/H$_2$O, then MeSO$_4$;
(iv) NaBO$_3$·4H$_2$O/AcOH;
(v) DPPA/Et$_3$N/t-BuOH;
(vi) NBS/MeCN;
(vii) NAH/DMF, then 1,3-dichloropropene;

(viii) Bu₃SnH/AIBN/benzene;

(ix) conc. H₂SO₄, then KNO₃;

(x) 5,6,7-trimethoxyindole-2-carboxylic acid or 5-[2-(dimethylamino)ethoxy]indole-2-carboxylic acid/EDCI/TsOH/DMA.

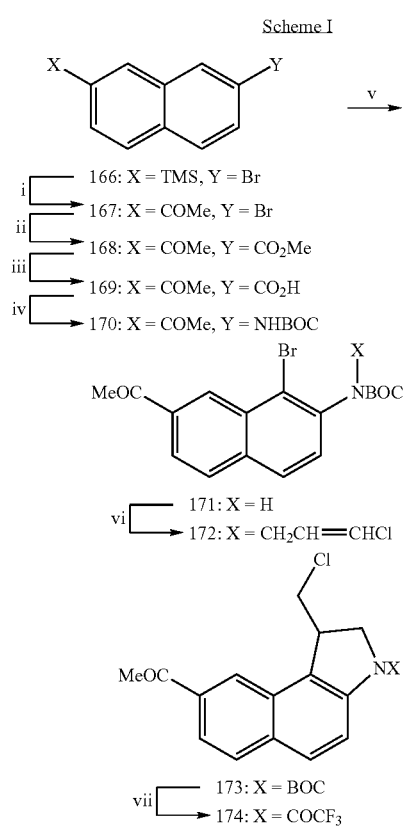

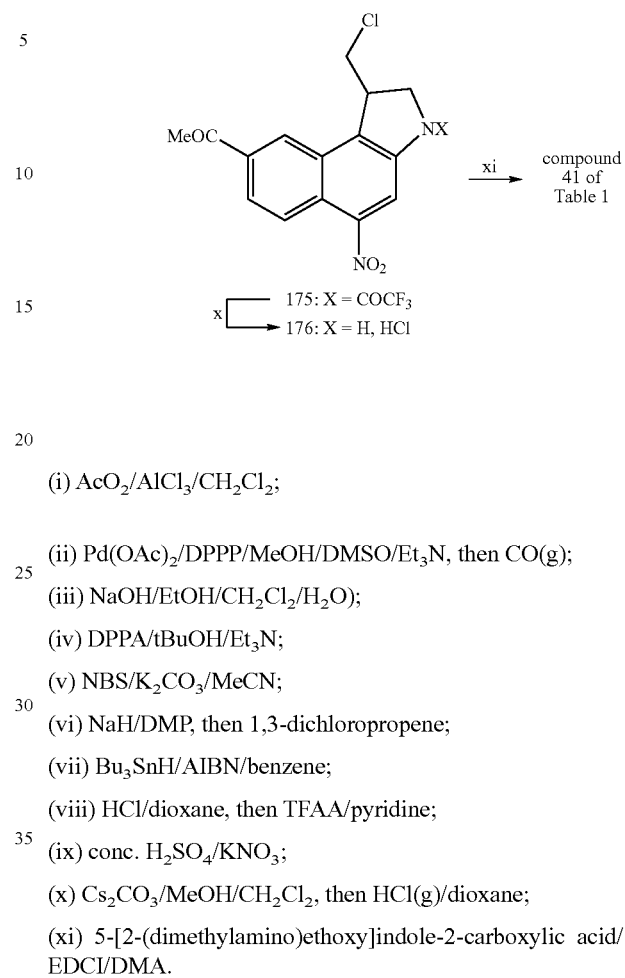

(i) AcO₂/AlCl₃/CH₂Cl₂;

(ii) Pd(OAc)₂/DPPP/MeOH/DMSO/Et₃N, then CO(g);

(iii) NaOH/EtOH/CH₂Cl₂/H₂O);

(iv) DPPA/tBuOH/Et₃N;

(v) NBS/K₂CO₃/MeCN;

(vi) NaH/DMP, then 1,3-dichloropropene;

(vii) Bu₃SnH/AIBN/benzene;

(viii) HCl/dioxane, then TFAA/pyridine;

(ix) conc. H₂SO₄/KNO₃;

(x) Cs₂CO₃/MeOH/CH₂Cl₂, then HCl(g)/dioxane;

(xi) 5-[2-(dimethylamino)ethoxy]indole-2-carboxylic acid/EDCI/DMA.

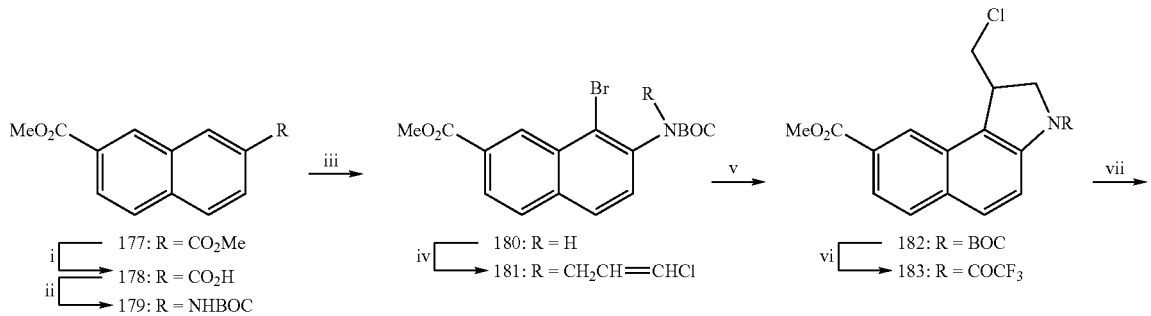

-continued
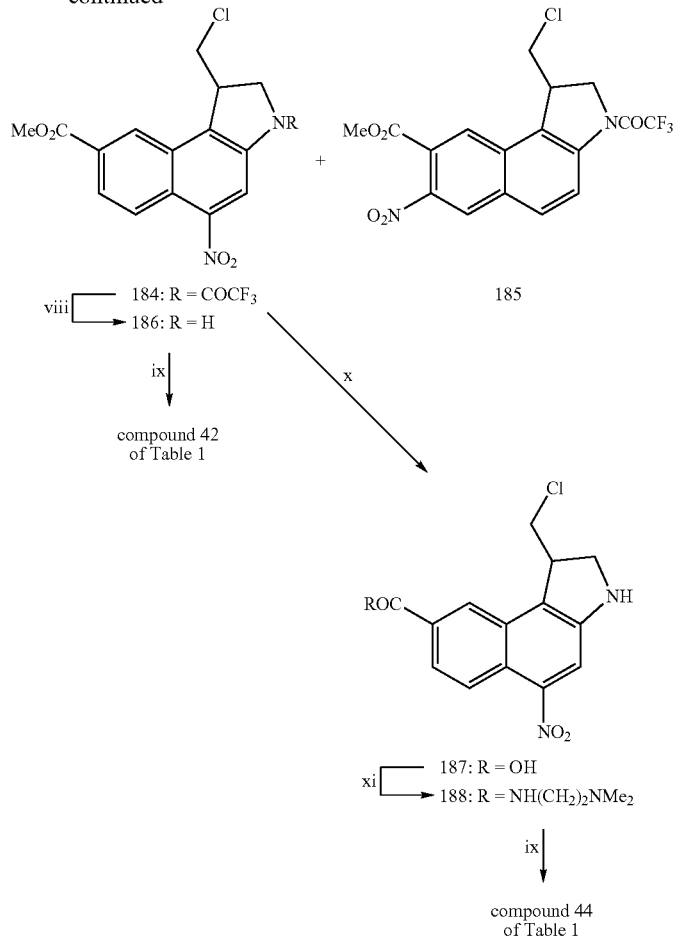
(i) KOH/MeOH/CH$_2$Cl$_2$/H$_2$O;
(ii) DPPA/tBuOH/Et$_3$N;
(iii) NBS/K$_2$CO$_3$/MeCN;
(iv) NaH/DMF, then 1,3-dichloropropene;
(v) Bu$_3$SnH/AIBN/benzene;
(vi) HCl(g)/dioxane, then TFAA/pyridine;
(vii) conc. H$_2$SO$_4$/KNO$_3$;
(viii) Cs$_2$CO$_3$/MeOH/CH$_2$Cl$_2$;
(ix) HCl(g)/dioxane, then RCO$_2$H/EDCI/DMA;
(x) 90% H$_2$SO$_4$;
(xi) N,N-dimethylethylenediamine/DMF, then DECP.
Scheme K
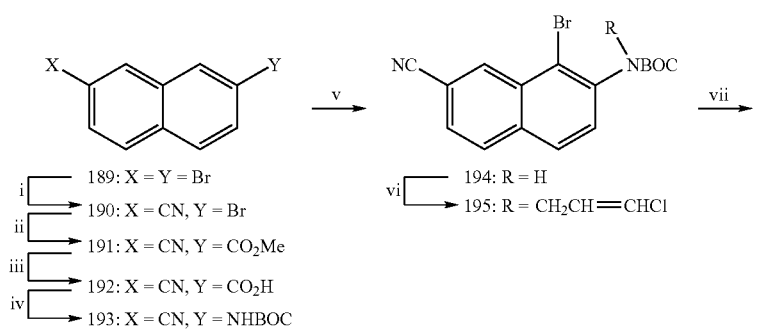

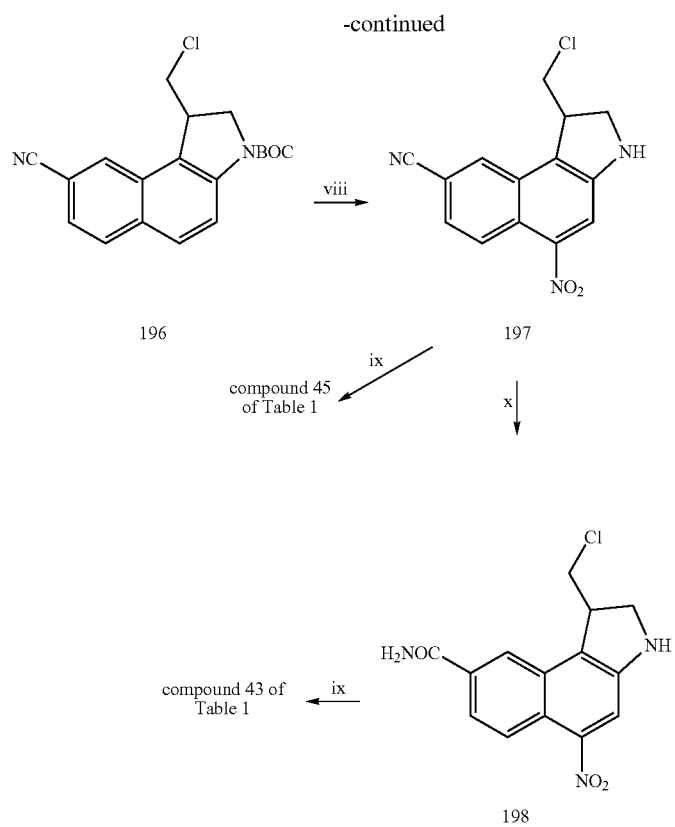
(i) CuCN/NMP;
(ii) Pd(OAc)₂/DPPP/MeOE/DMSO/Et₃N, then CO(g);
(iii) NaOH/EtOH/CH₂Cl₂/H₂O;
(iv) DPPA/tBuOH/Et₃N;
(v) NBS/K₂CO₃/MeCN;
(vi) NaH/DMF, then 1,3-dichloropropene;
(vii) Bu₃SnH/AIBN/benzene;
(viii) HCl/dioxane, evaporation, then conc. H₂SO₄/KNO₃;
(ix) HCG(g)/dioxane, then 5-[2-(dimethylamino)ethoxy]indole-2-carboxylic acid/EDCI/DMA;
(x) 90% H₂SO₄.
Scheme L
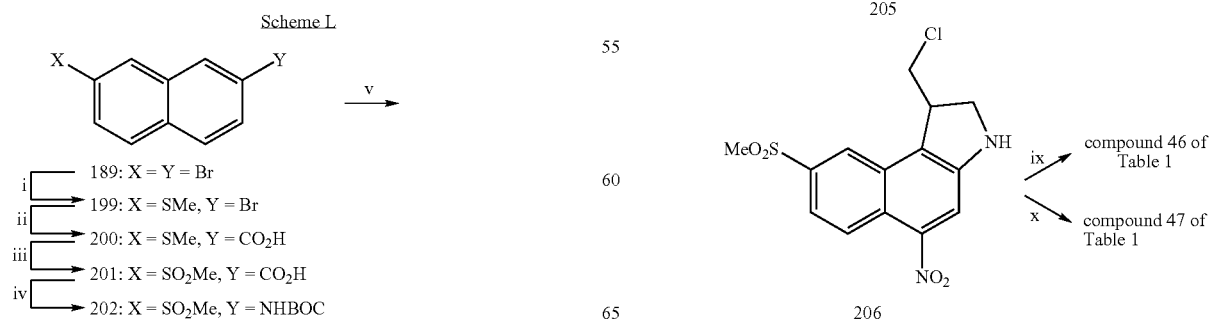

(i) BuLi/THF, then MeSSMe;
(ii) BuLi/THF, then CO$_2$;
(iii) NaBO$_3$·4H$_2$O/AcOH;
(iv) DPPA/Et$_3$N/t-BuOH;
(v) NBS/MeCN;
(vi) NaH/DMF, then 1,3-dichloropropene;
(vii) Bu$_3$SnH/AIBN/benzene;
(viii) conc. H$_2$SO$_4$, then KNO$_3$;
(ix) 5,6,7-trimethoxyindole-2-carbonyl chloride/DMAP/pyridine;
(x) 5-[2-(dimethylamino)ethoxy]indole-2-carboxylic acid/EDCI/TsOH/DMA.

(i) BuLi/THF, Den SO$_2$(g), then NCS/CH$_2$Cl$_2$;
(ii) Bn$_2$NH/Et$_3$NMEP;
(iii) Pd(OAc)$_2$/DPPP/MeOH/Et$_3$N/DMSO/CO(g);
(iv) KOH/H$_2$O/MeOH/CH$_2$Cl$_2$;
(v) DPPA/t-BuOH/Et$_3$N;
(vi) NBS/K$_2$CO$_3$/MeCN;
(vii) NaH/DMF, then 1,3-dichloropropene;
(viii) Bu$_3$SnH/AIBN/benzene;
(ix) HCl(g)/dioxane, then (CF$_3$CO)$_2$O/pyridine;
(x) conc. H$_2$SO$_4$;
(xi) conc. H$_2$SO$_4$/KNO$_3$;
(xii) Cs$_2$CO$_3$, then HCl(g)/dioxane, then RCO$_2$H/EDCI/DMA;

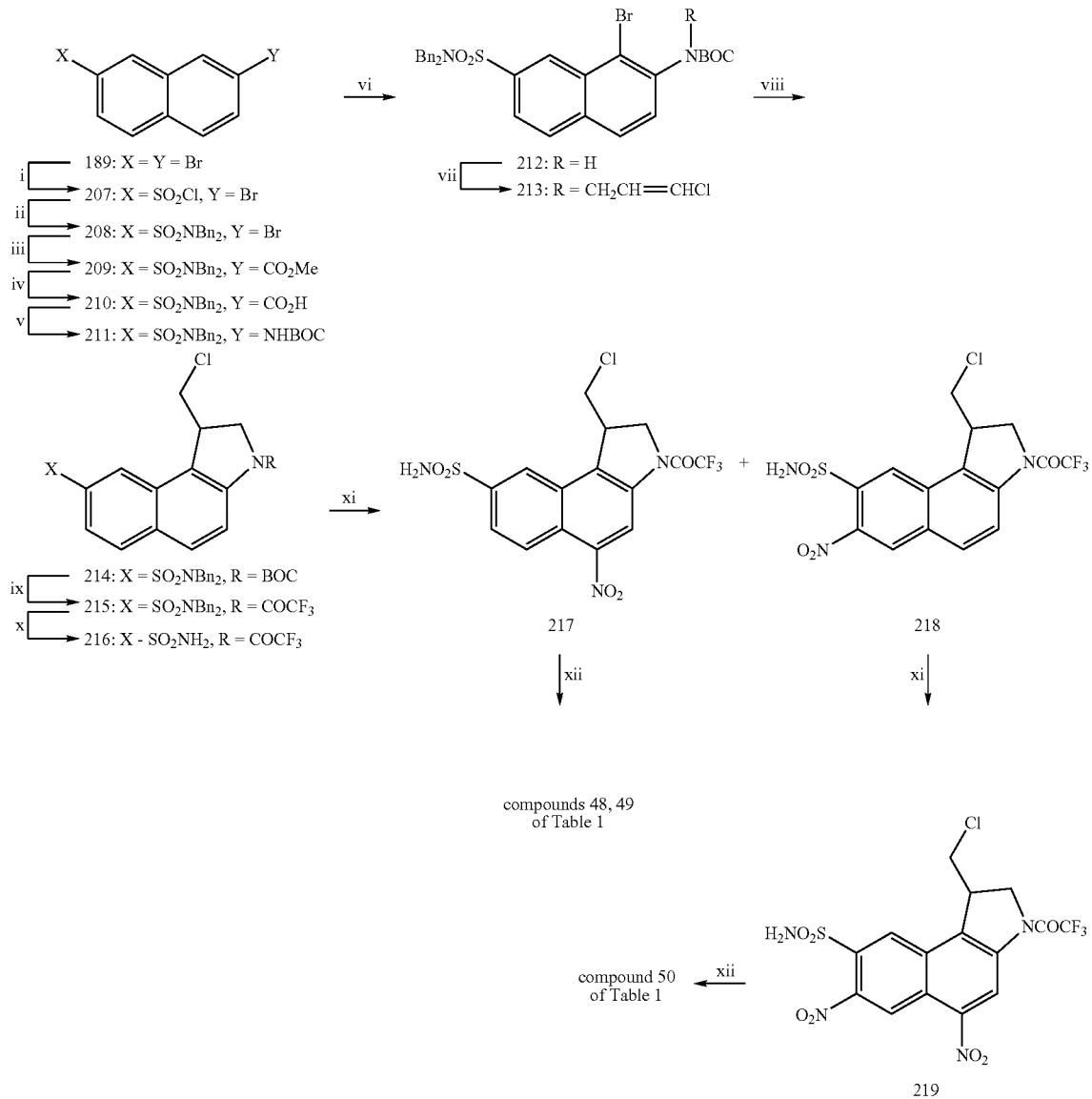

Scheme M

Scheme N
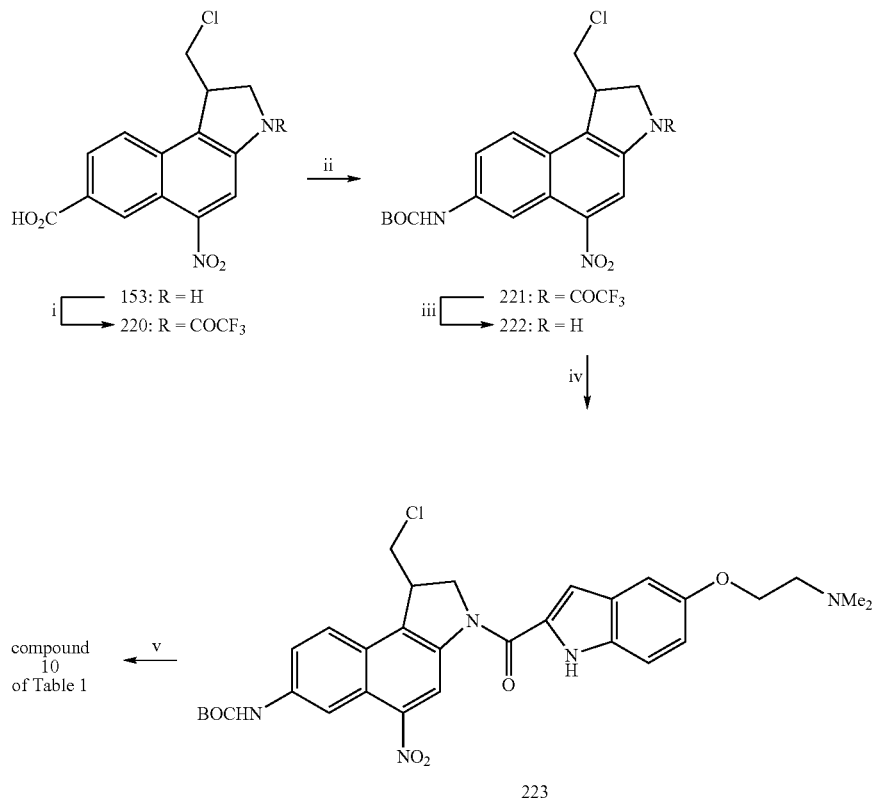
(i) TFAA/THF;
(ii) (COCl)$_2$/DMF then NaN$_3$ then toluene reflux then tBuOH;
(iii) Cs$_2$CO$_3$/MeOH;
(iv) 5-[2-(dimethylamino)ethoxy]indole-2-carboxylic acid/EDCI/TsOH/DMA;
(v) TFA then NH$_3$.
Scheme O
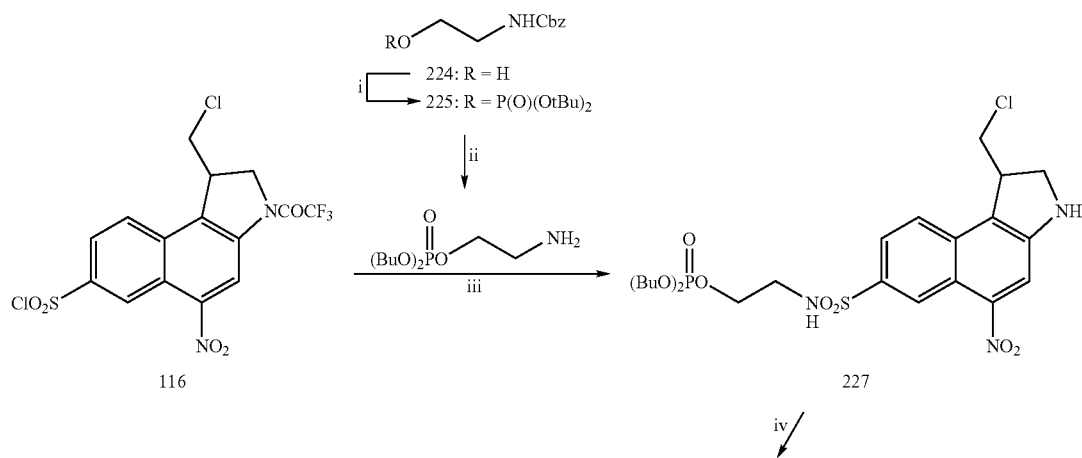

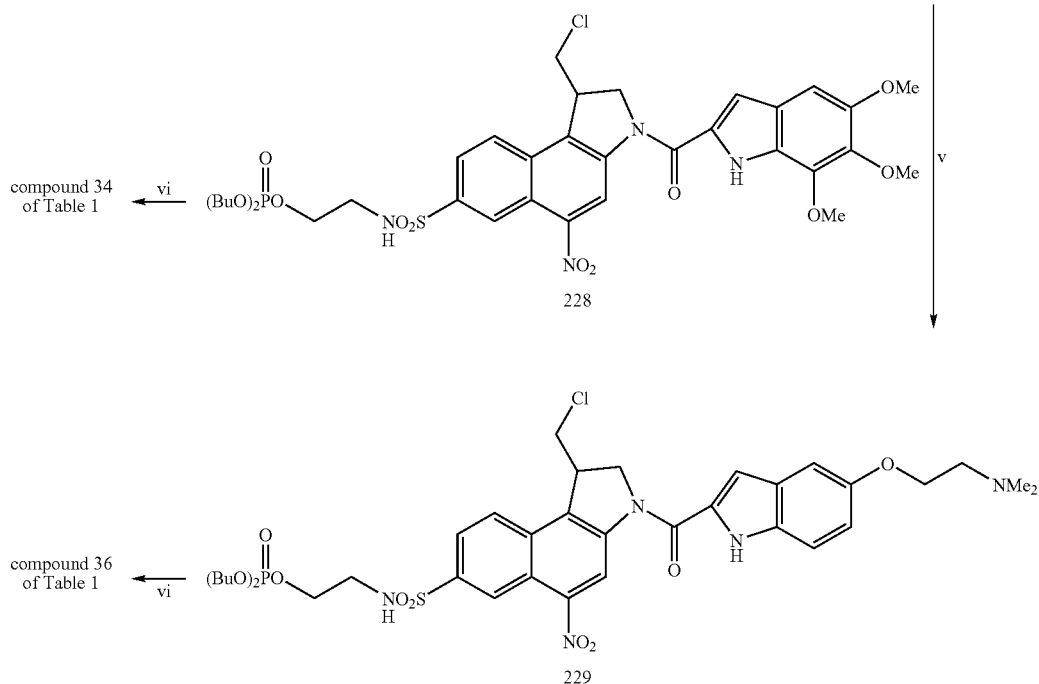
(i) iPr$_2$NP(OtBu)$_2$/tetrazole/THF/CH$_3$CN then H$_2$O$_2$;
(ii) H$_2$/Pd/C/MeOH;
(iii) Et$_3$N/THF then Cs$_2$CO$_3$/MeOH;
(iv) 5,6,7-trimethoxyindole-2-carboxylic acid/EDCI/TsOH/DMA;
(v) 5-[2-(dimethylamino)ethoxy]indole-2-carboxylic acid/EDCI/TsOH/DMA;
(vi) TFA/CH$_2$Cl$_2$
Scheme P
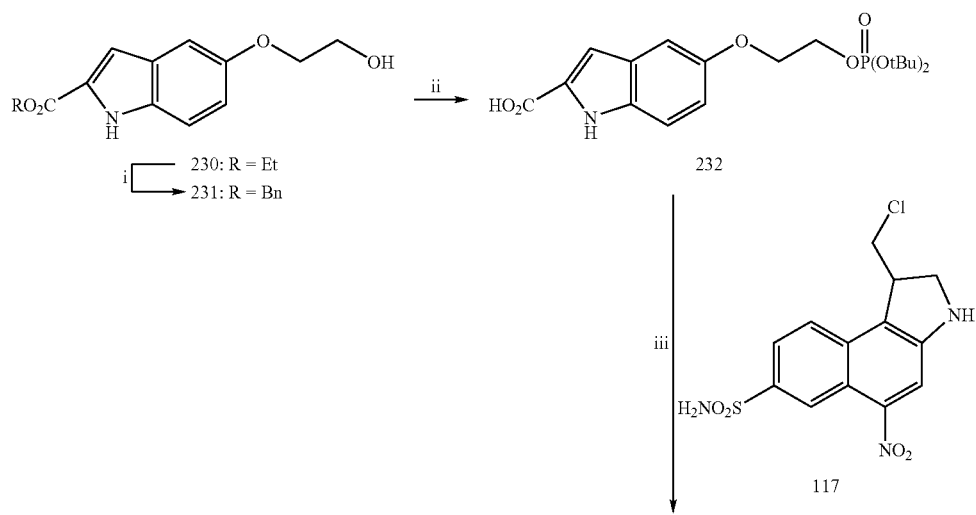

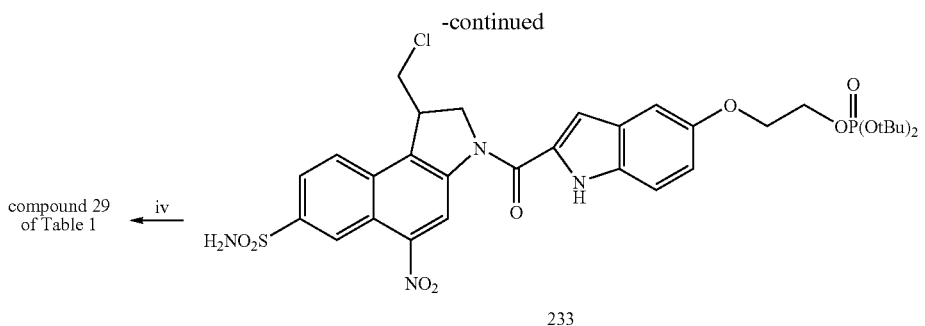

compound 29 of Table 1 ← iv

233

(i) Bu₂SnO/BnOH;

(ii) iPr₂NP(OtEu)₂/tetrazole/THF/CH₃CN then H₂O₂ then H₂/Pd/C/MeOH;

(iii) EDCI/TsOH/DMA;

(iv) TFA/CH₂Cl₂.

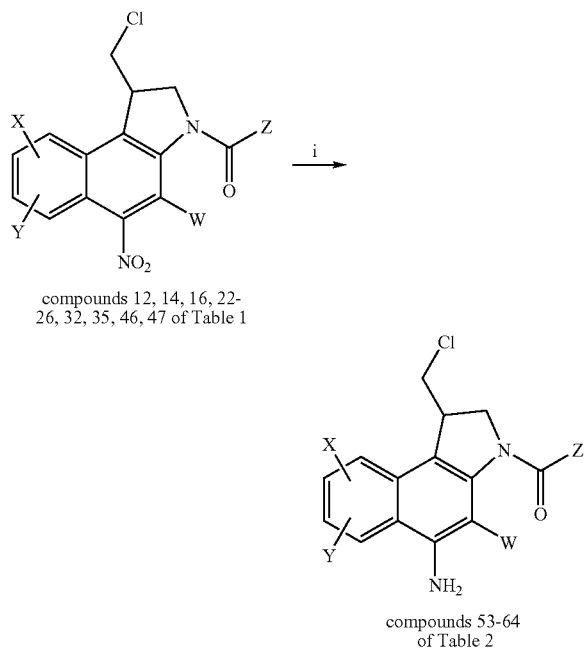

Scheme Q compounds 12, 14, 16, 22-26, 32, 35, 46, 47 of Table 1 compounds 53-64 of Table 2

(i) H₂/PtO/THF

Applications of the Compounds of the Present Invention

The compounds of formula I of the present invention can be used in a method of treatment of cancer of the human or animal body. Such treatment includes a method of treating the growth of cancer cells in hypoxic environments in a patient with cancer which comprises administering to a patient in need of treatment compounds of formula I of the invention. The compounds of formula I can be used in this context as single agents, or in combination with other cytotoxic drugs or other therapeutic agents/therapies, especially those that are relatively ineffective against hypoxic cells such as radiation therapy. When a compound of formula I is administered before radiation, therapeutic synergy can also arise because of radiosensitization of hypoxic cells resulting from reaction of the compound with radiation-induced DNA radicals (as described by Wardman, *Radiat. Phys. Chem.*, 1987, 30, 423-432) or as a result of reduction of the compound by radiation in hypoxie tissue as described by Wilson et al., *Anticancer Drug Design* 1998, 13, 663-685. These approaches are applicable to any cancer type that exhibits hypoxic regions. In addition, the compounds of formula I can be used in cancer therapy as part of an ADEPT or GDEPT therapy system, as discussed below. The treatment of cancer includes conditions such as leukaemia and solid tumours such as breast, bowel and lung tumours including small cell lung carcinoma and other cancer types It will be understood that where treatment of tumours is concerned, treatment includes any measure taken by the physician to alleviate the effect of the tumour on a patient. Thus, although complete remission of the tumour is a desirable goal, effective treatment will also include any measures capable of achieving partial remission of the tumour as well as a slowing down in the rate of growth of a tumour including metastases. Such measures can be effective in prolonging and/or enhancing the quality of life and relieving the symptoms of the disease.

(i) Compounds of the Formula I of the Present Invention

Compounds of Formula I of the present invention can be used in a method of treatment of cancer in a patient, which method comprises administering to a patient in need of treatment an effective amount of a compound of Formula I. The compounds of the invention may be administered in the form of a pharmaceutical composition.

While the exact dose of the compound will be at the discretion of the physician, taking into account the condition and needs of the patient, typical doses and administration schedules will he determined by experience in clinical trials. Total doses are expected to be in the range from about 0.1 to 200 mg/kg per subject, preferably about 10 mg/kg per subject.

(ii) GDEPT Therapy

GDEPT (gene-directed enzyme-prodrug therapy for cancer) is a tool that is envisaged as being suitable for use with compounds of the present invention. ODEPT therapies involve the administration of a vector (nucleic acid, virus, bacterium or bacterial spore) that is able to express, in tumours, an enzyme that activates a prodrug. Such prodrug-activating enzymes include nitroreductases that are capable of reducing the nitro group of compounds of Formula I, and thereby activating these as GDEPT prodrugs. An example of such an enzyme is the product of the nfsB gene of *E. coli*, which codes for a nitroreductase (NTR) that is able to reduce aromatic nitro groups under both aerobic and hypoxic conditions (Anlezark et al., *Biochem. Pharmacol.*, 1992, 44, 2289-

2295). A further example of a prodrug-activating nitroreductase enzyme for GDPET is human cytochrome P450 oxidoreductase (Patterson et al., *Gene Ther.*, 2002, 9, 946-954). Vectors suitable for GDEPT include human adenoviruses as illustrated by a replication-defective adenovirus that expresses NTR (Chen et al., *Gene Ther.*, 2004, 11, 1126-1136), and conditionally replicating adenoviruses that express the prodrug-activating enzyme cytosine deaminase (Zhan, *Cancer Gene Ther.*, 2005, 12, 19-25). An example of a bacterial spores which can be used as a GDEPT vector system is provided by recombinant *Clostridia* sp. which express NTR on germination in hypoxic regions of tumours (Lemmon et al., *Gene Ther.*, 1997, 4, 791-796).

Preferably, the GDEPT enzyme is a non-mammalian nitroreductase enzyme, such as a bacterial nitroreductase. An *E. coli* nitroreductase as disclosed in WO93/08288 may be suitable. The enzyme may be modified by standard recombinant DNA techniques, e.g. by cloning the enzyme, determining its gene sequence and altering the gene sequence by methods such as truncation, substitution, deletion or insertion of sequences for example by site-directed mutagenesis. Reference may be made to "Molecular Cloning" by Sambrook et al. (1989, Cold Spring Harbor) for discussion of standard recombinant DNA techniques. The modification made may be any which still leaves the enzyme with the ability to reduce the nitro group of Formula I but which alters other properties of the enzyme, for example its rate of reaction or selectivity.

In addition, small truncations in the N- and/or C-terminal sequence may occur as a result of the manipulations required to produce a vector in which a nucleic acid sequence encoding the enzyme is linked to the various other vector sequences.

One suitable route of administration is by injection of the particles in a sterile solution. Viruses, for example isolated from packaging cell lines may also be administered by regional perfusion or direct intratumoural direction, or direct injection into a body cavity (intracaviterial administration), for example by intraperitoneal injection.

In using a GDEPT system the prodrug will usually be administered following administration of the vector encoding an enzyme. Total doses of prodrug are expected to be in the range from about 0.1 to 200 mg/kg per subject, preferably about from 10 mg/kg per subject.

(iii) ADEPT Therapy

ADEPT (antibody-directed enzyme-prodrug therapy for cancer) is a tool suitable for use with some of the compounds of the present invention.

For applications in ADEPT systems, an antibody directed against a tumour specific marker is linked to the nitroreductase enzyme, which may be modified as described above. The antibody may be monoclonal or polyclonal. For the purposes of the present invention, the term "antibody", unless specified to the contrary, includes fragments of whole antibodies which retain their binding activity for a tumour target antigen. Such fragments include Fv, F(ab') and F(ab')2 fragments, as well as single chain antibodies. Furthermore, the antibodies and fragments thereof may be humanised antibodies, e.g. as described in EP-A-239400.

The antibodies may be produced by conventional hybridoma techniques or, in the case of modified antibodies or fragments, by recombinant DNA technology, e.g. by the expression in a suitable host vector of a DNA construct encoding the modified antibody or fragment operably linked to a promoter. Suitable host cells include bacterial (e.g. *E. coli*), yeast, insect and mammalian. When the antibody is produced by such recombinant techniques the enzyme may be produced by linking a nucleic acid sequence encoding the enzyme (optionally modified as described above) to the 3' or 5' end of the sequence of the construct encoding the antibody or fragment thereof.

The antibody/enzyme conjugate for ADEPT can be administered simultaneously but it is often found preferable, in clinical practice, to administer the enzyme/agent conjugate before the prodrug, e.g. up to 72 hours or even 1 week before, in order to give the enzyme/agent conjugate an opportunity to localise in the region of the tumour target. By operating in this way, when the prodrug is administered, conversion of the prodrug to the cytotoxic agent tends to be confined to the regions where the enzyme/agent conjugate is localised, i.e. the region of the target tumour and the premature release of the toxic fragment of Formula I is minimised.

In ADEPT the degree of localisation of the enzyme/agent conjugate (in terms of the ratio of localized to freely circulating active conjugate) can be further enhanced using the clearance and/or inactivation systems described in WO89/10140. This involves, usually following administration of the conjugate and before administration of the prodrug, the administration of a component (a "second component") which is able to bind to the part of the conjugate so as to inactivate the enzyme and/or accelerate the clearance of the conjugate from the blood. Such a component may include an antibody to the enzyme component of the system which is capable of inactivating the enzyme.

The second component may be linked to a macromolecule such as dextran, a liposome, albumin, macroglobulin or a blood group O erythrocyte so that the second component is restrained from leaving the vascular compartment. In addition or as an alternative, the second component may include a sufficient number of covalently bound galactose residues, or residues of other sugars such as lactose or mannose, so that it can bind the conjugate in plasma but be removed together with the conjugate from plasma by receptors for galactose or other sugars in the liver. The second component should be administered and designed for use such that it will not, to any appreciable extent, enter the extravascular space of the tumour where it could inactivate localised conjugate prior to and during administration of the prodrug.

In ADEPT systems, the dose of the prodrug and conjugate will ultimately be at the discretion of the physician, who will take into account such factors as the age, weight and condition of the patient. Suitable doses of prodrug and conjugate are given in Bagshawe et al. Antibody, Immunoconjugates, and Radiopharmaceuticals (1991), 4, 915-922. A suitable dose of conjugate may be from 500 to 200,000 enzyme units/m$^2$ (e.g. 20,000 enzyme units/m$^2$) and a suitable dose of prodrug may be from about 0.1 to 200 mg/kg, preferably about from 10 to 100 mg/kg per patient per day.

In order to secure maximum concentration of the conjugate at the site of desired treatment, it is normally desirable to space apart administration of the two components by at least 4 hours. The exact regime will be influenced by various factors including the nature of the tumour to be targeted and the nature of the prodrug, but usually there will be an adequate concentration of the conjugate at the site of desired treatment within 48 hours.

The ADEPT system when used with nitroreductase also preferably comprises a suitable cofactor for the enzyme. Suitable cofactors include a riboside or ribotide of nicotinic acid or nicotinamide.

The antibody/enzyme conjugate may be adminstered by any suitable route usually used in ADEPT therapy.

The exact dosage regime for ADEPT will, of course, need to be determined by individual clinicians for individual patients and this, in turn, will be controlled by the exact nature of the prodrug and the cytotoxic agent to be released from the prodrug but some general guidance can be given. Chemotherapy of this type will normally involve parenteral administration of modified virus and administration by the intravenous route is frequently found to be the most practical.

The following examples are representative of the invention, and provide detailed methods for preparing the compounds of the invention. In these examples, elemental analyses were carried out in the Microchemical Laboratory, University of Otago, Dunedin, NZ. Melting points were determined on an Electrothermal 2300 Melting Point Apparatus. NMR Epectra were obtained on a Bruker Avance400 spectrometer at 400 Mz for $^1$H and 100 Mgz for $^{13}$C spectra, referenced to Me$_4$Si. Mass spectra were determined on a VG-70SE mass spectrometer using an ionizing potential of 70 eV at a nominal resolution of 1000. High-resolution spectra were obtained at nominal resolutions of 3000, 5000, or 10000 as appropriate. All spectra were obtained as electron impact (EI) using PFK as the reference unless otherwise stated. Column chromatography was carried out on silica gel, (Merck 230-400 mesh) unless, otherwise stated

EXAMPLE 1

1-(Chloromethyl)-5,6-dinitro-3-(5,6,7-trimethoxyindol-2-carbonyl)-1,2-dihydro-3H-benzo[e]indole (1) (Scheme A). A solution of tert-butyl 1-(chloromethyl)-5-nitro-1,2-dihydro-3H-benzo[e]indole-3-carboxylate [J. Org. Chem., 1998, 63, 9414-9420] (101) (600 mg, 1.65 mmol) in dioxane (15 mL) was saturated with dry HCl, stirred at 20° C. for 1, and then evaporated under reduced pressure below 30° C. The residue was partitioned between CH$_2$Cl$_2$ and dilute aqueous KHCO$_3$ and the organic phase was washed with water, dried, and then filtered rough a column of silica gel to give 1-(chloromethyl)-5-nitro-1,2-dihydro-3H-benzo[e]indole (102) (372 mg, 86%) as a red solid: mp (CH$_2$Cl$_2$/petroleum ether) 100-101° C.; $^1$H NMR [(CD$_3$)$_2$SO] δ 8.11 (d, J—8.7 Hz, 1H), 7.87 (d, J=8.4 Hz, 1H), 7.65 (s, 1H), 7.55 (ddd, J=8.2, 7.0, 1.2 Hz, 1H), 7.40 (ddd, J=8.7, 6.8, 1.0 Hz, 1H), 6.27 (br s, 1H), 4.23-4.15 (m, 1H), 3.89 (dd, J=11.0, 3.7 Hz, 1H), 3.81 (t, J=9.7 Hz, 1H), 3.78-3.66 (m, 2H). Anal. (C$_{13}$H$_{11}$ClN$_2$O$_2$) C, H, N.

A stirred solution of 102 (500 mg, 1.90 mmol) in conc. H$_2$SO$_4$ (5 mL) was cooled to −5° C. and treated with powdered KNO$_3$ (288 mg, 2.85 mmol). The mixture was stirred at 0° C. for a further 15, in, then poured into ice-water and the solid was collected and dissolved in CH$_2$Cl$_2$. The solution was filtered through a column of silica gel and the product was recrystallised from EtOAc/iPr$_2$O to give 1-(chloromethyl)-5,6-dinitro-1,2-dihydro-3H-benzo[e]indole (103) (446 mg, 76%) as a red solid: mp 206-207° C.; $^1$H NMR [(CD$_3$)$_2$SO] δ 8.23 (dd, J=8.7, 1.0 Hz, 1H), 8.00 (dd, J=7.7, 0.9 Hz, 1H), 7.76 (s, 1H), 7.67 (dd, J=8.4, 7.6 Hz, 1H), 6.72 (s, 1H), 4.32-4.22 (m, 1H), 3.94-3.83 (m, 2H), 3.83-3.75 (m, 2). Anal. (C$_{13}$H$_{10}$ClN$_3$O$_4$) C, H, N.

A suspension of 5,6,7-trimethoxyindole-2-carboxylic acid (122 mg, 0.49 mmol) in dry CH$_2$Cl$_2$ (10 mL) was treated with oxalyl chloride (0.13 mL, 1.49 mmol) followed by DMF (10 mL). The mixture was stirred at room temperature for 15 min, then evaporated under reduced pressure and azeotroped dry with benzene. The resulting acid chloride was cooled to −5° C. and treated with an ice-cold solution of amine 103 (100 mg, 0.33 mmol) in dry pyridine (2 ml) containing DMAP (5 mg). The stirred mixture was warmed to room temperature for 30 min, then poured into dilute aqueous KHCO$_3$. The solid was collected, purified by chromatography on silica gel eluting with CH$_2$Cl$_2$/EtOAc (19:1), then crystallised from CH$_2$Cl$_2$/EtOAc to give 1 (84 mg, 48%) as a yellow solid: mp 278-279° C.; $^1$H NMR [(CD$_3$)$_2$SO] δ 11.67 (s, 1H), 9.16 (s, 1H), 8.61 (d, J=8.0 Hz, 1H), 8.38 (d, J=7.4 Hz, 1H), 7.92 (t, J=8.0 Hz, 1H), 7.21 (d, J=1.9 Hz, 1H), 6.99 (s, 1H), 4.94 (t, J=10.6 Hz, 1H), 4.73-4.60 (m, 2H), 4.19-0.05 (m, 2H), 3.94 (s, 3H) 3.83 (s, 3H), 3.81 (s, 3H). HRMS (FAB) calcd. for C$_{25}$H$_{21}$$^{35}$ClN$_4$O$_8$ (M$^+$) m/z 540.1048, found 540.1051. Anal. (C$_{25}$H$_{21}$ClN$_4$O$_8$) C, H, N.

EXAMPLE 2

1-(Chloromethyl)-3-(5-[2-(dimethylamino)ethoxy]indol-2-carbonyl)-5,6-dinitro-1,2-dihydro-3H-benzo[e]indole (2) (Scheme A). A mixture of amine 103 (100 mg, 0.33 mmol), 5-[2-(dimethylamino)ethoxy]indole-2-carboxylic acid hydrochloride (111 mg, 0.39 mmol), EDCI [1-ethyl-3-(3-dimethylaminopropyl)carbodiimide hydrochloride] (249 mg, 1.30 mmol) and anhydrous TsOH (40 mg, 0.23 mmol) in dry DMA (4 mL) was stirred at room temperature under N$_2$ for 3 h, then poured into dilute aqueous NH$_3$. The solid was collected, dissolved in CH$_2$Cl$_2$ at room temperature, died, and concentrated under reduced pressure below 30° C. The residue was triturated with EtOAc to give crude 2. Treatment of a solution of the free base in CH$_2$Cl$_2$ with HCl(g)/EtOAc/hexane, followed by crystallization from MeOH/Me$_2$CO/EtOAc, gave 2-HCl (129 mg, 69%) as a yellow solid: Mp 225-226° C.; $^1$H NMR [(CD$_3$)$_2$SO] δ 11.88 (d, J=1.6 Hz, 1H), 10.12 (br s, 1H), 9.22 (s, 1H), 8.63 (d, J=7.9 Hz, 1H), 8.40 (dd, J=7.6, 0.6 Hz, 1H), 7.93 (t, J=8.0 Hz, 1H), 7.47 (d, J=8.9 Hz, 1H), 7.27 (d, J=2.3 Hz, 1H), 7.26 (d, J=1.6 Hz, 1H), 7.04 (dd, J=8.9, 2.4 Hz, 1H), 4.99 (t, J=10.2 Hz, 1H), 4.79-4.66 (m, 2H), 4.36 (t, J=4.4 Hz, 2H), 4.20-4.07 (m, 2H), 3.53 (t, J=5.0 Hz, 2H), 2.87 (s, 6H). Anal. (C$_{26}$H$_{24}$ClN$_5$O$_6$·HCl.1½H$_2$O) C, H, N.

EXAMPLE 3

6-Acetyl-1-(chloromethyl)-5-nitro-3-(5,6,7-trimethoxy-indol-2-carbonyl)-1,2-dihydro-3H-benzo[e]indole (3) (Scheme B). A stirred solution of tert-butyl 2-naphthylcarbamate (104) [PCT Int. Appl. (2002) WO 02/067930, Searcey, M., Patterson, L. H.] (20.3 g, 83 mmol) in MeCN (150 mL) was treated portionwise at 0° C. with NBS (17.82 g, 100 mmol), then stirred for a further 2 h at 0° C. The mixture was concentrated under reduced pressure and the residue was dissolved in CH$_2$Cl$_2$. The solution was filtered through a short column of silica gel, and the product was recrystallised from MeOH to give tert-butyl 1-bromo-2-naphthylcarbamate (105) (24.09 g, 90%), as a white solid: mp 90-91° C.; $^1$H NMR [(CD$_3$)$_2$SO] δ 8.82 (s, 1H), 8.15 (d, J=8.5 Hz, 1H), 7.96 (d, J=9.6 Hz, 1H), 7.93 (d, J=9.3 Hz, 1H), 7.71 (d, J=8.8 Hz, 1H), 7.66 (t, J=7.7 Hz, 1H), 7.56 (t, J=7.4 Hz, 1H), 1.49 (s, 9H). Anal. (C$_{15}$H$_{16}$BrNO$_2$) C, H, N, Br.

A stirred solution of 105 (800 mg, 2.48 mmol) in DMF (6 mL) was treated portionwise at 0° C. with NaH (119 mg, 60% in oil, 2.98 mmol). The mixture was warmed to room temperature for 30 min, then cooled to 0° C. and treated with 1,3-dichloropropene (0.72 mL, 7.8 mmol, mixed isomers). The mixture was stirred at room temperature for a flirter 4 h, then diluted with 10% aqueous NaCl and extracted with EtOAc (×2). The combined organic extracts were washed with water (×3), dried, and concentrated under reduced pressure at 100° C. The residue was chromatographed, on silica gel, eluting with CH$_2$Cl$_2$/petroleum ether (7:3), to give tert-butyl 1-bromo-2-naphthyl (3-chloro-2-propen-1-yl)carbamate (106) (958 mg, 97%) as an oil; $^1$H [(CD$_3$)$_2$SO] (mixture of rotamers and Z forms) δ 8.23 (d, J=8.4 Hz, 1H), 8.07-7.94 (m, 2H), 7.71 (t, J=7.5 Hz, 1H), 7.65 (t, J=1.4 Hz, 1H), 7.51, 7.45 (2 d, J=8.6 Hz, 1H), 6.44-6.26 (m, 1 H), 6.21-5.99 (m, 1H), 4.58-4.46, 4.44-4.17, 4.14-3.96 (3 m, 2H), 1.50, 1.26 (2 s, 9H). HRMS (I) calcd. for $C_{18}H_{19}{}^{79}Br^{35}ClNO_2$ (M$^+$) m/z 395.0288, found 395.0261.

A mixture of 106 (23.0 g, 58 mmol), Bu$_3$SnH (16.4 mL, 61 mmol) and AIBN (1.2 g, 7.3 mmol) in dry benzene (200 mL) was stirred at reflux under N$_2$ for 2 h, then concentrated under reduced pressure. The residue was chromatograph on silica gel, eluting with CH$_2$Cl$_2$/petroleum ether, to provide an oil. This was dissolved in MeOH, and following prolonged refrigeration the precipitate was collected and recrystallised from petroleum ether to give tert-butyl 1-(chloromethyl)-1,2-dihydro-3H-benzo[e]indole-3-carboxylate (107) (13.6 g, 74%) as a white solid: mp 107-108° C.; $^1$H NMR [(CD$_3$)$_2$SO] δ 8.07 (v br, 1H), 7.94-7.80 (m, 3H), 7.52 (t, J=7.4 Hz, 1H), 7.39 (t, J=7.5 Hz, 1H), 4.29-4.11 (m, 2H), 4.08 (dd, J=11.1, 2.3 Hz, 1H), 4.03 (dd, J=11.1, 2.9 Hz, 1H), 3.88 (dd, J=11.0, 7.1 Hz, 1H), 1.55 (s, 9H). Anal. ($C_{18}H_{20}ClNO_2$) C, H, N.

A solution of 107 (400 mg, 1.26 mmol) in dioxane (15 mL) was saturated with dry HCl, stirred at room temperature for 1 h, and then evaporated under reduced pressure below 30° C. The residue was dissolved in pyridine. (3 mL), and treated dropwise at 0° C. with trifluoroacetic anhydride (0.21 mL, 1.49 mmol). The mixture was warmed to room temperature for 5 min, then diluted with water, and the precipitated solid was collected, dissolved in CH$_2$Cl$_2$ and filtered through a column of silica gel to give 1-(chloromethyl)-3-(trifluoroacetyl)-1,2-dihydro-3H-benz[e]indole (108) (363 mg, 92%) as a white solid: mp (CH$_2$Cl$_2$/petroleum ether) 157° C.; $^1$H NMR [(CD$_3$)$_2$S)] δ 8.32 (d, J=9.0 Hz, 1H), 8.07-7.96 (m, 3H), 7.62 (ddd, J=8.2, 6.9, 1.2 Hz, 1H), 7.53 (ddd, J=8.1, 6.9, 1.1 Hz, 1H), 4.61-4.52 (m, 1H), 4.51-4.39 (m, 2H), 4.15 (dd, J=11.3, 3.0 Hz, 1H), 4.04 (dd, J=11.3, 5.9 Hz, 1H). Anal. ($C_{15}H_{11}ClF_3NO$) C, H, N.

Solid 108 (4.7 g, 15 mmol) was added to a mixture of AlCl$_3$ (7.0 g, 52 mmol) and AcCl (2.5 mL, 35 mmol) in CS$_2$ (60 mL) at 0° C., and the stirred mixture was heated at 70° C. for 3 h. Solvent was boiled off at 60° C., and the black residue was cooled and treated with ice and conc. HCl. The mixture was extracted with CH$_2$Cl$_2$ (3×100 mL). The extracts were dried and concentrated under reduced pressures and the residue was chromatographed on silica gel. Elution with EtOAc/petroleum ether (1:4) gave a product (3.9 g, 73%) that was shown by NMR to be a mixture of 64% 6-acetyl-1-(chloromethyl)-3-(trifluoroacetyl)-1,2-dihydro-3H-benzo[e]indole (109) and 23% 7-acetyl-1-(chloromethyl)-3-(trifluoroacetyl)-1,2-dihydro-3H-benzo[e]indole (110), with the remainder of the material being a mixture of other acetylated products. Pure 109 was obtained by crystallization from EtOAc/petroleum ether as a white solid: mp 121-123° C.; $^1$H NMR [(CD$_3$)$_2$SO] δ 8.72 (d, J=1.6 Hz, 1H), 8.60 (d, J=9.4H, 1H), 8.38 (d, J=9.3 Hz, 1H), 8.25 (d, J=8.4 Hz, 1H), 8.00 (dd, J=7.1, 0.9 Hz, 1H), 7.70 (dd, J=8.3, 7.3 Hz, 1H), 4.60-4.40 (m, 3H), 4.18-4.10 (m, 1H), 4.07-3.99 (m, 1H), 2.76 (s, 3H); $^{13}$C NMR δ 201.8, 153.2 (q, J$_{C-F}$ 36.9 Hz), 139.9, 136.1, 129.6; 128.1, 127.8, 127.5, 127.2, 126.8, 126.3, 124.9, 116.1 (q, J$_{C-F}$ 288 Hz), 52.5, 47.6, 41.1, 30.0. Anal. ($C_{17}H_{13}ClF_3NO_2$) C, H, N.

A solution of 109 (1.0 g, 2.8 mmol) in CH$_2$Cl$_2$ (20 mL) was treated with fuming HNO$_3$ (6 mL). The mixture was stirred at room temperature for 30 min, and quenched with ice. The mixture was extracted with CH$_2$Cl$_2$ (3×50 ml) dried, and concentrated under reduced pressure. The residue was chromatographed on silica gel, eluting with EtOAc/petroleum ether (from 1:4 to 1:1) to give 6-acetyl-1 chloromethyl)-5-nitro-3-(trifluoroacetyl)-1,2-dihydro-3H-benzo[e]indole (111) (640 mg, 57%) as a brown solid: mp 182-184° C. (EtOAc/petroleum ether); $^1$H NMR (CDCl$_3$) δ 9.18 (s, 1H), 9.06 (d, J=1.4 Hz, 1H), 8.28 (dd, J=8.8, 1.6 Hz, 1H), 7.95 (d, J=8.8 Hz, 1H), 4.68-4.63 (m, 1H), 4.57-4.49 (m, 1H), 4.48-4.30 (m, 1H), 3.93-3.87 (m, 1H), 3.65-3.58 (m, 1H), 2.70 (s, 3H); $^{13}$C NMR 200.4, 154.7 (q, J$_{C-F}$ 39.2 Hz), 148.7, 139.2, 138.2, 130.9, 130.4, 127.7, 127.5, 125.9, 119.6, 115.7, 115.6 (q, J$_{C-F}$ 288H), 52.7, 45.4, 42.7, 28.5. Anal. ($C_{17}H_{12}ClF_3N_2O_4$) C, H, N.

A solution of 111 (53 mg, 0.13 mmol) in CH$_2$Cl$_2$/MeOH (1.1, 20 mL) was treated with Cs$_2$CO$_3$ (100 mg, 0.31 mmol), and the mixture was stirred at room temperature for 15 min, then poured into water (100 mL) and extracted with CH$_2$Cl$_2$ (3×50 mL). The extracts were dried and concentrated under reduced pressure, and the residue was dissolved in CH$_2$Cl$_2$ (5 mL). A solution of 5,6,7-trimethoxyindole-2-carboxylic acid chloride [prepared from 5,6,7-trimethoxyindole-2-carboxylic acid (60 mg, 0.24 mmol) as described above in the synthesis of 1] in pyridine (0.1 mL) was added, and the mixture was stirred for 30 min at room temperature, then washed with aqueous HCl (1N), dried, and concentrated under reduced pressure. The product was purified by chromatography on silica gel, eluting with EtOAc/petroleum ether (1:1), followed by crystallization from CH$_2$Cl$_2$/petroleum ether, to give 3 (40 mg, 57%) as a yellow solid: mp 180-183° C.; $^1$H NMR (CDCl$_3$) δ 9.41 (s, 1H), 9.11 (s, 1H), 7.89 (dd, J=8.4, 1.0 Hz, 1H), 7.72 (dd, J=6.9, 0.9 Hz, 1H), 7.61 (dd, J=8.3, 7.3 Hz, 1H), 7.00 (d, J=2.4 Hz, 1H), 6.86 (s, 1H), 4.85-4.80 (m, 1H), 4.74-4.67 (m, 1H), 4.33-4.25 (m, 1H), 4.08 (s, 3H), 3.94 (s, 3H), 3.91 (s, 3H), 3.93-3.87 (m, 1H), 3.59-3.51 (m, 1H), 2.70 (s, 3H); $^{13}$C NMR δ 200.5, 160.5, 150.5, 148.6, 141.4, 140.9, 138.9, 138.3, 130.6, 129.7, 128.7, 127.2, 126.6, 126.0, 125.7, 123.5, 118.8, 116.6, 107.1, 97.7, 61.5, 61.1, 56.3, 54.7, 45.6, 43.4, 28.5. Anal. ($C_{27}H_{24}ClN_3O_7 \cdot \frac{1}{2}H_2O$) C, H, N.

EXAMPLE 4

6-Acetyl-(chloromethyl)-3-{[2-dimethylamino)ethoxy]indol-2-carbonyl}-5-nitro-1,2-dihydro-3H-benzo[e]indole (4) (Scheme B). A solution of 111 (20.0 mg, 0.5 mmol) in CH$_2$Cl$_2$/MeOH (1:1, 50 mL) and Cs$_2$CO$_3$ (0.5 g, 1.5 mmol) was stirred at room temperature for 15 min, then poured into water (100 mL). The mixture was extracted with CH$_2$Cl$_2$ (3×50 mL), the extracts were dried, and a solution of dry HCl in dioxane was added. After 15 min, the mixture was concentrated under reduced pressure, and to the residue was added sequentially 5-[2-(dimethylamino)ethoxy]indole-2-carboxylic acid hydrochloride (180 mg, 0.63 mmol), EDCI (250 mg, 1.31 mmol), anhydrous TsOH (20 mg, 0.12 mmol) and DMA (3 mL). The reaction was stirred at room temperature for 16 h, then poured into ice-cold dilute aqueous NaHCO$_3$ and extracted with EtOAc (3×30 mL). The combined organic phases were washed with water (3×30 mL) and then brine, dried, and concentrated under reduced pressure to give 4 (200 mg, 75%): mp (CH$_2$Cl$_2$/MeOH)>300° C.; $^1$H NMR [(CD$_3$)$_2$SO] δ 11.71 (s, 1H), 9.01 (s, 1H), 8.35 (dd, J=8.5, 0.9 Hz, 1H), 8.13 (dd, J=7.2, 0.8 Hz, 1H), 7.80 (dd, J=8.5, 7.2 Hz, 1H), 7.41 (d, J=8.9 Hz, 1H), 7.20-7.15 (m, 2H), 6.94 (dd, J=8.9, 2.4 Hz, 1H), 4.98-4.89 (m, 1H), 4.73-4.68 (m, 1H), 4.67-4.60 (m, 1H), 4.16-4.04 (m, 4H), 2.69 (s, 3H), 2.68-2.63 (m, 2H), 2.24 (s, 6H); $^{13}$C NMR δ 200.7, 200.6, 160.5, 153.0, 147.2, 141.3, 136.8, 131.9, 131.7, 130.3, 129.7, 127.6, 127.4, 127.0, 117.4, 116.3, 115.7, 113.2, 196.1, 103.1, 66.1, 57.7, 54.7, 47.7, 45.4, 41.5, 28.5. Anal. ($C_{28}H_{27}ClN_4O_5 \cdot \frac{1}{2}H_2O$) C, H, N, Cl.

EXAMPLE 5

7-Acetyl-1-(chloromethyl)-5-nitro-3-(5,6,7-trimethoxyindol-2-carbonyl)-1,2-dihydro-3H-benzo[e]indole (11) (Scheme B). Acylation of 108 (0.88 g, 2.8 mmol) with $AlC_3$ and AcCl in $PhNO_2$ at 0° C., stirring at room temperature for 16 h, and workup as above, gave a crude product. Chromatography on silica gel, eluting with EtOAc/petroleum ether (from 0:1 to 1:3) gave 7-acetyl-1-(chloromethyl)-3-(trifluoroacetyl)-1,2-dihydro-3H-benzo[e]indole (110) (196 mg, 33% based on consumption of starting material): mp (EtOAc/petroleum ether) 168-170° C.; $^1$H NMR ($CDCl_3$) δ 8.52 (d, J=8.9 Hz, 1H), 8.51 (s, 1H), 8.14 (dd, J=8.8, 1.7 Hz, 1H), 8.02 (d, J=9.0 Hz, 1H), 7.84 (d, J=8.8H, 1H), 4.68-4.62 (m, 1H), 4.49-4.41 (m, 1H), 4.28-4.19 (m, 1H), −3.99-3.93 (m, 1H), 3.61-3.55 (m, 1H), 2.74 (s, 3H); $^{13}$C NMR δ 197.6, 182.8, 154.9 (q, $J_{C-F}$ 38.4 Hz), 142.1, 134.1, 132.2, 131.3, 131.1, 125.7, 125.5, 131.1, 118.1, 116.0 (q, $J_{C-F}$ 288 Hz), 52.7, 45.4, 42.6, 26.6. Anal. ($C_{17}H_{13}ClF_3NO_2$) C, H, N. Further elution gave recovered 108 (360 mg, 40%).

A solution of 110 (200 mg, 0.56 mmol) in conc. $H_2SO_4$ (10 mL) was cooled to 5° C. and treated with $KNO_3$ (60 mg, 0.6 mmol) in one portion. The mixture was stirred vigorously for 30 min at 5° C. The reaction was quenched with co water and the mixture was extracted with EtOAc (3×50 ml). The extracts were dried and concentrated under reduced pressure. Chromatography of the residue on silica gel fluting with EtOAc/petroleum ether (from, 1:4 to 1:1) gave 7-acetyl-1-(chloromethyl)-5-nitro-3-(trifluoroacetyl)-1,2-dihydro-3-benzo[e]indole 112)(177 mg, 86%) as an orange solid: mp (EtOAc/petroleum ether) 158-160.6° C.; $^1$H NMR ($CDCl_3$) δ 9.18 (s, 1H), 9.06 (d, J=1.4 Hz, 1H), 8.28 (dd, J=8.8, 1.6 Hz, 1H), 7.95 (d, J=8.8 Hz, 1H), 4.74-4.68 (m, 1H), 4.58-4.51 (m, 1H), 4.40-4.31 (m, 1H), 4.00-3.92 (m, 1H), 3.74-3.66 (m, 1H), 2.75 (s, 3H); $^{13}$C NMR δ 196.9, 149.1 (q, $J_{C-F}$ 38.8 Hz), 140.7, 136.5, 131.5, 130.9, 130.8, 127.0, 126.5, 123.6, 123.1, 115.7 (q, $J_{C-F}$ 288 Hz), 115.5, 52.8, 45.3, 42.7, 26.5. Anal. ($C_{17}H_{12}ClF_3N_2O_4$) C, H, N.

Deblocking of 112 (80 mg, 0.2 mmol) and reaction with 5,6,7-trimethoxyindole-2-carboxylic acid chloride as above, and purification of the crude product by chromatography, gave 11 (60 mg, 56%): mp ($CH_2Cl_2$/petroleum ether) 257-260° C.; $^1$H NMR [($CD_3$)$_2$SO] δ 11.58 (s, 1H), 9.17 (s, 1H), 8.96 (d, J=1.4 Hz, 1H), 8.29 (d, J=8.8 Hz, 1H), 8.15 (dd, J=8.8, 1.6 Hz, 1H), 7.18 (4, J=2.2 Hz, 1H), 6.97 (s, 1H), 4.95-4.87 (m, 1H), 4.67-4.58 (ra, 21H), 4.17-4.05 (m, 2H), 3.94 (s, 3H), 3.83 (s, 3H), 3.81 (s, 3H), 2.75 (s, 3H); $^{13}$C NMR δ 197.2, 160.6, 149.3, 147.5, 142.6, 140.3, 139.0, 134.9, 131.8, 131.3, 129.6, 126.0, 125.8, 125.1, 124.5, 123.1, 120.9, 115.5, 107.2, 98.0, 61.0, 60.8, 55.9, 54.9, 47.5, 41.2, 26.6. Anal. ($C_{27}H_{24}ClN_3O_7$) C, H, N.

EXAMPLE 6

7-Acetyl-1-(chloromethyl)-3-{5-[2-(dimethylamino) ethoxy]indol-2-carbonyl}-5-nitro-1,2-dihydro-3H-benzo[e]indole (12) (Scheme B). Similar deblocking of 112 (177 mg, 0.44 mmol) and reaction with 5-[2-(dimethylamino)ethoxy]indole-2-carboxylic acid hydrochloride gave 12 (230 mg, 98%): mp ($CH_2Cl_2$MeO)>350° C.; $^1$H NMR [($CD_3$)$_2$SO] δ 11.71 (s, 1H), 9.23 (s, 1H), 8.97 (d, J=1.3 Hz, 1H), 8.33 (d, J=8.8 Hz, 1H), 8.16 (dd, J=8.8, 1.5 Hz, 1H), 7.40 (d, J=8.9 Hz, 1H), 7.20 (d, J=1.7 Hz, 1H), 7.18 (d, J=2.3 Hz, 1H), 6.94 (dd, J=8.9, 2.4 Hz, 1H), 4.92-4.80 (m, 1H), 4.74-4.60 (m, 2H), 4.18-4.03 (m, 4H), 2.73 (s, 3H), 2.66 (t, J=7.8 Hz, 2H), 2.24 (s, 6H). Anal. ($C_{28}H_{27}ClN_4O_5 \cdot H_2O$) C, H, N, Cl.

EXAMPLE 7

7-(Chloromethyl)-3-{5-[2-(dimethylamino)ethoxy]indol-2-carbonyl}-5-nitro-1,2-dihydro-3H-benzo[e]indole-6-sulfonamide (7) (Scheme C). Solid 108 (1.6 g, 5.1 mmol) was gradually added to chlorosulfonic acid (6.0 mL, 90 mmol) with ice bath cooling. The mixture was then heated to 60° C. for 2 h, and the reaction was quenched by pouring slowly, with stirring, into ice-water. The precipitated solid was collected, washed with water, dried and chromatographed on silica gel. Elution with EtOAc/petroleum ether (from 1:4 to 1:1) gave 1-(chloromethyl)-3-(trifluoroacetyl)-1,2-dihydro-3H-benzo[e]indole-7-sulfonyl chloride (113) (0.53 g, 25%) as a pale yellow solid: mp (EtOAc/petroleum ether) 189-192° C.; $^1$H NMR ($CDCl_3$) δ 8.70-8.64 (m, 2H), 8.13-8.08 (m, 2H), 8.00 (d, J=9.0 Hz, 1H), 4.72-4.68 (m, 1H), 4.55-4.48 (m, 1H), 4.33-4.25 (m, 1H), 3.98-3.93 (m, 1H), 3.68-3.61 (m, 1H), $^{13}$C NMR δ 154.9 (q, $J_{C-F}$ 38.4 Hz), 143.9, 140.7, 132.7, 131.8, 130.1, 130.0, 125.8, 124.8, 123.2, 119.6, 115.9 (q, $J_{C-F}$ 288 Hz), 52.8, 45.4, 42.4. Anal. ($C_{15}H_{10}Cl_2F_3NO_3S$) C, H, N, Cl.

Later eluates gave 1-(chloromethyl)-3-(trifluoroacetyl)-1,2-dihydro-3H-benzo[e]indole-6-sulfonyl chloride (114) (1.54 g, 73%); mp (EtOAc/petroleum ether) 181-183° C.; $^1$H NMR ($CDCl_3$) δ 8.87 (d, J=9.5 Hz, 1H), 8.73 (d, J=9.5 Hz, 1H), 8.36 (dd, J=7.5, 1.0 Hz, 1H), 8.19 (d, J=8.4 Hz, 1H), 7.72 (dd, J=8.3, 7.5 Hz, 1H), 4.72-4.66 (m, 1H), 4.52-4.44 (m, 1H), 4.31-4.23 (m, 1H), 3.95-3.81 (m, 1H), 3.63-3.56 (m, 1H); $^{13}$C NMR 154.8 (q, $J_{C-F}$ 38.3 Hz), 141.5, 140.9, 131.0, 130.6, 128.6, 126.7, 126.5, 125.8, 125.5, 120.3, 115.9 (q, $J_{C-F}$ 288 Hz), 52.6, 45.4, 43.0. Anal. ($C_{15}H_{10}Cl_2F_3NO_3S$) C, H, N, Cl.

The 6-sulfonyl chloride 114(750 mg, 1.9 mmol) was dissolved in conc. $H_2SO_4$ (20 mL), the solution was cooled in an ice bath, and a solution of $KNO_3$ (195 mg, 1.95 mmol) in $H_2SO_4$ (5 mL) was added slowly. The mixture was vigorously for 30 min, quenched with cold water, and extracted with EtOAc (3×50 mL). The extracts were dried and concentrated under reduced pressure, and the resulting solid was separated by column chromatography on silica gel. Elution with EtOAc/petroleum ether (from 1:4 to 1:1) gave 1-(chloromethyl)-5-nitro-3-(trifluoroacetyl)-1,2-dihydro-3H-benzo[e]indole-6-sulfonyl chloride (115) (202 mg, 59%, based on consumption of starting material): mp (EtOAc/petroleum ether) 169° C. (dec.); $^1$H NMR [($CD_3$)$_2$SO] δ 8.63 (s, 1H), 8.22 (dd, J=7.6, 0.9 Hz, 1H), 8.13 (dd, J=8.4 Hz, 1H), 7.71 (dd, J=7.8, 7.8 Hz, 1H), 4.66-4.56 (m, 2H), 4.49-4.43 (m, 1H), 4.17-4.02 (m, 2H); $^{13}$C NMR δ 153.4 (q, $J_{C-F}$ 37.4 Hz), 149.2, 145.2, 137.7, 131.4, 130.5, 129.9, 127.7, 124.9, 118.6, 115.6 (q, $J_{C-F}$ 288 Hz) 114.3, 52.6, 47.5, 41.4. Anal. ($C_{15}H_9Cl_2F_3N_2O_5S$) C, H, N. 114 (457 mg, 61%) was also recovered.

A solution of 115 (300 mg, 0.66 mmol) in $CH_2Cl_2$/THF (1:1, 50 mL) was treated with conc. ammonia (0.5 μL) at room temperature for 30 m followed by $Cs_2CO_3$ (0.5 g, 1.5 mmol) and stirring for another 15 min. The mixture was poured into water (100 mL) and extracted with $CH_2Cl_2$ (3×50 mL), and the extracts were dried. To this solution was added a solution of dry methanolic HCl (10 mL). After 10 min the mixture was evaporated to dryness under reduced pressure. To the residue was added 5-[2-(dimethylamino)ethoxy]indole-2-carboxylic acid hydrochloride (160 mg, 0.55 mmol), EDCI (200 mg, 1.1 mmol), anhydrous TsOH (20 mg, 0.12 mmol) and DMA (5 mL).

The mixture was stirred at room temperature overnight, then poured into a dilute solution of NaHCO$_3$ in ice-water, and extracted with ETOAc (3×50 mL). The combined organic phases were washed with water (3×30 mL) and then brine, dried, concentrated under reduced pressure and the residue was crystallised from CH$_2$Cl$_2$/MeOH to give 7 (200 mg, 53%): mp>320° C.; $^1$H NMR [(CD$_3$)$_2$SO] δ 11.73 (s, 1H), 9.03 (s, 1H), 8.44 (d, J=7.5 Hz, 1H), 8.40 (d, J=8.3 Hz, 1H), 7.92 (dd, J=8.0, 7.8 Hz, 1H), 7.47 (s, 2H), 7.41 (d, J=8.9 Hz, 1H), 7.16-7.21 (m, 2H), 6.95 (dd, J=8.7, 2.4 Hz, 1H), 4.98-4.89 (m, 1H), 4.73-4.61 (m, 2H), 4.17-4.02 (m, 4H), 2.68-2.63 (m, 2H), 2.24 (s, 6H); $^{13}$C NMR δ 160.4, 153.0, 147.3, 141.1, 140.8, 131.9, 131.5, 130.6, 130.3, 129.7, 127.8, 127.5, 127.4, 116.8, 116.7, 116.4, 113.2, 106.1, 103.1, 66.0, 57.7, 54.7, 47.8, 45.4, 41.6. Anal. (C$_{26}$H$_{26}$ClN$_5$O$_6$S) C, H, N, Cl.

EXAMPLE 8

1-(Chloromethyl)-5-nitro-3-(5,6,7-trimethoxyindol-2-carbonyl)-1,2-dihydro-3H-benzo[e]indole-7-sulfonamide (25) (Scheme C). A solution of 113(250 mg, 0.63 mmol) in conc. H$_2$SO$_4$ (10 mL) was nitrated with KNO$_3$ (65 mg, 0.65 mmol) in H$_2$SO$_4$ (5 mL) as above, to give 1-(chloromethyl)-5-nitro-3-(trifluoroacetyl)-1,2-dihydro-3H-benzo[e]indole-7-sulfonyl chloride (116) (192 mg, 67%) as a red solid: mp (EtOAc/petroleum ether) 184-189° C.; $^1$H NMR [(CDCl$_3$)] a 9.34 (s, 1H), 9.28 (d, J=1.8 Hz, 1H), 8.22 (dd, J=9.0, 1.9 Hz, 1H), 8.11 (d, J=9.0 Hz, 1H), 4.77-4.71 (m, 1H), 4.58 (dd, J=11.5, 8.8 Hz, 1H), 4.42-4.33 (m, 1H), 3.95 (dd, J=11.7, 3.5 Hz, 1H 3.73 (dd, J=11.7, 7.7 Hz, 1H); $^{13}$C NMR δ 153.4 (q, J$_{C-F}$ 38 Hz), 153.0, 148.2, 147.0, 138.7, 133.2, 129.1, 126.7, 124.5, 122.0, 119.3, 115.9 (q, J$_{C-F}$ 288 Hz), 52.6, 47.3, 41.2. Anal. (C$_{15}$H$_9$Cl$_2$F$_3$N$_2$O$_5$S) C, H, N, Cl.

Conc. aqueous NH$_3$ (0.5 mL, 7.3 mmol) was added to a solution of 116 (299 mg, 0.65 mmol) in THF (10 mL) at 0° C., and the ice bath was removed. The mixture was stirred for 7 min and then Cs$_2$CO$_3$ (0.55 g, 1.7 mmol) and MeOH (4 mL) were added. After stirring for a further 15 min the mixture was diluted with brine and extracted with CH$_2$Cl$_2$ (×3). The combined extracts were dried and evaporated to give 1-(chloromethyl)-5-nitro-1,2-dihydro-3H-benzo[e]indole-7-sulfonamide (117) (214 mg, 96%) as an orange solid. A sample was triturated with EtOAc: mp 183-187° C. (dec.); $^1$H NMR [(CD$_3$)$_2$SO] δ 8.59 (d, J=1.7 Hz, 1H), 8.03 (d, J=8.9 Hz, 1H), 7.85 (dd, J=8.9, 1.7 Hz, 1H), 7.75 (s, 1H), 7.42 (s, 2H), 6.68 (s, 1H), 4.28-4.21 (m, 1H), 3.95-3.85 (m; 2H), 3.81 (dd, J=11.2, 8.3 Hz, 1H), 3.73 (dd, J=10.4, 3.0 Hz, 1H). Anal. (C$_{13}$H$_{12}$ClN$_3$O$_4$S) C, H, N.

A mixture of 117 (161 mg, 0.47 mmol), 5,6,7-trimethoxyindole-2-carboxylic acid (154 mg, 0.61 mmol), EDCI (361 mg, 1.88 mmol), and TsOH (16 mg, 0.09 mmol) in DMA (3 mL) was stirred at room temperature for 22 h and then cooled to 0° C. Ice-cold aqueous NaHCO$_3$ was added. The precipitated solid was filtered off and washed with aqueous NaHCO$_3$, water, and then dried in a vacuum desiccator. The crude product was triturated with EtOAc to give 25 (228 mg, 84%) as a yellow-brown solid: mp 280-285° C. (dec.); $^1$H NMR [(CD$_3$)$_2$SO] δ 11.60 (d, J=1.7 Hz, 1H), 9.23 (s, 1H), 8.87 (d, J=1.7 Hz, 1H), 8.43 (d, J=8.9 Hz, 1H), 8.06 (dd, J=8.9, 1.7 Hz, 1H), 7.62 (s, 2H), 7.19 (d, J=2.2 Hz, 1H), 6.98 (s, 1H), 4.93 (dd, J=11.1, 10.0 Hz, 1H), 4.68-4.59 (m, 2H), 4.17-4.09 (m, 2H), 3.94 (s, 3H), 3.83 (s, 3H), 3.81 (s, 3H). Anal. (C$_2$H$_{23}$ClN$_4$O$_8$S) C, H, N.

EXAMPLE 9

1-(Chloromethyl)-3-{5-[2-(dimethylamino)ethoxy]indol-2-carbonyl}-5-nitro-1,2-dihydro-3H-benzo[e]indole-7-sulfonamide (26) (Scheme C). The amine 117 was reacted with 5-[2-(dimethylamino)ethoxy]indole-2-carboxylic acid as described in Example 7. The product crystallised from CH$_2$Cl$_2$/MeOH to give 26. This proved to be unstable as the free base and was immediately dissolved in CH$_2$Cl$_2$/MeOH (1:1, 20 mL) and treated with methanolic HCl (5 L), followed by precipitation with petroleum ether. The solid was collect by filtration and air-dried to give 26-HCl (110 mg, 59%): mp>350° C.; $^1$H NMR [(CD$_3$)$_2$SO] δ 11.82 (s, 1H), 10.05 (br, 1H), 9.28 (s, 1H), 8.85 (d, J=1.7 Hz, 1H), 8.44 (d, J=8.9 Hz, 1H), 8.06 (dd, J=8.9, 1.7 Hz, 1H), 7.63 (s, 2H), 7.47 (d, J=8.8 Hz, 1H), 7.28 (d, J=2.4 Hz, 1H), 7.24 (d, J=1.7 Hz, 1H), 7.04 (dd, J=8.9, 2.4 Hz, 1H), 5.02-4.94 (m, 1H), 4.74-4.62 (m, 2H), 4.38-4.33 (m, 2H), 4.18-4.12 (m, 2H), 3.57-3.51 (m, 2H), 2.88 (s, 6H); $^{13}$C NMR δ 160.6, 152.1, 147.0, 142.6, 142.5, 132.3, 132.2, 130.4, 130.0, 127.3, 125.6, 124.4, 121.3, 120.5, 116.2, 116.0, 113.4, 106.0, 104.0, 62.7, 55.5, 54.8, 47.6, 42.8, 41.4. Anal. (C$_{26}$H$_{26}$ClN$_5$O$_6$S.HCl.½H$_2$O) C, H, N.

EXAMPLE 10

1-(Chloromethyl)-3-[(2E)-3-(3-hydroxy-4-methoxyphenyl)-2-propenoyl]-5-nitro-1,2-dihydro-3H-benzo[e]indole-7-sulfonamide (27). (Scheme C). The amine 117 was reacted with (2E)-3-(4-hydroxy-3-methoxyphenyl)-2-propenoic acid as described in Example 7. The crude product was chromatographed on silica gel, eluting with EtOAc/petroleum ether (from 1:1 to 1:0) to give 27 (82%): mp (EtOAc/petroleum ether) 220-225° C.; $^1$H NMR [(CD$_3$)$_2$SO] δ 9.33 (s, 1H), 9.12 (s, 1H), 8.84 (d, J=1.7 Hz, 1H), 8.38 (d, J=8.9 Hz, 1H), 8.04 (dd, J=8.9, 1.7 Hz, 1H), 7.68-7.60 (m, 3H), 7.28 (d, J=2.0 Hz, 1H), 7.23 (dd, J=8.4, 1.9 Hz, 1H), 7.02-6.96 (m, 2H), 4.70-4.58 (m, 3H), 4.11-4.07 (m, 2H), 3.88 (s, 3H); $^{13}$C NMR δ 164.7, 150.0, 147.1, 146.6, 144.1, 142.4, 142.3, 131.9, 130.4, 127.4, 125.4, 124.3, 121.6, 121.3, 120.2, 115.9, 115.5, 114.4, 111.9, 55.6, 52.8, 47.7, 40.8. Anal. (C$_{23}$H$_{20}$ClN$_3$O$_7$S.½.H$_2$O) C, H, N.

EXAMPLE 11

1-(Chloromethyl)-3-[5-(2-hydroxyethoxy)indol-2-carbonyl]-5-nitro-1,2-dihydro-3H-benzo[e]indole-7-sulfonamide (28). (Scheme C). The amine 117 was reacted with 5-(2-hydroxyethoxy)-1H-indole-2-carboxylic acid as described in Example 7. The reaction mixture was poured into ice-water and the precipitate was collected to give 28 (88%): mp (EtOAc) 231-234° C.; $^1$H NMR [(CD$_3$)$_2$SO] δ 11.72 (s, 1H), 9.28 (s, 1H), 8.87 (d, J=1.6 Hz, 1H), 8.44 (d, J=8.9 Hz, 1H), 7.97 (dd, J=8.9, 1.6 Hz, 1H), 7.63 (s, 1H), 7.42 (d, J=8.9 Hz, 1H), 7.22 (d, J=1.7 z, 1H), 7.17 (d, J=2.2 Hz, 1H), 6.97 (dd, J=8.9, 2.4 Hz, 1H), 5.00-4.93 (m, 1H), 4.188-4.81 (m, 1H), 4.74-4.70 (m, 1H), 4.69-4.60 (m, 1H), 4.19-4.12 (m, 2H), 4.05-3.98 (m, 2H), 3.79-3.71 (m, 2H), 2.94 (s, 1H), 2.79 (s, 1H), 1.95 (s, 1H); $^{13}$C NMR δ 160.6, 153.2, 147.0, 142.6, 142.5, 132.2, 131.9, 130.4, 129.7, 127.4, 125.6, 124.4, 121.3, 120.5, 116.5, 116.1, 113.2, 106.3, 103.1, 69.8, 59.6, 54.8, 47.6, 41.4. Anal. (C$_{24}$H$_{21}$ClN$_4$O$_7$S.⅓H$_2$O) C, H, N.

EXAMPLE 12

1-(Chloromethyl)-3-{5-[2-(dimethylamino)ethoxy]indol-2-carbonyl}-N-hydroxy-5-nitro-4,2-dihydro-3H-benzo[e]indole-7-sulfonamide hydrochloride (30) (Scheme C). A solution of hydroxylamine hydrochloride (55 mg, 0.8 mmol) in water (1 mL) and then a solution of NaHCO$_3$ (132 mg, 1.6 mmol) in water (2 mL) were added to a solution of 116 (90 mg, 0.20 mmol) in DE (5 mL) at 0° C. The orange solution was stirred at 0° C. for 10 min, and then Cs$_2$CO$_3$ (0.12 g, 0.4 mmol) and MeOH (3 mL) were added. The cooling bath was removed and the mixture was stirred for a further 1 h. The mixture was diluted with brine and extracted with CH$_2$Cl$_2$ (×4). The combined extracts were dried and evaporated to give 1-(chloromethyl)-N-hydroxy-5-nitro-1,2-dihydro-3H-benzo[e]indole-7-sulfonamide (118) (43 mg, 61%) as a red-brown solid. A sample was recrystallised from EtOAc/petroleum ether as an orange solid: mp 170-175° C. (dec.); $^1$H NMR [(CD$_3$)$_2$SO] δ 9.63-9.58 (m, a H), 8.63 (d, J=1.6 Hz, 1H), 8.04 (d, J=8.9 Hz, 1H), 7.82 (dd, J=8.9, 1.7 Hz, 1H), 7.78 (s, 1H), 6.80 (s, 1H), 4.30-4.22 (m, 1H), 3.95-3.87 (m, 2H), 3.82 (dd, J=11.0, 8.2 Hz, 1H), 3.75 (dd, J=10.5, 3.1 Hz, 1H). Anal. (C$_{13}$H$_{12}$ClN$_3$O$_5$S) C, H, N.

A mixture of 118 (28 mg, 0.078 mmol), 5-[2-(dimethylamino)ethoxy]indole-2-carboxylic acid hydrochloride (29 mg, 0.10 mmol), EDCI (60 mg, 0.31 mmol), and TsOH (3 mg, 0.016 mmol) in DMA (2 mL) was stirred at room temperature for 4 h and then cooled to 0° C. Ice-cold aqueous NaHCO$_3$ was added and the mixture was extracted with EtOAc (×3). The combined extracts were washed with water and dried, and the EtOAc solution was evaporated onto silica. Chromatography, eluting with EtOAc/MeOH (9:1 then 4:1 then 3:2), gave crude 30 (24 mg, 52%). The crude product was suspended in CH$_2$Cl$_2$ (4 mL) and MeOH (4 mL) and treated with methanolic HCl (1 mL). After 90 min the precipitate was filtered off and dried to give 30·HCl (18 mg, 37%) as a yellow solid: mp 260-265° C. (dec.); $^1$H NMR [(CD$_3$)$_2$SO] δ 11.83 (s, 1H), 9.90 (br s, 1H), 9.86 (d, J=3.3 Hz, 1H), 9.76 (d, J=3.2 Hz, 1H), 9.31 (s, 1H), 8.92 (d, J=1.6 Hz, 1H), 8.47 (d, J=8.9 Hz, 1H), 8.05 (dd, J=8.9, 1.7 Hz, 1H), 7.47 (d, J=8.9H, 1H), 728 (d, J=2.2 Hz, 1H), 7.25 (d, J=1.7 Hz, 1H), 7.05 (dd, J=8.9, 2.4 Hz, 1H), 5.04-4.96 (m, 1H), 4.72 (dd, J=10.9, 2.4 Hz, 1H), 4.70-4.64 (m, 1H), 4.40-4.34 (m, 2H), 4.20-4.11 (m, 2H), 3.59-3.50 (m, 2H), 2.89 (s, 6H). Anal. (C$_{26}$H$_{26}$ClN$_5$O$_7$S·HCl·H$_2$O) C, H. HRMS (FAB) calcd. for C$_{26}$H$_{27}^{35}$ClN$_5$O$_7$S (MH$^+$) m/z 588.1320, found 588.1334.

EXAMPLE 13

1-(Chloromethyl)-3-{5-[2-(dimethylamino)ethoxy]indol-2-carbonyl}-5-nitro-1,2-dihydro-3H-benzo[e]indole-7-sulfonohydrazide dihydrochloride (31) (Scheme C). t-Butyl carbazate (86 mg, 0.65 mmol) was added to a solution of 116 (107 mg, 0.23 mmol) in ThF (5 mL) and the mixture was stirred at room temperature for 16 h. Cs$_2$CO$_3$ (150 mg, 0.46 mmol) and MeOH (2 mL) were added and the mixture was stirred for a further 2 h. The mixture was diluted with water and extracted with CH$_2$Cl$_2$ (×2). The combined extracts were dried and evaporated and the residue was purified by chromatography, eluting with EtOAc/petroleum ether (1:4 then 2:3). The product was recrystallised from EtOAc/petroleum ether to give tert-butyl 2-{[1-(chloromethyl)-5-nitro-1,2-dihydro-3H-benzo[e]indol-7-yl]sulfonyl}hydrazinecarboxylate (119) (72 mg, 67%) as an orange crystalline solid: mp 179° C. (dec.); $^1$H NMR [(CD$_3$)$_2$SO] δ 9.60 (br s, 1H), 9.18 (v br s, 1H), 8.54 (d, J=1.4 Hz, 1H), 8.00 (d, J=8.9 Hz, 1H), 7.75 (s, 1H), 7.74 (dd, J=8.9, 1.8 Hz, 1H), 6.74 (s, 1H), 4.29-4.22 (m, 1H), 3.94-3.85 (m, 2H), 3.80 (dd, J=11.0, 8.0 Hz, 1H), 3.74 (dd, J=10.5, 3.0 Hz, 1H), 1.10 (br s, 9H). HRMS (FAB) calcd. for C$_{18}$H$_{21}^{35}$ClN$_4$O$_6$S (M$^+$) m/z 456.0870, found 456.0877.

A mixture of 119 (59.4 mg, 0.13 mmol), 5-[2-(dimethylamino)ethoxy]indole-2-carboxylic acid hydrochloride (48 mg, 0.17 mmol), EDCI (100 mg, 0.52 mmol), and TsOH (4.5 mg, 0.03 mmol) in DMA (2 mL) was stirred at room temperature for 4.5 h and then cooled to 0° C. Ice-cold aqueous NaHCO$_3$ was added and the precipitate was filtered off, washed with water, and dried to give tert-butyl 2-{[1-(chloromethyl)-3-({5-[2-(dimethylamino)ethoxy]indol-2-yl}carbonyl)-5-nitro-1,2-dihydro-3H-benzo[e]indol-7-yl]sulfonyl}hydrazinecarboxylate (120) (84 mg, 94%) as a yellow solid: mp 175-180° C. (dec.); $^1$H NMR [(CD$_3$)$_2$SO] δ 11.72 (d, J=1.8 Hz, 1H), 9.85 (br s, 1H), 9.30 (v br s, 1H), 9.29 (s, 1H), 8.83 (d, J=1.5 Hz, 1H), 8.44 (d, J=8.9 Hz, 1H), 7.98 (dd, J=8.9, 1.7 Hz, 1H), 7.42 (d, J=8.9 Hz, 1H), 7.21 (d, J=1.6 Hz, 1H), 7.18 (d, J=2.4H, 1H), 6.95 (dd, J=8.9, 2.4 Hz, 1H), 5.02-4.96 (1,1H), 4.72 (dd, J=10.9, 2.4 Hz, 1H), 4.70-4.64 (m, 1H), 4.17-4.09 (m, 2H), 4.07 (t, J=5.9 Hz, 2H), 2.66 (t, J=5.7 Hz, 2H), 2.25 (s, 6H), 1.10 (br s, 9H). HRMS (FAB) calcd. for C$_3$H$_{36}^{35}$ClN$_6$O$_8$S (MH$^+$) m/z 687.2004, found 687.2002.

Compound 120 (77 mg, 0.11 mmol) was stirred with HCl/dioxane (4M, 2.5 mL) for 16 h, and the solvent was evaporated. The residue was triturated with EtOAc to give 31 (74 mg, 100%) as a yellow solid: mp 280-285° C. (dec.); $^1$H NMR [(CD$_3$)$_2$SO] δ 511.82 (d J=1.7 Hz, 1H), 10.02 (br s, 1H), 9.29 (s, 1H), 8.88 (d, J=1.7 Hz, 1H), 8.74 (br s, 1H), 8.45 (d, J=8.9 Hz, 1H), 8.02 (dd, J=8.9, 1.7 Hz, 1H), 7.47 (d, J=8.9 Hz, 1H), 7.28 (d, J=2.3 Hz, 1H), 7.24 (d, J=1.7 Hz, 1H), 7.04 (dd, J=8.9, 2.4 Hz, 1H), 5.02-4.96 (m, 1H), 4.73 (dd, J=10.8, 2.4 Hz, 1H), 4.69-4.64 (m, 1H), 4.37 (t J=5.0 Hz, 2H), 4.20-4.11 (m, 2H), 3.51 (t, J=5.0 Hz, 2H), 2.88 (d, J=4.9 Hz, 6H).

EXAMPLE 14

1-(Chloromethyl)-3-{5-[2-(dimethylamino)ethoxy]indol-2-carbonyl}-N-methyl-5-nitro-1,2-dihydro-3H-benzo[e]indole-7-sulfonamide (32) (Scheme C). Treatment of 116 (50 mg, 0.11 mmol) with aqueous methylamine, followed by treatment as for the synthesis of 7 above, gave the free base of 32, which was immediately converted to the HCl salt (51 mg, 75%); mp>350° C.; $^1$H NMR [(CD$_3$)$_2$SO] δ 11.81 (s, 1H), 9.9 (br s, 1H), 9.29 (s, 1H), 8.85 (d, J=1.7 Hz, 1H), 8.44 (d, J=8.9 Hz, 1H), 8.01 (dd, J=8.9, 1.7 Hz, 1H), 7.76 (m, 1H), 7.47 (d, J=8.8 Hz, 1H), 7.28 (d, J=2.4 Hz, 1H), 7.24 (d, J=1.7 Hz, 1H), 7.04 (dd, J=8.9, 2.4 Hz, 1H), 5.02-4.93 (m, 1H), 4.74-4.61 (m, 2H), 4.39-4.32 (m, 2H), 4.17-4.12 (m, 2H), 3.55-3.50 (m, 2H), 2.87 (s, 6H), 2.48 (s, 3H); $^{13}$C NMR B (one C not observed) 160.7, 152.2, 147.0, 142.8, 138.0, 132.4, 130.7, 130.1, 127.3, 125.9, 124.7, 123.3, 120.7, 116.4, 116.3, 113.4, 106.4, 104.1, 62.8, 55.6, 54.9, 47.7, 42.9, 41.4, 28.6. Anal. (C$_{27}$H$_{28}$ClF$_3$N$_5$O$_6$S·HCl·¾H$_2$O) C, H, N.

EXAMPLE 15

1-(Chloromethyl)-N-(2-hydroxyethyl)-5-nitro-3-(5,6,7-trimethoxyindol-2-carbonyl)-1,2-dihydro-3H-benzo[e]indole-7-sulfonamide (33). (Scheme C). A solution of 116 (456 mg, 1.00 mmol) in TV (5 mL) and CH$_2$Cl$_2$ (5 mL) was treated at 0° C. with a solution of ethanolamine (134 mg, 2.19 mmol) in THF (0.5 mL). The mixture was stirred at 0° C. for 5 min, then warmed to room temperature for 10 min and treated with a solution of Cs$_2$CO$_3$ (980 mg, 3 mmol) in MeOH (20 mL). After stirring at room temperature for a further 10 min, the mixture was diluted with water and extracted with EtOAc (×2). The combined organic layers were washed with water (×2), dried, filtered through a short column of silica gel, and then concentrated to a small volume and diluted with i-Pr$_2$O/hexane to give 1-(chloromethyl)-N-(2-hydroxyethyl)-5-nitro-1,2-dihydro-3H-benzo[e]indole-7-sulfonamide (121) (346 mg, 90%): mp 173-174° C.; $^1$H NMR [(CD$_3$)$_2$SO] δ 8.57 (d, J=1.6 Hz, 1H), 8.03 (d, J=8.9 Hz, 1H), 7.80 (dd, J=8.9, 1.7

Hz, 1H), 7.77 (s, 1H), 7.69 (br s, 1H), 6.73 (s, 1H), 4.64 (t, J=5.6 Hz, 1H), 4.29-4.19 (m, 1H), 3.95-3.84 (m, 2H), 3.80 (dd, J=11.0, 8.4 Hz, 1H), 3.74 (dd, J=10.4, 3.3 Hz, 1H), 3.35 (after $D_2O$ exchange, t, J=6.3 Hz, 2H), 2.81 (t, J=6.3 Hz, 2H). Anal. ($C_{15}H_{16}C_{11}N_3O_5S$) C, H, N.

Amine 121 (75 mg, 0.19 mmol) was dissolved in MeOH/HCl(g) at room temperature and the solution was evaporated to dryness under reduced pressure. 5,6,7-Trimethoxyindole-2-carboxylic acid (59 mg, 0.23 mmol), EDCI (149 mg, 0.78 mmol), anhydrous TsOH (30 mg, 0.17 mmol) and dry DMA (3 mL) were then added, and the mixture was stirred at room temperature for 1 h. The mixture was poured into water and the precipitate was collected and washed with water, dried, and dissolved in the minimum volume of DMW at room temperature. The solution was diluted with EtOAc, filtered, and then diluted with hexane and refrigerated to give 33 (89 mg, 74%): mp 257-258° C.; $^1H$ NMR [$(CD_3)_2SO$] δ 11.61 (s, 1H), 9.24 (s, 1H), 8.86 (d, J=1.6 Hz, 1H), 8.43 (d, J=8.9 Hz, 1H), 8.02 (dd, J=8.9, 1.7 Hz, 1H), 7.91 (t, J=5.7 Hz, 1H), 7.20 (d, J=2.1 Hz, 1H), 6.99 (s, 1H), 4.93 (t, J=10.1 Hz, 1H), 4.70-4.58 (m, 3H), 4.18-4.07 (m, 2H), 3.94 (s, 3H), 3.83 (s, 3H), 3.81 (s, 3H, 3.39 (q, J=6.0 Hz, 2H), 2.88 (q, J=6.1 Hz, 2H). Anal. ($C_{27}H_{27}ClN_4O_9S$) C, H, N.

EXAMPLE 16

1-(Chloromethyl)-3-{5-[2-(dimethylamino)ethoxy]indol-2-carbonyl}-N-(2-hydroxyethyl)-5-nitro-1,2-dihydro-3H-benzo[e]indole-7-sulfonamide (35). (Scheme C). A mixture of compound 121 (46 mg, 0.11 mmol), 5-[2-(dimethylamino)ethoxy]indole-2-carboxylic acid hydrochloride (37 mg, 0.13 mmol) and EDCI (83 mg, 0.44 mmol) in DMA (3 mL) was stirred under a $N_2$ atmosphere for 4 h. The mixture was then partitioned between $CH_2Cl_2$ and cold (0° C.) 5% aqueous $KHCO_3$. The aqueous portion was extracted with cold $CH_2Cl_2$ (×4) and the combined extracts were washed with $H_2O$ (×2), brine (×2), dried and evaporated. The residue was dissolved in $CH_2Cl_2$/MeOH and the solvents were evaporated under reduced pressure until precipitation began. The precipitate was filtered off and washed with MeOH to give 35 (14 mg, 21%): mp 205-210° C.; $^1H$ NMR [$(CD_3)_2SO$] δ 11.73 (s, 1H), 9.30 (s, 1H), 8.85 (d, J=1.6 Hz, 1H), 8.43 (d, J=8.9 Hz, 0.1H), 8.03 (dd, J=8.9, 1.6 Hz, 1H), 7.92 (t, J=5.4 Hz, 1H), 7.41 (d, J=8.9 Hz, 1H), 7.22 (d, J=1.4 Hz, 1H), 7.21 (d, J=2.3 Hz, 1H), 6.94 (dd, J=8.9, 2.4 Hz, 1H), 4.97 (t, J=10.3 Hz, 1H), 4.74 (dd, J=10.9, 2.3 Hz, 1H), 4.68-4.61 (m, 2H), 4.19-4.09 (m, 2H), 4.07 (t, J=5.9 Hz, 2H), 3.43-3.35 (m, 21H), 2.88 (q, J=5.8 Hz, 21H), 2.66 (t J=5.8 Hz, 2H), 224 (s, 6H). HRMS (FAB) calcd. for $C_{28}H_{30}^{35}ClN_5O_7S$ (MH+) m/z 616.1633, found 616.1630.

EXAMPLE 17

1-(Chloromethyl)-N-(2-hydroxyethyl)-3-[(E)-4-methoxycinnamoyl]-5-nitro-1,2-dihydro-3H-benzo[e]indole-7-sulfonamide (37). (Scheme C). Amine 121 (75 mg, 0.19 mmol) was dissolved in MeOH/HCl(g) at room temperature and the solution was evaporated to dryness under reduced pressure. (E)-4-methoxycinnamic acid (41 mg, 0.23 mmol), EDCI (149 mg, 0.78 mmol), anhydrous TsOH (30 mg, 0.17 mmol) and dry DMA (3 mL) were then added and the mixture was sired at room temperature for 2 h. The mixture was poured into water and the precipitate was collected, washed with water, dried and dissolved in the minimum volume of DMW at room temperature. The solution was diluted with EtOAc, filtered and then diluted with hexane and refrigerated to give 37 (68 mg, 64%): mp 250-251° C.; $^1H$ NMR [$(CD_3)_2SO$)] δ 9.35 (s, 1H), 8.83 (d, J=1.6 Hz, 1H), 8.38 (d, J=8.9 Hz, 1H) 8.00 (dd, J=8.9, 1.7 Hz, 1H), 7.90 (t, J=5.8 Hz, 1H), 7.80 (d, J=8.8 Hz, 2H), 7.74 (d, J=15.3 Hz, 1H), 7.10 (d, J=15.3 z, 1H), 7.03 (d, J=8.81 Hz, 2H), 4.72-4.48 (m, 4 H), 4.13-4.06 (m, 2H), 3.83 (s, 3H), 3.38 (q, J=6.0 Hz, 2H), 2.87 (q, J=6.1 Hz, 2H). Anal. ($C_{25}H_{24}ClN_3O_7S$) C, H, N.

EXAMPLE 18

1-(Chloromethyl)-3-{5-[2-(dimethylamino)ethoxy]indol-2-carbonyl}-N,N-dimethyl-5-nitro-1,2-dihydro-3H-benzo[e]indole-7-sulfonamide (38) (Scheme C). Dimethylamine (40% w/w aqueous solution, 0.12 mL, 0.9 mmol) was added to a solution of 116 (104 mg, 0.23 mmol) in THF (5 mL) at 0° C. After 10 min the cooling bath was removed and $Cs_2CO_3$ (0.15 g, 0.46 mmol) and MeOH (2 mL) were added. After 30 min the mixture was diluted with water and extracted with $CH_2Cl_2$ (×2). The combined extracts were dried and evaporated and the resulting red oil was crystallised from EtOAc to give to give 1-(chloromethyl)-5-nitro-1,2-dihydro-3H-benzo[e]indole-7-dimethylsulfonamide (122) (57 mg, 68%) as a red powder: mp 170-172° C.; $^1H$ NMR [$(CD_3)_2SO$] δ 8.54 (d, J=1.6 Hz, 1H), 8.05 (d, J=9.0 Hz, 1H), 7.82 (s, 1H), 7.73 (dd, J=8.9, 1.8 Hz, 1H), 6.81 (s, 1H), 4.30-4.22 (m, 1H), 3.95-3.86 (m, 2H), 3.83-3.73 (m, 2H), 2.66 (s, 6H). Anal. ($C_{15}H_{16}ClN_3O_4S$) C, H, N. The mother liquor was evaporated and the residue purified by chromatography, eluting with EtOAc/petroleum ether (3:7) to give more 122 (18 mg, 21%).

Reaction of 122 with 5-[2-(dimethylamino)ethoxy]indole-2-carboxylic acid hydrochloride as described for the synthesis of 7 above, gave the free base of 38 (97%), which was immediately converted to the HCl salt: mp>350° C.; $^1H$ NMR [$(CD_3)_2SO$] δ 11.83 (s, 1H), 9.88 (br, 1H), 9.33 (s, 1H), 8.82 (d, J=1.7 Hz, 1H), 8.46 (d, J=8.9 Hz, 1H), 7.97 (dd, J=8.9, 1.7 Hz, 1H), 7.47 (d, J=8.8 Hz, 1H), 7.28 (d, J=2.4 Hz, 1H), 7.24 (d, J=1.7 Hz, 1H), 7.04 (dd, J=8.9, 2.4 Hz, 1H), 5.02-4.93 (m, 1H), 4.77-4.62 (m, 2H), 4.38-4.31 (m, 2H), 4.20-4.08 (m, 2H), 3.56-3.46 (m, 2H), 2.87 (s, 6H), 2.73 (s, 6H). $^{13}C$ NMR δ 160.6, 152.1, 147.0, 142.9, 138.0, 133.9, 132.3, 130.8, 130.1, 127.2, 125.7, 125.0, 124.3, 120.7, 116.5, 116.3, 113.4, 106.3, 104.0, 62.8, 55.6, 54.8, 47.5, 42.9, 41.4, 37.4 Anal. ($C_{28}H_{30}ClN_5O_6S \cdot HCl \cdot \frac{1}{2}H_2O$) C, H, N.

EXAMPLE 19

1-(Chloromethyl)-3-{5-[2-(dimethylamino)ethoxy]indol-2-carbonyl}-N-[2-(dimethylamino)ethyl]-5-nitro-1,2-dihydro-3H-benzo[e]indole-7-sulfonamide (39). (Scheme C). A solution of 116 (50 mg, 0.11 mmol) in $CH_2Cl_2$/THF (1:1, 20 mL) was treated with N,N-dimethylethylenediamine (25 mg, 0.28 mmol), and stirred at room temperature for 30 min. $Cs_2CO_3$ (0.5 g, 1.5 mmol) was then added, and the mixture was stirred at room temperature for another 15 min, then poured in water (100 mL) and extracted with $CH_2Cl_2$ (3×50 mL). The combined organic layers were dried, HCV/MeOH (10 mL) was added, and the solution was evaporated under reduced pressure. The residue, 5-[2-(dimethylamino)ethoxy]indole-2-carboxylic acid hydrochloride (80 mg, 0.28 mmol), EDCI (100 mg, 0.52 mmol), anhydrous TsOH (20 mg, 0.12 mmol) and DMA (3 mL) were mixed and stirred at room temperature overnight. The mixture was poured to a dilute $NaHCO_3$ at 0° C. and extracted with EtOAc (3×50 mL). The combined organic phases were washed with water (3×30 ml) and brine, dried, and evaporated. The residue was crystallised from $CH_2Cl_2$/MeOH to give unstable 39. This was dissolved in $CH_2Cl_2$/MeOH (1:1, 20 my) and HCl/MeOH (2 mL) was added. Precipitation with petroleum ether gave 39-HCl (54 mg, 69%): mp>350° C.; $^1$H NMR [(CD$_3$)$_2$SO$_2$] δ 11.83 (s, 1H), 10.25 (br, 1H), 10.11 (br, 1H), 9.31 (s, 1H), 8.90 (d, J=1.7 Hz, 1H), 8.48 (d, J=8.9 Hz, 1H), 8.44-8.38 (m, 1H), 8.06 (dd, J=8.9, 1.7 Hz, 1 H), 7.47 (d, J=8.8 Hz, 1H), 7.28 (d, J=2.4 Hz, 1H), 7.25 (d, J=1.7 Hz, 1H), 7.04 (dd, J=8.9, 2.4 Hz, 1H), 5.03-4.95 (m, 1H), 4.77-4.64 (m, 2H), 4.41-4.33 (m, 2H), 4.19-4.10 (m, 2H), 3.59-3.50 (m, 2H), 3.19-3.16 (m, 4H), 2.89 (s, 3H), 2.87 (s, 3H), 2.78 (s, 6H), 2.77 (s, 3H); $^{13}$C NMR δ (one C not observed) 160.6, 152.1, 147.0, 143.0, 138.0, 132.3, 130.8, 130.0, 127.3, 126.0, 124.4, 123.4, 120.6, 116.3, 116.2, 113.4, 106.3, 104.0, 62.7, 55.6, 55.4, 54.8, 47.6, 42.7, 42.3, 41.3, 37.5. Anal. (C$_{30}$H$_{35}$ClN$_6$O$_5$S.3HCl.½H$_2$O) C, H, N.

EXAMPLE 20

1-(Chloromethyl)-3-{5-[2-(dimethylamino)ethoxy]indol-2-carbonyl}-5-nitro-N-propionyl-1,2-dihydro-3H-benzo[e]indole-7-sulfonamide (40) (Scheme C). Conc. aqueous NH$_3$ (0, 32 mL, 4.7 mmol) was added to a solution of 116 (215 mg, 0.47 mmol) in THF (10 mL) at −78° C. After 10 min water (10 mL), aqueous HCl (2 N, 5 mL, 9.4 mmol), and EtOAc (20 mL) were added and the mixture was allowed to warm to room temperature. Brine was added and the mixture was extracted with EtOAc (×2). The combined extracts were washed with brine and dried, and the EtOAc solution was evaporated onto silica. Chromatography eluting with EtOAc/petroleum ether (1:10 then 1:3 then 2:1) gave 1-(chloromethyl)-5-nitro-3-(trifluoroacetyl)-1,2-dihydro-3H-benzo[e]indole-7-sulfonamide (123) (158 mg, 77%) as a pale yellow solid: mp (EtOAc) 274-278° C. (dec.); $^1$H NMR [(CD$_3$)$_2$SO] δ 9.11 (s, 1H), 8.89 (d, J=1.6 Hz, 1H), 8.50 (d, J=8.9 Hz, 1H), 8.11 (dd, J=8.9, 1.7 Hz, 1H), 7.66 (s, 1H), 4.73-4.64 (m, 2H), 4.57-4.49 (m, 1H), 4.24-4.11 (m, 2H). Anal. (C$_{15}$H$_{11}$ClF$_3$N$_3$O$_5$S) C, H, N.

Propionic anhydride (83 μL, 0.64 mmol) was added to a solution of 123 (141 mg, 0.32 mmol) and DMAP (4 mg, 0.03 mmol) in THF (10 mL) and Et$_3$N (0.18 mL, 1.3 mmol) and the mixture was stirred at room temperature for 1.5 h. Cs$_2$CO$_3$ (0.21 g, 0.64 mmol) and MeOH (10 mL) were added and the mixture was stirred for a further 16 h. Aqueous HCl (2 N, 4 mL) was added, and the organic solvents were evaporated under reduced pressure. The aqueous residue was diluted with brine and extracted with EtOAc (×2). The combined extracts were washed with brine, dried, and evaporated. The residue was triturated with EtOAc/petroleum ether to give 1-(chloromethyl)-5-nitro-N-propionyl-1,2-dihydro-3H-benzo[e]indole-7-sulfonamide (124) (1.00 mg, 78%) as a red-brown solid: mp 173-177° C.; $^1$H NMR [(CD$_3$)$_2$SO] δ 12.06 (s, 1H), 8.73 (d, J=1.6 Hz, 1H), 8.03 (d, J=9.0 Hz, 1H), 7.86 (dd, J=9.0, 1.8 Hz, 1H), 7.80 (s, 1H), 6.85 (s, 1H), 4.28-4.21 (m, 1H), 3.95-3.86 (m, 2H), 3.81 (dd, J=11.1, 8.2 Hz, 1H), 3.75 (dd, J=10.5, 3.1 Hz, 1H), 2.22 (q, J=7.5 Hz, 2H), 0.88 (t, J=7.5 Hz, 3H). Anal. (C$_{16}$H$_{16}$ClN$_3$O$_5$S.½EtOAc) C, H, N.

A mixture of 124 (89 mg, 0.22 mmol), 5-[2-(dimethylamino)ethoxy]indole-2-carboxylic acid hydrochloride (83 mg, 0.29 mmol), EDCI (172 mg, 0.88 mmol), and TsOH (7.7 mg, 0.04 mmol) in DMA (2 mL) was stirred at room temperature for 4.5 h, and then cooled to 0° C. Ice-cold aqueous NaHCO$_3$ was added, causing a fine precipitate to separate. The mixture was centrifuged at 0° C. (3000 rpm, 10 min) and the resulting pellet resuspended and recentrifuged, firstly using aqueous NaHCO$_3$ and then water. The resulting solid was dried and then triturated with EtOAC to give 40 (116 mg, 83%) as an orange solid: mp 221-225° C.; $^1$H NMR [(CD$_3$)$_2$SO] δ 11.75 (d, J=2.0 Hz, 1H), 9.21 (s, 1H), 8.78 (d, J=1.1 Hz, 1H), 8.26 (d, J=8.8 Hz, 1H), 8.04 (dd, J=8.8, 1.6 Hz, 1H), 7.43 (d, J=8.9 Hz, 1H), 7.22 (d, J=2.3 Hz, 1H), 7.20 (d, J=1.8 Hz, 1H), 6.97 (dd, J=8.9, 2.4 Hz, 1H), 4.98-4.91 (m, 1H), 4.70 (dd, J=10.9, 2.4 Hz, 1H), 4.65-4.58 (m, 1H), 4.19 (t, J=5.5 Hz, 2H), 4.17-4.09 (m, 2H), 3.06 (br s, 2H), 2.54 (s, 6H), 2.03 (q, J=7.5 Hz, 2H), 0.87 (t, J=7.5 Hz, 3H). HRMS (FAB) calcd. for C$_{29}$H$_{31}$$^{35}$ClN$_5$O$_7$S (MH$^+$) m/z 628.1633, found 628.1634.

EXAMPLE 21

1-(Chloromethyl)-3-{5-[2-(dimethylamino)ethoxy]indol-2-carbonyl}-5-nitro-1,2-dihydro-3H-benzo[e]indole-6-carbonitrile (6) (Scheme D). Diglyme (10 mL) and Ti(OiPr)$_4$ (200 mg, 0.7 mmol) were added to a mixture of 114 (660 mg, 1.6 mmol), ZnI$_2$ (653 mg, 2.4 mmol), LiCl (63 mg, 1.45 mmol), and PdCl$_2$(PhCN)$_2$ (16 mg, 0.04 mmol) under N$_2$, and the mixture was stirred and heated at 155° C. for 30 min. The reaction mixture was poured into aqueous HCl (0.05M, 50 mL) and filtered through a wad of Celite. The filter cake was mixed with CH$_2$Cl$_2$ (50 mL, then 3×30 mL), and each time the mixture was filtered. The filtrate was dried and concentrated, and the residue was chromatographed on silica gel. Elution with EtOAc/petroleum ether (from 1:5 to 1:2) gave 1-(chloromethyl)-6-iodo-3-(trifluoroacetyl)-1,2-dihydro-3H-benzo[e]indole (125) as a pale yellow solid (630 mg, 90%): mp (EtOAc/petroleum ether) 174-177° C.; $^1$H NMR (CDCl$_3$) δ 8.48 (d, J=9.3 Hz, 1H), 8.14 (d, J=9.3 Hz, 1H), 8.08 (d, J=7.3 Hz, 1H), 7.76 (d, J=8.4 Hz, 1H), 7.28-7.22 (m, 1H), 4.70-4.62 (m, 1H), 4.48-4.39 (m, 1H), 4.21-4.13 (m, 1H), 3.96-3.89 (m, 1H), 3.56-3.48 (m, 1H); $^{13}$C NMR δ 154.6 (q, J$_{C-F}$ 38.3 Hz), 140.8, 137.3, 135.0, 132.8, 129.5, 128.4, 125.8, 123.4, 118.6, 116.0 (q, J$_{C-F}$ 288 Hz), 100.6, 52.8, 45.4, 42.8. Anal. (C$_{15}$H$_{10}$ClF$_3$INO) C, H, N.

A mixture of 125 (148 mg, 0.34 mmol), KCN (120 mg, 1.9 mmol), Pd(PPh$_3$)$_4$ (10 mg, 0.01 mmol), and CuI (50 mg, 0.26 mmol) in dry THF (30 mL) was heated to reflux under N$_2$ with vigorous stirring for 30 min. The mixture was cooled to room temperature, diluted with EtOAc (50 mL), and then filtered through Celite. The filtrate was washed with water and brine, dried and concentrated under reduced pressure. Chromatography of the residue on silica gel eluting with EtOAc/petroleum ether (from 1:5 to 1:2) gave 1-(chloromethyl)-3-(trifluoroacetyl)-1,2-dihydro-3H-benzo[e]indole-6-carbonitrile (126) (97 mg, 85%): mp (EtOAc/petroleum ether) 158-160° C.; $^1$H NMR (CDCl$_3$) δ 8.63 (d, J=9.1 Hz, 1H), 8.26 (d, J=9.2 Hz, 1H), 8.05 (d, J=8.5 Hz, 1H), 7.90 (dd, J=7.2, 1.0 Hz, 1H), 7.64 (dd, J=8.2, 7.2 Hz, 1H), 4.70-4.63 (m, 1H), 4.51-4.43 (m, 1H), 4.28-4.20 (m, 1H), 3.95-3.89 (m, 1H), 3.64-3.55 (m, 1H); $^{13}$C NMR S 154.7 (q, J$_{C-F}$ 38.3 Hz), 141.5, 132.0, 130.7, 129.0, 127.7, 127.5, 126.7, 119.7, 117.2, 115.9 (q, J$_{C-F}$ 288 Hz), 111.7, 52.7, 45.4, 42.6. Anal. (C$_{16}$H$_{10}$ClF$_3$N$_2$O.⅓H$_2$O) C, H, N.

A solution of 126 (60 mg, 0.18 mmol) in CH$_2$Cl$_2$ (10 mL) was treated with fuming HNO$_3$ (1.5 mL) and stirred for 30 min at room temperature. The reaction was quenched with ice and extracted with CH$_2$Cl$_2$ (3×50 ml). The extracts were dried and concentrated under reduced pressure. The residue was chromatographed on silica gel, eluting with EtOAc/petroleum ether (from 1:4 to 1:1), to give 1-(chloromethyl)-5-nitro-3-(trifluoroacetyl)-1,2-dihydro-3H-benzo[e]indole-6-carbonitrile (127) (28 mg, 41%) as a brown solid: mp EtOAc/petroleum ether) 201-205° C. (dec.); $^1$H NMR [(CD$_3$)$_2$SO] δ 8.87 (s, 1H), 8.63 (dd, J=8.5, 1.1 Hz, 1H), 8.40 (dd, J=7.3, 1.0 Hz, 1H), 7.93 (dd, J=8.5, 7.3 Hz, 1H), 4.73-4.61 (m, 2H), 4.55-4.49 (m, 1H), 4.22-4.15 (m, 1H), 4.12-4.07 (m, 1H); $^{13}$C NMR δ 153.8 (q, $J_{C-F}$ 37.6 Hz), 146.8, 139.8, 137.7, 132.6, 130.3, 129.4, 128.3, 118.7, 115.4 (q, $J_{C-F}$ 288 Hz), 115.1, 114.8, 105.4, 52.7, 47.4, 41.1. Anal. ($C_{16}H_9ClF_3N_3O_3$) C, H, N.

$Cs_2CO_3$ (0.5 g, 1.5 mmol) was added to a solution of 127 (100 mg, 0.26 mmol) in $CH_2Cl_2$/MeOH (1:1, 20 mL). The mixture was stirred at room temperature for 15 min, then poured into water (100 mL) and extracted with $CH_2Cl_2$ (3×50 mL). The extracts were dried and the solution was mixed with a solution of dry HCl in dioxane (10 mL). After 30 min the mixture was evaporated under reduced pressure. To the residue was added 5-[2-dimethylamino)ethoxy]indole-2-carboxylic acid hydrochloride (100 mg, 0.34 mmol) was added, followed by EDCI (100 mg, 0.55 mmol), anhydrous TsOH (20 mg, 0.12 mmol) and DMA (3 mL), and the mixture was sired at room temperature overnight. The mixture was poured into dilute ice-cold aqueous $NaHCO_3$ and extracted with EtOAc (3×50 mL). The combined organic phases were washed with water (3×30 mL) and then brine, dried, and evaporated to give 6 (88 mg, 66%): mp ($CH_2Cl_2$/MeOH) >300° C.; $^1$H NMR (CDCl$_3$) δ 9.26 (br, 1H), 9.10 (s, 1H), 8.14 (dd, J=8.5, 1.0 Hz, 1H), 8.02 (dd, J=8.2, 0.9 Hz, 1H), 7.73 (dd, J=8.5, 7.3 Hz, 1H), 7.38 (d, J=8.9 Hz, 1H), 7.15-7.05 (m, 3H), 4.95-4.90 (m, 1H), 4.84-4.77 (m, 1H), 4.37-4.29 (m, 1H), 4.17-4.11 (m, 2H), 3.96-3.90 (m, 1H), 3.67-3.58 (m, 1H), 2.81-2.76 (m, 2H), 2.37 (s, 6H); $^{13}$C NMR δ 160.7, 154.3, 148.3, 142.4, 135.9, 131.7, 130.2, 129.1, 128.7, 128.2, 127.9, 127.6, 119.2, 118.3, 116.3, 115.2, 112.8, 107.9, 106.8, 103.7, 66.8, 58.5, 54.8, 46.0, 45.5, 43.4. Anal. ($C_{27}H_{24}ClN_5O_4 \cdot ¼H_2O$) C, H, N.

EXAMPLE 22

1-(Chloromethyl)-3-{5-[2-(dimethylamino)ethoxy]indol-2-carbonyl}-5-nitro-1,2-dihydro-3H-benzo[e]indole-6-carboxamide (5) (Scheme D). Solid 126 (500 mg, 1.48 mmol), was added to 90% $H_2SO_4$ (5 μL) and heated to 70° C. for 1 h. After cooling to room temperature, the mixture was poured into ice-water and extracted with EtOAc (3×50 mL). The extracts were dried and concentrated under reduced pressure. Chromatography of the residue on silica gel (EtOAc/petroleum ether, from 1:1 to 1:0) gave 1-(chloromethyl)-3-(trifluoroacetyl)-1,2-dihydro-3H-benzo[e]indole-6-carboxamide (128) (410 mg, 78%) as a white solid: mp (EtOAc/petroleum ether) 190-193° C.; $^1$H NMR (CDCl$_3$) δ 8.54-8.45 (m, 2H), 7.89 (d, J=5.8 Hz, 1H), 7.69 (dd, J=7.1, 1.1 Hz, 1H), 7.59 (dd, J=8.4, 7.1 Hz, 1H), 5.91 (br, 2H), 4.69-4.61 (m, 1H), 4.48-4.40 (m, 1H), 4.25-4.17 (m, 1H), 3.97-3.89 (m, 1H), 3.58-3.50 (m, 1H; $^{13}$C NMR δ 170.7, 153.8 (q, $J_{C-F}$ 38.0 Hz), 140.5, 134.6, 129.7, 128.6, 126.5, 125.6, 125.4, 124.8, 118.4, 115.4 (q, $J_{C-F}$ 288 Hz), 53.4, 45.4, 43.0. Anal. ($C_{16}H_{12}ClF_3N_2O_2$) C, H, N, Cl.

A stirred solution of 128 (300 mg, 0.84 mmol) in $CH_2Cl_2$ (20 mL) was treated with filming $HNO_3$ (2 mL) for 30 min at room temperature, then quenched with ice and extracted with $CH_2Cl_2$ (3×50 ml). The extracts were dried and concentrated under reduced pressure, and the residue was chromatographed on silica gel. Elution with EtOAc/petroleum ether/methanol (from 5:1:0 to 9:0:1) gave 1-(chloromethyl)-5-nitro-3-(trifluoroacetyl)-1,2-dihydro-3H-benzo[e]indole-6-carboxamide (129) (150 mg, 45%) as yellow solid: mp 272-277° C. (EtOAc/petroleum ether); $^1$H NMR [(CD$_3$)$_2$SO] δ 8.78 (s, 1H), 8.30 (dd, J=8.4, 1.1 Hz, 1H), 8.24 (s, 1H), 7.91 (dd, J=7.1, 1.0 Hz, 1H), 7.80 (dd, J=8.4, 7.1 Hz, 1H), 7.57 (s, 1H), 4.69-4.61 (m, 2H), 4.52-4.47 (m, 1H), 4.21-4.15 (m, 1H), 4.13-4.07 (m, 1H); $^{13}$C NMR δ 169.3, 153.6 (q, $J_{C-F}$ 37.8 Hz), 148.1, 138.6, 133.4, 132.4, 130.1, 128.7, 127.9, 126.1, 119.3, 115.6 (q, $J_{C-F}$ 288 Hz), 114.4, 52.7, 47.5, 41.2. Anal. ($C_{16}H_{11}ClF_3N_3O_4$) C, H, N, Cl.

Further elution gave 1-(chloromethyl)-9-nitro-3-(trifluoroacetyl)-1,2-dihydro-3H-benzo[e]indole-6-carboxamide 130 (100 mg, 30%), characterized only by NMR: $^1$H NMR (CDCl$_3$) δ 8.71 (d, J=9.2 Hz, 1H), 8.49 (d, J=9.2 Hz, 1H), 7.83 (d, J=7.6 Hz, 1H), 7.67 (d, J=7.6 Hz, 1H), 6.30 (br, 1H), 6.13 for, 1H), 4.57-4.50 (m, 1H), 4.47-4.39 (m, 1H), 4.02 (s, 1H), 3.59-3.57 (m; 1H), 3.33-3.25 (m, 1H).

$Cs_2CO_3$ (0.5 g, 1.5 mmol) was added to a stirred solution of 129 (50 mg, 0.12 mmol) in $CH_2Cl_2$/MeOH (1:1, 20 mL), and after 15 min at room temperature the mixture was poured into water (100 mL) and extracted with $CH_2Cl_2$ (3×50 mL). The extracts were dried and the solution was mixed with a solution of dry HCl in dioxane (5 mL). After 15 min the solvents were removed under reduced pressure. To the residue was added, in sequence, 5-[2-(dimethylamino)ethoxy]indole-2-carboxylic acid hydrochloride (50 mg, 0.18 mmol), EDCI (80 mg, 0.42 mmol), anhydrous TsOH (20 mg, 0.12 mmol) and DMA (3 mL). The mixture was stirred at room temperature for 16 h, then poured into a dilute solution of $NaHCO_3$ in ice-water, and extracted with EtOAc (3×50 mL). The combined organic extracts were washed with water (3×30 mL) and then brine, dried, and evaporated under reduced pressure to give 5 (48 mg, 72%): mp ($CH_2Cl_2$MeOH)>350° C.; $^1$H NMR [(CD$_3$)$_2$SO] δ 11.7 (s, 1H), 8.95 (s, 1H), 8.26 (dd, J=8.4, 1.0 Hz, 1H), 8.20 (s, 1H), 7.84 (dd, J=7.1, 1.0 Hz, 1H), 7.76 (dd, J=8.3, 7.1 Hz, 1H), 7.52 (s, 1H), 7.40 (d, J=8.9 Hz, 1H), 7.18 (d, J=2.1 Hz, 2H), 6.95 (dd, J=8.9, 2.4 Hz, 1H), 4.97-4.90 (m, 1H), 4.72-4.58 (m, 2H), 4.16-4.04 (m, 4H), 2.68-2.63 (m, 2H), 2.24 (s, 6H); $^{13}$C NMR (one C not observed) 169.5, 160.4, 153.0, 147.9, 140.8, 133.4, 131.8, 131.0, 130.3, 129.9, 127.7, 127.4, 125.7, 118.3, 116.3, 115.2, 113.2, 106.0, 103.1, 66.2, 57.7, 54.7, 47.8, 45.5, 41.5. Anal. ($C_{27}H_{26}ClN_5O_5$) C, H, N, Cl.

EXAMPLE 23

1-(Chloromethyl)-5,7-dinitro-(5,6,7-trimethoxyindol-2-carbonyl)-1,2-dihydro-3H-benzo[e]indole (8) (Scheme E). A stirred solution of 108 (5.24 g, 16.7 mmol) in dry $CH_2Cl_2$ (70 mL) was treated dropwise at 10° C. with fuming $HNO_3$ (2.0 mL, 48 mmol) and then warmed to room temperature for 5 min. The mixture was diluted with $CH_2Cl_2$ (100 mL) and the resulting solution was washed with water, dried, filtered through a column of silica gel, then concentrated to 25 mL and diluted with EtOAc (25 mL). Following refrigeration the precipitate was collected and washed with EtOAc to give 1-(chloromethyl)-3-(trifluoroacetyl)-7-nitro-1,2-dihydro-3H-benzo[e]indole (131) (2.31 g, 39%) as a pale yellow solid: mp ($CH_2Cl_2$/iPr$_2$O) 213-214° C.; $^1$H NMR [(CD$_3$)$_2$SO] δ 9.06 (s, 1H), 8.48 (d, J=9.0 Hz, 1H), 8.36 (d, J=9.1 Hz, 1H), 8.33-8.25 (m, 2H) 4.67-4.51 (m, 2H), 4.46 (br d, J=10.6 Hz, 1H), 4.17 (dd, J=11.3, 3.0 Hz, 1H), 4.07 (dd, J=11.3, 5.5 Hz, 1H). Anal. ($C_{15}H_{10}ClF_3N_2O_3$) C, H, N.

The mother liquor from the above crystallization was evaporated under reduced pressure, and the residue was chromatographed on silica gel. Elution with $CH_2Cl_2$/petroleum ether (1:1) gave 1-(chloromethyl)-3-(trifluoroacetyl)-9-nitro-1,2-dihydro-3H-benzo[e]indole (132) (1.67 g, 28%) as a pale yellow solid: mp (EtOAc/petroleum ether) 139-140° C.; $^1$H NMR [(CD$_3$)$_2$SO] δ 8.58 (d, J=9.1 Hz, 1H), 8.39 (d, J=8.1 Hz, 1H), 8.30 (d, J=9.1 Hz, 1H), 8.20 (dd, J=7.6, 0.9 Hz, 1H), 7.69 (t, J=7.9 Hz, 1H), 4.60 (dd, J=11.1, 8.7 Hz, 1H), 4.33 (d, J=11.3 Hz, 1H), 4.03-3.90 (m, 1H), 3.73 (dd, J=11.4, 3.3 Hz, 1H), 3.51 (dd, J=11.4, 6.8 Hz, 1H). Anal. ($C_{15}H_{10}ClF_3N_2O_3$) C, H, N.

Further elution gave 1-(chloromethyl)-3-(trifluoroacetyl)-5-nitro-1,2-dihydro-3H-benzo[e]indole (133) (165 mg, 3%) [J. Med. Chem., 1999, 42 3400-3411].

A solution of 131 (1.00 g, 2.79 mmol) in dioxane (30 mL) was treated with a solution of $Cs_2CO_3$ (3.26 g, 10 mmol) in water (3 mL) and MeOH (17 mL), and the mixture was stirred vigorously at room temperature for 15 min. The resulting solution was treated with AcOH (1.2 mL), then concentrated to a small volume under reduced pressure and partitioned between water and $CH_2Cl_2$. The organic phase was washed with water (×2), dried, and filtered through a column of silica gel. Evaporation and trituration with petroleum ether/$iPr_2O$ gave 1-(chloromethyl)-7-nitro-1,2-dihydro-3H-benzo[e]indole (134) (702 mg, 96%) as an orange-red solid: mp ($CH_2Cl_2$/petroleum ether) 121-122° C.; $^1$H NMR [$(CD_3)_2$SO] δ 8.76 (d, J=2.2 Hz, 1H), 8.05 (dd, J=9.3, 2.3 Hz, 1H), 7.97 (d, J=8.7 Hz, 1H), 7.76 (d, J=9.3 Hz, 1H), 7.09 (d, J=8.7 Hz, 1H), 6.79 (s, 1H), 4.17-4.04 (m, 1H), 3.95-3.78 (m, 2H, 3.76-3.63 (m, 2H). Anal. ($C_{13}H_{11}ClN_2O_2$) C, H, N.

A stirred solution of 134 (901 mg, 3.43 mmol) in conc. $H_2SO_4$ (10 mL) was cooled to −5° C. and treated with powdered $KNO_3$ (520 mg, 5.14 mmol). The mixture was stirred at 0° C. for a further 15 min, then poured into ice-water and the solid was collected. This was dissolved in water EtOAc, and the solution was diluted with an equal volume of $CH_2Cl_2$ and filtered through a short column of silica gel. The eluate was concentrated to a small volume and MeOH was added to precipitate 1-(chloromethyl)-5,7-dinitro-1,2-dihydro-3H-benzo[e]indole (135) (824 mg, 78%) as a red solid: mp (EtOAc/$iPr_2O$) 239-240° C.; $^1$H NMR [$(CD_3)_2$SO] δ 9.06 (d, J=2.3 Hz, 1H), 8.17 (dd, J=9.3, 2.2 Hz, 1H), 8.00 (d, J=−9.3 Hz, 1H), 7.83 (s, 1H), 7.14 (s, 1H), 4.33-4.24 (m, 1H), 3.98-3.88 (m, 2H), 3.84 (dd, J=11.1, 7.9 Hz, 1H), 3.77 (dd, J=10.7, 3.2 Hz, 1H). Anal. ($C_{13}H_{10}ClN_3O_4$) C, H, N, Cl.

A suspension of 5,6,7-trimethoxyindole-2-carboxylic acid (122 mg, 0.49 mmol) in dry $CH_2C_2$ (10 mL) was treated with oxalyl chloride (0.13 mL, 1.49 mmol) followed by DMF (10 μL). The mixture was stirred at room temperature for 15 min, then evaporated under reduced pressure and azeotroped dry with benzene. The resulting acid chloride was cooled to −5° C. and treated with an ice-cold solution of amine 135 (100 mg, 0.33 mmol) in dry pyridine (2 mL) containing DMAP (5 mg). The stirred mixture was warmed to room temperature for 30 min, then poured into dilute aqueous $KHCO_3$. The precipitate was collected, purified by chromatography on silica gel eluting with $CH_2Cl_2$/EtOAc (19:1), then crystallised from $CH_2Cl_2$/EtOAc to give 8 (124 mg, 71%) as an orange solid: mp 251-252° C.; $^1$H NMR [$(CD_3)_2$SO] δ 11.66 (d, J=1.6 Hz, 1H), 9.33 (d, J=2.2 Hz, 1H), 9.31 (s, 1H), 8.45 (d, J=9.3 Hz, 1H), 8.39 (dd, J=9.3, 2.2 Hz, 1H), 7.20 (d, J=2.2 Hz, 1H), 6.97 (s, 1H), 4.95 (dd, J=11.1, 10.3 Hz, 1H), 4.72-4.58 (m, 2H), 4.18-4.06 (m, 2H), 3.94 (s, 3H), 3.83 (s, 3H), 3.81 (s, 3 M. HRMS (FAB) calcd. for $C_{25}H_{21}{}^{35}ClN_4O_8$ ($M^+$) m/z 540.1048, found 540.1043. Anal. ($C_{25}H_{21}ClN_4O_8$) C, H, N.

EXAMPLE 24

1-(Chloromethyl)-3-{5-[2-(dimethylamino)ethoxy]indol-2-carbonyl}-5,7-dinitro-1,2-dihydro-3H-benzo[e]indole (9) (Scheme E). A mixture of amine 135 (100 mg, 0.33 mmol), 5-[2-(dimethylamino)ethoxy]indole-2-carboxylic acid hydrochloride (111 mg, 0.39 mmol), EDCI (249 mg, 1.30 mmol) and anhydrous TsOH (4.0 mg, 0.02 mmol) in dry DMA (8 mL) was stirred at room temperature under N2 for 6 h, then poured into dilute aqueous $NH_3$. The basic mixture was stirred for 1 h, then the precipitate was collected and dissolved in EtOAc (300 mL) at room temperature. The solution was washed with water, dried, and then concentrated to 10 mL under reduced pressure below 30° C. to give crude 9. Treatment of a suspension of the free base in MeOH with HCl(g)/EtOAc, followed by crystallization from MeOH/$Me_2CO$/EtOAc gave 9.HCl (114 mg, 60%) as a yellow solid: mp 263-264° C.; $^1$H NMR [$(CD_3)_2$SO] δ 11.88 (s, 1H), 10.15 (br s, 1H), 9.36 (s, 1H), 9.34 (d, J=2.2 Hz, 1H, 8.48 (d, J=9.3 Hz, 1H), 8.41 (dd, J=9.3, 2.2 Hz, 1H), 7.46 (d, J=8.9 Hz, 1H), 7.26 (s, 2H), 7.03 (dd, J=8.9, 2.3 Hz, 1H), 5.00 (t, J=10.5 Hz, 1H), 4.78-4.65 (m, 2H), 4.36 (t, J=4.9 Hz, 2H), 4.22-4.09 (m, 2H), 3.52 (t, J=4.5 Hz, 2H), 2.80 (s, 6H). Anal. ($C_{26}H_{24}ClN_5O_6$.HCl) C, H, N.

EXAMPLE 25

1-(Chloromethyl)-5,9-dinitro-(5,6,7-trimethoxyindol-2-carbonyl)-1,2-dihydro-3H-benzo[e]indole (51) (Scheme E). A solution of 132 (1.54 g, 4.29 mmol) in dioxane (10 mL) was treated with a solution of $Cs_2CO_3$ (3.26 g, 10 mmol) in water (3 mL) and MeOH (7 mL) and the mixture was stirred at room temperature for 10 min. The mixture was treated with AcOH (12 mL), then concentrated under reduced pressure to a small volume and partitioned between water and $CHCl_2$. The organic phase was washed with water (×2), dried, and filtered through a column of silica gel. The resulting oil was crystallised from EtOAc/petroleum ether to give 1-(chloromethyl)-9-nitro-1,2-dihydro-3H-benzo[e]indole (136) (1.03 g, 91%) as a red solid: mp 100° C.; $^1$H NMR [$(CD_3)_2$SO] δ 8.07 (dd, J=8.0, 1.1 Hz, 1H), 7.94 (dd, J=7.6, 1.3 Hz, 1H), 7.87 (d, J=8.7H, 1H), 7.21 (t, J=7.8 Hz, 1H), 7.13 (d, J=8.7 Hz, 1H), 6.63 (s, 1H), 3.81-3.71 (m, 1H), 3.71-3.62 (m, 1H), 3.62-3.54 (m, 1H), 3.33-3.25 (m, 2H). Anal. ($C_{13}H_{11}ClN_2O_2$) C, H, N.

A stirred solution of amine 136 (900 mg, 3.43 mmol) in conc. $H_2SO_4$ (9 mL) was cooled to −5° C. and treated with powdered $KNO_3$ (520 mg, 5.14 mmol). The mixture was stirred at 0° C. for a further 15 min, then poured into ice-water and the solid was collected Chromatography on silica gel, eluting with petroleum ether/EtOAc (3:1), followed by two recrystallizations from $CH_2Cl_2$/$iPr_2O$ gave 1-(chloromethyl)-5,9-dinitro-1,2-dihydro-3H-benzo[e]indole (137) (394 mg, 37%) as a red solid: mp 130-131° C.; $^1$H [$(CD_3)_2$SO] δ 8.21 (dd, J=8.6, 1.1 Hz, 1H), 8.10 (dd, J=7.6, 1.1 Hz, 1H), 7.75 (s, 1H), 7.44 (dd, J=−8.6, 7.6 Hz, 1H), 7.02 (s, 1H), 3.89-3.81 (m, 1H), 3.72-3.62 (m, 2H), 3.41-3.35 (m, 2H). Anal. ($C_{13}H_{10}ClN_3O_4$) C, H, N, Cl.

Further elution with petroleum ether/EtOAc (2:1) gave 1-(chloromethyl)-7,9-dinitro-1,2-dihydro-3H-benzo[e]indole (138) (122 mg, 12%) as a red solid: mp (EtOAc/$iPr_2O$) 216-218° C.; $^1$H NMR [$(CD_3)_2$SO] δ 9.00 (d, J=2.4 Hz, 1H), 8.65 (d, J=2.5 Hz, 1H), 8.19 (d, J=8.9 Hz, 1H), 7.74 (s, 1H), 7.24 (d, J=8.9 Hz, 1H, 3.93 (dd, J=10.8, 9.0 Hz, 1H), 3.76-3.68 (m, 1H), 3.67 (dd, J=11.0, 2.4 Hz, 1H), 3.38-3.24 (after $D_2O$ exchange, m, 2 M). Anal. ($C_{13}H_{10}ClN_3O_4$) C, H, N, Cl.

A suspension of 5,6,7-trimethoxyindole-2-carboxylic acid (122 mg, 0.49 mmol) in dry $CH_2Cl_2$ (10 mL) was treated with oxalyl chloride (0.13 mL, 1.49 mmol) followed by DMF (10 μL). The mixture was stirred at room temperature for 15 min, then evaporated under reduced pressure and azeotroped dry with benzene. The resulting acid chloride was cooled to −5° C. and treated with an ice-cold solution of amine 137 (100 mg, 0.33 mmol) in dry pyridine (2 mL) containing DMAP (5 mg). The stirred mixture was warmed to room temperature for 30 min, then poured into dilute aqueous $KHCO_3$. The precipitate was collected, purified by chromatography on silica gel eluting with $CH_2Cl_2$/EtOAc (19:1), then crystallised from $CH_2Cl_2$/EtOAc to give 51 (106 mg, 60%) as a yellow solid: mp 270-271° C.; $^1$H NMR [$(CD_3)_2$SO] δ 11.67 (d, J=1.0 Hz, 1H), 9.22 (s, 1H), 8.53 (dd, J=8.8, 0.9 Hz, 1H), 8.34 (dd, J=7.4, 0.9 Hz, 1), 7.84 (dd, J=8.7, 7.6 Hz, 1H), 7.17 (d, J=2.1 Hz, 1H), 6.99 (s, 1H), 4.93 (dd, J=10.9, 9.0 Hz, 1 H), 4.53 (dd, J=11.0, 1.8 Hz, 1H), 3.99-3.89 (m, 4H), 3.83 (s, 3H), 3.81 (s, 3H), 3.70 (dd, J=11.5, 3.3 Hz, 1H), 3.55 (dd, J=11.5, 7.0 Hz, 1H). HRMS NAB) calcd. for $C_{25}H_{21}^{35}ClN_4O_8$ (M+) m/z 540.1048, found 540.1034. Anal. ($C_2H_{21}ClN_4O_8$) C, H, N.

EXAMPLE 26

1-(Chloromethyl)-3-{5-[2-(dimethylamino)ethoxy]indol-2-carbonyl}-5,9-dinitro-1,2-dihydro-3H-benzo[e]indole (52) (Scheme E). A mixture of amine 137 (100 mg, 0.33 mmol), 5-[2-dimethylamino)ethoxy]indole-2-carboxylic acid hydrochloride (111 mg, 0.39 mmol), EDCI (249 mg, 1.30 mmol) and anhydrous TsOH (40 mg, 0.23 mmol) in dry DMA (6 mL) was stirred at room temperature under $N_2$ for 6 h, then poured into dilute aqueous $NH_3$. The solid was collected, dissolved in $CH_2Cl_2$ at room temperature, dried, and concentrated under reduced pressure below 30° C. to a small volume and diluted with EtOAc/iPr$_2$O to give 52. Treatment of a solution of the free base in $CH_2Cl_2$ with HCl(g)/EtOAc/hexane, followed by crystallization from MeOH/Me$_2$CO/EtOAc, gave 52-HCl (99 mg, 53%) as a yellow solid: mp 187-191° C.; $^1$H NMR [(CD$_3$)$_2$SO] δ 11.87 (d, J=1.6 Hz, 1H), 10.01 (br s, 1H), 9.28 (s, 1H), 8.53 (dd, J=8.8, 1.0 Hz, 1H), 8.36 (dd, J=7.5, 1.0 Hz, 1H), 7.85 (dd, J=8.7, 7.6 Hz, 1 H), 7.46 (d, J=8.9 Hz, 1H), 7.28 (d, J=2.3 Hz, 1H), 7.21 (d, J=1.6 Hz, 1H), 7.04 (dd, J=8.9, 2.4 Hz, 1H), 4.99 (dd, J=10.8, 9.0 Hz, 1H), 4.60 (dd, J=10.9, 1.7 Hz, 1 H), 4.35 (t, J=5.0 Hz, 2H), 4.02-3.92 (m, 1H), 3.70 (dd, J=11.4, 3.3 Hz, 1H), 3.58 (dd, J=11.4, 7.2 Hz, 1H), 3.52 (t, J=4.8 Hz, 2H), 2.87 (s, 6H). Anal. ($C_{26}H_{24}ClN_5O_6 \cdot HCl$) C, H, N.

EXAMPLE 27

1-(Chloromethyl)-5-nitro-3-[5,6,7-trimethoxyindol-2-carbonyl]-1,2-dihydro-3H-benzo[e]indole-7-carboxamide (15) (Scheme F). A suspension of 6-cyano-2-naphthoic acid [J. Med. Chem., 2004, 47, 303-324] (139) (4.62 g, 23.4 mmol) in dry t-BuOH (120 mL) containing powdered molecular sieves (2 g) was treated with Et$_3$N (3.91 mL, 28.1 mmol) and the mixture was stirred at room temperature under $N_2$ for 30 min. DPPA (5.55 mL, 25.8 mmol) was added, and the mixture was stirred at reflux for 6 h, then concentrated to half volume and poured into dilute aqueous NaHCO$_3$. The resulting solid was purified by chromatography on silica gel, eluting with $CH_2Cl_2$, to give tert-butyl 6-cyano-2-naphthylcarbamate (140) (4.68 g, 74%): mp (MeOH/H$_2$O) 135-136° C.; $^1$H NMR [(CD$_3$)$_2$SO] δ 9.85 (s, 1H), 8.42 (d, J=0.9 Hz, 1H), 8.23 (d, J=1.0H, 1H), 7.95 (d, J=8.7H, 2H), 7.68 (dd, J=8.5, 1.6 Hz, 1H), 7.64 (dd, J=9.0, 2.0 Hz, 1H), 1.52 (s, 9H). Anal. ($C_{16}H_{16}N_2O_2$) C, H, N.

A solution of 140 (4.48 g, 18 mmol) and NBS (3.85 g, 21.6 mmol) in MeCN (80 mL) was stirred at reflux for 1 h, then concentrated under reduced pressure. The residue was dissolved in $CH_2Cl_2$, washed with 10% aqueous Na$_2$SO$_3$, water, dried, and concentrated under reduced pressure. The residue was purified by chromatography on silica gel, eluting with $CH_2Cl_2$, to give tert-butyl 1-bromo-6-cyano-2-naphthylcarbamate (141) (5.69 g, 91%): mp (iPr$_2$O/hexane) 164-166° C.; $^1$H NMR [(CD$_3$)$_2$SO] δ 9.01 (s, 1H), 8.63 (d, J=1.5 Hz, 1H), 8.27 (d, J=9.0 Hz, 1H), 8.07 (d, J=9.0 Hz, 1H), 7.94 (d, J=8.9 Hz, 1H), 7.93 (dd, J=8.9, 1.8 Hz, 1H), 1.50 (s, 9H). Anal. ($C_{16}H_{15}BrN_2O_2$) C, H, N, Br.

A stirred solution of nitrile 141 (5.78 g, 16.6 mmol) in dry DMF (50 mL) was treated at 0° C. with NaH (0.80 g, 20.0 mmol, 60% in oil). The resulting suspension was warmed to room temperature for 30 min, then cooled to 0° C. again and treated with 1,3-dichloropropene (4.8 mL, 52 mmol, mixed isomers). After stirring at room temperature for a further 6 h, the mixture was diluted with water and extracted with EtOAc (×3). The combined organic extracts were washed with water (×3), dried, and concentrated to dryness under high vacuum at 80° C. The residue was chromatographed on silica gel, eluting with $CH_2Cl_2$, to give tert-butyl 1-bromo-6-cyano-2-naphthyl (3-chloro-2-propenyl)carbamate (142) (6.77 g, 96%) as a foam; $^1$H NMR [(CD$_3$)$_2$SO] (mixture of rotamers and E and Z forms) δ 8.69 (s, 1H), 8.35 (d, J=8.8 Hz, 1H), 8.13, 8.12 (2 d, J=8.6 Hz, 1H), 7.96 (d, J=8.9 Hz, 1H), 7.69, 7.63 (2d, J=8.7 Hz, 1H), 6.42-6.29 (m, 1H), 6.17-5.99 (m, 1H), 4.55-4.45, 4.40-4.19, 4.15-3.98 (3 m, 2H), 1.48, 1.24 (2 s, 9H). HRMS (FAB) calcd. for $C_{19}H_{19}^{79}Br^{35}ClN_2O_2$(m/z 421.0318, found 421.0306.

A solution of 142 (6.78 g, 16.1 mmol) in dry benzene (80 mL) was treated with Bu$_3$SnH (4.33 mL, 16.1 mmol), followed by AIBN (0.3 g, 1.8 mmol). The mixture was stirred at reflux under $N_2$ for 2 h, then concentrated under reduced pressure, and the residue was chromatographed on silica gel. Elution with $CH_2Cl_2$ gave an oil that was triturated with iPr$_2$O, to provide 143 contaminated with tert-butyl 7-cyano-1-methyl-1,2-dihydro-3H-benzo[e]indole-3-carboxylate. Two recrystallizations from $CH_2Cl$/Pr$_2$O gave pure tert-butyl 1-(chloromethyl)-7-cyano-1,2-dihydro-3H-benzo[e]indole-3-carboxylate (143) (4.49 g, 81%): mp 171-172° C.; $^1$H MR [(CD$_3$)$_2$SO] δ 8.55 (d, J=1.4 Hz, 1H), 8.18 (v br, 1H), 8.07 (d, J=8.7 Hz, 1H), 8.01 (d, J=8.9 Hz, 1H), 7.75 (dd, J=8.7, 1.7 Hz, 1 H), 4.34-4.25 (m, 1H), 4.21 (t, J=10.5 Hz, 1H), 4.09 (dd, J=11.3, 2.8 Hz, 1H), 4.03 (dd, J=11.1, 3.1 Hz, 1H), 3.93 (dd, J=11.1, 6.7 Hz, 1H), 1.55 (s, 9H). Anal. ($C_{19}H_{19}ClN_2O_2 \cdot \frac{1}{4}H_2O$) C, H, N.

Powdered carbamate 143 (1.00 g, 2.9 mmol) was added portionwise to stirred conc. $H_2SO_4$ (10 mL) at 0° C., and the mixture was warmed to room temperature for 10 min. The resulting solution was cooled to −5° C. and treated dropwise with a solution of KNO$_3$ (324 mg, 3.2 mmol) in conc. $H_2SO_4$ (2 mL). After siting for a flirter 5 min at 0° C., the mixture was poured into ice/water and neutralized with dilute aqueous $NH_3$. The resulting solid was purified by chromatography on silica gel, eluting with $CH_2Cl_2$, followed by recrystallization from $CH_2Cl_2$, then EtOAc, to give 1-(chloromethyl)-7-cyano-5-nitro-1,2-dihydro-3H-benzo[e]indole (144) (522 mg, 62%) as a red solid: mp 237-238° C.; $^1$H NMR [(CD$_3$)$_2$SO] δ 8.55 (d, J=1.4 Hz, 1H), 7.98 (d, J=8.8 Hz, 1H), 7.77 (s, 1H), 7.74 (dd, J=8.8, 1.5 Hz, 1H), 6.87 (s, 1H), 4.29-4.21 (m, 1H), 3.94-3.85 (m, 2H), 3.80 (dd, J=11.1, 8.1 Hz, 1H), 3.75 (dd, J=10.6, 3.1 Hz, 1H). Anal. ($C_{14}H_{10}ClN_3O_2$) C, H, N, Cl.

A solution of 144 (100 mg, 0.35 mmol) in a mixture of conc. $H_2SO_4$ (1.8 mL) and water (0.2 mL) was heated at 65° C. for 1 h, then cooled and neutralized with saturated aqueous KHCO$_3$. The precipitate was collected, washed with water, and dissolved in warm EtOAc. The solution was filtered through a column on silica gel and then concentrated and diluted with iPr$_2$O to give 1-(chloromethyl)-5-nitro-1,2-dihydro-3H-benzo[e]indole-7 carboxamide (145) (92 mg, 86%) as a red solid: mp (EtOAc/iPr$_2$O)>300° C.; $^1$H NMR [(CD$_3$)$_2$SO] δ 8.61 (d, J=1.3 Hz, 1H), 8.09, 7.39 (2 br s, 2H), 7.95 (dd, J=8.8, 1.7 Hz, 1H), 7.89 (d, J=8.7 Hz, 1H), 7.66 (s, 1H), 6.54 (s, 1H), 426-4.18 (m, 1H), 3.91 (dd, J=11.0, 3.8 Hz, 1H), 3.86 (td, J=9.9, 2.3 Hz, 1H), 3.78 (dd, J=11.0, 8.5 Hz, 1H), 3.72 (dd, J=10.3, 2.6 Hz, 1H). Anal. ($C_{14}H_{12}ClN_3O_3$) C, H, N.

A suspension of 5,6,7-trimethoxyindole-2-carboxylic acid (63 mg, 025 mmol) in dry $CH_2Cl_2$ (2 mL) was treated with oxalyl chloride (65 μL, 0.75 mmol), followed by DMF (10

μL), and the mixture was stirred at room temperature for 30 min. The mixture was evaporated under reduced pressure and then azeotroped with benzene. The resulting acid chloride was cooled to −5° C. and treated with an ice-cold solution of amine 145 (50 mg, 0.16 mmol) in dry pyridine (1 mL) containing DMAP (4 mg). After stirring at room temperature for 30 min the mixture was poured into dilute aqueous $KHCO_3$, and the precipitate was collected, washed with water, and dissolved in EtOAc/THF (4:1). This solution was filtered through a column of silica gel and then concentrated to give 15 (74 mg, 84%) as a yellow solid: mp (THF/EtOAc) 287-289° C.; $^1$H NMR [$(CD_3)_2$SO] δ 11.58 (d, J=1.6 Hz, 1H), 9.12 (s, 1H), 8.85 (d, J=1.4 Hz, 1H), 8.28 (d, J=8.7 Hz, 1H), 8.27, 7.60 (2 s, 2H), 8.15 (dd, J=8.8, 1.6 Hz, 1H), 7.18 (d, J=2.2 Hz, 1H), 6.99 (s, 1H), 4.92 (dd, J=10.7, 9.5 Hz, 1H), 4.68-4.56 (m, 2H), 4.18-4.06 (m, 2H), 3.94 (s, 3H), 3.83 (s, 3H), 3.81 (s, 3H). Anal. ($C_{26}H_{23}ClN_4O_7$) C, H, N.

EXAMPLE 28

1-(Chloromethyl)-3-{5-[2-(dimethylamino)ethoxy]indol-2-carbonyl}-5-nitro-1,2-dihydro-3H-benzo[e]indole-7-carboxamide (16) (Scheme F). A mixture of 145 (86 mg, 0.28 mmol), 5-[2-(dimethylamino)ethoxy]indole-2-carboxylic acid hydrochloride (96 mg, 0.34 mmol), EDCI (216 mg, 1.13 mmol) and anhydrous TsOH (30 mg, 0.17 mmol) in dry DMA (4 mL) was stirred at room temperature under $N_2$ for 2 h, then poured into dilute aqueous $NH_3$. The precipitate was collected, washed with water, stirred as a suspension in MeCN (30 mL) for 1 h, and then re-collected to provide crude 16. Treatment of a suspension of the free base in MeOH with HCl(g)/EtOAc/hexane, followed by crystallization from MeOH, gave 16·HCl (109 mg, 68%) as a yellow solid: mp>300° C.; $^1$H NMR [$(CD_3)_2$SO] δ 11.80 (d, J=1.7 Hz, 1H), 10.09 (br s, 1H), 9.16 (s, 1H), 8.85 (d, J=1.5 Hz, 1H), 8.30 (d, J=8.7 Hz, 1H), 8.29, 7.61 (2 br s, 2H), 8.16 (dd, J=8.8, 1.6 Hz, 1H), 7.47 (d, J 8.9 Hz, 1H), 7.28 (d, J=2.4 Hz, 1H), 7.23 (d, J=1.7 Hz, 1H), 7.04 (dd, J=8.9, 2.4 Hz, 1H), 4.96 (dd, J=10.7, 9.7 Hz, 1H), 4.70 (dd, J=10.9, 2.5 Hz, 1H), 4.68-4.59 (m, 1H), 4.36 (t, J=5.1 Hz; 2H), 420-4.07 (m, 2H), 3.50 (t, J=4.9 Hz, 2H), 2.87 (s, 6H). Anal. ($C_{26}H_{26}ClN_5O_5HCl·H_2O$) C, H, N.

EXAMPLE 29

1-(Chloromethyl)-nitro-3-(5,6,7-trimethoxyindol-2-carbonyl)-1,2-dihydro-3H-benzo[e]indole-7-carbonitrile (21) (Scheme F). A suspension of 5,6,7-trimethoxyindole-2-carboxylic acid (79 mg, 0.31 mmol) in dry $CH_2Cl_2$ (6 mL) was treated with oxalyl chloride (80 μL, 0.92 mmol) followed by DMF (10 μL). The mixture was stirred at room temperature for 30 min then evaporated to dryness under reduced pressure and re-evaporated after addition of benzene. The resulting acid chloride was cooled to −5° C. and treated with an ice-cold solution of amine 144 (60 mg, 0.21 mmol) in dry pyridine (1.5 mL) containing DMAP (5 mg). The mixture was stirred at room temperature for 15 min, then poured into dilute aqueous $KHCO_3$. The resulting solid was purified by chromatography on silica gel, eluting with $CH_2Cl_2$/EtOAc (9:1), to give 21 (81 mg, 75%) as a yellow solid: mp ($CH_2Cl_2$/EtOAc) 257-258° C.; $^1$H NMR [$(CD_3)_2$SO]δ 11.62 (s, 1H), 9.23 (s, 1H), 8.86 (d, J=1.4 Hz, 1H), 8.39 (d, J=8.8 Hz, 1H), 8.02 (dd, J=8.8, 1.4 Hz, 1H), 7.19 (d, J=2.1 Hz, 1H), 6.98 (s, 1H), 4.93 (t, J=10.6 Hz, 1H), 4.69-4.59 (m, 2H), 4.16-4.05 (m, 2H), 3.94 (s, 3H), 3.83 (s, 3H), 3.81 (s, 3H). Anal. ($C_{26}H_{21}ClN_4O_6$) C, H, N.

EXAMPLE 30

1-(Chloromethyl)-3-{5-[2-(dimethylamino)ethoxy]indol-2-carbonyl}-5-nitro-1,2-dihydro-3H-benzo[e]indole-7-carbonitrile (22) (Scheme F). A mixture of amine 144 (60 mg, 0.21 mmol), 5-[2-(dimethylamino)ethoxy]indole-2-carboxylic acid hydrochloride (71 mg, 0.25 mmol), EDCI (160 mg, 0.83 mmol) and anhydrous TsOH (25 mg, 0.15 mmol) in dry DMA (3 mL) was stirred under $N_2$ at room temperature for 6 h, then poured into dilute aqueous $NH_3$. The precipitated solid was collected, washed with water, and dissolved in $CH_2Cl_2$. The dried solution was concentrated under reduced pressure below 25° C. to a small volume and diluted with i-$Pr_2O$ to give crude 22. Treatment of a solution of the free base in $CH_2Cl_2$ with HCl(g)/EtOAc/hexane, gave 22·HCl (94 mg, 81%) as a yellow solid: mp (MeOH/EtOAc)>300° C.; $^1$H NMR [$(CD_3)_2$SO] δ 11.86 (s, 1H), 10.04 (v br s, 1H), 9.31 (s, 1H), 8.90 (d, J=1.2 Hz, 1H), 8.44 (d, J=8.8 Hz, 1H), 8.06 (dd, J=8.8, 1.5 Hz, 1H), 7.50 (d, J=8.9 Hz, 1H), 7.31 (d, J=2.3 Hz, 1H), 7.28 (d, J=1.7 Hz, 1H), 7.08 (dd, J=8.9, 2.4 Hz, 1H), 5.00 (t, J=10.2 Hz, 1H), 4.79-4.65 (m, 2H), 4.39 (t J=5.1 Hz 2H), 421-4.10 (m, 2H), 3.56 (t, J=5.0 Hz, 2H), 2.90 (s, 6H). Anal. ($C_{27}H_{24}ClN_5O_4$—HCl) C, H, N.

EXAMPLE 31

1-(Chloromethyl)-N-(2-hydroxyethyl)-5-nitro-3-(5,6,7-trimethoxyindol-2-carbonyl)-1,2-dihydro-3H-benzo[e]indole-7-carboxamide (17) (Scheme G). A stirred solution of 153 [for preparation see Example 36] (178 mg, 0.58 mmol) in dry THF (6 mL) was treated at 0° C. with ethanolamine (142 mg, 2.32 mmol) followed by benzotriazol-1-yloxytripyrrolidinophosphonium hexafluorophosphate (394 mg, 0.76 mmol). The mixture was warmed to room temperature for 10 min, then diluted with water and extracted with EtOAc (×2). The combined organic layers were washed with 1 M aqueous AcOH, 10% aqueous $KHCO_3$ and warm water, then dried and filtered through a short column of silica gel. Solvent removal followed by two recrystallizations from EtOAc gave 1-(chloromethyl)-N-(2-hydroxyethyl)-5-nitro-1,2-dihydro-3H-benzo[e]indole-7-carboxamide (155) (166 mg, 82%): mp 150-151° C.; $^1$H NMR [$(CD_3)_2$SO] δ 8.60-8.52 (m, 2H), 7.95 (dd, J=8.9, 1.5 Hz, 1H), 7.89 (d, J=8.8 Hz, 1 H), 7.65 (s, 1H), 6.53 (s, 1H), 4.73 (t, J=5.5 Hz, 1H), 4.27-4.17 (m, 1H), 3.93-3.81 (m, 2H), 3.78 (dd, J=11.0, 8.6 Hz, 1H), 3.72 (dd, J=10.4, 2.8 Hz, 1H), 3.54 (q, J=5.9 Hz, 2H), 3.36 (after $D_2O$ exchange, t, J=5.9 Hz, 2H). Anal. ($C_{16}H_{16}ClN_3O_4$) C, H, N.

Amine 155 (75 mg, 0.21 mmol) was dissolved in MeOH/HCl(g) at room temperature and the solution was evaporated to dryness under reduced pressure. 5,6,7-Trimethoxyindole-2-carboxylic acid (65 mg, 0.26 mmol), EDCI (163 mg, 0.85 mmol), anhydrous, TsOH (30 mg, 0.17 mmol) and dry DMA (3 mL) were added and the mixture was stirred at room temperature for 3 h. The mixture was poured into 10% aqueous NaCl and the precipitate was collected, washed with water, and dried, then dissolved in the minimum volume of DMF at room temperature. The solution was diluted with EtOAc, filtered, then diluted with hexane and refrigerated to give 17 (76 mg, 61%): mp 244-245° C.; $^1$H NMR [$(CD_3)_2$SO] δ 11.57 (s, 1H), 9.11 (s, 1H), 8.81 (s, 1H), 8.76 (t, J=5.5 Hz, 1H), 828 (d, J=8.8 Hz, 1H), 8.13 (d, J=8.8 Hz, 1H), 7.18 (d, J=2.0 Hz, 1H), 6.98 (s, 1H), 4.91 (t, J=10.1 Hz, 1H), 4.77 (t J=5.5 Hz, 1H), 4.67-4.56 (m, 2H), 4.17-4.06 (m, 2H), 3.94 (s, 3H), 3.83 (s, 3H), 3.81 (s, 3H), 3.57 (q, J=5.9 Hz, 2H), 3.39 (after D$_2$O exchange, t, J=5.9 Hz, 2H). Anal. (C$_{28}$H$_{27}$ClN$_4$O$_8$) C, H, N.

EXAMPLE 32

1-(Chloromethyl)-N-(2-hydroxyethyl)-3-[(E)-4-methoxycinnamoyl]-5-nitro-1,2-dihydro-3H-benzo[e]indole7-carboxamide (18) (Scheme G). Amine 155 (75 mg, 0.21 mmol) was converted to the hydrochloride salt, then reacted with (E)-4-methoxycinnamic acid, EDCI and TsOH and worked up as in Example 31, to give 18 (69 mg, 63%): mp 240-241° C.; $^1$H NMR [(CD$_3$)$_2$SO] δ 9.22 (s, 1H), 8.79 (s, 1H), 8.75 (t, J=5.5 Hz, 1H), 8.24 (d, J=8.8 Hz, 1H), 8.12 (d, J=8.8 Hz, 1H), 7.80 (d, J=8.8 Hz, 2H), 7.72 (d, J=15.3 Hz, 1H), 7.09 (d, J=15.3 Hz, 1H), 7.02 (d, J=8.8 Hz, 2 H), 4.76 (t, J=5.5 Hz, 1H), 4.70-4.56 (m, 3H), 4.13-4.04 (m, 2H), 3.83 (s, 3H), 3.56 (q, J=5.9 Hz, 2H), 3.39 (after D$_2$O exchange, t, J=6.0H, 2H). Anal. (C$_{26}$H$_{24}$ClN$_3$O$_6$) C, H, N.

EXAMPLE 33

1-(Chloromethyl)-3-(5-[2-(dimethylamino)ethoxy]indol-2-carbonyl)-N-(2-hydroxyethyl)-5-nitro-1,2-dihydro-3H-benzo[e]indole-7-carboxamide (19) (Scheme G). Amine 155 (75 mg, 0.21 mmol) was converted to the hydrochloride salt, then reacted with 5-[2-(dimethylamino)ethoxy]indol-2-carboxylic acid hydrochloride as in Example 31. The mixture was poured into 10% aqueous KHCO$_3$ and extracted with EtOAc (×2). The combined organic layers were washed with 10% aqueous KHCO$_3$ and saturated aqueous NaCl, then dried and concentrated under reduced pressure below 30° C. to provide the crude 19. This was dissolved in MeOH and diluted with excess EtOAc, filtered, then treated with EtOAc/hexane/HCl(g). The resulting precipitate was crystallised from MeOH/EtOAc to give 19·HCl (68 mg, 51%): mp 231-233° C. (dec.); $^1$H NMR [(CD$_3$)$_2$SO] δ 11.80 (s, 1H), 9.98 (v br, 1H), 9.16 (s, 1H), 8.83 (s, 1H), 8.78 (t, J=5.5 Hz, 1H), 8.30 (d, J=8.8 Hz, 1H), 8.15 (d, J=8.8 Hz, 1H), 7.47 (d, J=8.9 Hz, 1H), 7.28 (d, J=1.9 Pa, 1H), 7.23 (s, 1H), 7.04 (dd, J=8.9, 2.3 Hz, 1H), 4.96 (t, J=10.2 Hz, 1H), 4.78 (t, J=5.3 Hz, 1H), 4.74-4.59 (m, 2H), 4.35 (t, J=4.9 Hz, 2H), δ 4.19-4.07 (m, 2H), 3.57 (q, J=5.7 Hz, 2H), 3.46-3.36 (after D$_2$O exchange, m, 4H), 2.86 (s, 6H). Anal (C$_{29}$H$_{30}$ClN$_5$O$_6$HCl) C, H, N, Cl.

EXAMPLE 34

Methyl 1-(chloromethyl)-3-(5,6,7-trimethoxyindol-2-carbonyl)-5-nitro-1,2-dihydro-3H-benzo[e]indole-7-carboxylate (13) (Scheme G). A suspension of 6-(methoxycarbonyl)-2-naphthoic acid [J. Med. Chem., 2004, 47, 303-324] (146) (1.21 g, 5.26 mmol) in dry t-BuOH (20 mL) containing powdered molecular sieves (1 g) was treated with Et$_3$N (0.88 mL, 6.31 mmol) and stud under N$_2$ at room temperature for 30 min. DPPA (1.25 mL, 5.80 mmol) was added and the mixture was sired at reflux for 7 h, then cooled and poured into dilute aqueous NaHCO$_3$. The resting solid was purified by chromatography on silica gel, eluting with CH$_2$Cl$_2$, followed by trituration with iPr$_2$O and recrystallization from EtOAc to give methyl 6-[(tert-butoxycarbonyl)amino]-2-naphthoate (147) (1.24 g, 78%) as a white solid: mp 178-180° C.; $^1$H NMR [(CD$_3$)$_2$SO] δ 9.76 (s, 1H), 8.51 (s, 1H), 8.19 (s, 1H), 8.02 (d, J=9.0 Hz, 1H), 7.90 (dd, J=8.6, 1.6 Hz, 1H), 7.86 (d, J=8.7 Hz, 1H), 7.59 (dd, J=8.9, 2.1 Hz, 1H), 3.89 (s, 3H), 1.52 (s, 9H). Anal. (C$_{17}$H$_{19}$NO$_4$) C, H, N.

A mixture of ester 147 (977 mg, 3.24 mmol) and NBS (664 mg, 3.73 mmol) in CH$_3$CN (25 mL) was stirred at reflux for 45 min, then concentrated under reduced pressure. The residue was dissolved in CH$_2$Cl$_2$ and the solution was washed with 10% aqueous Na$_2$SO$_3$ and water (×2), dried, and concentrated under reduced pressure. The residue was purified by chromatography on silica gel, eluting with CH$_2$Cl$_2$, to give methyl 2-[(tert-butoxycarbonyl)amino]-1-bromo-6-naphthoate (148) (1.12 g, 91%) as a white solid: mp (petroleum ether) 130-131° C.; $^1$H NMR [(CD$_3$)$_2$SO] δ 8.93 (s, 1H), 8.65 (d, J=1.6 Hz, 1H), 8.64 (d, J=8.9 Hz, 1H), 8.16 (d, J=8.9 Hz, 1H), 8.11 (dd, J=8.9, 1.7 Hz, 1H), 7.86 (d, J=8.9 Hz, 1H), 3.93 (s, 3H), 1.50 (s, 9H). Anal. (C$_{17}$H$_{18}$BrNO$_4$) C, H, N, Br.

A stirred solution of bromide 148 (1.05 g, 2.76 mmol) in dry DMF (8 mL) was treated at 0° C. with NaH (132 mg, 60% in oil, 3.30 mmol). The resulting suspension was warmed to room temperature for 30 min, then cooled to 0° C. and treated with 1,3-dichloropropene (0.80 mL, 8.7 mmol, mixed isomers). The mixture was stirred at room temperature for a further 4 h then poured into dilute aqueous AcOH and exacted with EtOAc (×2). The combined organic layers were washed with dilute aqueous NaHCO$_3$ and water (×2), dried, and concentrated to dryness under reduced pressure at 100° C. The residue was chromatographed on silica gel, eluting with CH$_2$Cl$_2$/EtOAc (19:1) to give methyl 2-[(tert-butoxycarbonyl)(3-chloro-2-propen-1-yl)amino]-1-bromo-6-naphthoate (149) (1.19 g, 95%) as a gum; $^1$H NMR [(CD$_3$)$_2$SO] (mixture of rotamers and E and Z forms) δ 8.73 (s, 1H), 8.34 (d, J=8.9 z, 1H), 8.16 (d, J=8.9 Hz, 1H), 7.63, 7.58 (2 d, J=8.7 Hz, 1H), 8.25, 8.24 (2 d, J=8.6 Hz, 1H), 6.45-6.31 (m, 1H), 6.20-6.00 (m, 1H), 4.58-4.48, 4.43-4.21, 4.16-4.00 (3 m, 2H), 3.95 (s, 3H), 1.50, 1.27 (2 s, 9H). HRMS (FAB) calcd. for C$_{20}$H$_{22}$$^{79}$Br$^{35}$ClNO$_4$ (MH$^+$) m/z 454.0421, found 454.0410.

A mixture of 149 (1.16 g, 2.55 mmol), Bu$_3$SnH (0.69 mL, 2.56 mmol) and AIBN (50 mg, 0.30 mmol) in dry benzene (15 mL) under N$_2$ was stirred at reflux for 2 h, then concentrated under reduced pressure. The residue was triturated with i-Pr$_2$O and the resulting solid was purified by chromatography on silica gel, eluting with CH$_2$Cl$_2$/EtOAc (19:1), to give methyl 3-(tert-butoxycarbonyl)-1-(chloromethyl)-1,2-dihydro-3H-benzo[e]indole-7-carboxylate (150) (817 mg, 85%) as a white solid. mp EtOAc) 187-189° C.; $^1$H NMR [(CD$_3$)$_2$SO] δ 8.60 (d, J=1.2 z, 1H), 8.1 (v br, 1H), 8.09 (d, J=8.6 Hz, 1H), 8.00 (d, J=8.8 Hz, 1H), 7.97 (dd, J=8.8, 1.6 Hz, 1H), 4.31-4.23 (m, 1H), 4.20 (t, J=10.4 Hz, 1H), 4.09 (dd, J=11.2, 2.5 Hz, 1H), 4.04 (dd, J=11.1, 3.1 Hz, 1H), 3.96-3.88 (m, 4H), 1.55 (s, 9H). Anal. (C$_{20}$H$_{22}$ClNO$_4$) C, H, N.

Powdered 150 (900 mg, 2.39 mmol) was added to stirred conc. H$_2$SO$_4$ (6 mL) at 0° C. and the mixture was warned to room temperature for 15 nm. The resulting solution was cooled to −5° C. and treated dropwise with a solution of KNO$_3$ (266 mg, 2.63 mmol) in conc. H$_2$SO$_4$ (1.5 mL). The mixture was stirred at −5° C. for a further 5 min, then poured into ice/water and neutralized with dilute aqueous NH$_3$. The resulting solid was chromatographed on silica gel, eluting with CH$_2$Cl$_2$ to give crude methyl 1-(chloromethyl)-9-nitro-1,2-dihydro-3H-benzo[e]indole-7-carboxylate (151) (102 mg, 13%) as an orange-brown solid; $^1$H NMR [(CD$_3$)$_2$SO] δ 8.66 (d, J=1.7 Hz, 1H), 8.30 (d, J=1.7 Hz, 1H), 8.08 (d, J=8.8 Hz, 1H), 7.25 (s, 1H), 7.18 (d, J=8.8 Hz, 1H), δ 3.92-3.83 (m, 4H), 3.74-3.67 (m, 1H), 3.63 (dd, J=10.6, 2.3 Hz, 1H), 3.39-3.28 (m, 2 H).

Further elution with CH$_2$Cl$_2$ gave methyl 1-(chloromethyl)-5-nitro-1,2-dihydro-3H-benzo[e]indole-7-carboxylate (152) (228 mg, 30%) as a red solid: mp (CH$_2$Cl$_2$/i-Pr$_2$O) 191-192° C.; $^1$H NMR [(CD$_3$)$_2$SO] δ 8.77 (s, 1H), 7.96 (dd, J=8.9, 1.5 Hz, 1H), 7.93 (dd, J=8.9, 0.7 Hz, 1H), 7.73 (s, 1H), 6.74 (s, 1H), 4.27-4.19 (m, 1H), 3.94-3.85 (m, 5H), 3.79 (dd, J=11.0, 8.4 Hz, 1H), 3.74 (dd, J=10.5, 3.1 Hz, 1H). Anal. ($C_{15}H_{13}ClN_2O_4$) C, H, N, Cl.

A suspension of 5,6,7-trimethoxyindole-2-carboxylic acid (47 mg, 0.19 mmol) in dry $CH_2Cl_2$ (2 mL) was treated with oxalyl chloride (50 µl, 0.57 mmol) followed by DMF (10 µl). The mixture was stirred at room temperature for 30 min, then evaporated to dryness under reduced pressure and re-evaporated after addition of benzene. The resulting acid chloride was cooled to −5° C. and treated with an ice-cold solution of amine 152 (40 mg, 0.12 mmol) in dry pyridine (1 mL) containing DMAP (4 mg). The mixture was stirred at room temperature for 15 min, then poured into dilute aqueous $KHCO_3$. The precipitated solid was purified by chromatography on silica gel, eluting with $CH_2Cl_2$/EtOAc (9:1), to give 13 (49 mg, 71%) as an orange solid: mp ($CH_2Cl_2$/i$Pr_2$O) 256-257° C.; $^1$H NMR [($CD_3$)$_2$SO] δ 11.60 (d, J=1.8 Hz, 1H), 9.19 (s, 1H), 9.03 (d, J=1.5 Hz, 1H), 8.34 (d, J=8.8 Hz, 1H), 8.16 (dd, J=8.8, 1.6 Hz, 1H), 7.19 (d, J=2.2 Hz, 1H), 6.98 (s, 1H), 4.92 (dd, J=10.6, 9.6 Hz, 1H), 4.69-4.57 (m, 2H), 4.18-4.05 (m, 2H), 3.96 (s, 3H), 3.94 (s, 3H), 3.83 (s, 3H), 3.81 (s, 3H). Anal. ($C_{27}H_{24}ClN_3O_8$) C, H, N.

EXAMPLE 35

Methyl 1-(chloromethyl)-3-{5-[2-(dimethylamino) ethoxy]indol-2-carbonyl}-5-nitro-1,2-dihydro-3H-benzo[e] indole-7-carboxylate (14) (Scheme G). A mixture of amine 152 (80 mg, 0.25 mmol), 5-[2-(dimethylamino)ethoxy]indole-2-carboxylic acid hydrochloride (85 mg, 0.30 mmol), EDCI (191 mg, 1.00 mmol) and anhydrous TsOH (25 mg, 0.15 mmol) in dry DMA (4 mL) was stirred under $N_2$ at room temperature for 7 h, then poured into dilute aqueous $NH_3$. The resulting solid was recrystallised twice from $CH_2Cl_2$/EtOAc/ i-$Pr_2$O to give 14. Treatment of a solution of 14 in $CH_2Cl_2$ with HCl(g)/EtOAc/hexane gave 14·HCl (106 mg, 72%) as a yellow solid: mp>300° C.; $^1$H NMR [($CD_3$)$_2$SO] δ 11.82 (d, J=1.8 Hz, 1H), 10.14 (br s, 1H), 9.24 (s, 1H), 9.03 (d, J=1.4 Hz, 1H), 8.35 (d, J=8.7 Hz, 1H, 8.17 (dd, J=8.8, 1.6 Hz, 1H), 7.47 (d, J=8.9 Hz, 1H), 7.28 (d, J=2 Hz, 1H), 7.24 (d, J=1.6 Hz, 1H), 7.04 (dd, J=8.9, 2.4 Hz, 1H), 4.97 (dd, J=10.7, 9.7 Hz, 1H), 4.71 (dd, J=10.9, 2.4 Hz, 1 H), 4.68-4.61 (m, 1H), 4.37 (t, J=5.1 Hz, 2H), 4.18-4.08 (m, 2H), 3.96 (s, 3H), 3.53 (t, J=5.0 Hz, 2H), 2.87 (s, 6H). Anal. ($C_{28}H_{27}ClN_4O_6$·HCl·0.5$H_2$O) C, H, N.

EXAMPLE 36

1-(Chloromethyl)-N-[2-(dimethylamino)ethyl]-5-nitro-3-(5,6,7-trimethoxyindol-2-carbonyl)-1,2-dihydro-3H-benzo [e]indole-7-carboxamide (20) (Scheme G). A solution of 152 (142 mg, 0.44 mmol) in conc. HCl (15 mL) was heated at reflux for 1 h, then evaporated to dryness under reduced pressure and re-evaporated after addition of water. The residue was triturated with water and the collected solid was dissolved in EtOAc. The solution was filtered through a column of silica gel and the product was recrystallised twice from EtOAc/hexane to give 1-(chloromethyl)-5-nitro-1,2-dihydro-3H-benzo[e]indole-7-carbolic acid (153) (106 mg, 78%) as a red solid: mp 214-217° C.; $^1$H NMR [($CD_3$)$_2$SO] δ 13.0 (v br, 1H) 8.75 (d, J=1.1 Hz, 1H), 7.96 (dd, J=8.8, 1.6 Hz, 1H), 7.91 (d, J=8.8 Hz, 1H), 7.71 (s, 1H), 6.68 (s, 1H), 4.27-4.18 (m, 1H), 3.94-3.83 (m, 2H), 3.78 (dd, J=11.1, 8.6 Hz, 1H), 3.73 (dd, J=10.5, 3.1 Hz, 1H). Anal. ($C_{14}H_{11}ClN_2O_4$) C, H, N.

A stirred solution of 153 (124 mg, 0.40 mmol) in dry DMF (1.5 mL) was treated at 0° C. with N,N-dimethyl-1,2-ethanediamine (111 µL, 1.01 mmol), followed by dropwise addition of diethyl cyanophosphonate (132 µl, 93%, 0.81 mmol). The mixture was warmed to room temperature for 30 min, then poured into dilute aqueous $NH_3$ saturated with NaCl. The precipitated solid was collected, washed with water and recrystallised twice from $CH_2Cl_2$/i-$Pr_2$O to give 1-(chloromethyl)-N-[2-(dimethylamino)ethyl]5-nitro-1,2-dihydro-3H-benzo[e]indole-7-carboxamide (154) (102 mg, 67%) as a red solid: mp 155-158° C.; $^1$H NMR [($CD_3$)$_2$SO] δ 8.57 (d, J=0.7 Hz, 1H), 8.51 (t, J=5.6 Hz, 1H), 7.93 (dd, J=8.9, 1.5 Hz, 1H), 7.90 (d, J=8.7 Hz, 1H), 7.66 (s, 1H), 6.54 (s, H), 4.26-4.18 (m, 1H), 3.91 (dd, J=11.0, 3.8 Hz, 1H), 3.86 (td, J=9.8, 2.3 Hz, 1H), 3.78 (dd, J=11.0, 8.6 Hz, 1H), 3.72 (dd, J=10.2, 2.8 Hz, 1H), 3.39 (q, J=6.5 Hz, 2H), 2.42 (t J=6.9 Hz, 2H), 2.49 (s, 6H). Anal. ($C_{18}H_{21}ClN_4O_3$·½$H_2$O) C, H, N.

A suspension of 154 (45 mg, 0.12 mmol) in dioxane (10 mL) was treated at 20° C. with HCl gas until colorless, then evaporated to dryness under reduced pressure. To the resulting dihydrochloride salt was added 5,6,7-trimethoxyindole-2-carboxylic acid (36 mg, 0.14 mmol), EDCI (92 mg, 0.48 mmol) and dry DMA (1 mL) and the mixture was stirred at room temperature for 2 h and then poured into saturated aqueous $KHCO_3$. The precipitated solid was collected, dissolved in $CH_2Cl_2$, and the solution was washed with water, dried and concentrated under reduced pressure below 25° C. The residue was triturated with EtOAc/i-$Pr_2$O to give crude 20. Treatment of a solution of the free base in $CH_2Cl_2$ with HCl(g)/EtOAc/hexane followed by crystallization from MeOH/EtOAc gave 20·HCl (61 mg, 79%) as a yellow solid: mp 246-248° C. (dec.); $^1$H NMR [($CD_3$)$_2$SO] δ 11.58 (d, J=1.8 Hz, 1H), 9.84 (br s, 1H), 9.14 (s, 1H), 9.07 (t, J=5.5 Hz, 1H), 8.86 (d, J=1.4 Hz, 1H), 8.33 (d, J=8.8 Hz, 1H, 8.19 (dd, J=8.9, 1.6 Hz, 1H), 7.19 (d, J=2.2 Hz, 1H), 6.98 (s, 1H), 4.93 (t, J=10.6 Hz, 1H), 4.68-4.57 (m, 2H), 4.18-4.07 (m, 2H), 3.94 (s, 3H), 3.83 (s, 3H), 3.81 (s, 3H), 3.69 (q, J=5.8 Hz, 2H), 3.23 (after $D_2$O exchange, t, J=5.7 Hz, 2H), 2.85 (s, 6H). Anal. ($C_{30}H_{32}ClN_5O_7$·HCl) C, H, N.

EXAMPLE 37

1-(Chloromethyl)-7-(methylsulfonyl)-5-nitro-3-(5,6,7-trimethoxyindol-2-carbonyl)-1,2-dihydro-3H-benzo[e]indole (23) (Scheme H). A mixture of methyl 6-hydroxy-2-naphthoate [J. Med. Chem., 2001, 44, 2869-2878] (156) (5.95 g, 29.4 mmol), DABCO (6.61 g, 58.9 mmol) and dimethylthiocarbamoyl chloride (5.46 g, 44.2 mmol) in dry DMF (40 mL) was stirred at room temperature for 8 h. The precipitated solid was collected, washed with water and dissolved in $CH_2Cl_2$. The solution was filtered through a column of silica gel and the product was triturated with i-$Pr_2$O and recrystallised from $CH_2Cl_2$/hexane to give methyl 6-{[(dimethylamino)carbothioyl]oxy}-2-naphthoate (157) (7.47 g, 88%) as a white solid: mp 144-147° C.; $^1$H NMR [($CD_3$)$_2$SO] δ 8.66 (s, 1H), 8.16 (d, J=9.0 Hz, 1H), 8.03 (d, J=8.7 Hz, 1H), 8.00 (dd, J=−8.6, 1.5 Hz, 1H), 7.70 (d, J=−2.3 Hz, 1H), 7.389 (dd, J=8.9, 2.3 Hz, 1H), 3.93 (s, 3H), 3.40 (s, 3H), 3.38 (s, 3H). Anal. ($C_{15}H_{15}NO_3S$) C, H, N.

Thiocarbamate 157 (8.10 g, 28 mmol) was heated under $N_2$ at 225° C. for 3 h. The cooled mixture was purified by chromatography on silica gel, eluting with $CH_2Cl_2$/EtOAc, followed by trituration with i-$Pr_2$O to give methyl 6-{[(dimethylamino)carbonyl]sulfanyl}-2-naphthoate (158) (6.91 g, 85%) as a white solid: mp ($CH_2Cl_2$/petroleum ether) 130-132° C.; $^1$H NMR [($CD_3$)$_2$SO] δ 8.67 (s, 1H), 8.1 (d, J=0.8 Hz, 1), 8.16 (d, J=8.8 Hz, 1H), 8.07 (d, J=8.7 Hz, 1H), 8.03 (dd, J=8.5, 1.16 Hz, 1H), 7.60 (dd, J=−8.5, 1.8 Hz, 1H), 3.93 (s, 3H), 3.09 (br s, 3H), 2.97 (br s, 3H). Anal. ($C_{15}H_{15}NO_3S$) C, H, N.

A suspension of 158 (6.36 g, 22-mmol) in a mixture of aqueous KOH (5N, 340 mL, 1.7 mol) and MeOH (205 mL) was stirred at reflux for 3 h, then cooled to 5° C. and treated dropwise with $Me_2SO_4$ (26 mL. 275 mmol). After stirring at room temperature for a further 4 h the mixture was concentrated to half volume, acidified with dilute aqueous HCl, and the precipitated product was crystallised from EtOAc/hexane to give 6-(methylsulfanyl)-2-naphthoic acid (159) (4.39 g, 91%) as a white solid: mp (MeOH) 231-233° C.; $^1$H NMR [$(CD_3)_2SO$] δ ($CO_2H$ not observed) 8.53 (s, 1H), 8.01 (d, J=8.9 Hz, 1H), 7.96 (dd, J=8.6, 1.7 Hz, 1H), 7.90 (d, J=8.7 Hz, 1H), 7.77 (d, J=1.7 Hz, 1H), 7.47 (dd, J=+8.7, 1.9 Hz, 1H), 2.61 (s, 3H). Anal. ($C_{12}H_{10}O_2S$) C, H.

A mixture of 159 (4.24 g, 19.4 mmol) and $NaBO_3.4H_2O$ (20.0 g, 130 mmol) in AcOH (150 mL) was stirred at 55° C. for 21 h. Additional $NaBO_3.4H_2O$ (5.4 g, 35 mmol) was added and the mixture was stirred at 55° C. for a further 211, then diluted with water (1 L). The precipitated solid was collected, washed with water, and recrystallised from MeOH then $DMF/H_2O$ to give 6-(methylsulfonyl)-2-naphthoic acid (160) (3.98 g, 82%) as a white solid: mp 301-304° C.; $^1$H NMR [$(CD_3)_2SO$)] δ ($CO_2H$ not observed) 8.74 (s, 1H), 8.66 (s, 1H), 8.39 (d, J=8.8 Hz, 1H), 8.30 (d, J=8.8 Hz, 1H), 8.13 (dd, J=8.6, 1,7 Hz, 1H), 8.03 (dd, J=8.7, 1.9 Hz, 1H), 3.32 (s, 3H). Anal. ($C_{12}H_{10}O_4S$) C, H.

A suspension of acid 160 (4.08 g, 16.30 mmol) in dry t-BuOH (70 mL) containing powdered molecular sieves (2 g) was treated with $Et_3N$ (2.73 mL, 19.59 mmol) and stirred under N2 at room temperature for 30 min. DPPA (3.87 mL, 17.96 mmol) was added and the mixture was stirred at reflux for 6 h, then concentrated to a small volume under reduced pressure and poured into dilute aqueous $NaHCO_3$. The resulting solid was purified by chromatography on silica gel, eluting with $CH_2Cl_2$, to give tert-butyl 6-(methylsulfonyl)-2-naphthylcarbamate (161) (4.57 g, 87%) as a white solid: mp (EtOAc/hexane) 203-204° C.; $^1$H NMR [$(CD_3)_2SO$] δ 9.81 (s, 1H); 8.44 (d, J=1.2 Hz, 1H), 8.26 (s, 1H), 8.08 (d, J=9.0 Hz, 1H), 8.01 (d, J=8.7 Hz, 1H), 7.84 (dd, J=8.7, 1.8 Hz, 1H), 7.66 (dd, J=8.9, 2.0 Hz, 1H), 3.25 (s, 3H), 1.52 (s, 9H). Anal. ($C_{16}H_{19}NO_4S$) Cl, N.

A mixture of 161 (4.47 g, 13.91 mmol) and NBS (2.72 g, 1528 mmol) in MeCN (80 mL) was stirred at reflux for 3 h, then concentrated under reduced pressure. The residue was dissolved in $CH_2Cl_2$ and the solution was washed with 10% aqueous $Na_2SO_3$ and water, dried, and concentrated under reduced pressure. The residue was purified by chromatography on silica gel, eluting with $CH_2Cl_2$, to give tert-butyl 1-bromo-6-(methylsulfonyl)-2-naphthylcarbamate (162) (4.79 g, 86%) as a white solid: mp (MeOH) 190° C.; $^1$H NMR [$(CD_3)_2SO$] δ 8.95 (s, 1H), 8.61 (d, J=1.8 Hz, 1H), 8.36 (d, J=9.0 Hz, 1H), 8.22 (d, J=8.8 Hz, 1H), 8.08 (dd, J=9.0, 1.9 Hz, 1H), 7.96 (d, J=8.9 Hz, 1H), 3.25 (after $D_2O$ exchange, s, 3H), 1.50 (s, 9H). Anal. ($C_{16}H_{18}BrNO_4S$) C, H, N.

A stirred suspension of 162 (4.70 g, 11.74 mmol) in dry DMF (40 mL) was treated portionwise at 0° C. with NaH (564 mg, 60% in oil, 14.10 mmol). The mixture was warmed to room temperature for 1 h then cooled to O—C and treated with 1,3-dichloropropene (3.4 mL, 37 mmol, mixed isomers). The mixture was stirred at room temperature for a further 6 h, then diluted with 10% aqueous NaCl and extracted with EtOAc (×2). The combined organic layers were washed with water (×2), dried, and concentrated to dryness under reduced pressure at 100° C. The residue was chromatographed on silica gel, eluting with $CH_2Cl_2$/EtOAc (9:1) to give tert-butyl 1-bromo-6-(methylsulfonyl)-2-naphthyl(3-chloro-2-propen-1-yl)carbamate (163) (5.41 g, 970%) as a foam; $^1$H NMR [$(CD_3)_2SO$] (mixture of rotamers and E and Z forms) δ 8.73-8.69 (m, 1H), 8.46 (d, J=9.0 Hz, 1H, 8.30, 8.29 (2 d, J=8.6 Hz, 1H), 8.14 (dd, J=9.0, 1.8 Hz, 1H), 7.71, 7.68 (2 d, J=8.6 Hz, 1H), 6.43-6.28 (m, 1H), 6.19-6.01 (m, 1 H), 4.59-4.48, 4.44-4.23, 4.19-4.05 (3 m, 2H), 327 (after $D_2O$ exchange, s, 3H), 1.50, 1.26 (2 s, 9H). HRMS (FAB) calcd. for $C_{19}H_{22}^{79}Br^{35}ClNO_4S$ (MH$^+$) m/z 474.0141, found 474.0142.

A mixture of 163 (5.38 g, 11.33 mmol), $Bu_3SnH$ (3.05 mL, 11.34 mmol) and AIBN (0.25 g, 1.5 mmol) in dry benzene (80 mL) under $N_2$ was stirred at reflux for 2 h, then concentrated under reduced pressure. The residue was dissolved in $CH_2Cl_2$ and the solution was diluted with excess hexane and refrigerated. The precipitated semisolid was purified by chromatography on silica gel, eluting with $CH_2Cl_2$/EtOAc (19:1), to give tert-butyl 1-(chloromethyl)-7-(methylsulfonyl)-1,2-dihydro-3H-benzo[e]indole 3-carboxylate (164) (3.53 g, 79%) as a white solid: mp (iPr$_2$O) 125-126° C.; $^1$H NMR [$(CD_3)_2SO$] δ 8.54 (d, J=1.8 Hz, 1H), 8.25-8.05 (m, 3H), 7.91 (dd, J=8.9, 1.9 Hz, 1H), 4.36-4.27 (m, 1H), 4.23 (t, f=10.5 Hz, 1H), 4.10 (dd, J=11.4, 2.9 Hz, 1H), 4.05 (dd, J=11.1, 3:2 Hz, 1H), 3.94 (dd, J=11.1, 6.7 Hz, 1H, 3.21 (after $D_2O$ exchange, s, 3H, 1.56 (s, 9H). Anal. ($C_{19}H_{22}ClNO_4S$) C, H, N.

Powdered 164 (1.50 g, 3.79 mmol) was added to stirred conc. $H_2SO_4$ (16 mL) at 0° C., and the mixture was warmed to room temperature for 30 min. The resulting solution was cooled to −5° C. and treated dropwise with a solution of $KNO_3$ (421 mg, 4.16 mmol) in conc. $H_2SO_4$ (3 mL). The mixture was stirred at 0° C. for a further 10 min then poured into ice/water and neutralized with aqueous $NH_3$. The resulting solid was purified by chromatography on silica gel, eluting with $CH_2Cl_2$, to give 1-(chloromethyl)-7-(methylsulfonyl)-5-nitro-1,2-dihydro-3H-benzo[e]dole (165) (926 mg, 72%) as a red solid: mp (EtOAc) 199-200° C.; $^1$H NMR [$(CD_3)_2SO$] δ 8.68 (d, J=1.6 Hz, 1H), 8.06 (dd, J=8.9, 0.4 Hz, 1H), 7.90 (dd, J=8.9, 1.8 Hz, 1H), 7.79 (s, 1H), 6.83 (s, 1H), 4.31-4.23 (m, 1H), 3.95-3.86 (m, 2H), 3.82 (dd, J=11.1, 8.1 Hz, 1H), 3.76 (dd, J=10.1, 3.1 Hz, 1H), 3.25 (s, 3H). Anal. ($C_{14}H_{13}ClN_2O_4S$) C, H, N, Cl.

A mixture of amine 165 (250 mg, 0.73 mmol), 5,6,7-trimethoxyindole-2-carboxylic acid (221 mg, 0.88 mmol), EDCI (563 mg, 2.94 mmol) and anhydrous TsOH (100 mg, 0.58 mmol) in dry DMA (8 mL) was stirred at room temperature for 4 h, then poured into dilute aqueous $KHCO_3$. The precipitate was collected and crystallised from $DMF/H_2O$ to give 23 (353 mg, 84%) as a yellow solid: mp 296-297° C. (dec.); $^1$H NMR [$(CD_3)_2SO$] δ 11.62 (s, 1. H), 9.27 (s, 1H), 8.98 (d, J=1.7 Hz, 1H), 8.48 (d, J=8.9 Hz, 1H), 8.15 (dd, J=8.9, 1.8 Hz, 1H), 7.21 (d, J=2.2 Hz, 1H), 6.99 (s, 1H), 4.95 (t, J=10.7 Hz, 1H), 4.70-4.61 (m, 2H), 4.20-4.06 (m, 2H), 3.94 (s, 3H), 3.83 (s, 3H), 3.81 (s, 3H), 3.28 (s, 3H). Anal. ($C_{26}H_{24}ClN_3O_8S.½H_2O$) C, H, N.

EXAMPLE 38

1-(Chloromethyl)-3-{5-[2-(dimethylamino)ethoxy]indol-2-carbonyl}-7-(methylsulfonyl)-5-nitro-1,2-dihydro-3H-benzo[e]indole (24) (Scheme H). A mixture of amine 165 (350 mg, 1.03 mmol), 5-[2-dimethylamino)ethoxy]indol-2-carboxylic acid hydrochloride (351 mg, 123 mmol), EDCI (788 mg, 4.11 mmol) and anhydrous TsOH (140 mg, 0.81 mmol) in dry DMF (20 ml) was stirred under $N_2$ at room temperature for 6 h, then poured into dilute aqueous $NH_3$. The precipitated solid was collected, dissolved in $CH_2Cl_2$, and the dried solution was diluted with EtOAc and concentrated under reduced pressure below 25° C. to a small volume to give crude 24. Treatment of a suspension of the free base in MeOH with HCl(g)/EtOAc/hexane followed by crystallization from MeOH/EtOAc gave 24.HCl (484 mg, 78%) as a yellow solid: mp 250-252° C.; $^1$H NMR [(CD$_3$)$_2$SO] δ 11.83 (d, J=1.7 Hz, 1H), 10.19 (br s, 1H), 9.32 (s, 1H), 8.98 (d, J=1.7 Hz, 1H), 8.50 (d, J=8.9 Hz. 1H), 8.17 (dd, J=8.9, 1.8 Hz, 1H), 7.47 (d, J=8.9 Hz, 1H), 7.27 (d, J=2.3 Hz, 1H), 7.25 (d, J=1.7 Hz, 1H), 7.04 (dd, J=8.9, 2.4 Hz, 1H), 5.00 (t, J=10.1 Hz, 1H), 4.77-4.65 (m, 2H), 4.37 (t, J=5.0 Hz, 2H), 4.20-4.09 (m, 2H), 3.51 (br s, 2H); 3.36 (s, 3H), 2.86 (s, 6H). Anal. (C$_{27}$H$_{27}$ClN$_4$O$_6$S.HCl) C, H, N.

EXAMPLE 39

8-Acetyl-1-(chloromethyl)-3-{5-[2-(dimethylamino) ethoxy]indol-2-carbonyl}-5-nitro-1,2-dihydro-3H-benzo[e] indole (41) (Scheme 1). A solution of Ac$_2$O (340 mg, 3.35 mmol) in CH$_2$Cl$_2$ (2.5 mL) was added dropwise to a suspension of AlCl$_3$ (490 mg, 3.66 mmol, 99.99%) in CH$_2$Cl$_2$ (15 mL) at 0° C. A solution of 7-bromo-2-(timethylsilyl)naphthalene (166) [J. Am. Chem. Soc., 1993, 115, 3182] (850 mg, 3.05 mmol) in CH$_2$Cl$_2$ (2.5 mL) was added dropwise. After 15 min, the mixture was poured into ice water and extracted with CH$_2$Cl$_2$ (×3). The combined organic extracts were washed with brine and dried. Filtration through Celite followed by chromatography eluting with petroleum ether/EtOAc (95:5 then 4:1) gave 2-acetyl-7-bromonaphthene-(167) (120 mg, 88%) as a colorless solid; $^1$H NMR (CDCl$_3$) δ 8.36 (d, J=6.9 Hz, 1H), 8.13 (d, J=1.7 Hz, 1H), 8.04 (dd, J=8.6, 1.7 Hz, 1H), 7.87 (d, J=8.6 Hz, 1H), 7.75 (d, J=8.7 Hz, 1H), 7.67 (dd, J=8.7, 1.9 Hz, 1H), 2.72 (s, 3H) [identical to that reported: Bull. Chem. Soc. Japan, 1979, 52, 3033].

A mixture of 167 (750 mg, 3.01 mmol), Pd(OAc)$_2$ (68 mg, 0.30 mmol), 1,3-bis(diphenylphosphino)propane (124 mg, 0.30 mmol), MeOH (10 mL), Et$_3$N (5 mL) and DMSO (5 mL) were placed in a Berghof reactor (R-200) and purged with CO(g) for 5 min. The reactor was then pressurized with CO(g) (25 bar) and heated at 70° C. for 15 h. After cooling, EtOAc was added and the mire was filtered through Celite/silica gel. Solvents were removed under reduced pressure, and CH$_2$Cl$_2$ and water were added. The mixture was extracted with CH$_2$Cl$_2$ (×3) and the combined organic extracts were washed with brine and dried. Filtration through silica gel, followed by chromatography eluting with petroleum ether/EtOAc (4:1 then 1:1 then 2:3) gave methyl 7-acetyl-2-naphthoate (168) (640 mg, 93%) as a white solid. A sample was recrystallised from petroleum ether/CH$_2$Cl$_2$: mp 103-105° C.; $^1$H NMR (CDCl$_3$) δ 8.72 (s, 1H), 8.55 (s, 1H), 8.18 (dd, J$_1$=8.6, 1.7 Hz, 1H), 8.13 (dd, J=8.6, 1.7 Hz, 1H), 7.93 (d, J=8.6 Hz, 1H), 7.92 (d, J=8.6 Hz, 1H), 4.00 (s, 3H), 2.74 (s, 3H); $^{13}$C NMR δ 197.5, 166.7, 137.5, 135.2, 132.4, 131.8, 131.3, 128.5, 128.3, 128.1, 127.8, 126.2, 52.4, 26.6. Anal. (C$_{14}$H$_{12}$O$_3$) C, H.

A solution of KOH 70 mg, 10 mmol) in water (3.5 mL) was added dropwise to a cooled solution of the ester 168 (640 mg, 2.81 mmol) in MeOH (10 mL) and CH$_2$Cl$_2$ (10 mL) at 0° C. After allowing the mixture to warm to room temperature and stirring for 96 h, excess CH$_2$Cl$_2$ and water were added. The aqueous portion was acidified (pH 2) with 2N HCl and the resulting white precipitate was extracted with EtOAc (×2). The combined EtOAc extracts were washed with water, brine, and dried, to give 7-acetyl-2-naphthoic acid (169). (575 mg, 96%) as a colorless solid. A sample was recrystallised from petroleum ether/CH$_2$Cl$_2$/Et$_2$O: mp 224-228° C.; $^1$H NMR: (CDCl$_3$) δ (CO$_2$H not observed) 8.82 (s, 1H), 8.60 (s, 1H), 8.23 (dd, J=8.6, 1.6 Hz, 1H), 8.18 (dd, J=8.7, 1.7 Hz, 1H), 7.97 (c, J=8.7 Hz, 2H), 2.76 (s, 3H). Anal. (C$_{13}$H$_{10}$O$_3$) C, H.

A solution of acid 169 (550 mg, 2.57 mmol), DPPA (850 mg, 3.08 mmol) and Et$_3$N (570 mg, 5.65 mmol) in t-BuOH (20 mL) was heated under reflux for 15 h. The mixture was poured into EtOAc and filtered through Celite. Chromatography on silica gel eluting with petroleum ether/CH$_2$Cl$_2$/EtOAc (8:1:1) gave tert-butyl 7-acetyl-2-naphthylcarbamate (170) (451 mg, 62%) as a colorless solid: mp (EtOAc) 161-163° C.; $^1$H NMR (CDCl$_3$) δ 8.38 (br s, 1H), 8.16 (br s, 1H), 7.91 (dd, J=8.5, 1.7 Hz, 1H), 7.80 (d, J=8.6 Hz, 1H), 7.78 (d, J=8.8 Hz, 1H), 7.43 (dd, J=8.8, 2.2 Hz, 1H), 6.68 (br s, 1H), 2.70 (s, 3H), 1.55 (s, 9H); $^{13}$C NMR δ 198.2, 152.7, 136.7, 135.0, 133.2, 132.0, 1297, 128.5, 128.0, 122.4, 121.6, 115.8, 81.0, 28.3, 26.6. Anal. (C$_{17}$H$_{19}$NO$_3$) C, H, N.

A mixture of carbamate 170 (420 mg, 1.47 mmol), NBS (292 mg, 1.62 mmol) and K$_2$CO$_3$ (244 mg, 1.77 mmol) in MeCN (10 mL) was heated at 40° C. under N$_2$ for 30 min then concentrated under reduced pressure. EtOAc and water were added to the residue, and the EtOAc portion was washed with water, brine and dried to give tert-butyl 7-acetyl-1-bromo-2-naphthylcarbamate (171) (530 mg, 99%) as a colorless solid: mp (petroleum ether/EtOAc) 114-117° C.; $^1$H NMR (CDCl$_3$) δ 8.70 (s, 1H), 8.50 (d, J=9.0 Hz, 1H), 7.97 (dd, J=3.5, 1.6 Hz, 1H), 7.84 (d, J=8.8 Hz, 1H), 7.81 (d, J=9.6 Hz, 1H), 7.34 (br s, 1H), 2.76 (s, 3H), 1.58 (s, 9H); $^{13}$C NMR δ 197.9, 152.4, 136.0, 135.8, 133.0, 131.5, 128.7, 128.5, 128.0, 123.1, 122.0, 111.0, 81.6, 28.3, 26.7. Anal. (C$_{17}$H$_{18}$BrNO$_3$) C, H, N.

NaH (7 mg, 0.17 mmol, 60% in oil) was added to a solution of 171 (50 mg, 0.14 mmol) in DMF (3 mL) at 40° C. 1,3-Dichloropropene (25 mg, 0.21 mmol) was added and the mixture was allowed to warm to room temperature over 1 h, then concentrated under reduced pressure. CH$_2$Cl$_2$ and water were added and the organic layer was washed with water, brine and dried. Chromatography eluting with petroleum ether/EtOAc (4:1) gave tert-butyl 7-acetyl-1-bromo-2-naphthyl-(3-chloro-2-propen-1-yl)carbonate (172) (55 mg, 92%) as a yellow oil; $^1$H NMR (CDCl$_3$) (mixture of rotamers and E and Z forms) δ 8.94 (s, 1H), 8.13-8.07 (m, 1H), 7.94-7.79 (m, 2H), 7.50-7.35 (m, 1H), 6.15-6.02 (m, 2H), 4.66-4.28, 4.02-3.91 (2 m, 2H), 2.78 (s, 3H), 1.34 (s, 9H). HRMS (CI) calcd. for C$_{20}$H$_{21}$$^{79}$Br$^{35}$ClNO$_3$ (MH$^+$) m/z 438.0472, found 438.0460.

A mixture of 172 (470 mg, 1.07 mmol), Bu$_3$SnH (380 mg, 1.29 mmol) and AIBN (18 mg, 0.11 mmol) in benzene (10 mL) was heated under reflux for 15 h, then concentrated under reduced pressure. EtOAc and water were added and the EtOAc portion was washed with water (×2), brine and dried. Chromatography eluting with petroleum ether/EtOAc (4:1) followed by recrystallization (MeOH) gave tert-butyl 8-acetyl-1-(chloromethyl)-1,2-dihydro-3H-benzo[e]indole-3-carboxylate (173) (320 mg, 82%) as colorless needles: mp 98-100° C.; $^1$H NMR (CDCl$_3$) δ 8.34 (s, 1H), 8.26 (br s, 1H), 7.91-7.84 (m, 2H), 7.81 (d, J=8.9 Hz, 1H), 436-428 (m, 1H), 4.21-4.09 (m, 2H), 3.97-3.90 (m, 1H), 3.59-3.51 (m, 1H), 2.72 (s, 3H), 1.61 (s, 9H); $^{13}$C NMR δ (one C not observed) 198.0, 142.4, 135.4, 132.2, 129.7, 129.5, 129.2, 123.6, 122.2, 119.1, 118.2, 68.2, 52.7, 46.5, 28.5, 26.9, 25.2. Anal. (C$_{20}$H$_{22}$ClNO$_3$) C, H, N.

A solution of 173 (100 mg, 0.28 mmol) in HCl(g): saturated dioxane (10 mL) was stirred for 4 h. The solvent was removed under reduced pressure to give the crude amine hydrochloride (82 mg, 0.26 mmol, 100%). This was immediately dissolved in pyridine (5 mL), cooled (0° C.) and treated with TFAA (88 mg, 0.42 mmol). After 1 h, the mixture was poured into ice water and extracted with CH$_2$Cl$_2$ (×3). The combined organic extracts were washed with aqueous HCl (1N, ×3), water, brine, and dried. Chromatography eluting with petroleum ether/EtOAc (1:1) gave 8-acetyl-1-(chloromethyl)-3-(trifluoroacetyl)-1,2-dihydro-3H-benzo[e]indole (174) (92 mg, 93%) as a colorless solid: mp petroleum ether/Et$_2$O) 161-163° C.; $^1$H NMR (CDCl$_3$) δ 8.55 (d, J=9.0

Hz, 1H), 8.41 (s, 1H), 8.02-7.95 (m, 2H), 7.92 (d, J=9.0 Hz, 1H), 4.68 (dt, J=11.5, 1.4 Hz, 1H), 4.47 (dd, J=11.4, 8.6 Hz, 1H), 4.34-4.26 (m, 1H), 3.98 (dd, J=11.5, 3.5 Hz, 1H), 3.63 (dd, J=11.5, 8.9 Hz, 0.1H), 2.74 (s, 3H); $^{13}C$ NMR δ 197.7, 154.6 (q, $J_{C-F}$ 37.8 Hz), 140.9, 135.8, 134.0, 130.2, 129.7, 128.6, 127.1, 124.0, 123.8, 119.5, 116.1 (q, $J_{C-F}$ 288 Hz), 52.6 (q, $J_{C-F}$ 4.1 Hz), 45.7, 42.7, 26.9. Anal. ($C_{17}H_{13}ClF_3NO_2$) C, H, N.

Solid 174 (57 mg, 0.16 mmol) was dissolved in conc. $H_2SO_4$ (5 mL) at 0° C., then treated dropwise with a cold (0° C.) solution of $KNO_3$ (16 mg, 0.16 mmol) in conc. $H_2SO_4$ (0.5 mL). After 15 min, the mixture was poured into ice water and extracted with $CH_2Cl_2$ (×6). The combined organic extracts were washed with water (×2), brine and dried. Chromatography eluting with petroleum ether/EtOAc (7:3) gave 8-acetyl-1-(chloromethyl)-5-nitro-3-(trifluoroacetyl)-1,2-dihydro-3H-benzo[e]indole (175) (25 mg, 39%) as an orange powder: mp (petroleum ether/EtOAc) 196-198° C.; $^1H$ NMR (CDCl$_3$) δ 9.23 (s, 1H), 8.58 (d, J=9.1 Hz, 1H, 8.49 (d, J=1.3 Hz, 1H), 8.17 (dd, J=9.1, 1.6 Hz, 1H), 4.73 (d, J=11.5 Hz, 1H), 4.56 (dd, J=11.4, 8.8 Hz, 1H), 4.47-4.39 (m, 1H), 3.98 (dd, J=11.6, 3.6 Hz, 1H), 3.77 (dd, J=11.6, 7.8 Hz, 1H), 2.78 (s, 3H). Anal. ($C_{17}H_{12}ClF_3N_2O_4$) C, H, N.

A solution of 175 (45 mg, 0.11 mmol) and $Cs_2CO_3$ (38 mg, 0.11 mmol) in MeOH (3 mL) and $CH_2Cl_2$ (6 mL) was stirred for 15 min. Water w added and the mixture was extracted with EtOAc (×3). The combined EtOAc extras were washed with water (×2), brine (×3), dried, and evaporated. The residue was dissolved in HCl(g) saturated dioxane (5 mL) and stirred for 1 h. The dioxane was evaporated to give 8-acetyl-1-(chloromethyl)-5-nitro-1,2-dihydro-3H-benzo[e]indole hydrochloride (176) (38 mg, 100%): mp>300° C.; $^1H$ NMR [(CID$_3$)$_2$SO] (two H not observed) 8.42 (d, J=1.3 Hz, 1 H), 8.19 (d, J=9.1 Hz, 1H), 7.80 (dd, J=9.1, 1.7 Hz, 1H), 7.77 (s, 1H), 4.41-4.33 (m, 1H), 3.96 (dd, J=11.0, 4.1 Hz, 1H), 3.85 (t, J=10.1 Hz, 1H), 3.77 (dd, J=11.0, 2.6 Hz, 1H), 3.73 (dd, J=10.3, 2.7 Hz, 1H), 2.74 (s, 3H); $^{13}C$ NMR δ 197.9, 150.0, 147.1, 135.3, 130.0, 127.1, 124.3, 123.6, 121.6, 119.8, 111.0, 50.8, 46.6, 42.7, 26.8. This material was used directly in the next step.

A mixture of 176 (35 mg, 0.10 mmol), 5-[2-(dimethylamino)ethoxy]indole-2-carboxylic acid hydrochloride (35 mg, 0.12 mmol) and EDCI (79 mg, 0.41 mmol) in DMA (3 mL) was stirred under a N$_2$ atmosphere for 15 h. The mixture was then partitioned between $CH_2Cl_2$ and cold (0° C.) 5%-aqueous $KHCO_3$. The aqueous portion was extracted with cold $CH_2Cl_2$ (×4) and the combined extracts were washed with water (×3), brine (×2) and dried. The solvent was evaporated and the residue was dissolved in $CH_2Cl_2$/MeOH and solvents were evaporated until precipitation began. The precipitate was filtered off and washed with MeOH to give 41 (38 mg, 69%) as an orange powder: mp 210-215° C.; $^1H$ NMR [(CD$_3$)$_2$SO] δ 11.71 (s, 1H), 9.26 (s, 1H), 8.73 (s, 1H), 8.45 (d, J=9.1 Hz, 1H), 8.12 (dd, J=9.1, 1.5 Hz, 1H, 7.41 (d, J=8.9 Hz, 1H), 7.22 (d, J=1.4 Hz, 1H), 7.18 (d, J=2.2 Hz, 1H, 6.95 (dd, J=8.9, 2.4 Hz, 1H), 4.97 (t, J=10.1 Hz, 1H), 4.87-4.78 (m, 1H), 4.74 (dd, J=10.8, 2.0 Hz, 1H), 4.22-4.12 (m, 2H), 4.08 (t, J=5.9 Hz, 2H, 2.81 (s, 3H), 2.66 (t, J=5.8 Hz, 2H), 2.25 (s, 6H); $^{13}C$ NMR δ197.7, 160.5, 153.0, 146.3, 141.5, 135.6, 133.9, 131.9, 129.8, 129.0, 127.4, 125.7, 125.2, 123.9, 123.4, 116.4, 116.3, 113.2, 106.1, 103.2, 66.1, 57.6, 54.7, 48.1, 45.3, 41.2, 27.0. Anal. ($C_{28}H_{27}ClN_4O_5$·½$H_2O$) C, H, N.

EXAMPLE 40

Methyl 1-(chloromethyl)-3-{5-[2-(dimethylamino)ethoxy]indol-2-carbonyl}-5-nitro-1,2-dihydro-3H-benzo[e]indole-8-carboxylate (42) (Scheme J). A solution of KOH (340 mg, 6.17 mmol) in MeOH (8 mL) and water (1 mL) was added dropwise to a solution of dimethyl 2,7-naphthalenedicarboxylate (177) [Bioorg. Med. Chem., 1998, 6, 1799] (1.52 g, 6.23 mmol) in MeOH (8 mL) and $CH_2Cl_2$ (8 mL). After 20 h, more $CH_2Cl_2$ and water were added, and the separated aqueous phase was acidified (pH 2) with 2N HCl. The resulting white precipitate was filtered off, washed with water, and dried in a vacuum desiccator. Chromatography eluting with $CH_2Cl_2$/MeOH (9:1 then 4:1) gave recovered 177 (0.50 g, 33%) and 7-(methoxycarbonyl)-2-naphthoic acid (178) (672 mg, 47%) as colorless crystals: mp (MeOH) 262-264° C.; $^1H$ NMR [(CD$_3$)$_2$SO] δ 13.0 (br s, 1H), 8.802 (s, 1H), 8.796 (s, 1H), 8.17-8.05 (m, 4H), 3.95 (s, 3H); $^{13}C$ NMR δ (one C not observed) 167.0, 166.0, 136.8, 131.8, 131.3, 129.2, 128.3, 128.1, 127.7, 127.6, 126.9, 52.3. Anal. ($C_{13}H_{10}O_4$) C, H.

A solution of acid 178 (50 mg, 0.22 mmol), DPPA (72 mg, 0.26 mmol) and Et$_3$N (48 mg, 0.48 mmol) in t-BuOH (5 mL) was heated under reflux for 20 h. The solvents were removed under reduced pressure and the residue was purified by chromatography eluting with $CH_2Cl_2$/MeOH (49:1) followed by recrystallization (EtOAc/petroleum ether) to give methyl 7-[(tert-butoxycarbonyl)amino]-2-naphthoate (179) (52 mg, 80%) as colorless needles. A sample was recrystallised: mp ($CH_2Cl_2$/n-hexane) 181-183° C.; $^1H$ NMR (CDCB) δ 8.52 (br s, 1H), 8.05 (br s, 1H), 7.94 (dd, J=8.5, 1.7 Hz, 1H), 7.79 (d, J=8.7 Hz, 2H), 7.51 (dd, J=8.8, 2.1 Hz, 1H), 6.67 (or s, 1H), 3.97 (s, 3H), 1.56 (s 9H); $^{13}C$ NMR 167.3, 152.7, 136.6, 133.1, 132.0, 130.4, 128.6, 127.9, 127.8, 123.8, 121.5, 115.6, 80.9, 52.2, 28.3. Anal. ($C_{17}H_{19}NO_4$) C, H, N.

A mixture of 179 (50 mg, 0.17 mmol), NBS (33 mg, 0.18 mmol) and $K_2CO_3$ (28 mg, 0.20 mmol) in MeCN (3 mL) was heated at 60° C. under N$_2$ for 30 min. The solvent was removed under reduced pressure and the residue was purified by chromatography eluting with petroleum ether/EtOAc (9:1) followed by recrystallization (petroleum ether) to give methyl 8-bromo-7-[(tert-butoxycarbonyl)amino]-2-naphthoate (180) (57 mg, 90%) as colorless crystals: mp 137-140° C.; $^1H$ NMR (CDCl$_3$) δ 8.89 (d, J=1.2 Hz, 1H), 8.49 (d, J=9.1 Hz, 1H), 8.01 (dd, J=8.6, 1.7 Hz, 1H), 7.83 (d, J=8.6 Hz, 1H), 7.82 (d, J=9.0 Hz, 1H), 7.35 (br s, 1H), 4.00 (s, 3H), 1.57 (s, 9H). Anal. ($C_{17}H_{18}BrNO_4$) C, H, N, Br.

NaH (57 mg, 1.42 mmol, 60% in oil) was added to a solution of bromide 180 (450 mg, 1.18 mmol) in DMF (5 mL) at 0° C. 1,3-Dichloropropene (260 mg, 2.37 mmol) was added and the mixture was allowed to warm to room temperature over 1 h, then concentrated under reduced pressure $CH_2Cl_2$ and water were added and the organic phase was washed with water (×2), brine (×2), dried, and filtered through silica gel to give methyl 8-bromo-7-[(tert-butoxycarbonyl)(3-chloro-2-propen-1-yl)amino]-2-naphthoate (181) (520 mg, 97%) as a yellow oil; $^1H$ NMR (CDCl$_3$) (mixture of rotamers and E and Z forms) δ 9.07 (s, 10H), 8.18-8.08 (m, 1H), 7.93-7.78 (m, 2H), 7.42-7.32 (m, 1H), 6.15-5.98 (m, 2H), 4.01 (s, 3H), 4.63-4.48 (m, 2H), 1.26, 1.24 (2 s, 9H). HRMS (FAB) calcd. for $C_{20}H_{21}{}^{79}Br{}^{35}ClNO_4$ (MH$^+$) m/z 454.0421, found 454.0421.

A mixture of 181 (500 mg, 1.10 mmol), Bu$_3$SnH (350 mg, 1.21 mmol) and AIBN (19 mg, 0.11 mmol) in benzene (8 mL)

was heated under reflux for 1.5 h. The benzene was removed under reduced pressure, the residue was triturated with pentane, and the solid obtained was recrystallised (MeOH) to give 8-methyl-3-(tert-butoxycarbonyl) 1-chloromethyl)-1,2-dihydro-3H-benzo[e]indole-8-carboxylate (182) (369 mg, 78%) as colorless needles: mp 143-145° C.; $^1$H NMR (CDCl$_3$) δ 8.45 (s, 1H), 8.31 (br s, 1H), 7.93 (dd, J=8.6, 1.5 Hz, 1H), 7.87 (d, J=8.6 Hz, 1H), 7.82 (d, J=8.9 Hz, 1H), 4.36-4.27 (m, 1H), 4.20-4.08 (m, 2H), 4.00 (s, 3H), 3.99-3.92 (m, 1H), 3.57-3.48 (m, 1H), 1.61 (s, 9H); $^{13}$C NMR δ 167.1, 152.4, 142.0, 132.1, 129.6, 129.2, 129.0, 128.4, 124.9, 124.1, 123.2, 118.0, 81.4, 52.6, 52.3, 46.5, 41.6, 28.4. Anal. (C$_{20}$H$_{22}$ClNO$_4$) C, H, N, Cl.

A solution of ester 182 (200 mg, 0.53 mmol) in HCl(g) saturated dioxane (10 mL) was stirred for 4 h, then evaporated, to give the amine hydrochloride (169 mg, 100%). A cold (0° C.) solution of this (85 mg, 0.27 mmol) in pyridine (4 mL) was treated with TFAA (66 mg, 0.32 mmol). After 30 min at 0° C., the mixture was poured into ice water and extracted with CH$_2$Cl$_2$ (×3). The combined organic extracts were washed with HCl (1N, ×2), water, brine, and dried. Chromatography eluting with petroleum ether/EtOAc/CH$_2$Cl$_2$ (7:2:1 then 8:1:1) followed by trituration with n-hexane gave methyl 1-(chloromethyl)-3-(trifluoroacetyl)-1,2-dihydro-3H-benzo[e]indolo-8-carboxylate (183) (88 mg, 87%) as colorless crystals: mp 161-163° C.; $^1$H NMR (CDCl$_3$) δ 8.55 (d, J=9.0 Hz, 1H), 8.52 (s, 1H), 8.07 (dd, J=8.6, 1.5 Hz, 1H), 7.95 (d, J=8.6 Hz, 1H), 7.92 (d, J=9.0 Hz, 1 H), 4.68 (dt, J=11.5, 1.4 Hz, 1H), 4.45 (dd, J=11.4, 8.6 Hz, 1H), 4.32-4.27 (m, 1H), 4.02 (s, 3H), 4.00 (dd, J=11.6, 3.3 Hz, 1H), 3.62 (dd, J=11.5, 9.2 Hz, 1H); $^{13}$C NMR δ 166.7, 154.8 (q, J$_{C-F}$ 37.4 Hz), 140.7, 134.0, 130.2; 129.4, 129.1, 128.4, 126.8, 125.4, 125.0, 119.4, 116.0 (q, J$_{C-F}$ 288 Hz), 76.7, 52.6 (q, J$_{C-F}$ 4.0 Hz), 45.7, 42.6. Anal. (C$_{17}$H$_{13}$ClF$_3$NO$_3$) C, H, N.

Cold (0° C.) conc. H$_2$SO$_4$ (8 mL) was added to cooled (0° C.) 183 (350 mg, 0.94 mmol). A cooled (0° C.) solution of KNO$_3$ (95 mg, 0.94 mmol) in 98% H$_2$SO$_4$ (0.5 mL) was then added dropwise. After 15 min, the mixture was poured into ice water and extracted with CH$_2$Cl$_2$ (×3). The combined CH$_2$Cl$_2$ extracts were washed with water (×2), brine and dried. Chromatography eluting with EtOAc/petroleum ether (4:1) gave methyl 1-(chloromethyl)-7-nitro-3-(trifluoroacetyl)-1,2-dihydro-3H-benzo[e]indole-8-carboxylate (185) (136 mg, 36%) as a brown powder: mp (CH$_2$Cl$_2$/MeOH), 165-168° C.; $^1$H NMR (CDCl$_3$) δ8.69 (d, J=9.0 Hz, 1H), 8.53 (s, 1H), 8.13 (s, 1H), 8.07 (d, J=9.0 Hz, 1H), 4.69 (d, J=11.5 Hz, 1H), 4.52 (dd, J=11.5, 8.6 Hz, 1H, 4.32-4.25 (m, 1H), 3.99 (s, 3H), 3.95 (dd, J=11.6, 3.5 Hz, 1H), 3.66 (dd, J=11.6, 8.5 Hz,1H); $^{13}$C NMR δ 165.9, 154.9 (q, J$_{C-F}$ 38.4 Hz), 144.8, 143.8, 132.1, 131.0, 130.0, 126.7, 126.11, 126.05, 125.7, 120.7, 115.8 (q, J$_{C-F}$ 288 Hz), 53.5, 52.8, 45.6, 42.3. Anal (C$_{17}$H$_{12}$ClF$_3$N$_2$O$_5$.¼EtOAC) C, H, N.

Further elution gave methyl 1-(chloromethyl)-5-nitro-3-(trifluoroacetyl)-1,2-dihydro-3H-benzo[e]indole-8-carboxylate (184) (140 mg, 36%) as a cream powder. A sample was triturated with MeOH to give colorless crystals: mp 243-245° C.; $^1$H NMR [(CD$_3$)$_2$SO] δ 9.09 (s, 1H), 8.75 (d, J=1.2 Hz, 1H), 8.51 (d, J=-9.2 Hz, 1H), 8.22 (dd, J=9.1, 1.6 Hz, 1H), 4.86-4.79 (m, 1H), 4.68-4.61 (m, 1H), 4.55-4.49 (m, 1H), 4.19 (dd, J=11.5, 3.5 Hz, 1H), 4.08 (dd, J=11.5, 5.5 Hz, 1H), 3.97 (s, 3H); $^{13}$C NMR δ 165.5, 150.3, 146.6, 139.3, 139.2, 134.8, 129.6, 128.7, 127.5, 126.3, 124.5, 123.0, 116.0, 52.8, 52.7, 47.6, 40.9. Anal. (C$_{17}$H$_{12}$ClF$_3$N$_2$O$_5$) C, H, N.

A solution of 184 (100 mg, 0.24 mmol) and Cs$_2$CO$_3$ (312 mg, 0.96 mmol) in MeOH (10 mL) and CH$_2$Cl$_2$ (15 mL) was stirred for 1.5 h. Water was added and the mixture was extracted with CH$_2$Cl$_2$ (×3). The combined organic extracts were washed with water, brine and dried. The solvent was evaporated and the residue was dissolved in CH$_2$Cl$_2$MeOH and, solvents were evaporated under reduced pressure until precipitation began. The precipitate was filtered off and washed with MeOH to give methyl 1-(chloromethyl)-5-nitro-1,2-dihydro-3H-benzo[e]indole-8-carboxylate (186) (76 mg, 100%): mp 161-163° C.; $^1$H NMR [(CD$_3$)$_2$SO] δ 8.40 (dd, J=1.6, 0.6 Hz, 1H), 8.22 (dd, J=9.1, 0.4 Hz, 1H), 7.82 (dd, J=9.1, 1.7 Hz, 1H), 7.78 (s, 1H), 6.49 (d, J=1.6 Hz, 1H), 4.35-4.28 (m, 1H), 3.93 (s, 3H), 3.89-3.82 (m, 2H), 3.79-3.69 (m, 2H). HRMS (CI) calcd. for C$_{15}$H$_{13}$$^{35}$ClN$_2$O$_4$ (M$^+$) m/z 320.0534, found 320.0563.

A solution of amine 186 (70 mg, 0.22 mmol) in HCl(g) saturated dioxane (5 mL) was stirred for 2 h. The dioxane was removed under reduced pressure to give the hydrochloride salt (78 mg, 100%). 5-[2-(Dimethylamino)ethoxy]indole-2-carboxylic acid hydrochloride (75 mg, 0.26 mmol), EDCI (126 mg, 0.66 mmol), and DMA (5 mL) were added and the mixture was stirred under a N$_2$ atmosphere for 5 h. The mixture was partitioned between CH$_2$Cl$_2$ and ice-cold 5% aqueous KHCO$_3$. The aqueous portion was extracted with cold CH$_2$Cl$_2$ (×3) and the combined extracts were washed with water, brine and dried. The solvent was evaporated and the residue was dissolved in CH$_2$Cl$_2$/MeOH and solvents were concentrated under reduced pressure until precipitation began. The precipitate was filtered off and washed with MeOH to give crude 42 (101 mg, 84%) as an orange powder: HRMS (FAB) calcd. for C$_{28}$H$_{27}$$^{35}$ClN$_4$O$_6$ (MH$^+$) m/z 551.1697, found 551.1696. $^1$H NMR analysis showed that this sample contained 8% of the corresponding exomethylene compound (methyl 3-{5-[2-(dimethylamino)ethoxy]indol-2-carbonyl}-1-methylene-5-nitro-1,2-dihydro-3H-benzo[e]indole-8-carboxylate). The sample was purified by HPLC (Synergi MAX column, CH$_3$CN/H$_2$O/TFA, pH 2.5) to give 42-TFA (38 mg, 99% purity by HPLC analysis) as an orange powder: mp>320° C.; $^1$H NMR [(CD$_3$)$_2$SO] δ 11.80 (d, J=1.8 Hz, 1H), 9.63 (br s, 1H), 9.26 (s, 1H), 8.74 (d, J=1.1 Hz, 1H), 8.49 (d, J=9.4 Hz, 1H), 8.17 (dd, J=9.1, 1.7 Hz, 1H), 7.48 (d, J=8.9 Hz, 1H), 7.28 (d, J=2.4 Hz, 1H), 7.25 (d, J=1.6 Hz, 1H), 7.05 (dd, J=8.9, 2.4 Hz, 1H), 4.96 (dd, J=10.6, 9.4 Hz, 1H), 4.83-4.74 (m, 1H), 4.70 (dd, J=10.8, 2.3 Hz, 1H), 4.35 (t, J=4.8 Hz, 2H), 4.14 (dd, J=11.4, 3.4 Hz, 1H), 4.05 (dd, J=11.4, 5.8 Hz, 1H), 3.98 (s, 3H), 3.57 (br s, 2H), 2.91 (br s, 6H); $^{13}$C NMR δ 165.5, 160.5, 152.0, 146.3, 141.5, 133.5, 132.3, 130.1, 129.1, 128.9, 127.3, 126.5, 125.9, 124.3, 123.5, 116.6, 116.1, 113.3, 106.2, 104.0, 62.6, 55.6, 54.8, 52.6, 47.8, 42.8, 41.4.

EXAMPLE 41

1-(Chloromethyl)-N-[2-(dimethylamino)ethyl]-5-nitro-3-(5,6,7-trimethoxyindol-2-carbonyl)-1,2-dihydro-3H-benzo[e]indole-8-carboxamide (44) (Scheme J). A suspension of 184 (314 mg, 0.75 mmol) in a mixture of conc. H$_2$SO$_4$ (4.5 mL) and water (0.5 mL) was stirred at 90° C. for 3 h, then cooled and diluted with water (80 mL). The solution was clarified by filtration and adjusted to pH 4 with aqueous NH$_3$. The resulting precipitate was collected, dissolved in EtOAc and the solution was then filtered, concentrated under reduced pressure to a small volume and diluted with hexane to give 1-(chloromethyl)-5-nitro-1,2-dihydro-3H-benzo[e]indole-8-carboxylic acid (187) (226 mg, 95%) as a red solid: mp 205-208° C.; $^1$H NMR [(CD$_3$)$_2$SO] δ 13.3 (v br, 1H), 8.38 (d, J=1.3 Hz, 1H), 8.19 (d, J=9.1 Hz, 1H), 7.82 (dd, J=9.1, 1.6 Hz, 1H), 7.76 (s, 1H), 6.45 (s, 1H), 4.35-4.28 (m, 1H), 3.91-3.80 (m, 2H), 3.76 (dd, J=11.2, 8.5 Hz, 2H), 3.72 (dd, J=10.3, 2.8 Hz, 1H). Anal. C$_{14}$H$_{11}$ClN$_2$O$_4$) C, H, N.

A stirred solution of 187 (120 mg, 0.39 mmol) in dry DMF (1.5 mL) was treated at 0° C. with N,N-dimethyl-1,2-ethanediamine (107 μL, 0.97 mmol), followed by the dropwise addition of diethyl cyanophosphonate (128 μL, 93%, 0.78 mmol). The mixture was warmed to room temperature for 45 min, then poured into dilute aqueous $NH_3$ saturated with NaCl. The resulting solid was collected, washed with water and recrystallised twice from $CH_2Cl_2$/i-$Pr_2O$ to give 1-(chloromethyl)-N-[2-(dimethylamino)ethyl]-5-nitro-1,2-dihydro-3H-benzo[e]indole-8-carboxamide (188) (88 mg, 60%) as a red solid: mp 178-180° C.; $^1$H NMR [$(CD_3)_2SO$] δ 8.68 (t, J=5.7 Hz, 1H), 8.22 (d, J=1.2 Hz, 1H), 8.16 (d, J=9.1 Hz, 1H), 7.77 (dd, J=9.1, 1.7 Hz, 1H), 7.72 (s, 1H), 6.41 (d, J=1.7 Hz, 1H), 4.28-4.18 (m, 1H), 3.98 (dd, J=10.9, 3.7 Hz, 1H), 3.84 (td, J=9.7, 2.4 Hz, 1H), 3.75 (dd, J=−11.0, 9.0 Hz, 2H), 3.49-3.37 (m, 2H), 2.45 (t, J=7.0 Hz, 2H), 2.21 (s, 6H). Anal. ($C_{18}H_{21}ClN_4O_3$) C, H, N.

A suspension of 188 (72 mg, 0.19 mmol) in dioxane (15 mL) was treated at 20° C. with HCl(g) until colorless, then evaporated to dryness under reduced pressure. To the resulting dihydrochloride salt was added 5,6,7-trimethoxyindole-2-carboxylic acid (58 mg, 0.23 mmol), EDCI (148 mg, 0.77 mmol) and dry DMA (2.0 mL), and the mixture was stirred at room temperature for 1.5 h. The mixture was poured into saturated aqueous $KHCO_3$ and the precipitated solid was collected and dissolved in $CH_2Cl_2$. The solution was washed with water, dried, concentrated under reduced pressure below 25° C., and then diluted with hexane to give crude 44. Treatment of a solution of 44 in $CH_2Cl_2$ with HCl(g)/EtOAc/hexane, followed by crystallization from MeOH/EtOAc, gave 44.HCl (71 mg, 57%) as a yellow solid: mp 228-229° C. (dec.); $^1$H NMR [$(CD_3)_2SO$]δ 11.58 (d, J=1.7 Hz, 1H), 9.87 (v br s, 1H), 9.28-9.14 (m, 2H), 8.71 (s, 1H), 8.46 (d, J=9.1 Hz, 1H), 8.14 (dd, J=−9.1, 1.5 Hz, 1H), 7.19 (d, J=2.2 Hz, 1H), 6.98 (s, 1H), 4.94 (t, J=10.7 Hz, 1H), 4.72-4.61 (ma, 2H), 4.25-4.15 (m, 2H), 3.95 (s, 3H), 3.83 (s, 3H), 3.81 (s, 3H), 3.76-3.68 (m, 2H), 3.26 (after $D_2O$ exchange, t, J=5.7 Hz, 2H), 2.87 (br s, 6H). Anal. ($C_{30}H_{32}ClN_5O_7$.HCl) C, H, N.

EXAMPLE 42

1-(Chloromethyl)-3-{5-[2-(dimethylamino)ethoxy]indol-2-carbonyl}-5-nitro-1,2-dihydro-3H-benzo[e]indole-8-carboxamide (43) (Scheme K). A solution of 2,7-dibromonaphthalene (189) (20.0 g, 0.07 mol) in 1-methyl-2-pyrrolidinone (60 mL) was purged with $N_2$ for 10 min. CUCN (7.52 g, 0.09 mol) and pyridine (0.5 mL) were added and the mixture was heated at 180° C. under $N_2$ for 1.5 h. After cooling to 80° C., $FeCl_3$ (40 g), water (200 mL) and conc. HCl (50 mL) were added and the mixture was stirred for 1 h at 80° C. The mixture was cooled, brine was added, and the mixture was extracted with $CH_2Cl_2$ (×3). The organic extracts were washed with aqueous HCl (2N, x2), water, 10% aqueous NaOH, brine, and dried. Chromatography eluting with $CH_2Cl_2$/petroleum ether (1:1, then 4:1) gave 7-bromo-2-naphthonitrile (190) (6.40 g, 39%) as a cream powder. A sample was recrystallised (petroleum ether) to give colorless needles: mp 126-128° C.; $^1$H NMR ($CDCl_3$) δ 8.13 (s, 1H), 8.06 (d, J=1.5 Hz, 1H), 7.89 (d, J=8.5 Hz, 1H), 7.76 (d, J=8.8 Hz, 1H), 7.71 (dd, J=8.8, 1.9 Hz, 1H), 7.62 (dd, J=8.4, 1.5 Hz, 1H); $^{13}$C NMR δ 133.2, 133.0, 132.4, 130.6, 130.3, 129.6, 129.2, 126.8, 121.9, 118.7, 110.6. Anal. ($C_{11}H_6BrN$) C, H, N, Br.

Nitrile 190 (6.0 g, 26 mmol), Pd(OAc)$_2$ (0.58 g, 2.59 mmol), 1,3-bis(diphenylphosphino)propane (1.07 g, 2.59 mmol), MeOH (30 mL), $Et_3N$ (12 mL) and DMSO (30 mL) were placed in a Berghof reactor (HR-200) and purged with CO(g) for 5 min. The reactor was then pressurized with CO(g) (15 bar) and heated at 70° C. for 20 h. After cooling, EtOAc was added and the mixture was filtered through Celite/silica gel. The solvents were removed under reduced pressure and the residue partitioned between $CH_2Cl_2$ and brine. The organic layer was dried and evaporated, and the residue was recrystallised (MeOH) to give methyl 7-cyano-2-naphthoate (191) (5.15 g, 92%), as a colorless solid: mp 136-136.5° C.; lit. mp. [Aust. J. Chem., 1965, 18, 1351] 137-139° C.; $^1$H NMR ($CDCl_3$) δ 8.65 (s, 1H), 8.34 (s, 1H), 8.22 (d, J=8.2 Hz, 1H), 7.97 (d, J=8.9 Hz, 1H), 7.95 (d, J=8.9 Hz, 1H), 7.72 (d, J=8.2 Hz, 1H), 4.01 (s, 3H).

A solution of NaOH (1.36 g, 34 mmol) in water (35 mL) was added dropwise to a solution of 191 (4.95 g, 24 mmol) in EtOH (100 mL) and $CH_2Cl_2$ (30 mL) and the mixture was stirred for 15 h. Water was added to dissolve the white solid and the mixture was extracted with $CH_2Cl_2$ (×2) and EtOAc. The aqueous portion was acidified (pH 2) with aqueous HCl (2N) and the resulting precipitate was filtered off, washed with water, and dried in a vacuum desiccator to give 7-cyano-2-naphthoic acid (192) (4.60 g, 99%), as a colorless powder: mp 279-283° C.; lit. mp [Aust. J. Chem., 1965, 18, 1351] 286-288° C.; $^1$H NMR [$(CD_3)_2SO$] δ 13.25 (br s, 1H), 8.81 (s, 1H), 8.75 (s, 1H), 8.20 (d, J=8.5 Hz, 1H), 8.17 (d, J=8.5 Hz, 2H), 8.15 (d, J=8.5 Hz, 2H), 7.92 (dd, J=8.5, 1.3 Hz, 1H).

A solution of acid 192 (6.60 g, 23 mmol), diphenyl phosphorazidate (7.71 g, 28 mmol) and $Et_3N$ (5.19 g, 51 mmol) in t-BuOH (50 mL) was heated under reflux for 6 h. The mixture was partitioned between EtOAc and brine. The EtOAc layer was dried and filtered through silica gel. Chromatography eluting with $CH_2Cl_2$/petroleum ether/MeOH (25:24:1) followed by recrystallization ($CH_2Cl_2$/petroleum ether) gave tert-butyl 7-cyano-2-naphthylcarbamate (193) (5.30 g, 85%) as colorless needles. A sample was recrystallised (EtOAc/n-hexane): mp 126-128° C.; $^1$H NMR ($CDCl_3$) δ 8.13 (s, 1H), 8.07 (s, 1H), 7.82 (d, J=8.1 Hz, 1H), 7.80 (d, J=8.1 Hz, 1H), 7.51-7.48 (m, 2H), 6.71 (br s, 1H), 1.56 (s, 9H); $^{13}$C NMR δ 152.5, 137.5, 133.4, 133.1, 131.0, 128.9, 128.8, 124.9, 122.0, 119.3, 114.4, 110.0, 81.3, 28.3. Anal. ($C_{16}H_{16}N_2O_2$) C, H, N.

A mixture of 193 (1.90 g, 7.09 mmol), NBS (1.41 g, 7.20 mmol) and $K_2CO_3$ (1.11 g, 8.50 mmol) in MeCN (20 mL) was heated at 60° C. under $N_2$ for 30 min. The solvent was removed under reduced pressure and the residue was partitioned between $CH_2Cl_2$ and water. The organic layer was washed with water (×2), brine and dried. Filtration through silica gel gave tert-butyl 1-bromo-7-cyano-2-naphthylcarbamate (194) (2.45 g, 100%) as a colorless powder. A sample was recrystallised (petroleum ether) to give colorless needles: mp 139-141° C.; $^1$H NMR ($CDCl_3$) δ 8.58 (d, J=9.1 Hz, 1H), 8.54 (d, J=1.0 Hz, 1H), 7.86 (d, J=8.4 Hz, 1H), 7.83 (d, J=9.1 Hz, 1H), 7.56 (dd; J=8.3, 1.4 Hz, 1H), 7.36 (br s, 1H), 1.57 (s, 9H); $^{13}$C NMR δ 152.3, 136.7, 132.5, 132.0, 131.4, 129.4, 128.3, 125.6, 122.4, 119.0, 111.3, 109.4, 81.9, 28.3. Anal. ($C_{16}H_{15}BrN_2O_2$) C, H, N, Br.

A solution of 194 (2.50 g, 7.21 mmol) in DMF (20 mL) was added to a suspension of NaH (350 mg, 8.65 mmol, 60% in oil) in DMF (20 mL) at 0° C. 1,3-Dichloropropene (1.60 g, 14 mmol) was added and the mixture was allowed to warm to room temperature over 2 h. The DMF was removed under reduced pressure and the residue was partitioned between $CH_2Cl_2$ and water. The organic layer was washed with water (×2), brine (×2) and dried. Filtration through silica gel gave tert-butyl 1-bromo-7-cyano-2-naphthyl(3-chloro-2-propen-1-yl)carbamate (195) (3.28 g, 100%) as a pale yellow oil; $^1$H NMR ($CDCl_3$) (mixture of rotamers and E and Z forms) δ 8.73 (s, 1H), 7.93-7.96 (m, 1H), 7.83-7.87 (m, 1H, 7.68-7.70 (m, 1H), 7.39-7.46 (m, 1H), 6.00-6.11 (m, 2 H), 4.49-4.62 (m, 1H), 4.33-4.43 (m, 1H), 1.33, 1.32 (2's, 9 W. HRMS (FAB) calcd. for $C_{19}H_{18}{}^{79}Br^{35}ClN_2O_2$ (MH$^+$) m/z 421.0318, found 421.0330.

A mixture of 195 (3.00 g, 7.13 mmol), Bu$_3$SnH (2.49 g, 8.55 mmol) and AIBN (120 mg, 0.71 mmol) in benzene (20 mL) was heated under reflux for 1.5 h. The benzene was removed under reduced pressure and the residue was triturated with pentane (×4) and recrystallised (MeOH) to give tert-butyl 1-(chloromethyl)-8-cyano-1,2-dihydro-3H-benzo[e]indole-3-carboxylate (196) (2.24 g, 92%) as colorless needles: mp 138-140° C.; $^1$H NMR (CDCl$_3$) δ 8.35 (br s, 1H), 8.09 (s, 1H), 7.90 (d, J=8.5 Hz, 1H), 7.82 (d, J=9.0 Hz, 1H), 7.48 (dd, J=8.5, 1.5 Hz, 1H), 430 (br d, J=11.2 Hz, 1H), 4.18 (dd, J=11.8, 8.7 Hz, 1H), 4.50 (tt, J=9.3, 3.0 Hz, 1H), 3.87 (dd, J=−11.3, 3.3 Hz, 1H), 3.53 (dd, J=11.2, 9.6 Hz, 1H), 1.61 (s, 9 M); $^{13}$C NMR δ 152.3, 142.9, 131.2, 130.2, 130.0, 128.9, 128.2, 124.2, 123.3, 119.2, 118.8, 110.5, 81.8, 52.8, 462, 41.5, 28.4. Anal. ($C_{19}H_{19}ClN_2O_2$) C, H, N.

A solution of 196 (30 mg, 0.088 mmol) in HCl(g) saturated dioxane (3 mL) was stirred for 1 h. The solvent was evaporated to provide the crude amine hydrochloride (24 mg, 100%). This solid was cooled to 0° C. and treated with conc. H$_2$SO$_4$ (2 mL). A cooled (O OC) solution of KNO$_3$ (9 mg, 0.088 mmol) in conc. H$_2$SO$_4$ (0.5 mL) was then added dropwise. After 15 min, the mixture was poured into ice water and conc. aqueous ammonia was carefully added until the pH of the mixture was 3-4. Solid KHCO$_3$ was then carefully added until the pH of the mixture was 8. The mixture was partitioned between CH$_2$Cl$_2$ and water, and the aqueous layer was extracted with CH$_2$Cl$_2$ (×3). The combined organic extracts were washed with brine and dried. The CH$_2$Cl$_2$ was removed under reduced pressure and the residue was triturated with MeOH to give 1-(chloromethyl)-5-nitro-1,2-dihydro-3H-benzo[e]indole-8-carbonitrile (197) (18 mg, 72%) as red crystals: mp 231-234° C.; $^1$H NMR [(CD$_3$)$_2$SO] δ 8.54 (dd, J=1.5, 0.5 Hz, 1 H), 8.22 (dd, J=9.0, 0.4 Hz, 1H), 7.80 (s, 1H), 7.59 (dd, J=9.0, 1.6 Hz, 1H), 6.63 (d, J=1.3 Hz, 1H), 4.32-4.23 (m, 1H), 3.95 (dd, J=11.0, 3.8 Hz, 1H), 3.84 (td, J=10.3, 2.3 Hz, 1H), 3.79-3.70 (m, 2H); $^{13}$C NMR δ 151.8, 148.1, 130.6, 129.9, 126.8, 125.7, 125.0, 120.0, 119.6, 112.8, 111.4, 51.8, 47.5, 43.5. Anal. ($C_{14}H_{10}ClN_3O_2$) C, H, N.

A solution of 197.HCl (81 mg, 0.25 mmol) in couc. H$_2$SO$_4$ (9 mL) and water (1 mL) was heated at. 60° C. for 1 h, then poured into cold water. Conc. aqueous NH$_3$ was carefully added until the pH of the mixture was 3, followed by careful addition of solid KHCO$_3$ until the pH of the mixture was 8. The mixture was extracted with cold CH$_2$Cl$_2$ (×3), and the combined organic extracts were washed with water, brine and dried. The solvent was evaporated and the residue was dissolved in CH$_2$Cl$_2$MeOH. The solvents were concentrated until precipitation began. The precipitate was filtered off and washed with MeOH to give crude 1-(chloromethyl)-5-nitro-1,2-dihydro-3H-benzo[e]indole-8-carboxamide (198) (37 mg, 48%) as red crystals: mp>300° C.; $^1$H NMR [(CD$_3$)$_2$SO] δ (two H not observed) 8.32 (d, J=1.3 Hz, 1H), 8.17 (d, J=9.1 Hz, 1H), 7.80 (dd, J=9.1, 1.7 Hz, 1H), 7.72 (s, 1H), 7.53 (br s, 1H), 4.26-4.18 (m, 1H), 3.99 (dd, J=10.9, 3.8 Hz, 1H), 3.83 (t, J=10.1 Hz, 1H), 3.77-3.69 (m, 2H). $^1$H NMR also showed the presence of an unidentified impurity (ca. 10%) which was not removed by chromatography. HRMS (CI) calcd. for $C_{14}H_{12}{}^{35}ClN_3O_3$ $_{(M}{}^+)$ m/z 305.0567, found 305.0564.

A solution of 198 (30 mg, 0.098 mmol) in HCl(g) saturated dioxane (5 mL) was stirred for 1 h, then evaporated to give the amine hydrochloride (34 mg, 0.098 mmol, 100%). 5-[2-(Dimethylamino)ethoxy]indole-2-carboxylic acid hydrochloride (34 mg, 0.098 mmol), EDCI (57 mg, 0.30 mmol), and DMA (4 mL) were added and the mixture was stirred under a N$_2$ atmosphere for 15 h. The mixture was partitioned between EtOAc and cold (0° C.) 5% aqueous KHCO$_3$. The aqueous portion was extracted with cold EtOAc (×3) and the combined extracts were washed with water, brine and dried. The solvent was evaporated and the residue was dissolved in CH$_2$Cl$_2$/MeOH, and solvents were concentrated until precipitation began. The precipitate was filtered off and washed with MeOH to give crude 43 (35 mg, 66%) as an orange powder: HRMS (FAB) calcd. for $C_{27}H_{26}{}^{35}ClN_5O_5$ (MH$^+$) m/z 536.1701, found 536.1710. $^1$H NMR analysis showed that this sample contained 13% of the corresponding exomethylene compound (3-{5-[2-(dimethylamino)ethoxy]indol-2-carbonyl}-1 methylene-5-nitro-1,2-dihydro-3H-benzo[e]indole-8-carboxamide). The sample was purified by HPLC (Synergi MAX column, CH$_3$CN/H$_2$O/TFA, pH 2.5) to give 43-TFA (38 mg) as an orange powder: mp>320° C.; $^1$H NMR [(CD$_3$)$_2$SO] δ 11.71 (d, J=1.7 Hz, 1H), 9.60 (br s, 1H), 9.21 (s, 1H), 8.62 (d, J=1.2 Hz, 1H), 8.43 (d, J=9.1 Hz, 1H), 8.40 (s, 1H), 8.14 (dd, J=7.3, 1.7 Hz, 1H), 7.70 (fr s, 1H), 7.47 (d, J=8.9 Hz, 1H), 7.27 (d, J=2.4 Hz, 1H), 7.23 (d, J=1.7 Hz, 1H), 7.04 (dd, J=. 8.9, 2.4 Hz, 1H), 4.97 (dd, J=10.8, 9.5 Hz, 1H), 4.72 (dd, J=10.8, 2.2 Hz, 1H), 4.68-4.61 (m, 1H), 4.33 (t, J=5.0 Hz, 2H), 4.21 (dd, J=11.3, 3.2 Hz, 1H), 4.13 (dd, J=11.1, 6.1 Hz, 1H), 3.48 (br s, 2H), 2.85 (s, 6H); $^{13}$C NMR δ 166.9, 160.5, 152.1, 146.3, 141.1, 133.6, 133.2, 132.2, 130.2, 129.0, 127.3, 126.5, 123.6, 123.0, 122.8, 116.1, 115.8, 113.3, 106.0, 104.0, 63.0, 55.8, 54.7, 47.7, 43.0, 41.5. Anal. ($C_{27}H_{26}ClN_5O_6$.TFA.1½H$_2$O) C, H.

EXAMPLE 43

1-Chloromethyl)-3-{5-[2-dimethylamino)ethoxy]indol-2-carbonyl}-5-nitro-1,2-dihydro-3H-benzo[e]indole-8-carbonitrile (45) (Scheme K). A solution of nitrile 197 (160 mg, 0.56 mmol) in HCl(G) saturated dioxane (15 mL) was stirred for 1 h, then the dioxane was removed under reduced pressure to give the crude amine hydrochloride (180 mg, 0.56 mmol, 100%). 5-[2-(Dimethylamino)ethoxy]indole-2-carboxylic acid hydrochloride (190 mg, 0.67 mmol), EDCI (319 mg, 1.67 mmol), and DMA (5 mL) were added and the mixture was stirred under a N2 atmosphere for 4 h. The mixture was then partitioned between CH$_2$Cl$_2$ and cold (0° C.) 5% aqueous KHCO$_3$. The aqueous layer was extracted with cold CH$_2$Cl$_2$ (×4) and the combined extracts were washed with water (×3), brine and dried. The solvent was evaporated and the residue was dissolved in CH$_2$Cl$_2$/MeOH and solvents were concentrated under reduced pressure until precipitation began. The precipitate was filtered off and washed with MeOH to give 45 (256 mg, 89%) as an orange powder: mp>340° C.; $^1$H NMR [(CD$_3$)$_2$SO] δ 11.67 (d, J=1.5 Hz, 1H), 9.29 (s, 1H), 8.91 (d, J=−1.0 Hz, 1H), 8.49 (d, J=9.1 Hz, 1H), 7.97 (dd, J=9.1, 1.5 Hz, 1H), 7.40 (d, J=8.9 Hz, 1H), 7.20 (d, J=1.7 Hz, 1H), 7.17 (d, J=2.3 Hz, 1H), 6.95 (dd, J=8.9, 2 Hz, 1H), 4.95 (dd, J=10.6, 9.5 Hz, 1H), 4.75-4.63 (m, 2H), 4.19-4.09 (m, 2H), 4.07 (t, J=5.9 Hz, 2H), 2.67 (t, J=5.9 Hz, 2H), 2.25 (s, 6H); $^{13}$C NMR δ 160.5, 152.9, 146.2, 142.1, 133.0, 131.9, 130.5, 129.6, 128.5, 127.9, 127.3, 124.9, 122.8, 118.2, 117.3, 116.4, 113.2, 111.0, 106.2, 103.1, 65.9, 57.6, 54.7, 47.9, 45.3, 41.2. Anal. ($C_{27}H_{24}ClNsO_4$) C, H, N.

EXAMPLE 44

1-(Chloromethyl)-8-(methylsulfonyl)-5-nitro-3-(5,6,7-trimethoxyindol-2-carbonyl)-1,2-dihydro-3H-benzo[e]indole (46) (Scheme L). A stirred solution of 189 (5.72 g, 20.0 mmol) in THF (80 mL) was treated dropwise at −78° C. with n-BuLi (2.5 M in hexanes, 8.40 mL, 21.0 mmol) under N$_2$.

The mixture was stirred at −78° C. for 20 min, then treated slowly with dimethyl disulfide (2.16 mL, 24 mmol) and allowed to warm to room temperature. The solvent was removed under reduced pressure to give a residue that was shaken with water, and the resulting solid was crystallised fom petroleum ether to give 2-bromo-7-(methylsulfanyl) naphthalene (199) (4.14 g, 82%): mp 80-81° C.; $^1$H NMR [(CD$_3$)$_2$SO] δ 8.11 (d, J=1.9 Hz, 1H), 7.86 (d, J=9.1 Hz, 1H), 7.83 (d, J=9.1 Hz, 1H), 7.71 (d, J=1.8 Hz, 1H), 7.54 (dd, J=8.72, 2.0 Hz, 1H), 7.44 (dd, J=8.6, 2.0 Hz, 1H), 2.58 (s, 3H). Anal. (C$_{11}$H$_9$BrS) C, H, S.

A stirred solution of 199 (850 mg, 3.36 mmol) in THF (10 mL) was treated at −78° C. with n-BuLi (2.5 M in hexanes, 1.48 mL, 3.70 mmol) under N$_2$. The mixture was stirred at −78° C. for 15 nm in, then treated with excess CO$_2$(g) and allowed to warm to room temperature. The solvent was removed under reduced pressure, and the residue was partitioned between water and EtOAc. The aqueous layer was acidified, and the resulting solid was crystallised from MeOH to give 7-(methylsulfanyl)-2-naphthoic acid (200) (577 mg, 79%): mp 217° C.; $^1$H NMR [(CD$_3$)$_2$SO] δ 13.0 (v br, 1H), 8.53 (d, J=0.7 Hz, 1H), 7.98-7.87 (m, 4H), 7.53 (dd, J=8.7, 1.9 Hz, 1H), 2.60 (s, 3H). Anal. (C$_{12}$H$_{10}$O$_2$S) C, H.

A mixture of 200 (2.00 g, 9.16 mmol) and NaBO$_3$.4H$_2$O (8.00 g, 52 mmol) in AcOH (50 mL) was stirred at 55° C. for 2 h, then cooled and diluted with water. The resulting solid was recrystallised twice from EtOAc to give 7-(methylsulfonyl)-2-naphthoic acid (201) (2.02 g, 88%) as a white solid: mp 273-274° C.; $^1$H NMR [(CD$_3$)$_2$SO] δ 13.3 (br s, 1H), 8.85 (d, J=0.5 Hz, 1H), 8.79 (d, J=1.8 Hz, 1H), 8.27 (d, J=8.7 Hz, 1H), 8.18 (2 s, 2H), 8.08 (dd, J=8.7, 1.9 Hz, 1H), 3.25 (after D$_2$O exchange, s, 3H). Anal. (C$_{12}$H$_{10}$O$_4$S) C, H.

A suspension of acid 201 (2.08 g, 8.31 mmol) in dry t-BuOH (30 mL) containing powdered molecular sieves (1 g) was treated with Et$_3$N (1.39 mL, 9.97 mmol) and stirred under N$_2$ at room temperature for 30 min. DPPA (1.97 mL, 9.14 mmol) was added and the mixture was stirred at reflux for 7 h, then concentrated to half volume under reduced pressure and poured into dilute aqueous KHCO$_3$. The resulting solid was purified by chromatography on silica gel, eluting with CH$_2$Cl$_2$/EtOAc (19:1), followed by recrystallization from CH$_2$Cl$_2$/iPr$_2$O to give tert-butyl 7-(methylsulfonyl)-2-naphthylcarbamate (202) (2.11 g, 79%) as a white solid: mp 179-180° C.; $^1$H NMR [(CD$_3$)$_2$SO] δ 9.76 (s, 1H), 8.39 (d, J=1.5 Hz, 1H), 8.28 (d, J=1.5 Hz, 1H), 8.06 (d, J=8.6 Hz, 1H), 7.98 (d, J=9.0 Hz, 1H), 7.77 (dd, J=8.6, 1.9 Hz, 1H), 7.74 (dd, J=9.2, 2.0 Hz, 1H), 3.27 (s, 3H), 1.52 (s, 9H). Anal. (C$_{16}$H$_{19}$NO$_4$S) C, H, N.

A mixture of 202 (2.05 g, 6.38 mmol) and NBS (1.31 g, 7.36 mmol) in MeCN (40 mL) was stirred at reflux for 2 h, then concentrated under reduced pressure. The residue was dissolved in CH$_2$Cl$_2$, and the solution was washed with 10% aqueous Na$_2$SO$_3$ and water, dried and concentrated under reduced pressure. The residue was purified by chromatography on silica gel, eluting with CH$_2$Cl$_2$/EtOAc (19:1), followed by recrystallization from MeOH to give tert-butyl 1-bromo-7-(methylsulfonyl)-2-naphthylcarbamate (203) (2.37 g, 93%) as a white solid: mp 166-167° C.; $^1$H NMR [(CD$_3$)$_2$SO] δ 8.99 (s, 1H), 8.70 (d, J=1.7 Hz, 1H), 8.25 (d, J=8.5 Hz, 1H), 8.10 (d, J=8.8 Hz, 1H), 8.00 (dd, J=8.5, 1.8 Hz, 1H), 7.97 (d, J=8.9 Hz, 1H), 3.32 (s, 3H), 1.50 (s, 9H). Anal. (C$_{16}$H$_{18}$BrNO$_4$S) C, H, N.

A stirred solution of 203 (2.29 g, 5.72 mmol) in dry DMF (20 mL) was treated portionwise at 0° C. with NaH (275 mg, 60% in oil, 6.88 mmol). The mixture was warmed to room temperature for 30 min, then cooled to 0° C. and treated with 1,3-dichloropropene (1.66 mL, 18 mmol, mixed isomers). The mixture was stirred at room temperature for a further 6 h, then diluted with 10% aqueous NaCl and extracted with EtOAc (×2). The combined organic layers were washed with water (×2), dried, and concentrated to dryness under reduced pressure at 100° C. The residue was chromatographed on silica gel, eluting with CH$_2$Cl$_2$/EtOAc (19:1) to give crude tert-butyl 1-bromo-7-(methylsulfonyl)-2-naphthyl(3-chloro-2-propen-1-yl)carbamate (204) (2.63 g, 97%) as a foam: $^1$H NMR [(CD$_3$)$_2$SO] (mixture of rotamers and B and Z forms) δ 8.78 (s, 1H), 8.32 (dd, J=8.6, 2.2 Hz, 1H), 8.18, 8.17 (2 d, J=8.7 Hz, 1H), 8.13-8.06 (1, 1H), 7.75, 7.70 (2 d, J=8.7 Hz, 1H), 6.44-6.29 (m, 1H), 6.20-6.01 (m, 1H), 4.58-4.48, 4.43-4.22, 4.16-4.05 (3 m, 21H), 3.35 (s, 3H), 1.50, 1.27 (2 s, 9H). HRMS (FAB) calcd. for C$_{19}$H$_{22}$$^{79}$Br$^{35}$ClNO$_4$S (m/z 474.0141, found 474.0143.

A solution of 204 (1.60 g, 3.37 mmol) in dry benzene (30 mL) was treated with Bu$_3$SnH (0.91 mL, 3.38 mmol) followed by AIBN (0.1 g, 0.6 mmol). The mixture was stirred under N$_2$ at reflux for 2 h, then concentrated under reduced pressure. The residue was dissolved in EtOAc, and the solution was diluted with hexane and refrigerated. The resulting semisolid was chromatographed on silica gel, eluting with CH$_2$Cl$_2$/EtOAc (19:1), and the product was triturated with i-Pr$_2$O/hexane to give tert-butyl 1-(chloromethyl)-8-(methylsulfonyl)-1,2-dihydro-3H-benzo[e]indole-3-carboxylate (205) (0.88 g, 66%) as an amorphous solid: $^1$H NMR [(CD$_3$)$_2$SO] δ 8.41 (d, J=1.6 Hz, 1H), 8.2 (v br, 1H), 8.17 (d, J=8.6 Hz, 1H), 8.03 (d, J=8.9. Hz. H), 7.80 (dd, J=8.6, 1.8 Hz, 1H), 4.42-4.33 (m, 1H), 4.21 (t, J=10.4 Hz, 1H), 4.12 (dd, J=11.6, 2.9 Hz, 1H), 4.07 (dd, J=11.2, 3.4 Hz, 1H). 3.89 (dd, J=11.2, 7.1 Hz; 1H), 3.33 (s, 3H), 1.55 (s, 9H). Anal. (C$_{19}$H$_{22}$ClNO$_4$S.½i-Pr$_2$O) C, H, N.

Powdered 205 (350 mg, 0.88 mmol) was added to stirred conc. H$_2$SO$_4$ (4 mL) at 0° C. and the mixture was warmed to room temperature for 20 min. The resulting solution of amine was cooled to −5° C. and treated dropwise with a solution of KNO$_3$ (98 mg, 0.97 mmol) in conc. H$_2$SO$_4$ (1 mL). The mixture was stirred at 0° C. for a further 5 min, then poured into ice/water and neutralized with dilute aqueous NH$_3$. The resulting solid was filtered off, dissolved in CH$_2$Cl$_2$, and the solution was filtered through a column of silica gel and evaporated to dryness. Recrystallization from CH$_2$Cl$_2$/i-Pr$_2$O followed by EtOAc gave 1-(chloromethyl)-8-(methylsulfonyl)-5-nitro-1,2-dihydro-3H-benzo[e]indole (206) (207 mg, 69%) as a red solid: mp 193-194° C.; $^1$H NMR [(CD$_3$)$_2$SO] δ 8.34 (d, J=1.5 Hz, 1H), 8.31 (d, J=9.1 Hz, 1H), 7.82 (s, 1H), 7.76 (dd, J=9.1, 1.9 Hz, 1H), 6.62 (br s, 1H), 4.37-4.28 (m, 1H), 3.93 (dd, J=11.1, 4.1 Hz, 1H), 3.87 (td, J=9.8, 2.3 Hz, 1H), 3.80-3.70 (1, 2H), 3.33 (s, 3H). Anal. (C$_{14}$H$_{13}$ClN$_2$O$_4$S) C, Ht N. The structure of 206 was confirmed by x-ray crystallography see FIG. 1.

A suspension of 5,6,7-trimethoxyindole-2-carboxylic acid (77 mg, 0.31 mmol) in dry CH$_2$Cl$_2$ (3 mL) was treated with oxalyl chloride (80 μL, 0.92 mmol) followed by DMF (10 μl). The mixture was stirred at room temperature for 30 min, then evaporated to dryness under reduced pressure and re-evaporated after addition of benzene. The resulting acid chloride was cooled to −5° C. and treated with an ice-cold solution of amine 206 (70 mg, 0.21 mmol) in dry pyridine (2 mL) containing DMAP (5 mg). The mixture was warmed to room temperature for 15 min then poured into dilute aqueous KHCO$_3$ and the precipitated solid was collected and dissolved in CH$_2$Cl$_2$/EtOAc (8:1). The solution was filtered through a column of silica gel and the product was recrystallised from CH$_2$Cl$_2$/EtOAc to give 46 (78 mg, 66%) as an orange solid: mp 265° C.; $^1$H NMR [(CD$_3$)$_2$SO] δ 11.61 (d, J=1.8 Hz, 1H), 9.26 (s, 1H), 8.69 (d, J=1.5 Hz, 1H), 8.59 (d, J=9.2 Hz, 1H), 8.13 (dd, J=9.2, 1.8 Hz, 1H), 7.21 (d, J=2.2 Hz, 1H), 6.98 (s, 1H), 4.93 (dd, J=10.7, 9.4 Hz, 1H), 4.78-4.70 (m, 1H), 4.66 (dd, J=10.9, 2.1 Hz, 1H), 4.16 (dd, J=11.3, 3.5 Hz, 1H), 4.07 (t, J=5.7 Hz, 1H), 3.94 (s, 3H), 3.83 (s, 3H), 3.81 (s, 3H), 3.42 (s, 3H). Anal. ($C_{26}H_{24}ClN_3O_8S$) C, H, N.

EXAMPLE 45

1-(Chloromethyl)-3-{5-[2-(dimethylamino)ethoxy]indol-2-carbonyl}-8-(methylsulfonyl)-5-nitro-1,2-dihydro-3H-benzo[e]indole (47) (Scheme L). A mixture of amine 206 (80 mg, 0.23 mmol), 5-[2-(dimethylamino)ethoxy]-indol-2-carboxylic acid hydrochloride (80 mg, 0.28 mmol), EDCI (180 mg, 0.94 mmol) and anhydrous TsOH (30 mg, 0.17 mmol) in dry DMA (5 mL) under $N_2$ was stirred at room temperature for 3 h, then poured into dilute aqueous $NH_3$. The precipitated solid was collected, stirred as a suspension in MeOH (10 mL) for 15 min. cooled to 0° C. and then recollected to give crude 47. Treatment of 47 in MeOH/$CH_2Cl_2$ with HCl(g)/EtOAc/hexane, followed by crystallization from MeOH gave 47-HCl (71 mg, 50%) as a yellow solid: mp>300° C.; $^1$H NMR [($CD_3)_2SO$] δ 11.82 (s, 1H), 10.0 (v br, 1H), 9.31 (s, 1H), 8.70 (d, J=1.5 Hz, 1H), 8.60 (d, J=9.2 Hz, 1H), 8.14 (dd, J=9.2, 1.8 Hz, 1H), 7.47 (d, J=8.9 Hz, 1H), 7.27 (d, J=2.3 Hz, 1H), 7.25 (d, J=1.7 Hz, 1H), 7.04 (dd, J=8.9, 2.4 Hz, 1H), 4.97 (t, J=9.8 Hz, 1H), 4.82-4.69 (m, 2H), 4.35 (t, J=5.0 Hz, 2H), 4.18 (dd, J=11.3, 3.2 Hz, 1H), 4.08 (dd, J=11.4, 5.7 Hz, 1H), 3.52 (br s, 2H), 3.42 (s, 31), 2.87 (s, 6H). Anal. ($C_{27}H_{27}ClN_4O_6S$.HCl) C, H, N.

EXAMPLE 46

1-(Chloromethyl)-5-nitro-3-(5,6,7-trimethoxyindol-2-carbonyl)-1,2-dihydro-3H-benzo[e]indole-8-sulfonamide (48) (Scheme M). n-BuLi (1.50 mL, 3.50 mmol, 2.3 M solution in hexanes) was added to a solution of 189 (1.00 g, 3.50 mmol) in THF (15 mL) under nitrogen at −78° C. After 20 min, $SO_2(g)$ was bubbled into the solvent and the resulting mixture was allowed to warm to room temperature and stirred for 12 h. The THF was evaporated, the resulting solid was suspended in $CH_2Cl_2$ (25 mL) at 0° C., and NCS (0.47 g, 3.50 mmol) was added. After 1 h the mixture was filtered through Celite and purified by chromatography on silica gel, eluting with petroleum ether/EtOAc (95:5), followed by recrystallization (petroleum ether/$Et_2O$) to give 7-bromo-2-naphthalenesulfonyl chloride (207) (1.86 g, 87%) as colorless crystals: mp 100-101° C.; $^1$H NMR (CDCl$_3$) δ 8.51 (d, J=1.3 Hz, 1H), 8.21 (d, J=1.2 Hz, 1H), 8.04 (d, J=8.8 Hz, 1H), 8.01 (dd, J=8.8, 1.8 Hz, 1H), 7.84 (d, J=8.8 Hz, 1H), 7.81 (dd, J=8.8, 1.8 Hz, 1H). Anal. ($C_{10}H_6BrClO_2S$) C, H.

A mixture of 207 (1.50 g, 4.92 mmol), dibenzylamine (1.45 g, 7.38 mmol), and Et$_3$N (0.75 g, 7.38 mmol) in THF (15 mL) was stirred at room temperature for 48 h. The solvents were evaporated under reduced pressure and the residue was extracted with EtOAc. The EtOAc extracts were washed with water and brine, then dried and evaporated. The residue was purified by chromatography on silica gel eluting with petroleum ether/EtOAc (95:5 then 1:1) to give N,N-dibenzyl-7-bromo-2-naphthalenesulfonamide (208) (2.11 g, 92%). A sample was recrystallised from petroleum ether/EtOAc as colorless crystals: mp 127-129° C.; $^1$H NMR (CDCl$_3$) δ 8.25 (d, J=1.4 Hz, 1H), 8.05 (d, J=1.6 Hz, 1H), 7.91 (d, J=8.7 Hz, 1H), 7.79 (dd, J=8.6, 1.8 Hz, 1H), 7.77 (d, J=8.5 Hz, 1H), 7.71 (dd, J=8.8, 1.9 Hz, 1H), 7.22-7.15 (m, 6H), 7.09-7.04 (m, 4H), 4.39 (s, 4H); $^{13}$C NMR δ 138.9, 135.4, 133.3, 133.0, 132.1, 131.4, 129.4, 129.3, 128.6, 128.5, 127.8, 127.3, 123.0, 121.6, 50.6. Anal. ($C_{24}H_{20}BrNO_2S$.¹/₁₀Bn$_2$NH) C, H, N.

A mixture of 208 (2.10 g, 4.51 mmol), Pd(OAc)$_2$ (101 mg, 0.45 mmol), 1,3-bis(diphenylphosphino)propane (186 mg, 0.45 mmol), MeOH (30 mL), Et$_3$N (10 mL), and DMSO (5 mL) were placed in a pressure vessel and purged with CO(g) for 5 rain. The reactor was then pressurized with CO(g) (50 bar) and heated at 70° C. for 12 h. After cooling EtOAc was added and the mixture was filtered through Celite. Solvents were removed under reduced pressure and the residue was partitioned between $CH_2Cl_2$ and brine. The $CH_2Cl_2$ layer was dried and evaporated, and the residue was purified by chromatography on silica gel, eluting with petroleum ther/EtOActCH$_2$Cl$_2$ (7:1:2) to give methyl 7-[(dibenzylamino)sulfonyl]-2-naphthoate (209) (1.75 g, 87%). A sample was recrystallised from petroleum ether/EtOAc as colorless crystals: mp 141-142° C.; $^1$H NMR (CDCl$_3$) δ 8.64 (s, 1H), 8.45 (s, 1H), 8.22 (dd, J=8.6, 1.6 Hz, 1H), 7.98 (d, J=8.4 Hz, 1H), 7.95 (d, J=7.0 Hz, 1H), 7.88 (dd, J=8.7, 1.8 Hz, 1H), 7.22-7.15 (m, 6H), 7.10-7.04 (m, 4H), 4.40 (s, 4H), 4.01 (s, 3H); $^{13}$C NMR δ 166.5, 138.7, 136.6, 135.4, 132.0, 131.5, 129.6, 129.2, 129.1, 128.6, 128.5, 128.2, 128.1, 127.8, 124.8, 52.5, 50.6. Anal. ($C_{26}H_{23}NO_4S$) C, H, N.

A solution of KOH (720 mg, 12.8 mmol) in MeOH (5 mL) and H2O (2 mL) was added dropwise to a solution of 209 (1.90 g, 4.27 mmol) in MeOH (10 mL) and CH$_2$Cl$_2$ (15 mL). After 48 h at room temperature CH$_2$Cl$_2$ and H$_2$O were added. The aqueous layer was separated and acidified to pH 2 with 2 M HCl. The resulting white precipitate was collected, dissolved in CH$_2$Cl$_2$, and the solution was washed with H$_2$O and brine. The CH$_2$Cl$_2$ layer was dried, the solvent was evaporated, and the residue was dried in a vacuum desiccator. Recrystallization from CH$_2$Cl$_2$/petroleum ether gave 7-[(dibenzylamino)sulfonyl]-2-naphthoic acid (210) (2.00 g, 99%) as colorless crystals: mp 189-190° C.; $^1$H NMR (CDCl$_3$) δ (CO$_2$H not observed) 8.76 (s, 1H), 8.47 (s, 1H), 8.29 (dd, J=8.6, 1.5 Hz, 1H), 8.01 (d, J=8.8 Hz, 1H), 7.92 (dd, J=8.7, 1.8 Hz, 1H), 7.23-7.15 (m, 6H), 7.12-7.05 (m, 4H), 5.29 (s, 1H), 4.42 (s, 4H); $^{13}$C NMR δ 170.8, 139.0, 137.0, 135.4, 133.1, 131.4, 129.7, 129.3, 128.6, 128.5, 128.4, 128.2, 128.1, 127.8, 125.3, 50.7. Anal. ($C_{25}H_{21}NO_4S$) C, H, N.

A solution of 210 (1.95 g, 4.52 mmol), DPPA (1.49 g, 5.43 mmol) and Et$_3$N (1.01 g, 9.95 mmol) in t-BuOH (40 mL) was heated at reflux for 15 h. The solvents were removed under reduced pressure and the residue purified by chromatography on silica gel, eluting with petroleum ether/EtOAc (4:1), to give tert-butyl 7-[(dibenzylamino)sulfonyl]-2-naphthylcarbamate (211) (1.37 g, 62%). A sample was recrystallised from Et$_2$O/petroleum ether as colorless needles: mp 139-140° C.; $^1$H NMR (CDCl$_3$) δ8.51 (d, J=1.2 Hz, 1H), 8.03 (d; J=1.3 Hz, 1H), 7.86 (d, J=8.7 Hz, 1H), 7.82 (d, J=8.9 Hz, 1H), 7.68 (dd, J=8.6, 1.8 Hz, 1H), 7.57 (dd, J=8.8, 2.1 Hz, 1H), 7.22-7.12 (m, 6H), 7.08-7.01 (m, 4H), 6.75 (s, 1H), 4.37 (s, 4H), 1.56 (s, 9H); $^{13}$C NMR δ 152.1, 137.7, 137.0, 135.1, 132.5, 130.6, 128.5, 128.2, 128.1, 127.9, 127.2, 127.1, 121.3, 120.6, 114.9, 80.6, 50.1, 27.8. Anal. ($C_{29}H_{30}N_2O_4S$) C, H, N.

A mixture of 211 (1.15 g, 2.29 mmol), NBS (450 mg, 2.52 mmol), and K$_2$CO$_3$ (380 mg, 2.75 mmol) in MeCN (25 mL) was stirred at 40° C. under nitrogen for 30 min. The solvent was removed under reduced pressure and the residue was partitioned between EtOAc and H$_2$O. The EtOAc layer was washed with H$_2$O, brine, then dried and evaporated. The residue was recrystallised from EtOAc/Et$_2$O/petroleum ether to give tert-butyl 1-bromo-7-[(dibenzylamino)sulfonyl]-2-naphthylcarbamate (212) as colorless crystals: mp 150-151° C.; $^1$H NMR (CDCl$_3$) δ 8.69 (d, J=1.6 Hz, 1H), 8.57 (d, J=9.1 Hz, 1H), 7.89 (d, J=8.6 Hz, 1H), 7.85 (d, J=9.1 Hz, 1H), 7.74 (dd, J=8.6, 1.8 Hz, 1H), 7.38 (s, 1H), 7.22-7.15 (m, 6H), 7.12-7.05 (m, 4H), 4.40 (s, 4H), 1.58 (s, 9H); $^{13}$C NMR δ

152.4, 139.6, 136.5, 135.5, 132.0, 131.5, 129.7, 128.6, 128.5, 128.1, 127.7, 126.8, 122.1, 121.8, 110.4, 81.8, 50.6, 28.3. Anal. ($C_{29}H_{29}BrN_2O_4S$) C, H, N.

NaH (107 mg, 2.69 mmol, 60% in oil) was added to a solution of 212 (1.3 g, 2.24 mmol) in DMF (15 mL) at 0° C. 1,3-Dichloropropene (414 mg, 3.36 mmol, mixed isomers) was added and the mixture was allowed to warm to room temperature over 12 h. The DMF was evaporated under reduced pressure and the residue was partitioned between EtOAc and $H_2O$. The EtOAc layer was washed with $H_2O$, brine, then dried and evaporated. The residue was purified by chromatography on silica gel, eluting with petroleum ether/EtOAc (4:1) to give tert-butyl 1-bromo-7-[(dibenzylamino)sulfonyl]-2-naphthyl(3-chloro-2-propen-1-yl)carbamate (213) (1.39 g, 95%) as a yellow foam: $^1$H NMR ($CDCl_3$) (mixture of rotamers and E and Z forms) δ 8.86 (s, 1H), 7.97-7.91 (m, 1H), 7.89-7.82 (m, 2H), 7.51-7.31, 7.26-7.16 (2 m, 7H), 7.13-7.06 (m, 4H), 6.14-6.01 (m, 2H), 4.64-4.48, 4.02-3.90 (2 m, 2H), 4.43 (s, 4H), 1.56, 1.33 (2 s, 9H). HRMS (FAB) calcd. for $C_{32}H_{32}{}^{79}Br^{35}ClN_2O_4S$ (M) 655.1033, found 655.1032.

A mixture of 213 (1.00 g, 1.53 mmol), $Bu_3SnH$ (550 mg, 1.83 mmol), and AIBN (50 mg, 0.31 mmol) in benzene (25 mL) was heated at reflux for 15 min, then concentrated under reduced pressure. The residue was partitioned between EtOAc and $H_2O$ and the EtOAc layer was washed with $H_2O$, brine and dried and evaporated. The residue was purified by chromatography on silica gel, eluting with petroleum ether/EtOAc (9:1) to give tert-butyl 1-(chloromethyl)-8-[(dibenzylamino)sulfonyl]-1,2-dihydro-3H-benzo[e]indole-3-carboxylate (214) (850 mg, 97%). A sample was recrystallised from $Et_2O$/petroleum ether as colorless needles: mp 131-133° C.; $^1$H NMR ($CDCl_3$) δ 8.30 (br s, 1H), 8.29 (d, J=1.5 Hz, 1H), 7.93 (d, J=8.7 Hz, 1H), 7.84 (d, J=9.0 Hz, 1H), 7.66 (dd, J=8.6, 1.8 Hz, 1H), 7.23-7.15 (m, 6H), 7.09-7.03 (m, 4H), 4.41 (s, 4H), 4.28 (d, J=11.5 Hz, 1H), 4.15 (dd, J=11.6, 9.0 Hz, 1H), 4.02 (tt, J=9.0, 2.9 Hz, 1H), 3.75 (dd, J=11.3, 3.5 Hz, 1H), 3.48 (dd, J=11.2, 9.3 Hz, 1H), 1.61 (s, 9H); $^{13}$C NMR δ 152.4, 142.7, 138.9, 135.5, 131.3, 130.5, 129.8, 128.9, 128.50, 128.46, 127.7, 124.3, 122.4, 120.3, 118.4, 81.8, 52.7, 50.5, 46.4, 41.4, 28.4. Anal. ($C_{32}H_{33}ClN_2O_4S$) C, H, N.

A solution of 214 (850 mg, 1.48 mmol) in HCl(g)-saturated dioxane (10 mL) was stirred for 4 h at room temperature. The dioxane was evaporated under reduced pressure and the resulting pale yellow solid was dissolved in pyridine (10 mL) at 0—C. Trifluoroacetic anhydride (470 mg, 2.23 mmol) was added and the mixture was stirred at 0° C. for 30 min, then poured into ice water and extracted with EtOAc (×3). The combined EtOAc extracts were washed with 1 M HCl (×3), $H_2O$, and brine, then dried and evaporated. The residue was purified by chromatography on silica gel, eluting with petroleum ether/EtOAc (9:1) to give N,N-dibenzyl-1-(chloromethyl)-3-(trifluoroacetyl)-1,2-dihydro-3H-benzo[e]indole-8-sulfonamide (215) (840 mg, 99%). A sample was recrystallised from EtOAc/$Et_2O$/petroleum ether as colorless crystals: mp 119-121° C.; $^1$H NMR ($CDCl_3$) δ 8.60 (d, J=9.0 Hz, 1H), 8.25 (d, J=8.7 Hz, 1H), 8.02 (d, J=8.7 Hz, 1H), 7.95 (d, J=9.0 Hz, 1H), 7.78 (dd, J=8.7, 1.8 Hz, 1H), 7.23-7.16 (m, 6H), 7.10-7.04 (m, 4H), 4.65 (d, J=11.6 Hz, 1H), 4.48-4.37 (m, 5H), 4.22-4.16 (m, 1H), 3.78 (dd, J=11.5, 3.5 Hz, 1H), 3.54 (dd, J=11.5, 8.5 Hz, 1H). Anal. ($C_{29}H_{24}ClF_3N_2O_3S$) C, H, N.

Sulfonamide 215 (750 mg, 1.31 mmol) was cooled to 0° C., dissolved in conc. $H_2SO_4$ (20 mL) at 0° C., and the solution was stirred at this temperature for 2 h. Ice water and EtOAc were added and the mixture was extracted with EtOAc (×3). The combined extracts were washed with brine (×3), dried, and evaporated to give 1-chloromethyl)-3-(trifluoroacetyl)-1,2-dihydro-3H-benzo[e]indole-8-sulfonamide (216) (490 mg, 96%). A sample was recrystallised from $CH_2Cl_2$/EtOAc as yellow crystals: mp 229-231° C.; $^1$H NMR [($CD_3)_2SO$] δ 8.45 (d, J=9.0 Hz, 1H), 8.42 (s, 1H), 8.21 (d, J=8.7 Hz, 1H), 8.11 (d, J=9.0 Hz, 1H), 7.87 (dd, J=8.7, 1.7H, 1H), 7.51 (s, 2H), 4.65-4.57 (m, 1H), 4.57-4.50 (m, 1H), 4.44 (d, J=10.8 Hz, 1H), 4.18 (dd, J=11.3, 3.1 Hz, 1H), 4.05 (dd, J=11.3, 5.9 Hz, 1H). Anal. ($C_{15}H_{12}ClF_3N_2O_3S \cdot \frac{1}{2}H_2O$) C, H, N.

Ice-cold conc. $H_2SO_4$ (14 mL) was added to 216 (450 mg, 1.15 mmol) at 0° C. with stirring. A solution of $KNO_3$ (128 mg, 1.26 mmol) in conc. $H_2SO_4$ (1 mL) at 0° C. was then added dropwise. After 15 min the mixture was poured into ice water and extracted with EtOAc (×3). The combined extracts were washed with $H_2O$, brine, dried, and evaporated under reduced pressure. The residue was purified by chromatography on silica gel, eluting with petroleum ether/EtOAc (3:2) to give 1-(chloromethyl)-7-nitro-3-(trifluoroacetyl)-1,2-dihydro-3H-benzo[e]indole-8-sulfonamide (218) (76 mg, 15%). A sample was recrystallised from petroleum ether/EtOAc as yellow crystals: mp 192-195° C.; $^1$H NMR [($CD_3)_2SO$] δ 8.79 (s, 1H), 8.65 (s, 1H), 8.59 (d, J=9.0 Hz, 1H), 8.31 (d, J=9.1 Hz, 1H), 7.88 (s, 2H), 4.66 (dd, J=10.5, 9.3 Hz, 1H), 4.58-4.51 (m, 1H), 4.47 (d, J=11.1 Hz, 1H), 4.19 (dd, J=11.3, 3.3 Hz, 1H), 4.08 (dd, J=11.3, 5.9 Hz, 1H). Anal. ($C_{15}H_{11}ClF_3N_3O_5S$) C, H, N.

Further elution gave 1-(chloromethyl)-5-nitro-3-(trifluoroacetyl)-1,2-dihydro-3H-benzo[e]indole-8-sulfonamide (217) (383 mg, 77%). A sample was recrystallised from petroleum ether/EtOAc as orange crystals: mp 251-254° C.; $^1$H NMR [($CD_3)_2SO$] δ 9.09 (s, 1H), 8.58 (d, J=8.9 Hz, 1H), 8.57 (d, J=2.0 Hz, 1H), 8.11 (dd, J=9.4, 1.6 Hz, 1H), 7.66 (s, 2H), 4.76-4.63 (m, 2H), 4.52 (d, J=10.5 Hz, 1H), 4.22 (dd, J=11.3, 3.1 Hz, 1H), 4.11 (dd, J=11.4, 5.3 Hz, 1H). Anal. ($C_{15}H_{11}ClF_3N_3O_5S$) C, H, N.

A solution of 217 (50 mg, 0.114 mmol) and $Cs_2CO_3$ (58 mg, 0.172 mmol) in MeOH (2 mL), THF (2 mL), and $CH_2Cl_2$ (2 mL) was stirred at room temperature for 15 min. Water was added and the mixture was extracted with EtOAc (×3). The combined EtOAc extracts were washed with $H_2O$ (×2), brine (×3), then dried and evaporated under reduced pressure. The resulting red solid was stirred in HCl(g)-saturated dioxane (5 mL) for 30 min then evaporated under reduced pressure. 5,6,7-Trimethoxyindole-2-carboxylic acid (34 mg, 0.137 mmol), EDCI (87 mg, 0.456 mmol), and DMA (3 mL) were added and the mixture was stirred at room temperature under nitrogen for 15 h. The mixture was partitioned between EtOAc and ice-cold 5% aqueous $KHCO_3$. The aqueous portion was extracted with cold EtOAc (×4) and the combined extracts were washed with $H_2O$ (×3), brine (×2) and dried. Addition of $Et_2O$ gave a precipitate of 48 (43 mg, 66%) as a red powder: mp 264-266° C. (dec.); $^1$H NMR [($CD_3)_2SO$] δ 11.60 (s, 1H), 9.21 (s, 1H), 8.54 (d, J=9.4 Hz, 1H), 8.53 (d, J=2.3 Hz, 1H), 8.04 (dd, J=9.2, 1.8 Hz, 1H), 7.64 (s, 2H), 7.19 (d, J=1.9 Hz, 1H), 6.98 (s, 1H), 4.94 (dd, J=11.1, 9.9 Hz, 1H), 4.70-4.60 (m, 2H), 4.17 (dd, J=11.4, 3.4 Hz, 1H), 4.08 (dd, J=11.4, 5.8 Hz, 1H), 3.94 (s, 3H), 3.83 (s, 3H), 3.81 (s, 3H). HRMS (FAB) calcd. for $C_{25}H_{23}{}^{35}ClN_4O_8S$ ($MH^+$) 575.1003, found 575.0989. Anal. ($C_{25}H_{23}ClN_4O_8S \cdot \frac{1}{2}EtOAc$) C, H, N.

EXAMPLE 47

1-(Chloromethyl)-3-{5-[2-(dimethylamino)ethoxy]indol-2-carbonyl}-5-nitro-1,2-dihydro-3H-benzo[e]indole-8-sulfonamide (49) (Scheme M). A solution of 217 (50 mg, 0.114 mmol) and $Cs_2CO_3$ (58 mg, 0.172 mmol) in MeOH (2 mL), THF (2 mL), and $CH_2Cl_2$ (2 mL) was stirred at room temperature for 15 min. Water was added and the mixture was extracted with EtOAc (×3). The combined EtOAc extracts were washed with $H_2O$ (×2), brine (×3), then dried and evaporated under reduced pressure. The resulting red solid was stirred in HCl(g)-saturated dioxane (5 mL) for 30 min then evaporated under reduced pressure. 5-[2-(Dimethylamino) ethoxy]indole-2-carboxylic acid hydrochloride (39 mg, 0.137 mmol), EDCI (87 mg, 0.456 mmol), and DMA (3 mL) were added and the mixture was stirred at room temperature under nitrogen for 15 h. The mixture was partitioned between $CH_2Cl_2$ and ice-cold 5% aqueous $KHCO_3$. The aqueous portion was extracted with cold $CH_2Cl_2$ (×4) and the combined extracts were washed with $H_2O$ (×3), brine (×2) and dried. Addition of $Et_2O$ gave a precipitate of 49 (43 mg, 66%) as an orange powder: mp 260-265° C. (dec.); $^1H$ NMR [$(CD_3)_2SO$] δ 11.71 (d, J=1.7 Hz, 1H), 9.26 (s, 1H), 8.55 (d, J=8.9 Hz, 1H), 8.53 (d, J=2.1 Hz, 1H), 8.04 (dd, J=9.3, 1.7 Hz, 1H, 7.64 (s, 2H), 7.42 (d, J=8.9 Hz, 1H), 7.19 (dd, J=10.2, 1.7 Hz, 2H), 6.95 (dd, J=8.9, 2.4 Hz, 1H), 4.98 (dd, J=10.1, 9.6 Hz, 1H), 4.72 (dd, J=11.0, 2.4 Hz, 1H), 4.71-4.63 (m, 1H), 4.18 (dd, J=11.5, 3.4 Hz, 1H), 4.10 (dd, J=11.4, 5.9 Hz, 2H), 4.08 (t, J=5.9 Hz, 2H), 2.66 (t, J=5.8 Hz, 2H), 2.24 (s, 6H). HRMS (FAB) calcd. for $C_{26}H_{26}{}^{35}ClN_5O_6S$ (MH$^+$) m/z 572.1371, found 572.1362. Anal. ($C_{26}H_{26}ClN_5O_6S.\frac{1}{2}H_2O$) C, H, N.

EXAMPLE 48

1-(Chloromethyl)-3-{5-[2-(dimethylamino)ethoxy]indol-2-carbonyl}-5,7-dinitro-1,2-dihydro-3H-benzo[e]indole-8-sulfonamide (50) (Scheme M). Ice cold $H_2SO_4$ (98%, 5 mL) was added to 218 (30 mg, 0.069 mmol) at 0° C. with stirring. An ice-cold solution of $KNO_3$ (9 mg, 0.089 mmol) in $H_2SO_4$ (98%, 1 mL) was then added dropwise. After 1 h the mixture was poured into ice water and extracted with EtOAc (×3). The combined EtOAc extracts were washed with $H_2O$, brine and dried. Chromatography eluting with petroleum ether/EtOAc (1:1) gave 1-(chloromethyl)-5,7-dinitro-3-(trifluoroacetyl)-1,2-dihydro-3H-benzo[e]indole-8-sulfonamide (219) (7 mg, 21%) as an orange powder: mp 201-204° C.; $^1H$ NMR (CDCl$_3$) δ 9.49 (s, 1H), 9.29 (s, 1H), 8.71 (s, 1H), 5.67 (s, 2H), 4.73 (d, J=10.8 Hz, 1H), 4.62 (dd, J=11.3, 8.8 Hz, 1H), 4.52-4.45 (m, 1H), 3.97 (dd, J=11.8, 3.5 Hz, 1H), 3.85 (dd, J=11.8, 6.3 Hz, 1H). HRMS (FAB) calcd. for $C_{15}H_{11}{}^{35}ClF_3N_4O_7S$ (MH$^+$) m/z 482.9989, found 482.9988.

A solution of 219 (10 mg, 0.021 mmol) and $Cs_2CO_3$ (21 mg, 0.062 mmol) in MeOH (2 mL) and $CH_2Cl_2$ (2 mL) was stirred for 15 min. Water was added and the mixture was extracted with EtOAc (×3). The combined extracts were washed with water, brine, and dried and evaporated. The resulting red solid was stirred in HCl(g) saturated dioxane (3 mL) for 30 min. The dioxane was removed under reduced pressure. 5-[2-(Dimethylamino)ethoxy]indole-2-carboxylic acid hydrochloride (7 mg, 0.025 mmol), TsOH (1 mg) and EDCI (16 mg, 0.082 mmol) in DMA (1 mL) were added and the mixture was stirred for 56 h under $N_2$. The mixture was then partitioned between EtOAc and ice-cold aqueous $KHCO_3$ (5%). The aqueous portion was extracted with cold EtOAc (×4) and the combined extracts were washed with water (×3), brine (×2) and dried to give 50 (containing 20% eliminated product) as an orange powder (3 mg, 25%): $^1H$ NMR [$(CD_3)_2SO$] δ 11.78 (d, J=1.2 Hz, 1H), 9.44 (s, 1H), 9.02 (s, 1H), 8.75 (s, 1H), 8.02 (s, 2H), 7.42 (d, J=8.9 Hz, 1H), 7.24 (d, J=1.8 Hz, 1H), 7.19 (d, J=2.2 Hz, 1H), 6.95 (dd, J=8.9, 2.4 Hz, 1H), 5.03 (t, J=9.9 Hz, 1H), 4.75 (dd, J=10.9, 2.5 Hz, 1H), 4.70-4.63 (m, 1H), 4.19 (dd, J=11.5, 3.5 Hz, 1H), 4.12 (dd, J=11.4, 5.9 Hz, 1H), 4.08 (t, J=5.8 Hz, 2H), 2.68 (t, J=5.8 Hz, 2H), 2.25 (s, 6H). HRMS (FAB) calcd. for $C_{26}H_{26}{}^{35}ClN_6O_8S$ (MH$^+$) m/z 617.1221, found 617.1219.

EXAMPLE 49

7-Amino-1-(chloromethyl)-3-{5-[2-(dimethylamino) ethoxy]indol-2-carbonyl}-5-nitro-1,2-dihydro-3H-benzo[e] indole (10) (Scheme N). A stirred solution of 153 (400 mg, 1.30 mmol) in TBP (20 mL) was treated with TFAA (0.74 mL, 5.24 mmol) and stirred at 20° C. for 30 min. Concentration under reduced pressure left a residue which was shaken with water and the resulting solid was collected and crystallised from EtOAc/i-Pr$_2$O to give 1-chloromethyl)-5-nitro-3-(trifluoroacetyl)-1,2-dihydro-3H-benzo[e]indole-7-carboxylic acid (220) (484 mg, 92%) as a tan solid: mp 246-247° C.; $^1H$ NMR [$(CD_3)_2SO$] δ 13.3 (br s, 1H), 9.06 (s, 1H), 9.02 (d, J=1.1 Hz, 1H), 8.37 (d, J=8.8 Hz, 1H), 8.20 (dd, J=8.8, 1.5 Hz, 1H), 4.72-4.62 (m, 2H), 4.56-4.48 (m, 1H), 4.20 (dd, J=11.2, 2.6 Hz, 1H), 4.17-4.09 (m, 1H). Anal. ($C_{16}H_{10}ClF_3N_2O_5$) C, H, N.

A suspension of 220 (410 mg, 1.02 mmol) in $CH_2Cl_2$ (15 mL) containing DMF (1 drop) was treated with oxalyl chloride (0.27 mL, 3.10 mmol) and stirred at room temperature for 30 min. The mixture was evaporated under reduced pressure and azeotroped dry with benzene. The resulting acid chloride was dissolved in acetone (5 mL) and treated at 0° C. with a solution of $NaN_3$ (300 mg, 4.6 mmol) in water (1 mL). The mixture was shaken at room temperature for 1 min, and the precipitate was collected, dried, and stirred in toluene (15 mL) at reflux for 1.5 h. After addition of t-BuOH (1.0 mL, 10 mmol) the mixture was heated at reflux for 5 min then concentrated under reduced pressure. The residue was purified by chromatography, eluting with $CH_2Cl_2$, followed by crystallisation from $CH_2Cl_2$/hexane to give tert-butyl 1-(chloromethyl)-5-nitro-3-(trifluoroacetyl)-1,2-dihydro-3H-benzo[e] indole-7-carbamate (221) (347 mg, 72%) as an orange solid: mp 219-220° C.; $^1H$ NMR [$(CD_3)_2SO$] δ 9.93 (s, 1H), 8.94 (s, 1H), 8.71 (d, J=1.9 Hz, 1H), 8.19 (d, J=9.2 Hz, 1H), 7.82 (dd, J=9.2, 2.0 Hz, 1H), 4.65-4.42 (m, 3H), 4.17 (dd, J=11.3, 2.8 Hz, 1H), 4.09 (dd, J=11.3, 5.2 Hz, 1H), 1.52 (s, 9H). Anal. ($C_{20}H_{19}ClF_3N_3O_5$) C, H, N.

A suspension of 221 (218 mg, 0.46 mmol) in dioxane (5 mL) was treated at room temperature with a solution of $Cs_2CO_3$ (0.33 g, 1.0 mmol) in water (1 mL) and MeOH (9 mL). The mixture was stirred at room temperature for 5 min and then treated with AcOH (0.15 mL) and diluted with water. The precipitate was collected and crystallised from $CH_2Cl_2$/hexane to give tert-butyl 1-(chloromethyl)-5-nitro-1,2-dihydro-3H-benzo[e]indole-7-carbamate (222) (164 mg, 94%) as a red solid: mp 162-163° C. (dec.); $^1H$ NMR [$(CD_3)_2SO$] δ 9.57 (s, 1H), 8.46 (d, J=1.7 Hz, 1H), 7.81 (d, J=9.1 Hz, 1H), 7.65-7.57 (m, 2H), 6.09 (d, J=2.1 Hz, 1H), 4.19-4.10 (m, 1H), 3.88 (dd, J=10.9, 3.7 Hz, 1H), 3.81-3.63 (m, 3H), 1.50 (s, 9H). Anal. ($C_{18}H_{20}ClN_3O_4$) C, H, N.

A mixture of 222 (75 mg, 0.20 mmol), 5-[2-(dimethylamino)ethoxy]indole-2-carboxylic acid hydrochloride (73 mg, 0.26 mmol), EDCI (152 mg, 0.79 mmol) and TsOH (5 mg, 0.03 mmol) in DMA (1.5 mL) was stirred at room temperature for 1 h, then poured into dilute aqueous $NH_3$. The precipitate was collected, washed with water, and dissolved in $CH_2Cl_2$ (250 mL). The solution was dried, filtered, concentrated under reduced pressure to a small volume, and then diluted with i-Pr$_2$O to give tert-butyl 1-(chloromethyl)-3-{5-[2-(dimethylamino)ethoxy]indol-2-carbonyl}-5-nitro-1,2-dihydro-3H-benzo[e]indole-7-carbamate (223) (91 mg, 75%) as a yellow solid: mp (THF/$CH_2Cl_2$/hexane)>250° C.; $^1H$ NMR [$(CD_3)_2SO$] δ 11.67 (d, J=1.6 Hz, 1H), 9.85 (s, 1H), 9.12 (s, 1H), 8.69 (d, J=1.9 Hz, 1H), 8.14 (d, J=9.2 Hz, 1H), 7.79 (dd, J=9.2, 2.0 Hz, 1H), 7.41 (d, J=−8.9 Hz, 1H), 7.18 (d, J=2.3 Hz, 1H), 7.15 (d, J=1.7 Hz, 1H), 6.93 (dd, J=8.9, 2.4 Hz, 1H), 4.90 (t, J=10.2 Hz, 1H), 4.67 (dd, J=10.9, 2.4 Hz, 1H), 4.58-4.51 (m, 1H), 4.16-4.03 (m, 4H), 2.66 (t, J=5.8 Hz, 2H), 2.24 (s, 6H), 1.53 (s, 9H). Anal. ($C_{31}H_{34}ClN_5O_6$) C, H, N.

A suspension of 223 (72 mg, 0.12 mmol) in TFA (3 mL) was stirred at room temperature for 30 min and the resulting solution was evaporated to dryness under reduced pressure below 30° C. The residue was stirred in dilute aqueous $NH_3$ at room temperature for 30 min, and the resulting base was collected, washed with water, and dried. This was dissolved in DMP (0.2 mL) and the solution was diluted with excess $CH_2Cl_2$, clarified by filtration, and then refrigerated to provide 10 (54 mg, 90%) as a red solid: mp>300° C.; $^1$H NMR [$(CD_3)_2SO$] 811.62 (d, J=1.4 Hz, 1H), 9.09 (s, 1H), 7.93 (d, J=9.1 Hz, 1H), 7.56 (d, J=2.1 Hz, 1H), 7.40 (d, J=8.9 Hz, 1H), 7.21-7.13 (m, 2H), 7.11 (d, J=1.7 Hz, 1H), 6.93 (dd, J=8.9, 2.4 Hz, 1H), 6.12 (s, 2H), 4.83 (dd, J=10.8, 9.4 Hz, 1H), 4.62 (dd, J=11.0, 2.2 Hz, 1H), 4.50-4.42 (m, 1H), 4.13-3.97 (m, 4H), 2.66 (t, J=5.9 Hz, 2H), 2.24 (s, 6H). Anal. (C26H26ClN5O4.1½H2O) C, H.

EXAMPLE 50

2-{[1-(Chloromethyl)-5-nitro-3-(5,6,7-trimethoxyindol-2-carbonyl)-1,2-dihydro-3H-benzo[e]indol-7-yl]sulfonyl}aminoethyl dihydrogen phosphate (34) (Scheme O). Tetrazole (3 wt % solution in $CH_3CN$, 32 mL, 11.0 mmol) and di-tert-butyl N,N-diisopropylphosphoramidite (95%, 2.73 mL, 8.2 mmol) were added to a solution of benzyl N-2-hydroxyethylcarbamate (224) (1.07 g, 5.48 mmol) in THF (20 mL) and the mixture was stirred at room temperature for 16 h. The mixture was cooled to 0° C. and $H_2O_2$ (70% aqueous, 1.0 mL, 24 mmol) was added. After 15 min. the cooling bath was removed and the mixture was stirred for a further 6 h, then aqueous $Na_2SO_3$ (10%, 50 mL) was added with water bath cooling. After 25 min the organic solvents were removed under reduced pressure and the aqueous residue was extracted with EtOAc (×2). The combined extracts were washed with brine, dried, and evaporated. The residue was purified by chromatography, eluting with EtOAc/petroleum ether (1:1) to give benzyl 2-{[di(tert-butoxy)phosphoryl]oxy}ethylcarbamate (225) (1.36 g, 64%) as a colourless oil: $^1$H NMR [$CDCl_3$] δ 7.37-7.28 (m, 5H), 5.43 (br 9, 1H), 5.11 (s, 2H), 4.07-4.00 (m, 2), 3.46 (q, J=5.1 Hz, 2H), 1.47 (s, 18H). HRMS (FAB) calcd. for $C_{18}H_{31}NO_6P$ (M$^+$) m/z 388.1889, found 388.1889.

A solution of 225 (1.17 g, 3.02 mmol) in MeOH (30 mL) with Pd/C (5%, 0.21 g) was hydrogenated at 50 psi for 2.5 h. The mixture was filtered through Celite, washing with MeOH, and the filtrate was evaporated. The residue was dissolved in $CH_2Cl$ and the solution was filtered once more, then evaporated to give 2-aminoethyl di(tert-butyl) phosphate (226) (604 mg, 79%) as a colourless oil: $^1$H NMR [$CDCl_3$] δ 4.01-3.94 (m, 2H), 2.96-2.90 (m, 2H), 1.58 (br s, 2H), 1.49 (s, 18H). HRMS (FAB) calcd. for $C_{10}H_{25}NO_4P$ (MH$^+$) m/z 254.1521, found 254.1519.

A solution of amine 226 (203 mg, 0.80 mmol) and $Et_3N$ (0.11 mL, 0.80 mmol) in THF (2 mL) was added to solution of 116 (306 mg, 0.67 mmol) in THF (8 mL) at 0° C. After 5 min the cooling bath was removed and after 10 min $Cs_2CO_3$ (0.44 g, 1.3 mmol) and MeOH (4 mL) were added. After a further 25 min the mixture was diluted with water and extracted with $CH_2C_2$ (×3). The combined extracts were dried and evaporated and the residue was purified by chromatography, eluting with EtOAc/petroleum ether (1:1 then 2:1) to give di(tert-butyl) 2-({[1-(chloromethyl)-5-nitro-1,2-dihydro-3H-benzo[e]indol-7-yl]sulfonyl}amino)ethyl phosphate (227) (351 mg, 91%) as a red-orange foam: $^1$H NMR [$(CD_3)_2SO$] δ 8.59 (d, J=1.6 Hz, 1H), 8.04 (d, J=8.9 Hz, 1H), 7.95 (br s, 1H), 7.79 (dd, J=8.9, 1.8 Hz, 1H), 7.77 (s, 1H), 6.74 (s, 1H), 4.28-4.20 (m, 1H), 3.95-3.86 (m, 2H), 3.83-3.72 (m, 4H), 2.99 (t, J=6.0 Hz, 2H), 1.35 (s, 18H). HMS (FAB) calcd. for $C_{23}H_{33}{}^{35}ClN_3O_8PS$ (M$^+$) m/z 577.1415, found 577.1412.

A mixture of 227 (77 mg, 0.13 mmol), 5,6,7-trimethoxyindole-2-carboxylic acid (44 mg, 0.17 mmol), EDCI (102 mg, 0.52 mmol), and TsOH (5 mg, 0.03 mmol) in DMA (1.5 mL) was stirred at room temperature for 2 h. Ice-cold aqueous $NaHCO_3$ was added and the mixture was extracted with EtOAc (×2). The combined extracts were washed with brine (×2), dried, and the solution was evaporated onto silica Chromatography, eluting with EtOAc/petroleum ether (3:2 then 4:1 then EtOAc alone) gave di(tert-butyl) 2-[({1-(chloromethyl)-5-nitro-3-(5,6,7-trimethoxyindol-2-carbonyl)-1,2-dihydro-3H-benzo[e]indol-7-yl}sulfonyl)amino]ethyl phosphate (228) (71 mg, 66%) as a yellow solid. A sample was triturated with $CH_2Cl_2$: mp 231-236° C. (dec.); $^1$H NMR [$(CD_3)_2SO$] δ 11.60 (d, J=1.6 Hz, 1H), 9.24 (s, 1H, 8.87 (d, J=1.7 Hz, 1H), 8.44 (d, J=8.9 Hz, 1H), 8.15 (br s, 1H), 8.01 (dd, J=8.9, 1.8 Hz, 1H), 7.20 (d, J=2.1 Hz, 1H), 6.98 (s, 1H), 4.96-4.90 (m, 1H), 4.68-4.59 (m, 2H), 4.18-4.07 (m, 2H), 3.95 (s, 3H), 3.87-3.82 (ni 2H), 3.84 (s, 3H), 3.81 (s, 3H), 3.10-3.04 (m, 2H), 1.36 (s, 18H). Anal, ($C_{35}H_{44}ClN_4O_{12}PS$) C, H, N.

TFA (0.06 mL, 0.7 mmol) was added to a solution of 228 (60 mg, 0.074 mmol) in $CH_2Cl_2$ (10 mL) and the solution was allowed to stand at room temperature for 16 h. The mixture was evaporated, the residue was redissolved in $CH_2Cl_2$ and evaporated once more, and the residue was triturated with EtOAc/MeOH to give 34 (45 mg, 87%) as a yellow solid: mp 228-2#3° C. (dec.); $^1$H NMR [$(CD_3)_2SO$] δ 11.60 (d, J=1.6 Hz, 1H), 9.24 (s, 1H), 8.87 (d, J=1.7 Hz, 1H), 8.43 (d, J=8.9 Hz, 1H), 8.17 (br s, 1H), 8.02 (dd, J=8.9, 1.7 Hz, 1H), 7.20 (d, J=2.2 Hz, 1H), 6.99 (s, 1H), 4.96-4.89 (m, 1H), 4.68-4.58 (m, 2H), 4.17-4.06 (m, 2H), 3.94 (s, 3H), 3.83 (s, 3H), 3.81 (s, 3H), 3.82-3.78 (m, 2H), 3.04 (br s, 2H). Anal. ($C_{27}H_{28}ClN_4O_{12}PS$) C, H, N.

EXAMPLE 51

2-{[1-(Chloromethyl)-5-nitro-3-{5-[2-(dimethylamino)ethoxy]indol-2-carbonyl}-1,2-dihydro-3H-benzo[c]indol-7-yl]sulfonyl}aminoethyl dihydrogen phosphate trifluoroacetate (36) (Scheme O). A mixture of 227 (351 mg, 0.61 mmol), 5-[2-(dimethylamino)ethoxy]indole-2-carboxylic acid hydrochloride (225 mg, 0.79 mmol), EDCI (466 mg, 2.4 mmol) and TsOH (21 mg, 0.12 mmol) in DMA (3 mL) was stirred at room temperature for 3.5 h and then cooled to 0° C. Ice-cold aqueous $NaHCO_3$ was added, and the resulting precipitate was filtered off, washed with aqueous $NaHCO_3$ and water, and dried. Trituration with acetone gave di(tert-butyl) 2-({[1-(chloromethyl)-3-{5-[2-(dimethylamino)ethoxy]indol-2-carbonyl}-5-nitro-1,2-dihydro-3H-benzo[e]indol-7-yl]sulfonyl}amino)ethyl phosphate (229) (433 mg, 88%) as a yellow solid: mp 220-225° C. (dec.); $^1$H NMR [$(CD_3)_2SO$] δ 11.73 (s, 1H), 9.30 (s, 1H), 8.87 (d, J=1.7 Hz, 1H), 8.45 (d, J=8.9 Hz, 1H), 8.16 (br s, 1H), 8.02 (dd, J=8.9, 1.7 Hz, 1H), 7.42 (d, J=8.9 Hz, 1H), 7.22 (d, J=1.6 Hz, 1H), 7.18 (d, J=2.4 Hz, 1H), 6.96 (dd, J=−8.9, 2.4 Hz, 1H), 5.00-4.94 (m, 1H), 4.73 (dd, J=11.0, 2.4 Hz, 1H), 4.68-4.62 (m, 1H), 4.19-4.11 (m, 2H), 4.07 (t, J=5.9 Hz, 2H), 3.87-3.80 (m, 2H), 3.08-3.03 (m, 2H), 2.66 (t, J=5.9 Hz, 2H), 2.24 (s, 6H), 1.36 (s, 18H. Anal. ($C_{36}H_{47}ClN_5O_{10}PS$.½$H_2O$) C, H, N.

TFA (0.41 mL, 5.4 mmol) was added to a solution of 229 (433 mg, 0.54 mmol) in $CH_2Cl_2$ (10 mL) and the solution was stirred at room temperature for 16 h. The mixture was evaporated, the residue was redissolved in $CH_2Cl_2$ and evaporated once more, and the residue was triturated with EtOAc to give 36 (417 mg, 96%) as a yellow solid: mp 171-174° C. (dec.); $^1H$ NMR [$(CD_3)_2SO$] δ 11.77 (s, 1H), 9.25 (s, 1H), 8.85 (d, J=1.6 Hz, 1H), 8.45 (v br s, 1H), 8.40 (d, J=8.9 Hz, 1H), 8.02 (dd, J=8.9, 1.7 Hz, 1H), 7.37 (d, J=8.9 Hz, 1H), 7.24-7.19 (m, 2H), 6.93 (dd, J=8.9, 2.4 Hz, 1H), 4.98-4.90 (m, 1H), 4.77-4.66 (m, 1H), 4.64-4.56 (m, 1H), 4.30 (t, J=5.1 Hz, 2H), 4.17-4.06 (m, 2H), 3.85-3.76 (m, 2H), 3.55-3.50 (m, 2H), 3.07-3.03 (m, 2H), 2.83 (s, 6H). Anal. ($C_{28}H_{31}ClN_5O_{10}PS.TFA$) C, H, N.

EXAMPLE 52

2-({2-[7-(Aminosulfonyl)-1-(chloromethyl)-5-nitro-1,2-dihydro-3H-benzo[e]indol-3-carbonyl]indol-5-yl}oxy)ethyl dihydrogen phosphate (29) (Scheme P). A mixture of ethyl 5-(2-hydroxyethyl)indole-2-carboxylate (230) (1.22 g, 4.9 mmol) and dibutyltin oxide (0.12 g, 0.49 mmol) inbenzyl alcohol (12 mL) was heated at 110° C. for 20 h. The benzyl alcohol was evaporated and the residue was purified by chromatography, eluting with EtOAc/petroleum ether (1:2) to give benzyl 5-(2-hydroxyethyl)indole-2-carboxylate (231) (1.34 g, 88%) as a white solid: mp (PhH) 107-108° C. (dec.); $^1H$ NMR [$(CD_3)_2SO$] δ 11.74 (s, 1H), 7.51-7.47 (m, 2H), 7.44-7.33 (m, 4H), 7.12-7.09 (m, 2H), 6.94 (dd, J=9.0, 2.4 Hz, 1H), 5.37 (s, 2H), 4.81 (t, J=5.6 Hz, 1H), 3.97 (t, J=5.1 Hz, 2H), 3.73 (q, J=5.2 Hz, 2H). Anal. ($C_{18}H_{17}NO_4.¼PhH$) C, H, N.

Tetrazole (3 wt % solution in $CH_3CN$, 10.2 mL, 3,5 mmol) and di-tert-butyl N,N-diisopropylphosphoramidite (95%, 0.86 mL, 2.6 mmol) were added to a solution of 231 (432 mg, 1.73 mmol) in THF (10 mL) and the mixture was stirred at room temperature for 17 h. The mixture was cooled to 0° C. and $H_2O_2$ (35% aqueous, 0.63 mL, 7.6 mmol) was added. After 15 min the cooling bath was removed and the mixture was stirred for a further 50 min, then aqueous $Na_2SO_3$ (10%, 20 mL) was added. After 15 min the organic solvents were removed under reduced pressure and the aqueous residue was extracted with EtOAc (×2). The combined extracts were washed with brine, dried, and evaporated. The residue was purified by chromatography, eluting with EtOAc/petroleum ether (1:1) to give crude benzyl 5-(2-{[di(tert-butoxy)phosphoryl]oxy}ethoxy)indole-2-carboxylate (630 mg). This product was dissolved in MeOH (20 mL) and hydrogenated over Pd/C (5%, 170 mg) at 50 psi for 2 h. The mixture was filtered through Celite and the filtrate was evaporated. The residue was dissolved in EtOAc and this solution was extracted with aqueous $NaHCO_3$ (×2). The combined extracts were cooled to 0° C. and acidified with ice-cold aqueous HCl (1 N). The precipitated solid was filtered off, dried, and triturated with EtOAc to give 5-(2-{[di(tert-butoxy)phosphoryl]oxy}ethoxy)indole-2-carboxylic acid (232) (278 mg, 49% from 231) as a white solid: mp 197-201° C. (dec.); $^1H$ NMR [$(CD_3)_2SO$] δ 12.5 (v br s, 1H), 11.59 (s, 1H), 7.34 (d, J=8.9 Hz, 1H), 7.12 (d, J=2.4 Hz, 1H), 6.98 (dd, J=2.1, 0.7 Hz, 1H), 6.90 (dd, J=8.9, 2.4 Hz, 1H), 4.20-4.12 (m, 4 H), 1.42 (s, 18H). Anal. ($C_{19}H_{28}NO_7P$) C, H, N.

A mixture of 117 (145 mg, 0.42 mmol), 232 (210 mg, 0.50 mmol), EDCI (325 mg, 1.7 mmol) and TsOH (15 mg, 0.08 mmol) in DMA (2.5 mL) was stirred at room temperature for 2.5 h and then cooled to 0° C. Ice-cold aqueous $NaHCO_3$ was added and the mixture was extracted with EtOAc (×4). The combined extracts were washed with aqueous $NaHCO_3$, brine, and then dried. The EtOAc solution was evaporated onto silica. Chromatography, eluting with EtOAc, followed by trituration with EtOAc, gave 2-[(2-{[7-(aminosulfonyl)-1-(chloromethyl)-5-nitro-1,2-dihydro-3H-benzo[e]indol-3-carbonyl]-1H-indol-5-yl}oxy)ethyl di(tert-butyl)phosphate (233) (247 mg, 79%) as a yellow powder: mp 133° C. (dec.); $^1H$ NMR [$(CD_3)_2SO$] δ 11.76 (d, J=2 Hz, 1H), 9.29 (s, 1H), 8.87 (d, J=1.7 Hz, 1H), 8.45 (d, J=8.9 Hz, 1H), 8.08 (dd, J=8.9, 1.7 Hz, 1H), 7.62 (s, 2H), 7.44 (d, J=8.9 Hz, 1H), 7.23 (d, J=1.8 Hz, 1H, 7.20 (d, J=2.4 Hz, 1H), 6.97 (dd, J=8.9, 2.4 Hz, 1H), 5.02-4.94 (m, 1H), 4.73 (dd, J=10.9, 2.4 Hz, 1H), 4.69-4.63 (m, 1H), 4.24-4.11 (m, 6H), 1.44 (s, 18H). Anal. ($C_{32}H_{38}ClN_4O_{10}PS.DMA$) C, H, N. TFA (0.23 mL, 3.0 mmol) was added to a solution of 233 (218 mg, 0.30 mmol) in $CH_2Cl_2$ (35 mL) and the mixture was stirred at room temperature for 24 h. The mixture was evaporated, the residue was redissolved in $CH_2Cl_2$ and evaporated once more, and the residue was triturated with EtOAc to give 29 (161 mg, 87%) as a yellow powder: mp 207-211° C.; $^1H$ NMR [$(CD_3)_2SO$] δ 11.75 (d, J=1.6 Hz, 1H), 9.29 (s, 1H), 8.87 (d, J=1.7 Hz, 1H), 8.44 (d, J=8.9 Hz, 1H), 8.07 (dd, J=8.9, 1.7 Hz, 1H), 7.63 (s, 2H), 7.44 (d, J=8.9 Hz, 1H), 7.23 (d, J=1.7 Hz, 1H), 7.20 (d, J=2.3 Hz, 1H), 6.99 (dd, J=8.9, 2.4 Hz, 1H), 5.01-4.95 (m, 1H), 4.73 (dd, J=10.9, 2.5 Hz, 1H), 4.69-4.63 (m, 1H), 4.20-4.11 (m, 6H). Anal. ($C_{24}H_{22}ClN_4O_{10}PS.½H_2O$) C, H, N.

EXAMPLE 53

7-Acetyl-5-amino-1-(chloromethyl)-3-{5-[2-(dimethylamino)ethoxy]indol-2-carbonyl}-1,2-dihydro-3H-benzo[e]indole (53) (Scheme Q). A solution of 12 (24 mg, 0.045 mmol) in THF (15 mL) with $PtO_2$ (25 mg) was hydrogenated at 50 psi for 20 min. The mixture was filtered through Celite and the filtrate was evaporated under reduced pressure. The residue was purified by chromatography, eluting with EtOAc/MeOH (4:1), and the crude product was triturated with EtOAc to give 53 (7 mg, 31%) as a yellow solid: mp 220-224° C. (dec.); $^1H$ NMR [$(CD_3)_2SO$] δ 11.56 (s, 1H), 8.78 (d, J=1.2 Hz, 1H), 7.88 (dd, J=8.8, 1.5 Hz, 1H), 7.78 (d, J=8.8 Hz, 1H), 7.75 (s, 1H), 7.38 (d, J=8.9 Hz, 1H), 7.16 (d, J=2.3 Hz, 1H), 7.08 (d, J=1.5 Hz, 1H), 6.92 (dd, J=8.9, 2.4 Hz, 1H), 6.43 (s, 2H), 4.75 (dd, J=10.8, 9.0 Hz, 1H), 4.51 (dd, J=10.9, 1.9 Hz, 1H), 4.19-4.13 (m, 1H), 4.07 (t, J=5.9 Hz, 2H), 3.97 (dd, J=10.9, 3.1 Hz, 1H), 3.81-3.75 (m, 1H), 2.68 (s, 3H), 2.65 (t, J=5.9 Hz, 2H), 2.24 (s, 6H). HRMS (FAB) calcd. for $C_{28}H_{30}{}^{35}ClN_4O_3$ (M) m/z 505.2006, found 505.1999.

EXAMPLE 54

Methyl 5-amino-1-(chloromethyl)-3-{5-[2-(dimethylamino)ethoxy]indol-2-carbonyl}-1,2-dihydro-3H-benzo[e]indole-7-carboxylate (54) (Scheme Q). Compound 14 (as the free base) was hydrogenated as described in Example 53 (50 psi for 45 min) to give 54 (82%) as a yellow solid: mp 225-230° C.; $^1H$ NMR [$(CD_3)_2SO$] 11.57 (d, J=1.6 Hz, 1H), 8.80 (d, J=1.4 Hz, 1H), 7.90 (dd, J=8.8, 1.6 Hz, 1H), 7.82 (d, J=8.8 Hz, 1H), 7.76 (s, 1H), 7.40 (d, J=8.9 Hz, 1H), 7.17 (d, J=2.4 Hz, 1H), 7.08 (d, J=1.5 Hz, 1H), 6.91 (dd, J=8.9, 2.4 Hz, 1H), 6.34 (s, 2H), 4.75 (dd, J=10.8, 8.9 Hz, 1H), 4.52 (dd, J=10.9, 1.8 Hz, 1H), 4.18-4.11 (m, 1H), 4.06 (t, J=5.9 Hz, 2H), 3.98 (dd, J=11.0, 3.1 Hz, 1H), 3.90 (s, 3 H), 3.78 (dd, J=11.0, 7.9 Hz, 1H), 2.65 (t, J=5.9 Hz, 2H), 2.23 (s, 6H). Anal. ($C_{28}H_{29}ClN_4O_4$) C, H, N.

EXAMPLE 55

5-Amino-1-(chloromethyl)-3-{5-[2-(dimethylamino)ethoxy]indol-2-carbonyl}-1,2-dihydro-3H-benzo[e]indole-7-carboxamide (55) (Scheme Q). Compound 16 (as the free base) was hydrogenated as described in Example 53 (50 psi for 45 min) to give 55 (70%) as a green solid: mp 232-236° C. (dec.); $^1$H NMR [(CD$_3$)$_2$SO] δ 11.55 (d, J=1.6 Hz, 1H), 8.66 (s, 1H), 7.90 (dd, J=8.7, 1.5 Hz, 1H), 7.83 (br s, 1H), 7.78 (d, J=8.8 Hz, 1H), 7.73 (s, 1H, 7.39 (d, J=8.9 Hz, 1H), 7.32 (br s, 1H), 7.17 (d, J=2.3 Hz, 1H), 7.07 (d, J=1.4 Hz, 1H), 6.91 (dd, J=8.9, 2.4 Hz, 1H), 6.11 (s, 2H), 4.75 (dd, J=10.8, 9.0 Hz, 1H), 4.51 (dd, J=10.9, 1.8 Hz, 1H), 4.18-4.12 (m, 1H), 4.06 (t, J=5.9 Hz, 2H), 3.98 (dd, J=10.9, 3.1 Hz, 1H), 3.78 (dd, J=11.0, 7.9 Hz, 1H), 2.65 (t, J=5.9 Hz, 2H), 2.24 (s, 6H). Anal. (C$_{27}$H$_{28}$ClN$_5$O$_3$·½H$_2$O) C, H, N.

EXAMPLE 56

5-Amino-1-(chloromethyl)-3-{5-[2-(dimethylamino)ethoxy]indol-2-carbonyl}-1,2-dihydro-3H-benzo[e]indole-7-carbonitrile (56) (Scheme Q). Compound 22 (as the free base) was hydrogenated as described in Example 53 (50 psi for 60 min) to give 56 (48%) as a yellow solid: mp 250-255° C. (dec.); $^1$H NMR [(CD$_3$)$_2$SO] δ 11.57 (d, J=1.5 Hz, 1H), 8.67 (s, 1H), 7.89 (d, J=8.7 Hz, 1H), 7.80 (s, 1H), 7.64 (dd, J=8.7, 1.5 Hz, 1H), 7.39 (d, J=8.9 Hz, 1H), 7.17 (d, J=2.3 Hz, 1H), 7.09 (s, 1H), 6.91 (dd, J=8.9, 2.4 Hz, 1H), 6.40 (s, 2H), 4.75 (dd, J=10.7, 9.1 Hz, 1H), 4.52 (dd, J=10.9, 1.8 Hz, 1H), 4.20-4.14 (m, 1H), 4.06 (t, J=5.9 Hz, 2H), 3.96 (dd, J=11.0, 3.1 Hz, 1H), 3.77 (dd, J=11.0, 7.6 Hz, 1H), 2.65 (t, J=5.9 Hz, 2H), 2.24 (s, 6H). HRMS (FAB) calcd. for C$_{27}$H$_{27}$$^{35}$ClN$_5$O$_2$ (MH$^+$) m/z 488.1853, found 488.1847.

EXAMPLE 57

5-Amino-1-(chloromethyl)-7-(methylsulfonyl)-3-(5,6,7-trimethoxyindol-2-carbonyl)-1,2-dihydro-3H-benzo[e]indole (57) (Scheme Q). Compound 23 was hydrogenated as described in Example 53 (45 psi for 90 min) to give 57 (42%) as a yellow solid: mp 266-268° C.; $^1$H NMR [(CD$_3$)$_2$SO] δ 11.42 (s, 1H), 8.69 (d, J=1.7 Hz, 1H), 7.96 (d, J=8.9 Hz, 1H), 7.81 (dd, J=8.8, 1.8 Hz, 1H), 7.76 (s, 1H), 7.08 (d, J=2.0 Hz, 1H), 6.97 (s, 1H), 6.40 (s, 2H), 4.71 (dd, J=10.9, 9.0 Hz, 1H), 4.44 (dd, J=11.0, 1.8 Hz, 1H), 4.18-4.11 (m, 1H), 3.97 (dd, J=11.0, 3.2 Hz, 1H), 3.94 (s, 3H), 3.82 (s, 3H), 3.80 (s, 3H), 3.78 (dd, J=11.0, 7.6 Hz, 1H), 3.25 (s, 3H). Anal. (C$_{26}$H$_{26}$ClN$_3$O$_6$S) C, H, N.

EXAMPLE 58

5-Amino-1-(chloromethyl)-3-{5-[2-(dimethylamino)ethoxy]indol-2-carbonyl}-7-(methylsulfonyl)-1,2-dihydro-3H-benzo[e]indole (58) (Scheme Q). Compound 24 (as the free base) was hydrogenated as described in Example 53 (45 psi for 60 min) to give 58 (81%) as a yellow solid: mp (iPr$_2$O/THF) 280-285° C.; $^1$H NMR [(CD$_3$)$_2$SO] δ 11.57 (s, 1H), 8.70 (d, J=1.6 Hz, 1H), 7.97 (d, J=8.9 Hz, 1H), 7.85-7.79 (m, 2H), 7.40 (d, J=8.9 Hz, 1H), 7.17 (d, J=2.3 Hz, 1H), 7.10 (d, J=1.7 Hz, 1H), 6.93 (dd, J=−8.9, 2.4H, 1H), 6.40 (s, 2H), 4.77 (dd, J=10.8, 9.0 Hz, 1H, 4.54 (dd, J=10.9, 1.8 Hz, 1H), 4.24-4.16 (m, 1H), 4.06 (t, J=5.9H, 2H), 3.99 (dd, J=11.0, 3.0 Hz, 1H), 3.81 (dd, J=11.0, 7.5 Hz, 1H), 3.26 (s, 3H), 2.65 (t, J=5.9 Hz, 2H), 2.24 (s, 6H). Anal. (C$_{27}$H$_{29}$ClN$_4$O$_4$S) C, H, N, Cl.

EXAMPLE 59

5-Amino-1-(chloromethyl)-3-(5,6,7-trimethoxyindol-2-carbonyl)-1,2-dihydro-3H-benzo[e]indole-7-sulfonamide (59) (Scheme Q). Compound 25 was hydrogenated as described in Example 53 (50 psi for 60 min) to give 59 (65%) as a yellow powder: mp 240-245° C. (dec.); $^1$H NMR [(CD$_3$)$_2$SO] δ 11.40 (s, 1H), 8.55 (d, J=1.6 Hz, 1H), 7.92 (d, J=8.9 Hz, 1H), 7.80 (dd, J=8.9, 1.7 Hz, 1H), 7.73 (s, 1H), 7.24 (s, 2H), 7.06 (s, 1H), 6.97 (s, 1H), 6.21 (s, 2H), 4.70 (dd, J=10.9, 9.0 Hz, 1H), 4.43 (dd, J=11.0, 1.8 Hz, 1H), 4.16-4.09 (m, 1H), 3.98 (dd, J=11.0, 3.1 Hz, 1H), 3.94 (s, 3H), 3.82 (s, 3H), 3.80 (s, 3H), 3.76 (dd, J=11.0, 7.9 Hz, 1H). Anal. (C$_{25}$H$_{25}$ClN$_4$O$_6$S) C, H, N.

EXAMPLE 60

5-Amino-1-(chloromethyl)-3-{5-[2-(dimethylamino)ethoxy]indol-2-carbonyl}-1,2-dihydro-3H-benzo[e]indole-7-sulfonamide (60) (Scheme Q). Compound 26 (as the free base) was hydrogenated as described in Example 53 (50 psi for 60 min) to give 60 (43%) as a yellow solid: mp 260-266° C. (dec.); $^1$H NMR [(CD$_3$)$_2$SO] δ 8.56 (s, 1H), 8.56 (d, J=1.5 Hz, 1H), 7.93 (d, J=8.9 Hz, 1H), 7.81 (s, 1H), 7.80 (dd, J=8.8, 1.7 Hz, 1H), 7.40 (d, J=8.9 Hz, 1H), 7.24 (s, 2H), 7.17 (d, J=2.3 Hz, 1H), 7.08 (s, 1H), 6.91 (dd, J=8.9, 2.4 Hz, 1H), 6.22 (s, 2H), 4.77 (dd, J=10.8, 9.1 Hz, 1H), 4.53 (dd, J=10.9, 1.8 Hz, 1H), 4.22-4.14 (m, 1H), 4.06 (t, J=−5.9 Hz, 2H), 3.99 (dd, J=11.0, 3.0 Hz, 1H), 3.80 (dd, J=10.9, 7.7 Hz, 1H), 2.65 (t, J=5.8 Hz, 2H), 2.24 (s, 6H). HRMS (FAB) calcd. for C$_{26}$H$_{29}$$^{35}$ClN$_5$O$_4$S NO) m/z 542.1629, found 542.1625.

EXAMPLE 61

5-Amino-1-(chloromethyl)-3-{5-[2-(dimethylamino)ethoxy]indol-2-carbonyl}-N-methyl-1,2-dihydro-3H-benzo[e]indole-7-sulfonamide (61) (Scheme Q). Compound 32 (as the free base) was hydrogenated as described in Example 53(50 psi for 35 min) to give 61 (83%) as a yellow solid: mp 260-265° C. (dec.); $^1$H NMR [(CD$_3$)$_2$SO] δ 11.57 (s, 1H), 8.53 (d, J=1.5 Hz, 1H), 7.94 (d, J=8.9 Hz, 1H), 7.82 (s, 1H), 7.71 (dd, J=8.8, 1.7 Hz, 1H), 7.40 (d, J=8.9 Hz, 1H), 7.34-7.29 (m, 1H), 7.16 (d, J=2.3 Hz, 1H), 7.09 (s, 1H), 6.92 (dd, J=8.9, 24 Hz, 1H), 6.31 (s, 1H), 4.76 (dd, J=10.8, 9.1 Hz, 1H), 4.53 (dd, J=10.8, 1.8Hz, 1H), 4.21-4.15 (m, 1H), 4.07 (t, J=5.9 Hz, 2H), 4.00 (dd, J=11.0, 3.0 Hz, 1H), 3.81 (dd, J=11.0, 7.7 Hz, 1H), 2.65 (t, J=5.9 Hz, 2H), 2.45 (br d, J=4.2 Hz, 3H), 2.24 (s, 6H). Anal. (C$_{27}$H$_{30}$ClN$_5$O$_4$S·½H$_2$O·½EtOAc) C, H, N.

EXAMPLE 62

5-Amino-6-(chloromethyl)-3-{5-[2-(dimethylamino)ethoxy]indol-2-carbonyl}-N-(2-hydroxyethyl)-1,2-dihydro-3H-benzo[e]indole-1-sulfonamide (62) (Scheme Q). Compound 35 was hydrogenated as described in Example 53 (50 psi for 30 min) to give 62 (74%) as a yellow solid: mp 225-230° C.; $^1$H NMR [(CD$_3$)$_2$SO] δ 11.57 (d, J=1.7 Hz 1H) 8.54 (d, J=1.5 Hz, 1H) 7.94 (d, J=8.9 Hz, 1H), 7.81 (s, 1H), 7.73 (dd, J=8.8, 1.7 Hz, 1H), 7.44 (t, J=5.9 Hz, 1H), 7.40 (d, J=8.9 Hz, 1H), 7.17 (d, J=2.4 Hz, 1) 7.09 (d, J=1.5 Hz, 1H), 6.91 (dd, J=8.9, 2.4 Hz, 1H), 6.30 (s, 2H), 4.76 (dd, J=10.8, 9.0 Hz, 1H), 4.65 (t, J=5.6 Hz, 1H), 4.54 (dd, J=10.9, 1.8 Hz, 1H), 4.22-4.13 (m, 1H), 4.07 (t, J=5.9 Hz, 2H), 4.00 (dd, J=11.0, 3.1 Hz, 1H), 3.81 (dd, J=11.0, 7.7 Hz, 1H), 3.39 (q, J=6.1 Hz, 2H), 2.84 (q, J=6.2 Hz, 2H), 2.65 (t, J=5.9 Hz, 2H), 2.24 (s, 6H). Anal. ($C_{28}H_{32}ClN_5O_5S \cdot \frac{1}{2}H_2O$) C, H, N.

EXAMPLE 63

5-Amino-1-(chloromethyl)-8-(methylsulfonyl)-3-(5,6,7-trimethoxyindol-2-carbonyl)-1,2-dihydro-3H-benzo[e]indole (63) (Scheme Q). Compound 46 was hydrogenated as described in Example 53 (45 psi for 90 min) to give 63 (84%) as a yellow solid: mp (iPr$_2$O/THF) 165-170° C.; $^1$H NMR [(CD$_3$)$_2$SO] δ 11.41 (d, J=2.0 Hz, 1H), 8.33 (d, J=8.9 Hz, 1H), 8.26 (d, J=1.8 Hz, 1H), 7.81 (s, 1H), 7.66 (dd, J=8.9, 1.8 Hz, 1H), 7.08 (d, J=2.2 Hz, 1H), 6.96 (s, 1H), 6.26 (s, 2H), 4.71 (dd, J=10.9, 8.8 Hz, 1H), 4.45 (dd, J=11.0, 1.6 Hz, 1H), 4.24-4.17 (m, 1H), 4.00 (dd, J=11.0, 3.3 Hz, 1H), 3.95 (s, 3H), 3.83 (s, 3H), 3.81 (s, 3H), 3.74 (dd, J=11.0, 7.9 Hz, 1H), 3.32 (s, 3H). Anal. ($C_{26}H_{26}ClN_3O_6S \cdot \frac{1}{2}H_2O$) C, H, N.

EXAMPLE 64

5-Amino-1-(chloromethyl)-3-{5-[2-(dimethylamino)ethoxy]indol-2-carbonyl}-8-(methylsulfonyl)-1,2-dihydro-3H-benzo[e]indole (64) (Scheme Q). Compound 47 (as the free base) was hydrogenated as described in Example 53 (50 psi for 60 min) to give 6.4 as a pale yellow solid: mp (i-Pr$_2$O/THF) 235-240° C.; $^1$H NMR. [(CD$_3$)$_2$SO] δ 115.6 (4, J=1.6 Hz, 1H), 8.33 (d, J=8.9 Hz, 1H), 8.26 (d, J=1.8 Hz, 1H), 7.88 (s, 1H), 7.67 (dd, J=8.9, 1.8 Hz, 1H), 7.40 (d, J=8.9 Hz, 1H), 7.17 (d, J=2.3 Hz, 1H), 7.10 (d, J=1.4 Hz, 1H), 6.92 (dd, J=8.9, 2.4 Hz, 1H), 6.26 (s, 2H), 4.76 (dd, J=10.8, 8.9 Hz, 1H), 4.55 (dd, J=10.9, 1.6 Hz, 1H), 4.28-4.21 (m, 1H), 4.06 (t, J=5.9 Hz, 2H), 4.01 (dd, J=11.0, 3.3 Hz, 1H), 3.78 (dd, J=11.1, 7.8 Hz, 1H), 3.32 (s, 3H), 2.65 (t, J=5.9 Hz, 2H), 2.23 (s, 6H). Anal. ($C_{27}H_{29}ClN_4O_4S \cdot \frac{1}{2}H_2O$) C, H, N.

TABLE 3

Activity of Selected Compounds of Table 1
The following table shows that the compounds of Formula I of the invention as a class are selectively toxic to hypoxic cells, with virtually all of them showing some selectivity for hypoxia against one or both of the cell lines (SZKOV3 and TH29) in proliferation IC$_{50}$ assays (HCR ≧ 3), with some having selectivities of >200-fold. Selected compounds evaluated in the clonogenic assay also show substantial hypoxic selectivity. Generally, the most selective compounds are those bearing 7-SO$_2$NHR or 7-CONHR substituents. This activity, together with the high potency of these compounds, suggests they have utility as hypoxia-selective cytotoxins. The Table also shows that the compounds of Formula I are more selectively toxic to hypoxic cells than the known compounds R1 and R2, in which the nitro-1,2-dihydro-3H-benzo[e]indole structure carries no substituent in the positions 6-9. Both of these reference compounds exhibit HCRs ≦ 3 in this assay.

| | | | | IC$_{50}$ average (μM)$^c$ | | | | Clonogenic C$_{10}$ (μM)$^d$ | |
| | | | E(1)$^b$ | SKOV3$^e$ | | HT29$^f$ | | HT29/OK | |
| | W$^a$, Y$^a$ = H and X$^a$ | Z$^a$ | (mV) | oxic | HCR$^g$ | Oxic | HCR$^g$ | Oxic | HCR$^h$ |
|---|---|---|---|---|---|---|---|---|---|
| R1$^i$ | H | A | | 4.2 | 2.8 | 3.4 | 2.5 | | |
| R2$^i$ | H | B | −512 ± 8 | 1.4 | 1.9 | 0.47 | 1.1 | 4.8 | 2 |
| 1 | 6-NO$_2$ | A | | >20 | — | 18 | <1 | | |
| 2 | 6-NO$_2$ | B | −467 ± 8 | 4.1 | 2.9 | 2.8 | 2.2 | | |
| 3 | 6-COMe | A | | 0.50 | 3.4 | 0.68 | 2.0 | | |
| 4 | 6-COMe | B | | 0.64 | 12 | 0.20 | 5.2 | | |
| 5 | 6-CONH$_2$ | B | −481 ± 8 | 50 | 18 | 23 | 43 | | |
| 6 | 6-CN | B | −491 ± 8 | 0.17 | 1.7 | 0.12 | 1.1 | | |
| 7 | 6-SO$_2$NH$_2$ | B | −497 ± 8 | 3.7 | 4.6 | 2.7 | 2.3 | | |
| 8 | 7-NO$_2$ | A | | 16 | 78 | 14 | 12 | >25 | >16.2 |
| 9 | 7-NO$_2$ | B | | 1.1 | 9.3 | 0.89 | 9.6 | | |
| 10 | 7-NH$_2$ | B | | 2.5 | 2.0 | 1.8 | 2.4 | | |
| 11 | 7-COMe | A | | 5.1 | 19 | 4.1 | 5.2 | >25 | >13.5 |
| 12 | 7-COMe | B | | 0.64 | 4.0 | 0.17 | 1.5 | | |
| 13 | 7-CO$_2$Me | A | | 1.1 | 4.0 | 1.9 | 3.2 | | |
| 14 | 7-CO$_2$Me | B | −429 ± 8 | 0.44 | 1.9 | 0.32 | 1.2 | | |
| 15 | 7-CONH$_2$ | A | | 5.8 | 6.1 | 7.9 | 2.8 | | |
| 16 | 7-CONH$_2$ | B | −422 ± 10 | 3.9 | 77 | 4.1 | 60 | >25 | >14 |
| 17 | 7-CONH(CH$_2$)$_2$OH | A | | | 5.7 | | 1.7 | | |
| 18 | 7-CONH(CH$_2$)$_2$OH | D | | 4.8 | 4.7 | 4.4 | 4.4 | | |
| 19 | 7-CONH(CH$_2$)$_2$OH | B | | 8.9 | 160 | 12 | 490 | | |
| 20 | 7-CONH(CH$_2$)$_2$NMe$_2$ | A | −427 ± 12 | 2.0 | 24 | 1.5 | 5.9 | | |
| 21 | 7-CN | A | | 6.4 | 13 | 5.3 | 2.5 | | |
| 22 | 7-CN | B | −385 ± 8 | 0.81 | 4.2 | 0.70 | 1.7 | | |
| 23 | 7-SO$_2$Me | A | | 17 | 1.9 | 14 | 2.0 | | |
| 24 | 7-SO$_2$Me | B | −362 ± 8 | 1.3 | 11 | 0.97 | 4.0 | | |
| 25 | 7-SO$_2$NH$_2$ | A | | 37 | 10 | 43 | 3.6 | | |
| 26 | 7-SO$_2$NH$_2$ | B | −390 ± 9 | 6.9 | 280 | 4.6 | 330 | >42 | >30.9 |
| 27 | 7-SO$_2$NH$_2$ | E | | 13 | 31 | 2.4 | 1.8 | | |
| 30 | 7-SO$_2$NHOH | B | | 24 | 55 | 24 | 160 | | |
| 31 | 7-SO$_2$NHNH$_2$ | B | | 33 | 160 | 31 | 220 | | |
| 32 | 7-SO$_2$NHMe | B | | 2.6 | 21 | 2.7 | 24 | | |
| 33 | 7-SO$_2$NH(CH$_2$)$_2$OH | A | | 13 | 5.8 | | | | |
| 35 | 7-SO$_2$NH(CH$_2$)$_2$OH | B | −392 ± 7 | 9.2 | 250 | 5.5 | 90 | 115 | 74.4 |
| 37 | 7-SO$_2$NH(CH$_2$)$_2$OH | D | | 4.7 | 3.4 | 4.8 | 1.3 | | |
| 38 | 7-SO$_2$NMe$_2$ | B | | 0.50 | 2.4 | 1.1 | 3.6 | | |
| 39 | 7-SO$_2$NH(CH$_2$)$_2$NMe$_2$ | B | −357 ± 8 | 0.83 | 130 | 0.73 | 110 | 6.2 | 55 |

TABLE 3-continued

Activity of Selected Compounds of Table 1

The following table shows that the compounds of Formula I of the invention as a class are selectively toxic to hypoxic cells, with virtually all of them showing some selectivity for hypoxia against one or both of the cell lines (SZKOV3 and TH29) in proliferation $IC_{50}$ assays (HCR ≧ 3), with some having selectivities of >200-fold. Selected compounds evaluated in the clonogenic assay also show substantial hypoxic selectivity. Generally, the most selective compounds are those bearing 7-$SO_2$NHR or 7-CONHR substituents. This activity, together with the high potency of these compounds, suggests they have utility as hypoxia-selective cytotoxins. The Table also shows that the compounds of Formula I are more selectively toxic to hypoxic cells than the known compounds R1 and R2, in which the nitro-1,2-dihydro-3H-benzo[e]indole structure carries no substituent in the positions 6-9. Both of these reference compounds exhibit HCRs ≦ 3 in this assay.

| | | | $E(1)^b$ (mV) | $IC_{50}$ average (μM)$^c$ | | | | Clonogenic $C_{10}$ (μM)$^d$ | |
| | | | | SKOV3$^e$ | | HT29$^f$ | | HT29/OK | |
| | $W^a, Y^a$ = H and $X^a$ | $Z^a$ | | oxic | HCR$^g$ | Oxic | HCR$^g$ | Oxic | HCR$^h$ |
|---|---|---|---|---|---|---|---|---|---|
| 41 | 8-COMe | B | | 0.20 | 1.3 | 0.15 | 1.1 | | |
| 42 | 8-$CO_2$Me | B | | 0.52 | 2.4 | 0.55 | 1.6 | | |
| 43 | 8-$CONH_2$ | B | −447 ± 9 | 3.4 | 34 | 2.8 | 22 | 33 | 21.2 |
| 44 | 8-CONH($CH_2$)$_2$$NMe_2$ | A | | 2.5 | 16 | 1.3 | 2.4 | | |
| 45 | 8-CN | B | −419 ± 8 | 1.2 | 1.5 | 1.4 | 1.4 | | |
| 46 | 8-$SO_2$Me | A | | 11 | 4.2 | 14 | 2.5 | | |
| 47 | 8-$SO_2$Me | B | −420 ± 8 | 1.9 | 2.7 | 0.98 | 1.2 | | |
| 48 | 8-$SO_2NH_2$ | A | | 12 | 2.6 | 24 | 1.9 | | |
| 49 | 8-$SO_2NH_2$ | B | −456 ± 8 | 4.9 | 21 | 9 | 26 | | |
| 51 | 9-$NO_2$ | A | | 55 | | 34 | 1.2 | | |
| 52 | 9-$NO_2$ | B | −477 ± 7 | 1.2 | 1.5 | 1.4 | 1.3 | | |

Footnotes for Table 3
$^a$W, X, Y, Z as defined in Table 1 for a compound of Formula I
$^b$E(1): one-electron reduction potential, determined by pulse radiolysis.
$^c$$IC_{50}$: drug concentration to reduce cell numbers by 50% relative to controls on the same 96 well plate, following a 4 h exposure under aerobic conditions.
$^d$$C_{10}$: drag concentration to reduce the number of HT29 clonogens to 10% of controls, following a 4 hr exposure under aerobic conditions.
$^e$SKOV3: human ovarian carcinoma cell line.
$^f$HT29: human colon cancer cell line.
$^g$HCR: hypoxic cytotoxicity ratio = $IC_{50}$(aerobic)/$C_{10}$(hypoxic)
$^h$HCR: hypoxic cytotoxicity ratio = $C_{10}$(aerobic)/$C_{10}$(hypoxic)
$^i$Reference compounds R1 and R2 (Denny et al., PCT Int. Appl. WO 98/11101 A2, 1998) with structures as shown:

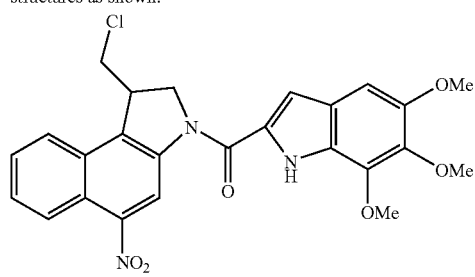

R1

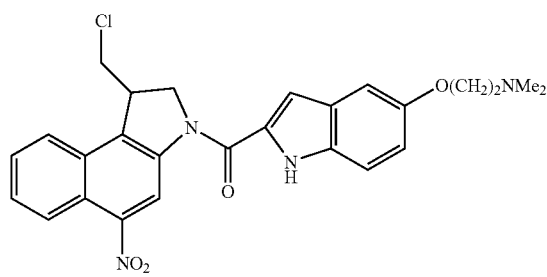

R2

TABLE 4

Activity of Compounds of Table 2
The following table shows that the compounds of Formula II of the invention as a class are potent cytotoxins, with $IC_{50}$s in the low nanomolar range in both of the cell proliferation assays. The table also shows that none of the compounds of Formula II have significant selective toxicity to hypoxic cells (HCR $\leq$ 3 for all compounds).

|  |  |  | $IC_{50}$ average (nM)[b] | | | |
|---|---|---|---|---|---|---|
|  |  |  | SKOV3[c] | | HT29[d] | |
|  | $W^a, Y^a$ = H and $X^a$ | $Z^a$ | oxic | HCR[e] | oxic | HCR[e] |
| 53 | 7-COMe | B | 11 | 1.4 | 7.6 | 1.5 |
| 54 | 7-CO$_2$Me | B | 7.7 | 0.91 | 8.6 | 1.7 |
| 55 | 7-CONH$_2$ | B | 13 | 1.0 | 61 | 1.4 |
| 56 | 7-CN | B | 13 | 1.1 | 17 | 2.0 |
| 57 | 7-SO$_2$Me | A | 32 | 1.2 | 32 | 0.86 |
| 58 | 7-SO$_2$Me | B | 14 | 1.7 | 11 | 1.6 |
| 59 | 7-SO$_2$NH$_2$ | A | 41 | 1.3 | 86 | 1.1 |
| 60 | 7-SO$_2$NH$_2$ | B | 23 | 1.4 | 35 | 1.8 |
| 61 | 7-SO$_2$NHMe | B | 20 | 1.8 | 24 | 1.2 |
| 62 | 7-SO$_2$NH(CH$_2$)$_2$OH | B | 34 | 1.1 | 94 | 1.0 |
| 63 | 8-SO$_2$Me | A | 19 | 1.4 | 25 | 1.0 |
| 64 | 8-SO$_2$Me | B | 18 | 1.5 | 29 | 1.9 |

Footnotes for Table 4
[a] W, X, Y, Z as defined in Table 2 for a compound of Formula II
[b] $IC_{50}$: drug concentration to reduce cell numbers by 50%, following a 4 h exposure under aerobic conditions.
[c] SKOV3: human ovarian carcinoma cell line.
[d] HT29: human colon cancer cell line.
[e] HCR: hypoxic cytotoxicity ratio = $IC_{50}$(aerobic)/$IC_{50}$(hypoxic)

Chart 1 and Table 5. Hypoxic Metabolism of Compounds of Formula I

Metabolism of compounds of Formula I was investigated using S9 preparations from HT29 tumours grown as xenografts in CD-1 mice. The chart below shows a representative example of HPLC chromatograms for compound 26 incubated at 10 μM with S9 (12 mg/mL protein) at 37-C in phosphate buffer (67 mM, pH 7.4 containing NADPH at 1 mM) for 2 h under oxic or hypoxic conditions. This chart shows that compound 60, which was identified by comparison with an authentic standard, is the major product of hypoxic metabolism. Under oxic conditions 60 was not detected.

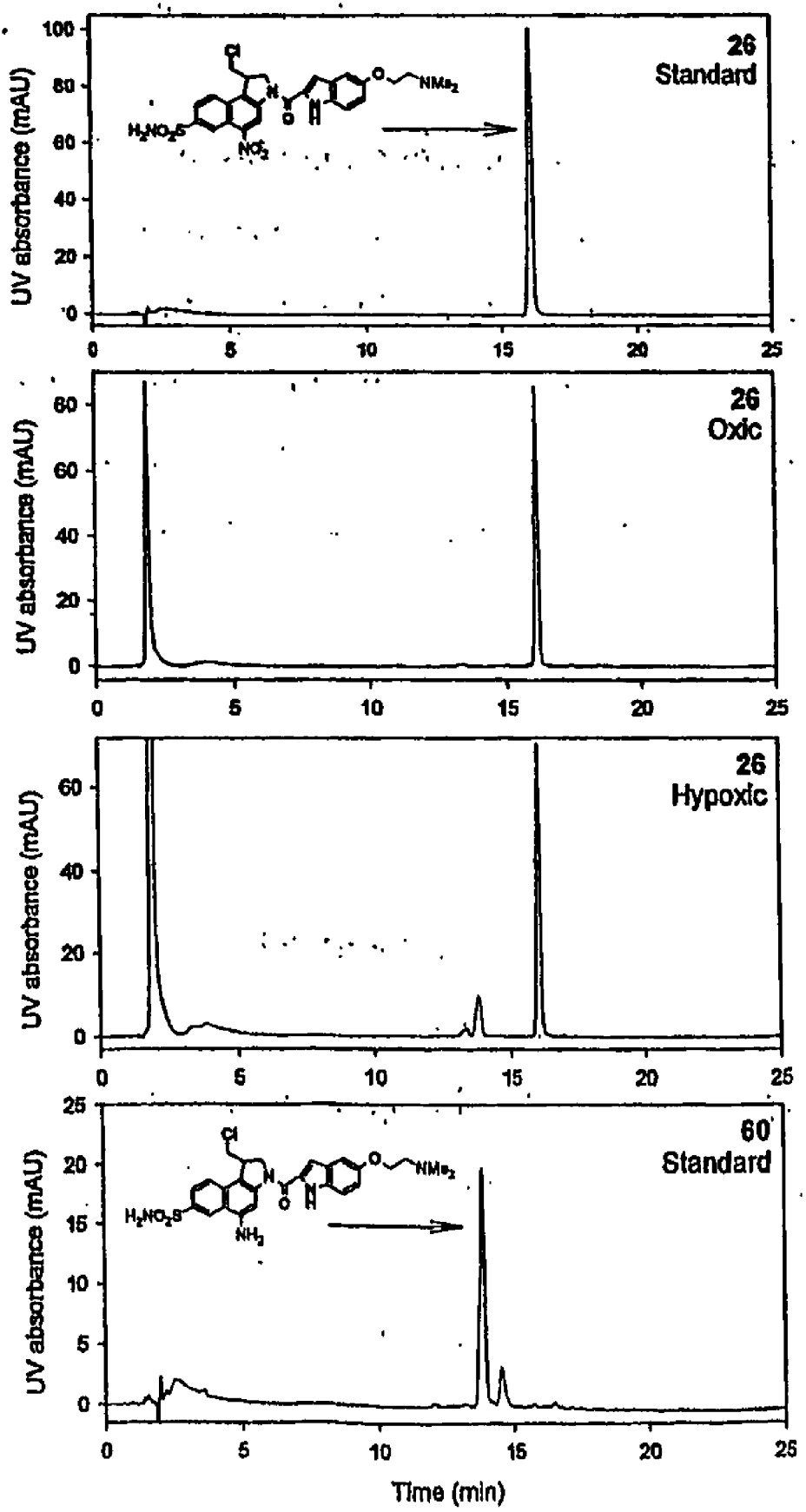

TABLE 5

The following table shows the rate of formation of compounds of Formula II from compounds of Formula I, where the compounds of Formula I are incubated at 10 μM with tumour S9 (12 mg/mL protein) at 37° C. in phosphate buffer (67 mM, pH 7.4 containing NADPH at 1 mM) for 2 h under hypoxic conditions. This table shows that hypoxic turnouts are able to metabolise compounds of Formula I to compounds of Formula II, and that the rate of formation of the compounds of Formula II appears to be dependent on the nature of the X substituent.

| No[a] | X[b] | HCR[c] | No[d] | k[e] (μM/h) |
|---|---|---|---|---|
| R2 | H | 1.1 | R3 | 0.49 |
| 22 | 7-CN | 1.7 | 56 | 1.27 |
| 16 | 7-CONH$_2$ | 60 | 55 | 1.48 |
| 26 | 7-SO$_2$NH$_2$ | 330 | 60 | 2.79 |

Footnotes for Table 5
[a]Compound of Formula I (or compound R2 as in Table 3).
[b]X substituent as defined in Table I.
[c]HCR: Hypoxic cytotoxicity ratio for HT29 cell line, as defined in Table 3.
[d]Compound of Formula II (or compound R3 of structure shown) produced by hypoxic metabolism. Identity confirmed by comparison to authentic standards.
[e]Rate of formation of compound of Formula II.

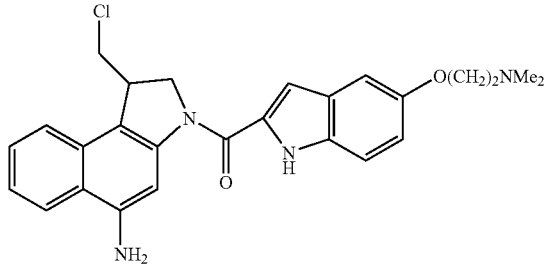

R3

Chart 2 and Table 6. Pharmacokinetic Properties of Phosphate 36 in Mice

The following chart shows that compound 36, as a representative example of the highly water soluble phosphates of Formula I, is hydrolysed to the corresponding alcohol (in this example, 35) following intravenous administration to CD-1 mice (nu/+ heterozygotes) at a well-tolerated dose (42.1 μmol/kg; the maximum tolerated dose following intravenous administration being 100 μmol/kg). Compound 36 was formulated for injection in phosphate buffered saline containing 2 equivalents of NaHCO$_3$, pH 7.5 (solubility limit in this medium 25 mM). The compounds were assayed in plasma, following precipitation of proteins with methanol, using an LC/MS/MS (triple quadrupole mass spectrometer).

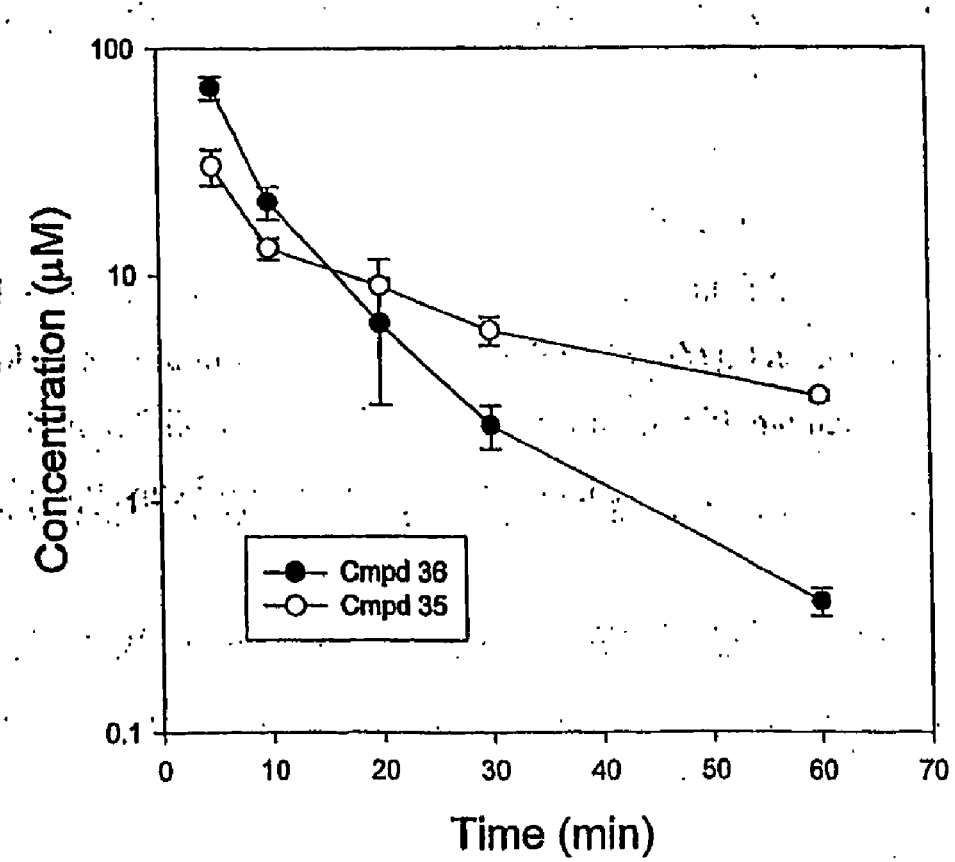

The non-compartmental plasma pharmacokinetic parameters for 36 and 35 are shown in the following Table. The data show that 35, derived from 36, exhibits favourable pharmacokinetic properties with a moderately long terminal half life (43 min) and an AUC of approximately 700 μM.min. The latter AUC value is greater than that required to kill hypoxic tumour cells in vitro (e.g. the AUC for 90% kill of HT29 cells under hypoxic conditions is estimated at 371 μM.min from the clonogenic assay data for 35 in Table 3).

TABLE 6

Plasma pharmacokinetic parameters for 36 and its metabolite 35.

| Parameter[a] | 36 Mean | 36 SEM | 35 Mean | 35 SEM |
|---|---|---|---|---|
| AUC (μM min) | 1208[b] | 143 | 701 | 68 |
| $T_{1/2}$ (min) | 27 | 0.9 | 43 | 2.0 |
| $V_d$ (L/kg) | 1.4 | 0.2 | 3.8 | 0.4 |
| Cl (L/kg min) | 0.036 | 0.005 | 0.061 | 0.006 |

Footnotes for Table 6
[a]Derived pharmacokinetic parameters: AUC: area under concentration-time curve, $T_{1/2}$: terminal half-life, $V_d$: volume of distribution based on the terminal phase, Cl: clearance.
[b]Values are for 3 mice per group.

APPENDIX

Combustion analyses for the new compounds of Table 1 and Table 2

| | Found | | | | Calculated | | | |
|---|---|---|---|---|---|---|---|---|
| No | C | H | N | other | C | H | N | other |
| 1 | 55.60 | 4.02 | 10.44 | | 55.51 | 3.91 | 10.36 | |
| 2 | 51.87 | 4.74 | 11.69 | | 51.92 | 4.69 | 11.65 | |
| 3 | 59.48 | 4.35 | 7.50 | | 59.29 | 4.57 | 7.68 | |
| 4 | 61.80 | 5.10 | 10.49 | 6.65 (Cl) | 61.86 | 5.09 | 10.47 | 6.65 (Cl) |
| 5 | 60.30 | 4.86 | 12.91 | 6.67 (Cl) | 60.50 | 4.89 | 13.07 | 6.61 (Cl) |
| 6 | 62.09 | 4.71 | 13.12 | | 62.09 | 4.69 | 13.41 | |
| 7 | 54.39 | 4.60 | 12.12 | 6.37 (Cl) | 54.59 | 4.58 | 12.24 | 6.20 (Cl) |
| 8 | 55.76 | 4.17 | 10.29 | | 55.51 | 3.91 | 10.36 | |
| 9 | 54.26 | 4.54 | 11.92 | | 54.37 | 4.39 | 12.19 | |
| 10 | 58.14 | 5.00 | 12.50 | | 58.37 | 5.46 | 13.09 | |
| 11 | 60.35 | 4.47 | 7.52 | | 60.28 | 4.50 | 7.81 | |
| 12 | 60.88 | 5.17 | 10.16 | 5.75 (Cl) | 60.82 | 5.24 | 10.13 | 6.40 (Cl) |
| 13 | 58.30 | 4.23 | 7.38 | | 58.54 | 4.37 | 7.59 | |
| 14 | 56.23 | 4.75 | 9.31 | | 56.38 | 4.90 | 9.40 | |
| 15 | 58.07 | 4.36 | 9.89 | | 57.94 | 4.30 | 10.40 | |
| 16 | 54.87 | 4.79 | 11.86 | | 54.92 | 4.95 | 11.86 | |
| 17 | 57.46 | 4.94 | 9.58 | | 57.69 | 4.67 | 9.61 | |
| 18 | 61.13 | 4.78 | 8.18 | | 61.24 | 4.74 | 8.24 | |
| 19 | 56.20 | 5.11 | 10.97 | 11.49 (Cl) | 56.50 | 5.07 | 11.36 | 11.50 (Cl) |
| 20 | 55.62 | 5.15 | 10.77 | | 55.73 | 5.14 | 10.83 | |
| 21 | 59.94 | 3.83 | 10.71 | | 59.94 | 4.06 | 10.76 | |
| 22 | 57.57 | 4.39 | 12.24 | | 57.56 | 4.65 | 12.43 | |
| 23 | 53.57 | 4.46 | 7.30 | | 53.56 | 4.32 | 7.21 | |
| 24 | 53.35 | 4.66 | 8.97 | | 53.38 | 4.65 | 9.22 | |
| 25 | 52.00 | 4.28 | 9.35 | | 52.22 | 4.03 | 9.74 | |
| 26 | 50.63 | 4.83 | 11.25 | | 50.57 | 4.57 | 11.34 | |
| 27 | 52.62 | 3.92 | 8.10 | | 52.43 | 4.02 | 7.98 | |
| 28 | 52.65 | 4.26 | 9.90 | | 52.40 | 4.40 | 10.19 | |
| 29 | 45.48 | 3.87 | 8.84 | | 45.47 | 3.66 | 8.84 | |
| 30 | 48.72 | 4.55 | 10.35 | | 48.60 | 4.55 | 10.90 | |
| 32 | 50.94 | 4.51 | 10.74 | | 50.98 | 4.68 | 11.01 | |
| 33 | 52.55 | 4.47 | 9.21 | | 52.39 | 4.40 | 9.05 | |
| 34 | 46.45 | 4.09 | 7.82 | | 46.39 | 4.04 | 8.02 | |
| 36 | 44.64 | 4.20 | 8.47 | | 44.48 | 3.98 | 8.65 | |
| 37 | 55.11 | 4.63 | 7.52 | | 54.99 | 4.43 | 7.70 | |
| 38 | 52.20 | 5.15 | 10.73 | | 52.10 | 5.00 | 10.83 | |
| 39 | 47.28 | 5.13 | 10.80 | | 47.31 | 5.16 | 11.04 | |
| 41 | 60.87 | 4.90 | 9.72 | | 60.81 | 5.29 | 10.13 | |
| 43 | 51.65 | 3.90 | 10.03 | | 51.79 | 4.42 | 10.41 | |
| 44 | 55.52 | 5.21 | 10.73 | | 55.73 | 5.14 | 10.83 | |
| 45 | 62.35 | 4.67 | 13.21 | | 62.61 | 4.67 | 13.52 | |

APPENDIX-continued

Combustion analyses for the new compounds of Table 1 and Table 2

| | Found | | | | Calculated | | | |
|---|---|---|---|---|---|---|---|---|
| No | C | H | N | other | C | H | N | other |
| 46 | 54.41 | 4.31 | 7.39 | | 54.40 | 4.21 | 7.32 | |
| 47 | 53.05 | 4.51 | 9.27 | | 53.38 | 4.65 | 9.22 | |
| 48 | 52.54 | 4.42 | 9.16 | | 52.39 | 4.40 | 9.05 | |
| 49 | 53.61 | 4.67 | 11.75 | | 53.75 | 4.68 | 12.05 | |
| 51 | 55.52 | 3.90 | 10.22 | | 55.51 | 3.91 | 10.36 | |
| 52 | 52.95 | 4.57 | 11.91 | | 52.71 | 4.59 | 11.82 | |
| 54 | 64.31 | 5.70 | 10.46 | | 64.55 | 5.61 | 10.75 | |
| 55 | 63.08 | 5.70 | 13.46 | | 62.97 | 5.68 | 13.60 | |
| 57 | 57.59 | 4.81 | 7.59 | | 57.40 | 4.82 | 7.73 | |
| 58 | 59.91 | 5.60 | 10.22 | 6.33 (Cl) | 59.93 | 5.40 | 10.36 | 6.55 (Cl) |
| 59 | 54.93 | 4.84 | 9.88 | | 55.10 | 4.62 | 10.28 | |
| 61 | 57.24 | 5.69 | 11.64 | | 57.18 | 5.79 | 11.50 | |
| 62 | 56.65 | 5.57 | 11.74 | | 56.51 | 5.59 | 11.77 | |
| 63 | 56.78 | 4.88 | 7.48 | | 56.46 | 4.92 | 7.60 | |
| 64 | 58.93 | 5.61 | 10.00 | | 58.96 | 5.50 | 10.19 | |

Combustion Analyses for Intermediates

The following are known from the literature: 101, 104, 133, 139, 146, 156, 166, 167, 191, 192, 224, 230.

| | Found | | | | Calculated | | | |
|---|---|---|---|---|---|---|---|---|
| No | C | H | N | Other | C | H | N | other |
| 102 | 59.59 | 4.17 | 10.47 | | 59.44 | 4.22 | 10.66 | |
| 103 | 50.98 | 3.27 | 13.67 | | 50.74 | 3.28 | 13.66 | |
| 105 | 56.10 | 5.11 | 4.38 | 24.66 (Br) | 55.92 | 5.01 | 4.35 | 24.80 (Br) |
| 107 | 68.02 | 6.15 | 4.48 | | 68.02 | 6.34 | 4.41 | |
| 108 | 57.40 | 3.65 | 4.44 | | 57.43 | 3.53 | 4.46 | |
| 109 | 57.13 | 3.54 | 3.79 | | 57.40 | 3.68 | 3.94 | |
| 110 | 57.48 | 3.44 | 3.83 | | 57.40 | 3.68 | 3.94 | |
| 111 | 50.96 | 2.75 | 6.71 | | 50.95 | 3.02 | 6.99 | |
| 112 | 51.25 | 2.86 | 7.00 | | 50.95 | 3.02 | 6.99 | |
| 113 | 43.81 | 2.16 | 3.28 | 17.10 (Cl) | 43.71 | 2.45 | 3.40 | 17.20 (Cl) |
| 114 | 43.85 | 2.15 | 3.27 | 17.27 (Cl) | 43.71 | 2.45 | 3.40 | 17.20 (Cl) |
| 115 | 39.22 | 1.76 | 6.13 | | 39.41 | 1.98 | 6.13 | |
| 116 | 39.63 | 1.74 | 6.16 | 15.96 (Cl) | 39.41 | 1.98 | 6.13 | 15.51 (Cl) |
| 117 | 45.95 | 3.80 | 12.15 | | 45.69 | 3.54 | 12.30 | |
| 118 | 43.90 | 3.49 | 11.99 | | 43.64 | 3.38 | 11.75 | |
| 121 | 46.98 | 4.19 | 10.71 | | 46.70 | 4.18 | 10.89 | |
| 122 | 48.84 | 4.38 | 11.27 | | 48.72 | 4.36 | 11.36 | |
| 123 | 41.45 | 2.62 | 9.45 | | 41.16 | 2.53 | 9.60 | |
| 124 | 48.93 | 4.66 | 9.61 | | 48.93 | 4.56 | 9.51 | |
| 125 | 41.20 | 1.99 | 2.97 | | 40.98 | 2.29 | 3.19 | |
| 126 | 55.73 | 2.76 | 8.07 | | 55.75 | 3.02 | 8.13 | |
| 127 | 50.01 | 2.15 | 10.68 | | 50.08 | 2.36 | 10.95 | |
| 128 | 54.03 | 3.27 | 7.87 | 9.95 (Cl) | 53.87 | 3.39 | 7.85 | 9.94 (Cl) |
| 129 | 48.23 | 3.28 | 9.98 | 8.48 (Cl) | 47.84 | 2.76 | 10.46 | 8.83 (Cl) |
| 131 | 50.12 | 3.00 | 7.54 | | 50.22 | 2.81 | 7.81 | |
| 132 | 50.44 | 2.94 | 7.76 | | 50.22 | 2.81 | 7.81 | |
| 134 | 59.72 | 4.25 | 10.76 | | 59.44 | 4.22 | 10.67 | |
| 135 | 51.03 | 2.99 | 13.45 | 11.55 (Cl) | 50.74 | 3.28 | 13.66 | 11.52 (Cl) |
| 136 | 59.47 | 4.25 | 10.51 | | 59.44 | 4.22 | 10.67 | |
| 137 | 50.67 | 3.56 | 13.86 | 11.62 (Cl) | 50.74 | 3.28 | 13.66 | 11.52 (Cl) |
| 138 | 50.86 | 3.20 | 13.39 | 11.83 (Cl) | 50.74 | 3.28 | 13.66 | 11.52 (Cl) |
| 140 | 71.47 | 5.93 | 10.16 | | 71.62 | 6.01 | 10.44 | |
| 141 | 55.61 | 4.28 | 8.08 | 23.24 (Br) | 55.35 | 4.36 | 8.07 | 23.01 (Br) |
| 143 | 66.00 | 5.43 | 7.96 | | 65.70 | 5.66 | 8.07 | |
| 144 | 58.74 | 3.44 | 14.53 | 12.13 (Cl) | 58.44 | 3.50 | 14.61 | 12.32 (Cl) |
| 145 | 55.30 | 4.18 | 13.49 | | 55.00 | 3.96 | 13.75 | |
| 147 | 68.04 | 6.38 | 4.64 | | 67.76 | 6.36 | 4.65 | |
| 148 | 53.93 | 4.70 | 3.59 | 20.97 (Br) | 53.70 | 4.77 | 3.68 | 21.01 (Br) |
| 150 | 64.21 | 6.07 | 3.62 | | 63.91 | 5.90 | 3.73 | |
| 152 | 56.37 | 3.83 | 8.67 | 10.98 (Cl) | 56.18 | 4.09 | 8.73 | 11.05 (Cl) |
| 153 | 55.58 | 3.80 | 9.10 | | 54.82 | 3.62 | 9.14 | |
| 154 | 56.22 | 5.63 | 14.69 | | 56.03 | 5.75 | 14.52 | |
| 155 | 54.64 | 4.84 | 11.67 | | 54.94 | 4.61 | 12.01 | |
| 157 | 62.32 | 5.49 | 4.92 | | 62.26 | 5.23 | 4.84 | |

-continued

| No | Found C | H | N | Other | Calculated C | H | N | other |
|---|---|---|---|---|---|---|---|---|
| 158 | 62.74 | 5.35 | 5.15 |  | 62.26 | 5.23 | 4.84 |  |
| 159 | 66.25 | 4.39 |  |  | 66.03 | 4.62 |  |  |
| 160 | 57.67 | 3.79 |  |  | 57.59 | 4.03 |  |  |
| 161 | 60.00 | 5.75 | 4.32 |  | 59.79 | 5.96 | 4.36 |  |
| 162 | 48.05 | 4.32 | 3.67 |  | 48.01 | 4.53 | 3.50 |  |
| 164 | 57.94 | 5.54 | 3.81 |  | 57.64 | 5.60 | 3.54 |  |
| 165 | 49.63 | 3.56 | 8.14 | 10.45 (Cl) | 49.34 | 3.84 | 8.22 | 10.40 (Cl) |
| 168 | 73.96 | 5.27 |  |  | 73.67 | 5.30 |  |  |
| 169 | 72.60 | 4.60 |  |  | 72.89 | 4.71 |  |  |
| 170 | 71.55 | 6.90 | 5.06 |  | 71.56 | 6.71 | 4.91 |  |
| 171 | 56.37 | 5.15 | 3.98 |  | 56.06 | 4.98 | 3.85 |  |
| 173 | 66.80 | 6.23 | 3.85 |  | 66.76 | 6.16 | 3.89 |  |
| 174 | 57.61 | 3.65 | 3.91 |  | 57.40 | 3.68 | 3.94 |  |
| 175 | 50.94 | 2.89 | 6.73 |  | 50.95 | 3.02 | 6.99 |  |
| 178 | 67.50 | 3.99 |  |  | 67.82 | 4.38 |  |  |
| 179 | 68.03 | 6.37 | 4.57 |  | 67.76 | 6.36 | 4.65 |  |
| 180 | 53.88 | 4.75 | 3.69 | 21.16 (Br) | 53.70 | 4.77 | 3.69 | 21.01 |
| 182 | 64.18 | 6.01 | 3.61 | 9.20 (Cl) | 63.91 | 5.90 | 3.73 | 9.43 (Cl) |
| 183 | 54.98 | 3.73 | 3.67 |  | 54.93 | 3.52 | 3.77 |  |
| 184 | 49.26 | 2.73 | 6.59 |  | 49.00 | 2.90 | 6.73 |  |
| 185 | 49.60 | 3.06 | 6.49 |  | 49.27 | 3.22 | 6.39 |  |
| 187 | 54.75 | 3.87 | 9.11 |  | 54.82 | 3.62 | 9.14 |  |
| 188 | 57.32 | 5.46 | 14.82 |  | 57.37 | 5.62 | 14.87 |  |
| 190 | 56.80 | 2.39 | 5.91 | 34.32 (Br) | 56.93 | 2.61 | 6.04 | 34.43 (Br) |
| 193 | 71.38 | 6.05 | 10.34 |  | 71.62 | 6.01 | 10.44 |  |
| 194 | 55.59 | 4.22 | 8.06 | 23.27 (Br) | 55.35 | 4.36 | 8.07 | 23.01 (Br) |
| 196 | 66.65 | 5.41 | 8.09 |  | 66.57 | 5.59 | 8.17 |  |
| 197 | 57.99 | 3.39 | 14.42 |  | 58.45 | 3.50 | 14.61 |  |
| 199 | 52.28 | 3.53 |  | 12.45 (S) | 52.19 | 3.58 |  | 12.66 (S) |
| 200 | 66.34 | 4.40 |  |  | 66.03 | 4.62 |  |  |
| 201 | 57.36 | 3.99 |  |  | 57.59 | 4.03 |  |  |
| 202 | 59.49 | 6.08 | 4.27 |  | 59.79 | 5.96 | 4.36 |  |
| 203 | 48.06 | 4.59 | 3.33 |  | 48.01 | 4.53 | 3.50 |  |
| 205 | 59.23 | 6.01 | 3.34 |  | 59.11 | 6.54 | 3.13 |  |
| 206 | 49.60 | 3.70 | 8.06 |  | 49.34 | 3.84 | 8.22 |  |
| 207 | 39.45 | 1.94 |  |  | 39.11 | 1.98 |  |  |
| 208 | 62.82 | 4.26 | 2.90 |  | 62.76 | 4.46 | 3.17 |  |
| 209 | 69.94 | 5.24 | 3.22 |  | 70.09 | 5.20 | 3.14 |  |
| 210 | 69.47 | 4.66 | 3.47 |  | 69.59 | 4.91 | 3.25 |  |
| 211 | 69.47 | 6.13 | 5.55 |  | 69.30 | 6.02 | 5.57 |  |
| 212 | 60.19 | 5.11 | 4.73 |  | 59.90 | 5.03 | 4.82 |  |
| 214 | 66.81 | 5.86 | 4.95 |  | 66.60 | 5.76 | 4.85 |  |
| 215 | 60.74 | 4.19 | 4.98 |  | 60.79 | 4.22 | 4.89 |  |
| 216 | 44.92 | 3.16 | 6.76 |  | 44.84 | 3.26 | 6.97 |  |
| 217 | 41.16 | 2.64 | 9.26 |  | 41.15 | 2.53 | 9.60 |  |
| 218 | 41.53 | 2.64 | 9.38 |  | 41.15 | 2.53 | 9.60 |  |
| 220 | 47.86 | 2.62 | 6.84 |  | 47.72 | 2.50 | 6.96 |  |
| 221 | 50.81 | 4.10 | 8.83 |  | 50.70 | 4.04 | 8.87 |  |
| 222 | 57.46 | 5.34 | 11.16 |  | 57.22 | 5.34 | 11.12 |  |
| 223 | 60.84 | 5.64 | 11.40 |  | 61.23 | 5.64 | 11.52 |  |
| 228 | 51.60 | 5.42 | 6.80 |  | 51.82 | 5.47 | 6.91 |  |
| 229 | 52.95 | 5.91 | 8.48 |  | 52.91 | 5.92 | 8.57 |  |
| 231 | 70.51 | 5.62 | 3.91 |  | 70.79 | 5.64 | 4.23 |  |
| 232 | 55.43 | 6.85 | 3.41 |  | 55.20 | 6.83 | 3.39 |  |
| 233 | 52.19 | 5.94 | 8.59 |  | 52.46 | 5.75 | 8.50 |  |

Wherein the foregoing description reference has been made to reagents, or integers having known equivalents thereof, then those equivalents are herein incorporated as if individually set forth.

While this invention has been described with reference to certain embodiments and examples, it is to be appreciated that further modifications and variations may be made to embodiments and examples without departing from the scope of the invention.

The invention claimed is:

1. A compound of Formula I,

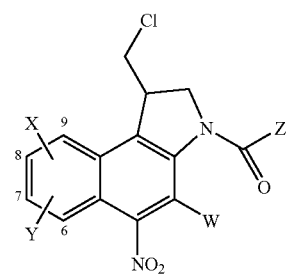

(I)

wherein X, Y, and W are independently selected from H, halogen, $C_{1-4}$alkyl, $OR^1$, $OP(O)(OH)_2$, $SR^1$, $NR^1_2$, $COR^1$, $SOR^1$, $SO_2R^1$, $SO_2NR^1_2$, $SO_2NR^1OR^1$, $SO_2NR^1NR^1_2$, $SO_2NHCOR^1$, $CO_2R^1$, $CONR^1_2$, $CONHSO_2R^1$, $CF_3$, $CN$, $NO_2$, where X and Y are located at any one of the available positions 6-9, and where each $R^1$ independently represents H or a $C_{1-4}$alkyl, optionally substituted with one or more hydroxyl or amino groups, each hydroxyl group being further optionally substituted with a phosphate $[P(O)(OH)_2]$ group, and each amino group being further optionally substituted with one or two $C_{1-4}$alkyl groups, and wherein Z may be selected from the following structures (Ia-Ic)

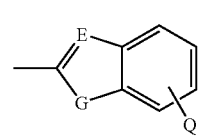

(Ia)

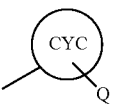

(Ib)

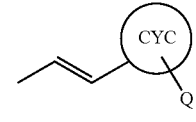

(Ic)

wherein E may be selected from —N= or —CH=, G may be-selected from O, S, or NH, Q may be independently selected from one to three of $R^2$, $OR^2$, $OP(O)(OH)_2$ halogen, $NR^2_2$, $NO_2$, $CO_2R^2$, $CONR_2^2$, $NR^2COR^2$, where each $R^2$ independently represents H, lower $C_{1-4}$ alkyl, optionally substituted with one or more hydroxyl or amino groups, each hydroxyl group being further optionally substituted with a phosphate $[P(O)(OH)_2]$ group, each amino group being optionally substituted with one or two $C_{1-4}$alkyl groups; and CYC may represent a 5- or 6-membered carbocycle, or heterocycle containing one or two atoms independently selected from N, O and S, and physiologically functional salt derivatives thereof, with the proviso that when W represents H, X and Y do not each represent H.

2. A compound of formula I as claimed in claim 1 wherein Z is selected from the following:

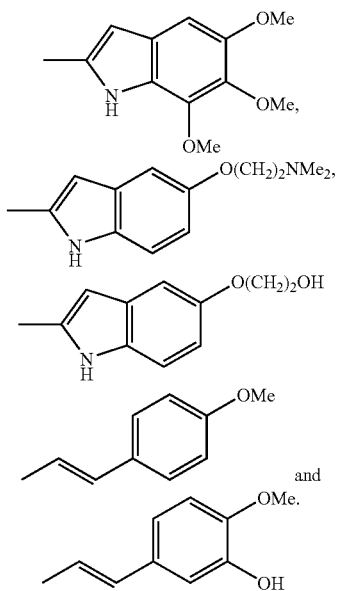

3. A compound of formula I as claimed in claim 1 selected from the following
- 1-(Chloromethyl)-5,6-dinitro-3-(5,6,7-trimethoxyindol-2-carbonyl)-1,2-dihydro-3H-benzo[e]indole;
- 1-(Chloromethyl)-3-{5-[2-(dimethylamino)ethoxy]indol-2-carbonyl}-5,6-dinitro-1,2-dihydro-3H-benzo[e]indole;
- 6-Acetyl-1-(chloromethyl)-5-nitro-3-(5,6,7-trimethoxyindol-2-carbonyl)-1,2-dihydro-3H-benzo[e]indole;
- 6-Acetyl-1-(chloromethyl)-3-{5-[2-(dimethylamino)ethoxy]indol-2-carbonyl}-5-nitro-1,2-dihydro-3H-benzo[e]indole;
- 7-Acetyl-1-(chloromethyl)-5-nitro-3-(5,6,7-trimethoxyindol-2-carbonyl)-1,2-dihydro-3H-benzo[e]indole;
- 7-Acetyl-1-(chloromethyl)-3-{5-[2-(dimethylamino)ethoxy]indol-2-carbonyl}-5-nitro-1,2-dihydro-3H-benzo[e]indole;
- 1-(Chloromethyl)-3-{5-[2-(dimethylamino)ethoxy]indol-2-carbonyl}-5-nitro-1,2-dihydro-3H-benzo[e]indole-6-sulfonamide;
- 1-(Chloromethyl)-3-{5-[2-(dimethylamino)ethoxy]indol-2-carbonyl}-5-nitro-1,2-dihydro-3H-benzo[e]indole-7-sulfonamide;
- 1-(Chloromethyl)-3-[(2E)-3-(3-hydroxy-4-methoxyphenyl)-2-propenoyl]-5-nitro-1,2-dihydro-3H-benzo[e]indole-7-sulfonamide;
- 1-(Chloromethyl)-3-[5-(2-hydroxyethoxy)indol-2-carbonyl]-5-nitro-1,2-dihydro-3H-benzo[e]indole-7-sulfonamide;
- 1-(Chloromethyl)-3-{5-[2-(dimethylamino)ethoxy]indol-2-carbonyl}-N-methyl-5-nitro-1,2-dihydro-3H-benzo[e]indole-7-sulfonamide
- 1-(Chloromethyl)-N-(2-hydroxyethyl)-5-nitro-3-(5,6,7-trimethoxyindol-2-carbonyl)-1,2-dihydro-3H-benzo[e]indole-7-sulfonamide;
- 1-(Chloromethyl)-N-(2-hydroxyethyl)-3-[(E)-4-methoxycinnamoyl]-5-nitro-1,2-dihydro-3H-benzo[e]indole-7-sulfonamide;
- 1-(Chloromethyl)-3-{5-[2-(dimethylamino)ethoxy]indol-2-carbonyl}-N-(2-hydroxyethyl)-5-nitro-1,2-dihydro-3H-benzo[e]indole-7-sulfonamide;
- 1-(Chloromethyl)-3-{5-[2-(dimethylamino)ethoxy]indol-2-carbonyl}-N,N-dimethyl-5-nitro-1,2-dihydro-3H-benzo[e]indole-7-sulfonamide;
- 1-(Chloromethyl)-3-{5-[2-(dimethylamino)ethoxy]indol-2-carbonyl}-N-[2-dimethylamino)ethyl]-5-nitro-1,2-dihydro-3H-benzo[e]indole-7-sulfonamide;
- 1-(Chloromethyl)-3-{5-[2-(dimethylamino)ethoxy]indol-2-carbonyl}-5-nitro-[2-dihydro-3H-benzo[e]indole-6-carbonitrile;
- 1-(Chloromethyl)-3-{5-[2-(dimethylamino)ethoxy]indol-2-carbonyl}-5-nitro-1,2-dihydro-3H-benzo[e]indole-6-carboxamide;
- 1-(Chloromethyl)-5,7-dinitro-(5,6,7-trimethoxyindol-2-carbonyl)-1,2-dihydro-3H-benzo[e]indole;
- 1-(Chloromethyl)-3-{5-[2-(dimethylamino)ethoxy]indol-2-carbonyl}-5,7-dinitro-1,2-dihydro-3H-benzo[e]indole; 1-(Chloromethyl)-5,9-dinitro-(5,6,7-trimethoxyindol-2-carbonyl)-1,2-dihydro-3H-benzo[e]indole;
- 1-(Chloromethyl)-3-{5-[2-(dimethylamino)ethoxy]indol-2-carbonyl}-5,9-dinitro-1,2-dihydro-3H-benzo[e]indole; 1-(Chloromethyl)-5-nitro-3-[5,6,7-trimethoxyindol-2-carbonyl]-1,2-dihydro-3H-benzo[e]indole-7-carboxamide;
- 1-(Chloromethyl)-3-{5-[2-(dimethylamino)ethoxy]indol-2-carbonyl}-5-nitro-1,2-dihydro-3H-benzo[e]indole-7-carboxamide;
- 1-(Chloromethyl)-5-nitro-3-(5,6,7-trimethoxyindol-2-carbonyl)-1,2-dihydro-3H-benzo[e]indole-7-carbonitrile;
- 1-(Chloromethyl)-3-{5-[2-(dimethylamino)ethoxy]indol-2-carbonyl}-5-nitro-1,2-dihydro-3H-benzo [e]indole-7-carbonitrile;
- 1-(Chloromethyl)-N-(2-hydroxyethyl)-5-nitro-3-(5,6,7-trimethoxyindol-2-carbonyl)-1,2-dihydro-3H-benzo[e]-indole-7-carboxamide;
- 1-(Chloromethyl)-N-(2-hydroxyethyl)-3-[(E)-4-methoxycinnamoyl]-5-nitro-1,2-dihydro-3H-benzo[e]indole-7-carboxamide;
- 1-(Chloromethyl)-3-{5-[2-(dimethylamino)ethoxy]indol-2-carbonyl}-N-(2-hydroxyethyl)-5-nitro-1,2-dihydro-3H-benzo[e]indole-7-carboxamide;
- Methyl 1-(chloromethyl)-3-(5,6,7-trimethoxyindol-2-carbonyl)-5-nitro-1,2-dihydro-3H-benzo[e]indole-7-carboxylate;
- Methyl 1-(chloromethyl)-3-{5-[2-(dimethylamino)ethoxy]indol-2-carbonyl}-5-nitro-1,2-dihydro-3H-benzo[e]indole-7-carboxylate;
- 1-(Chloromethyl)-N-[2-(dimethylamino)ethyl]-5-nitro-3-(5,6,7-trimethoxyindol-2-carbonyl)-1,2-dihydro-3H-benzo[e]indole-7-carboxamide;
- 1-(Chloromethyl)-7-(methylsulfonyl)-5-nitro-3-(5,6,7-trimethoxyindol-2-carbonyl)-1,2-dihydro-3H-benzo[e]indole;
- 1-(Chloromethyl)-3-{5-[2-(dimethylamino)ethoxy]indol-2-carbonyl}-7-(methylsulfonyl)-5-nitro-1,2-dihydro-3H-benzo[e]indole;
- 8-Acetyl-1-(chloromethyl)-3-{5-[2-(dimethylamino)ethoxy]indol-2-carbonyl}-5-nitro-1,2-dihydro-3H-benzolelindole;
- Methyl 1-(chloromethyl)-3-{5-[2-(dimethylamino)ethoxy]indol-2-carbonyl}-5-nitro-1,2-dihydro-3H-benzo[e]indole-8-carboxylate;
- 1-(Chloromethyl)-N-[2-(dimethylamino)ethyl]-5-nitro-3-(5,6,7-trimethoxyindol-2-carbonyl)-1,2-dihydro-3H-benzo[e]indole-8-carboxamide;

1-(Chloromethyl)-3-{5-[2-(dimethylamino)ethoxy]indol-2-carbonyl}-5-nitro-1,2-dihydro-3H-benzo[e]indole-8-carboxamide;
1-(Chloromethyl)-3-{5-[2-(dimethylamino)ethoxy]indol-2-carbonyl}-5-nitro-1,2-dihydro-3H-benzo[e]indole-8-carbonitrile;
1-(Chloromethyl)-8-(methylsulfonyl)-5-nitro-3-(5,6,7-trimethoxyindol-2-carbonyl)-1,2-dihydro-3H-benzo[e]indole;
1-(Chloromethyl)-3-{5-[2-(dimethylamino)ethoxy]indol-2-carbonyl}-8-(methylsulfonyl)-5-nitro-1,2-dihydro-3H-benzo[e]indole;
1-(Chloromethyl)-5-nitro-3-(5,6,7-trimethoxyindol-2-carbonyl)-1,2-dihydro-3H-benzo[e]indole-8-sulfonamide;
1-(Chloromethyl)-3-{5-[2-(dimethylamino)ethoxy]indol-2-carbonyl}-5-nitro-1,2-dihydro-3H-benzo[e]indole-8-sulfonamide;
7-Amino-1-(chloromethyl)-3-{5-[2-(dimethylamino)ethoxy]indol-2-carbonyl}-5-nitro-1,2-dihydro-3H-benzo[e]indole;
1-(Chloromethyl)-3-{5-[2-(dimethylamino)ethoxy]indol-2-carbonyl}-N-hydroxy-5-nitro-1,2-dihydro-3H-benzo[e]indole-7-sulfonamide;
1-(Chloromethyl)-3-{5-[2-(dimethylamino)ethoxy]indol-2-carbonyl}-5-nitro-1,2-dihydro-3H-benzo[e]indole-7-sulfonohydrazide;
1-(Chloromethyl)-3-{5-[2-(dimethylamino)ethoxy]indol-2-carbonyl}-5-nitro-N-propionyl-1,2-dihydro-3H-benzo[e]indole-7-sulfonamide; and
1-(Chloromethyl)-3-{5-[2-(dimethylamino)ethoxy]indol-2-carbonyl}-5,7-dinitro-1,2-dihydro-3H-benzo[e]indole-8-sulfonamide.

4. A compound of Formula I as claimed in claim 1 wherein at least one of X, Y, W or Q is substituted with a phosphate $[P(O)(OH)_2]$ group.

5. A compound of Formula I as claimed in claim 4 selected from the following:
2-{[1-(Chloromethyl)-5-nitro-3-(5,6,7-trimethoxyindol-2-carbonyl)-1,2-dihydro-3H-benzo[e]indol-7-yl]sulfonyl}aminoethyl dihydrogen phosphate;
2-{[1-(Chloromethyl)-5-nitro-3-{5-1,2-(dimethylamino)ethoxy]indol-2-carbonyl}-1,2-dihydro-3H-benzo[e]indol-7-yl]sulfonyl}aminoethyl dihydrogen phosphate; and
2-({2-[7-(Aminosulfonyl)-1-(chloromethyl)-5-nitro-1,2-dihydro-3H-benzo[e]indol-3-carbonyl]indol-5-yl}oxy)ethyl dihydrogen phosphate.

6. A compound of Formula II,

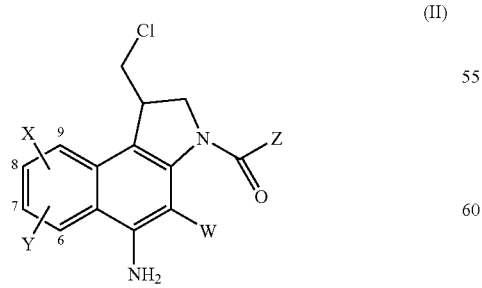

(II)

wherein X, Y, and W are independently selected from H, halogen, $C_{1-4}$alkyl, $OR^1$, $OP(O)(OH)_2$, $SR^1$, $NR^1_2$, $COR^1$, $SOR^1$, $SO_2R^1$, $SO_2NR^1_2$, $SO_2NR^1OR^1$, $SO_2NR^1NR^1_2$, $SO_2NHCOR^1$, $CO_2R^1$, $CONR^1_2$, $CONHSO_2R^1$, $OF_3$, CN, $NO_2$, where X and Y are located at any one of the available positions 6-9, and where each $R^1$ independently represents H or a $C_{1-4}$alkyl, optionally substituted with one or more hydroxyl or amino groups, each hydroxyl group being further optionally substituted with a phosphate $[P(O)(OH)_2]$ group, and each amino group being further optionally substituted with one or two $C_{1-4}$alkyl groups, and wherein Z may be selected from the following structures (Ia-Ic)

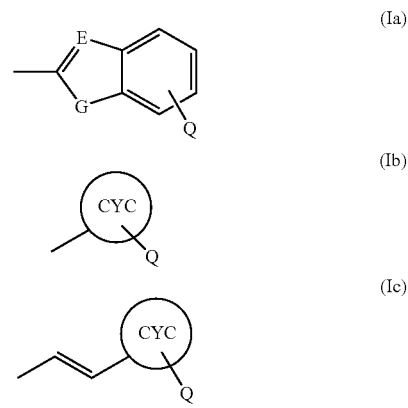

wherein E may be selected from —N= or CH=, G may be selected from O, S, or NH, Q may be independently selected from one to three of $R^2$, $OR^2OP(O)(OH)_2$ halogen, $NR^2_2$, $NO_2$, $CO_2R^2$, $CONR^2_2$, $NR^2COR^2$, where each $R^2$ independently represents H, lower $C_{1-4}$alkyl, optionally substituted with one or more hydroxyl or amino groups, each hydroxyl group being further optionally substituted with a phosphate $[P(O)(OH)_2]$ group, each amino group being optionally substituted with one or two $C_{1-4}$alkyl groups; and CYC may represent a 5- or 6-membered carbocycle, or heterocycle containing one or two atoms independently selected from N, O and S, and physiologically functional salt derivatives thereof, with the proviso that when W represents H, X and Y do not each represent H.

7. A compound of formula II as claimed in claim 6 wherein Z is selected from the following:

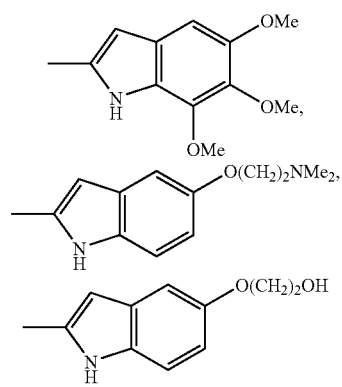

-continued

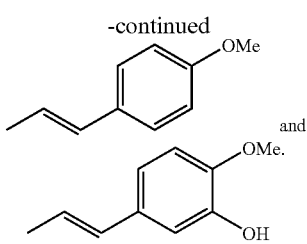
and

8. A compound of Formula II as claimed in claim 6 selected from 7-Acetyl-5-am mo-1-(chloromethyl)-3-{5-[2-(dimethylamino)ethoxy]indol-2-carbonyl}-1,2-dihydro-3H-benzo[e]indole;
  Methyl 5-amino-1-(chloromethyl)-3-{5-[2-(dimethylamino)ethoxy]indol-2-carbonyl}-1,2-dihydro-3H-benzo[e]indole-7-carboxylate;
  5-Amino-1-(chloromethyl)-3-{5-[2-(dimethylamino)ethoxy]indol-2-carbonyl}-1,2-dihydro-3H-benzo[e]indole-7-carboxamide;
  5-Amino-1-(chloromethyl)-3-{5-[2-(dimethylamino)ethoxy]indol-2-carbonyl}-1,2-dihydro-3H-benzo[e]indole-7-carbonitrile;
  5-Amino-1-(chloromethyl)-7-(methylsulfonyl)-3-(5,6,7-trimethoxyindol-2-carbonyl)-1,2-dihydro-3H-benzo[e]indole;
  5-Amino-1-(chloromethyl)-3-{5-[2-(dimethylamino)ethoxy]indol-2-carbonyl}-7-(methylsulfonyl)-1,2-dihydro-3H-benzo[e]indole;
  5-Amino-1-(chloromethyl)-3-(5,6,7-trimethoxyindol-2-carbonyl)-1,2-dihydro-3H-benzo[e]indole-7-sulfonamide;
  5-Amino-1-(chloromethyl)-3-{5-[2-(dimethylamino)ethoxy]indol-2-carbonyl}-1,2-dihydro-3H-benzo[e]indole-7-sulfonamide;
  5-Amino-1-(chloromethyl)-3-{5-[2-(dimethylamino)ethoxy]indol-2-carbonyl}-N-methyl-1,2-dihydro-3H-benzo[e]indole-7-sulfonamide;
  5-Amino-1-(chloromethyl)-3-{5-[2-(dimethylamino)ethoxy]indol-2-carbonyl}-N-(2-hydroxyethyl)-1,2-dihydro-3H-benzo[e]indole-7-sulfonamide;
  5-Amino-1-(chloromethyl)-8-(methylsulfonyl)-3-(5,6,7-trimethoxyindol-2-carbonyl)-1,2-dihydro-3H-benzo[e]indole and
  5-Amino-1-(chloromethyl)-3-(5-[2-(dimethylamino)ethoxy]indol-2-carbonyl)-8-(methylsulfonyl)-1,2-dihydro-3H-benzo[e]indole.

9. A method of treating a solid tumour, which comprises administering to a subject in need of such treatment a therapeutically effective amount of a compound of Formula I as claimed in claim 1.

10. The method as claimed in claim 9 wherein the subject has tumour cells in a hypoxic environment.

11. The method as claimed in claim 10 wherein the tumour cells are selected from the group consisting of breast, bowel, lung and small cell lung tumour cells.

12. The method as claimed in claim 9 further including the step of administering radiotherapy to the subject before, during or after the administration of the compound of Formula I.

13. The method as claimed in claim 9 further including the step of administering one or more chemotherapeutic agents to the subject before, during or after the administration of the compound of Formula I.

14. The method as claimed in claim 13 wherein the one or more chemotherapeutic agents are selected from Cisplatin or other platinum-based derivatives, Temozolomide or other DNA methylating agents, Cyclophosphamide or other DNA alkylating agents, Doxorubicin, mitoxantrone, camptotheoin or other topoisomerase inhibitors, Methotrexate, gemcitabine or other antimetabolites, Paclitaxel, Docetaxel or other tubulin-modifying agents; Tirapazamine, Bleomycin, or other DNA-breaking agents.

15. The method as claimed in claim 9 wherein the subject is a human or warm blooded animal.

16. A pharmaceutical composition including a therapeutically effective amount of a compound of formula I as claimed in claim 1 and a pharmaceutically acceptable excipient, adjuvant, carrier, buffer or stabiliser.

17. A method of nitrating a compound of formula VIII

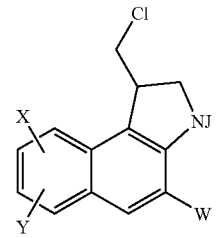

wherein W, X and Y are as defined above for Formula I, J represents H, t-butoxycarbonyl or trifluoroacetyl to provide a compound of Formula IX,

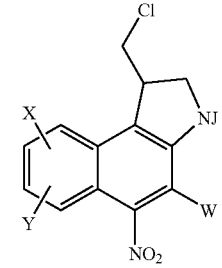

wherein W, X and Y are as defined above for Formula I, J represents H, or trifluoroacetyl.

18. The method as claimed in claim 17 wherein nitration is achieved with $KNO_3/H_2SO_4$ or with any other suitable nitrating agent.

19. A method of producing a compound of Formula II

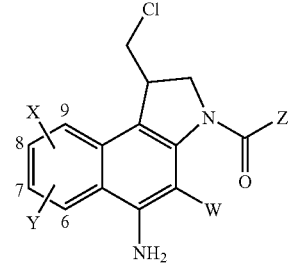

wherein X, Y, and W are independently selected from H, halogen, $C_{1-4}$alkyl, $OR^1$, $OP(O)(OH)_2$, $SR^1$, $NR^1{}_2$, $COR^1$, $SOR^1$, $SO_2R^1$, $SO_2NR^1{}_2$, $SO_2NR^1OR^1$, $SO_2NR^1NR^1{}_2$, $SO_2NHCOR^1$, $CO_2R^1$, $CONR^1{}_2$, $CONHSO_2R^1$, $OF_3$, ON, $NO_2$, where X and Y are located at any one of the available positions 6-9, and where each $R^1$ independently represents H or a $C_{1-4}$alkyl, optionally substituted with one or more hydroxyl or amino groups, each hydroxyl group being further optionally substituted with a phosphate [P(O)(OH)$_2$] group, and each amino group being further optionally substituted with one or two $C_{1-4}$alkyl, groups, and wherein Z may be selected from the following structures (Ia-Ic)

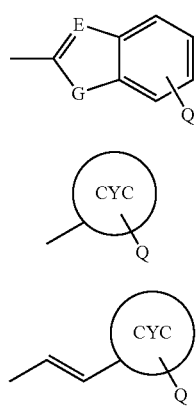

(Ia)
(Ib)
(Ic)

wherein E may be selected from —N= or —CH=, G may be selected from O, S, or NH, Q may be independently selected from one to three of $R^2$, $OR^2OP(O)(OH)_2$ halogen, $NR^2{}_2$, $NO_2$, $CO_2R^2$, $CONR^2{}_2$, $NR^2COR^2$, where each $R^2$ independently represents H, lower $C_{1-4}$alkyl, optionally substituted with one or more hydroxyl or amino groups, each hydroxyl group being further optionally substituted with a phosphate [P(O)(OH)$_2$] group, each amino group being optionally substituted with one or two $C_{1-4}$alkyl groups; and CYC may represent a 5- or 6-membered carbocycle, or heterocycle containing one or two atoms independently selected from N, O and S, and physiologically functional salt derivatives thereof, with the proviso that when W represents H, X and Y do not each represent H, said method comprising reducing a compound of Formula I as defined in claim 1.

20. A method as claimed in claim 19 whereby the reduction is carried out by chemical reduction or hypoxic metabolism.

21. A method as claimed in claim 19 wherein the reduction step is carried out under in vivo hypoxic conditions.

22. A compound of Formula I as defined in claim 1 but with the further proviso that when W is H, and one of X and Y represents H, the other of X and Y does not represent halogen, $CH_3$, $OR^1$, $SR^1$, $NR^1{}_2$, $SO_2R^1$, $CONHR^1$, CN or $CO_2R^1$, where for this proviso each $R^1$ can only independently represent H or $C_1$-$C_4$ alkyl, optionally substituted with one or more hydroxyl or amino groups, the amino groups being further optionally substituted with one or two $C_1$-$C_4$ alkyl groups.

23. A compound of Formula II as defined in claim 6 but with the further proviso that when W is H, and one of X and Y represents H, the other of X and Y does not represent halogen, $CH_3$, $OR^1$, $SR^1$, $NR^1{}_2$, $SO_2R^1$, $CONHR^1$, CN or $CO_2R^1$, where for this proviso each $R^1$ can only independently represent H or $C_1$-$C_4$ alkyl, optionally substituted with one or more hydroxyl or amino groups, the amino groups being further optionally substituted with one or two $C_1$-$C_4$ alkyl groups.

24. A compound of Formula I as defined in claim 1 but with the further proviso that when W is H, and one of X and Y represents H, then the other of X and Y is selected from halogen, $CH_3$, $OR^1$, $SR^1$, $NR^1{}_2$, $SO_2R^1$, $CONHR^1$, CN and $CO_2R^1$, where for this proviso each $R^1$ can only independently represent H or $C_1$-$C_4$ alkyl, optionally substituted with one or more hydroxyl or amino groups, the amino groups being further optionally substituted with one or two $C_1$-$C_4$ alkyl groups.

25. A compound of Formula II as defined in claim 6 but with the further proviso that when W is H, and one of X and Y represents H, then the other of X and Y is selected from halogen, $CH_3$, $OR^1$, $SR^1$, $NR^1{}_2$, $SO_2R^1$, $CONHR^1$, ON and $CO_2R^1$, where for this proviso each $R^1$ can only independently represent H or $C_1$-$C_4$ alkyl, optionally substituted with one or more hydroxyl or amino groups, the amino groups being further optionally substituted with one or two $C_1$-$C_4$ alkyl groups.

26. A compound of Formula I as defined in claim 1 but with the further proviso that when W is H; and one of X and Y represents H, then the other of X and Y is $CONR^1{}_2$, wherein $R^1$ is as defined in claim 1.

27. A compound of Formula II as defined in claim 6 but with the further proviso that when W is H, and one of X and Y represents H, then the other of X and Y is $CONR^1{}_2$, wherein $R^1$ is as defined in claim 6.

28. A compound of Formula I as defined in claim 1 but with the further proviso that when W is H, and one of X and Y represents H, then the other of X and Y is selected from $C_2$-$C_4$ alkyl, $OP(O)(OH)_2$, $COR^1$, $SOR^1$, $SO_2NR^1{}_2$, $SO_2NR^1OR^1$, $SO_2NR^1NR^1{}_2$, $SO_2NHCOR^1$, $CONHSO_2R^1$, $CF_3$ and $NO_2$, wherein $R^1$ is as defined in claim 1.

29. A compound of Formula II as defined in claim 6 but with the further proviso that when W is H, and one of X and Y represents H, then the other of X and Y is selected from $C_2$-$C_4$ alkyl, $OP(O)(OH)_2$, $COR^1$, $SOR^1$, $SO_2NR^1{}_2$, $SO_2NR^1OR^1$, $SO_2NR^1NR^1{}_2$, $SO_2NHCOR^1$, $CONHSO_2R^1$, $CF_3$ and $NO_2$, wherein $R^1$ is as defined in claim 6.

30. A compound of Formula I as defined in claim 1 but with the further proviso that when W is H, and one of X and Y represents H, then the other of X and Y is $SO_2NR^1{}_2$, wherein $R^1$ is as defined in claim 1.

31. A compound of Formula II as defined in claim 6 but with the further proviso that when W is H, and one of X and Y represents H, then the other of X and Y is $SO_2NR^1{}_2$, wherein $R^1$ is as defined in claim 6.

* * * * *